US011541070B2

(12) United States Patent
Han et al.

(10) Patent No.: US 11,541,070 B2
(45) Date of Patent: Jan. 3, 2023

(54) ADMINISTRATION OF AN ANTI-ACTIVIN-A COMPOUND TO A SUBJECT

(71) Applicants: AMGEN INC., Thousand Oaks, CA (US); Santa Maria Biotherapeutics, Inc., South San Francisco, CA (US)

(72) Inventors: Huiquan Han, Thousand Oaks, CA (US); Christopher Michael Haqq, Newbury Park, CA (US); Isaac Ciechanover, Burlingame, CA (US); Xiaolan Zhou, Newbury Park, CA (US); John Zhao-Nian Lu, Alhambra, CA (US)

(73) Assignee: Atara Biotherapeutics, Inc., South San Francisco, CA (US)

(*) Notice: Subject to any disclaimer, the term of this patent is extended or adjusted under 35 U.S.C. 154(b) by 0 days.

(21) Appl. No.: 16/714,407

(22) Filed: Dec. 13, 2019

(65) Prior Publication Data

US 2020/0108085 A1 Apr. 9, 2020

Related U.S. Application Data

(62) Division of application No. 14/764,288, filed as application No. PCT/US2014/014490 on Feb. 3, 2014, now abandoned.

(60) Provisional application No. 61/815,220, filed on Apr. 23, 2013, provisional application No. 61/759,961, filed on Feb. 1, 2013.

(51) Int. Cl.
| | |
|---|---|
| *A61K 38/17* | (2006.01) |
| *A61K 31/704* | (2006.01) |
| *A61K 45/06* | (2006.01) |
| *A61K 31/7068* | (2006.01) |
| *C07K 16/22* | (2006.01) |
| *A61K 39/395* | (2006.01) |
| *A61K 39/00* | (2006.01) |

(52) U.S. Cl.
CPC ........ *A61K 31/704* (2013.01); *A61K 31/7068* (2013.01); *A61K 38/177* (2013.01); *A61K 38/1796* (2013.01); *A61K 39/3955* (2013.01); *A61K 39/39558* (2013.01); *A61K 45/06* (2013.01); *C07K 16/22* (2013.01); *A61K 2039/505* (2013.01); *A61K 2039/545* (2013.01); *C07K 2317/76* (2013.01)

(58) Field of Classification Search
CPC .............................. A61K 38/179; A61K 45/06
See application file for complete search history.

(56) References Cited

U.S. PATENT DOCUMENTS

| | | | |
|---|---|---|---|
| 3,773,919 A | 11/1973 | Boswell et al. | |
| 4,411,993 A | 10/1983 | Gillis | |
| 4,543,439 A | 9/1985 | Frackelton et al. | |
| RE32,011 E | 10/1985 | Zimmerman et al. | |
| 4,816,567 A | 3/1989 | Cabilly et al. | |
| 4,902,614 A | 2/1990 | Wakabayashi et al. | |
| 4,973,577 A | 11/1990 | Vale et al. | |
| 5,011,912 A | 4/1991 | Hopp et al. | |
| 5,545,616 A | 8/1996 | Woodruff | |
| 5,567,584 A | 10/1996 | Sledziewski et al. | |
| 5,595,898 A | 1/1997 | Robinson et al. | |
| 5,627,052 A | 5/1997 | Schrader | |
| 5,693,493 A | 12/1997 | Robinson et al. | |
| 5,750,375 A | 5/1998 | Sledziewski et al. | |
| 5,827,733 A | 10/1998 | Lee et al. | |
| 5,859,205 A | 1/1999 | Adair et al. | |
| 5,863,738 A | 1/1999 | Dijke et al. | |
| 5,885,794 A | 3/1999 | Mathews et al. | |
| 5,994,618 A | 11/1999 | Lee et al. | |
| 6,096,506 A | 8/2000 | Lee et al. | |
| 6,162,896 A | 12/2000 | Mathews et al. | |
| 6,300,129 B1 | 10/2001 | Lonberg et al. | |
| 6,465,239 B1 | 10/2002 | Lee et al. | |
| 6,468,535 B1 | 10/2002 | Lee et al. | |
| 6,472,179 B2 | 10/2002 | Stahl et al. | |
| 6,500,664 B1 | 12/2002 | Lee et al. | |
| 6,599,876 B2 | 7/2003 | Kojima | |
| 6,607,884 B1 | 8/2003 | Lee et al. | |
| 6,656,475 B1 | 12/2003 | Lee et al. | |
| 6,812,339 B1 | 11/2004 | Venter et al. | |
| 6,858,208 B2 | 2/2005 | Lee et al. | |
| 6,891,082 B2 | 5/2005 | Lee et al. | |

(Continued)

FOREIGN PATENT DOCUMENTS

| | | |
|---|---|---|
| CA | 1219215 A | 3/1987 |
| CN | 1946382 A | 4/2007 |

(Continued)

OTHER PUBLICATIONS

Rudikoff et al., Proc. Natl. Acad. Sci. 79: 1979-1983, (1982).*

(Continued)

*Primary Examiner* — Gyan Chandra
(74) *Attorney, Agent, or Firm* — Lisa E. Alexander

(57) ABSTRACT

The present invention relates to methods of treating ovarian cancer in a subject by administering to the subject by evaluating the subject's expression levels of specific biomarkers or angiogenic an anti-activin-A compound, such as an anti-activin-A antibody or an activin-A-binding receptor. In some embodiments, at least two compounds are administered to the subject, where the first compound is an anti-activin A compound, and the second compound is a chemotherapeutic compound, for example capecitabine. The invention further relates to methods of identifying subjects for treatment factors.

1 Claim, 49 Drawing Sheets

Specification includes a Sequence Listing.

(56) References Cited

U.S. PATENT DOCUMENTS

| | | |
|---|---|---|
| 7,166,707 B2 | 1/2007 | Feige |
| 7,189,827 B2 | 3/2007 | Feige |
| 7,399,848 B2 | 7/2008 | Lee et al. |
| 7,442,778 B2 | 10/2008 | Gegg et al. |
| 7,507,412 B2 | 3/2009 | Burger et al. |
| 7,511,012 B2 | 3/2009 | Han et al. |
| 7,534,432 B2 | 5/2009 | Lee et al. |
| 7,566,772 B2 | 7/2009 | Green et al. |
| 7,585,500 B2 | 9/2009 | Foltz et al. |
| 7,645,861 B2 | 1/2010 | Gegg et al. |
| 7,655,764 B2 | 2/2010 | Gegg et al. |
| 7,655,765 B2 | 2/2010 | Gegg et al. |
| 7,662,931 B2 | 2/2010 | Gegg et al. |
| 7,709,605 B2 | 5/2010 | Knopf et al. |
| 7,736,653 B2 | 6/2010 | Kim et al. |
| 7,737,260 B2 | 6/2010 | Kim et al. |
| 7,750,127 B2 | 7/2010 | Gegg et al. |
| 7,750,128 B2 | 7/2010 | Gegg et al. |
| 7,803,923 B2 | 9/2010 | Han et al. |
| 7,842,663 B2 | 11/2010 | Knopf et al. |
| 7,928,075 B2 | 4/2011 | Han et al. |
| 7,947,646 B2 | 5/2011 | Sun et al. |
| 7,964,193 B2 | 6/2011 | Green et al. |
| 7,994,302 B2 | 8/2011 | Foltz et al. |
| 8,058,229 B2 | 11/2011 | Seehra et al. |
| 8,067,562 B2 | 11/2011 | Han et al. |
| 8,071,538 B2 | 12/2011 | Han et al. |
| 8,110,665 B2 | 2/2012 | Kim et al. |
| 8,124,094 B2 | 2/2012 | Kim et al. |
| 8,128,933 B2 | 3/2012 | Knopf et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,309,082 B2 | 11/2012 | Han et al. |
| 8,343,933 B2 | 1/2013 | Knopf et al. |
| 8,361,957 B2 | 1/2013 | Seehra et al. |
| 8,410,043 B2 | 4/2013 | Sun et al. |
| 8,501,678 B2 | 8/2013 | Sun et al. |
| 8,614,292 B2 | 12/2013 | Han et al. |
| 8,716,459 B2 | 5/2014 | Sun et al. |
| 8,753,627 B2 | 6/2014 | Han et al. |
| 8,999,917 B2 | 4/2015 | Sun et al. |
| 9,273,114 B2 | 3/2016 | Sun et al. |
| 9,284,364 B2 | 3/2016 | Han et al. |
| 2004/0209805 A1 | 10/2004 | Phillips et al. |
| 2004/0223966 A1 | 11/2004 | Wolfman et al. |
| 2005/0014733 A1 | 1/2005 | Whittemore et al. |
| 2005/0186593 A1 | 8/2005 | Mathews et al. |
| 2006/0034831 A1 | 2/2006 | Tobin |
| 2006/0068468 A1 | 3/2006 | Knopf et al. |
| 2007/0065444 A1 | 3/2007 | North et al. |
| 2007/0117130 A1 | 5/2007 | Han et al. |
| 2008/0089897 A1 | 4/2008 | Wolfman |
| 2008/0248047 A1 | 10/2008 | Das et al. |
| 2009/0005308 A1 | 1/2009 | Knopf et al. |
| 2009/0047281 A1 | 2/2009 | Sherman et al. |
| 2009/0087433 A1 | 4/2009 | Wolfman et al. |
| 2009/0118188 A1 | 5/2009 | Knopf et al. |
| 2009/0227497 A1 | 9/2009 | Sun et al. |
| 2009/0234106 A1* | 9/2009 | Han .................. A61P 7/00 530/387.9 |
| 2010/0008918 A1 | 1/2010 | Sherman et al. |
| 2010/0168020 A1 | 7/2010 | Sun et al. |
| 2010/0272734 A1 | 10/2010 | Berger et al. |
| 2010/0310506 A1 | 12/2010 | Coti et al. |
| 2011/0034372 A1 | 2/2011 | Lee et al. |
| 2011/0070233 A1 | 3/2011 | Seehra et al. |
| 2011/0183897 A1 | 7/2011 | Sun et al. |
| 2011/0243933 A1 | 10/2011 | Poradosu et al. |
| 2011/0281796 A1 | 11/2011 | Han et al. |
| 2012/0121576 A1 | 5/2012 | Seehra et al. |
| 2012/0128668 A1 | 5/2012 | Knopf et al. |
| 2012/0148588 A1 | 6/2012 | Seehra et al. |
| 2012/0156204 A1 | 6/2012 | Seehra et al. |
| 2012/0295814 A1 | 11/2012 | Cramer et al. |
| 2012/0328595 A1 | 12/2012 | Sun et al. |
| 2013/0030159 A1 | 1/2013 | Han et al. |
| 2013/0071393 A1 | 3/2013 | Seehra et al. |
| 2014/0194355 A1 | 7/2014 | Sun et al. |
| 2014/0220033 A1 | 8/2014 | Han et al. |
| 2014/0348827 A1 | 11/2014 | Sun et al. |
| 2015/0086556 A1 | 3/2015 | Han et al. |
| 2015/0231206 A1 | 8/2015 | Sun et al. |
| 2015/0359850 A1 | 12/2015 | Han et al. |
| 2016/0137718 A1 | 5/2016 | Sun et al. |
| 2016/0152683 A1 | 6/2016 | Han et al. |

FOREIGN PATENT DOCUMENTS

| | | |
|---|---|---|
| CN | 101679980 A | 3/2010 |
| EP | 0036676 A1 | 9/1981 |
| EP | 0058481 A1 | 8/1982 |
| EP | 0088046 A2 | 9/1983 |
| EP | 0133988 A2 | 3/1985 |
| EP | 0143949 A1 | 6/1985 |
| EP | 2064239 A2 | 6/2009 |
| EP | 2370463 A2 | 10/2011 |
| EP | 2559705 A2 | 2/2013 |
| JP | 1171495 A | 7/1989 |
| JP | 2006-516886 A | 7/2006 |
| JP | 2009-513162 A | 4/2009 |
| JP | 2010-518009 A | 5/2010 |
| JP | 2010-519931 A | 6/2010 |
| JP | 2010-539236 A | 12/2010 |
| JP | 2013-027391 A | 2/2013 |
| JP | 5349966 A | 11/2013 |
| JP | 2014-195469 A | 10/2014 |
| KR | 10-1428344 | 8/2014 |
| WO | 1992/002551 A1 | 2/1992 |
| WO | 1993/015722 A1 | 8/1993 |
| WO | 1994/009817 A1 | 5/1994 |
| WO | 1994/010332 A1 | 5/1994 |
| WO | 1994/020069 A1 | 9/1994 |
| WO | 1999/038890 A1 | 8/1999 |
| WO | 2000/029581 A1 | 5/2000 |
| WO | 2000/043781 A2 | 7/2000 |
| WO | 2000/043781 A3 | 7/2000 |
| WO | 2004/039948 A2 | 5/2004 |
| WO | 2004/039948 A3 | 5/2004 |
| WO | 2005/051299 A2 | 6/2005 |
| WO | 2005/105057 A1 | 11/2005 |
| WO | 2005/116052 A2 | 12/2005 |
| WO | 2006/012627 A2 | 2/2006 |
| WO | 2006/020884 A2 | 2/2006 |
| WO | 2006/020884 A3 | 2/2006 |
| WO | 2006/116269 A2 | 11/2006 |
| WO | 2007/053775 A1 | 5/2007 |
| WO | 2008/031061 A2 | 3/2008 |
| WO | 2008/097541 A2 | 8/2008 |
| WO | 2008/109167 A2 | 9/2008 |
| WO | 2008/113185 A1 | 9/2008 |
| WO | 2010/019261 A1 | 2/2010 |
| WO | 2010/062383 A2 | 6/2010 |
| WO | 2013/106175 A1 | 7/2013 |
| WO | 2014/121221 A1 | 8/2014 |
| WO | 2015/108972 A1 | 7/2015 |
| WO | 2015/192127 A2 | 12/2015 |

OTHER PUBLICATIONS

Chamow and Ashkenazi, TIBTECH 14: 52-60, (1996).*
Cooke and Brenton, Lancet Oncol 12: 1169-1174, (2011).*
Schmeler et al , J. Clin. Oncology (Meeting abstract), (2010).*
Abaza, MS., et al. "Effects of amino acid substitutions outside an antigenic site on protein binding to monoclonal antibodies of predetermined specificity obtained by peptide immunization: demonstration with region 94-100 (antigenic site 3) of myoglobin," J Protein Chem. Oct. 1992; 11 (5):433-44.
Akerstrom, B et al., "Protein G: A Powerful Tool for Binding and Detection of Monoclonal and Polyclonal Antibodies," Journal of lmmunoloav, 135(4):2589-2592, 1985.

(56) References Cited

OTHER PUBLICATIONS

Alibhai, SMH, et al., "Long-term side effects of androgen deprivation therapy in men with non-metastatic prostate cancer: a systematic literature review," Crit Rev Oncol/Hematol. 2006, vol. 60, pp. 201-215.
Anker, S., et al., "Cardiac Cachexia: A Syndrome With Impaired Survival and Immune and Neuroendocrine Activation," Chest, 1999, vol. 115, pp. 836-847.
Attisano, L., et al., "Activation of Signalling by the Activin Receptor Complex," Molecular and Cellular Biology, Mar. 1996, p. 1066-1073, vol. 16, No. 3.
Attisano, L., et al., "Novel Activin Receptors: Distinct Genes and Alternative mRNA Splicing Generate a Repertoire of Serine/Threonine Kinase Receptors," Cell, Jan. 1992, vol. 68, pp. 97-108.
Augustin, H.G., et al., "Control of vascular morphogenesis and homeostasis through the angiopoietin—Tie system," Nature Reviews Molecular Cell Biology, 2009, vol. 10, pp. 165-177.
Babcock, J., et al., "A Novel strategy for generating monoclonal antibodies from single, isolated lymphocytes producing antibodies of defined specificities," Proc. Natl. Acad. Sci., USA, Jul. 1996, vol. 93, pp. 7843-7848.
Barany, et al., "Solid-phase peptide syntheses: a silver anniversary report," Int. J. Peptide Protein Res., 30:705-739, 1987.
Barany, et al., "Solid-phase peptide synthesis," Ch. 1, The Peptides: Analysis, Synthesis, Biology, vol. 2, Gross and Meienhofer, eds., (Academic Press, New York, 1980), pp. 1-284.
Beiboer, et al.,"Guided selection of a pan carcinoma specific antibody reveals similar binding characteristics yet structural divergence between the original murine antibody and its human equivalent," J. Mol., Biol. (2000) 296:833-849.
Berrondo, M., "Predicting the structure and function of protein mutants," A Dissertation submitted to Johns Hopkins University in conformity with the requirements for the degree of Doctor of Philosophy Baltimore, Maryland, Jan. 2010, 176 Pages, Can be retrieved at <URL:http://graylab.jhu.edu/publications/dissertations/Berrondo2010.pdf>.
Birtalan, A., et al., "The intrinsic contributions of tyrosine, serine, glycine and arginine to the affinity and specificity of antibodies," J. Mol. Biology, Apr. 2008, pp. 1518-1528, vol. 377.
Bogdanovich, S., et al., "Myostatin blockade improves function but not histopathology in a murine model of limb-girdle muscular dystrophy 2C," Muscle Nerve, Mar. 2008, pp. 308-316, vol. 37, No. 3.
Bowie, J.U., et al., "Deciphering the message in protein sequences: tolerance to amino acid substitutions" Science, Mar. 16, 1990, pp. 1306-1310, vol. 247, No. 4948.
Brown, et al., "Tolerance of single, but not multiple, amino acid replacements in antibody VH CDR 2: a means of minimizing B cell wastage from somatic hypermutation?" J. Immuno, May 1996, 3285-91.
Campbell, K., et al., "Totipotency of Multipotentiality of Cultured Cells: Applications and Progress," Theriogenology, Jan. 1, 1997, vol. 47, Issue 1, pp. 63-72.
Casset, et al. "A peptide mimetic of an anti-CD4 monoclonal antibody by rational design," Biochem Biophys Res Commun. Jul. 18, 2003, 307(1):198-205.
Chang, K.P., et al., "Overexpression of activin A in oral squamous cell carcinoma: association with poor prognosis and tumor progression," Ann Surg Oncol. 2010, vol. 17, pp. 1945-1956.
Chaubert, et al., "Simultaneous Double Immunoenzymatic Labeling: A New Procedure for the Histopathologic Routine," Modern Pathology, 10(6):585-591, 1997.
Chien, et al., "Significant structural and functional change of an antigen-binding site by a distant amino acid substitution: proposal of a structural mechanism," Proc Natl Acad Sci U S A. Jul. 1989, 86(14):5532-6.
Choi, J.-H., et al., "Gonadotropins and ovarian cancer," Endocrine Reviews, 2007, vol. 28, pp. 440-461.

Choi, K.-C., et al., "Differential expression of activin/inhibin subunit and activin receptor mRNAs in normal neoplastic ovarian surface epithelium (OSE)," Molecular and Cellular Endocrinology, 2001, vol. 174, pp. 99-110.
Cipriano, S., et al., "Follistatin Is a Modulator of Gonadal Tumor Progression and the Activin-Induced Wasting Syndrome in Inhibin-Deficient Mice," Endocrinology, 2000, vol. 141, No. 7, pp. 2319-2327.
Clackson, T., et al., "Making antibody fragments using phage display libraries," Nature 352:624-628, 1991.
Cobellis, L., et al., "High Concentrations of Activin A in the Peritoneal Fluid of Women With Epithelial Ovarian Cancer," J. Soc. Gynecol. Investig. 2004, vol. 11, pp. 203-206.
Coerver, K. A. et al., "Activin Signaling through Activin Receptor Type II Causes the Cachexia-Like Symtoms in Inhibin-Deficient Mice," Molecular Endocrinology 10:534-543, 1996.
Colman, PM., "Effects of amino acid sequence changes on antibody-antigen interactions," Res Immunol. 145(1):33-36, 1994.
Communication Pursuant to Article 94(3) EPC for European Patent Application No. 06827481.0, dated Jul. 20, 2010, 2 pages.
Communication Pursuant to Article 94(3) EPC for European Patent Application No. 06827481.0, dated May 30, 2011, 3 pages.
Communication Pursuant to Article 94(3) EPC for European Patent Application No. 06827481.0, dated Sep. 9, 2008, 2 pages.
Communication Pursuant to Article 94(3) EPC for European Patent Application No. 07842088.2, dated Feb. 18, 2013, 4 Pages.
Communication pursuant to Article 94(3) EPC for European Patent Application No. 07842088.2, dated Feb. 4, 2010, 3 Pages.
Communication pursuant to Article 94(3) EPC for European Patent Application No. 07842088.2, dated Jan. 24, 2012, 6 Pages.
Communication pursuant to Article 94(3) EPC for European Patent Application No. 07842088.2, dated Jul. 31, 2012, 4 Pages.
Communication Pursuant to Article 94(3) EPC for European Patent Application No. 08742032.9, dated Apr. 18, 2013, 4 pages.
Communication pursuant to Article 94(3) EPC for European Patent Application No. 08742032.9, dated Aug. 21, 2015, 3 Pages.
Communication pursuant to Article 94(3) EPC for European Patent Application No. 09761055.4, dated Apr. 28, 2014, 3 Pages.
Communication pursuant to Article 94(3) EPC for European Patent Application No. 09761055.4, dated Sep. 13, 2012, 2 pages.
Communication pursuant to Article 94(3) EPC for European Patent Application No. 09761055.4, dated Sep. 3, 2013, 3 Pages.
Communication pursuant to Article 94(3) EPC for European Patent Application No. 09761055.4, dated Sep. 9, 2014, 4 Pages.
Communication pursuant to Article 94(3) EPC for European Patent Application No. 12154124.7, dated Feb. 17, 2014, 5 Pages.
Communication pursuant to Article 94(3) EPC for European Patent Application No. 12809999.1, dated Dec. 22, 2016, 6 Pages.
Communication Pursuant to Article 94(3) EPC for European Patent Application No. 12809999.1, dated Jan. 19, 2016, 4 Pages.
Database EMBL Accession No. AY421275, "*Homo sapiens* ACVR2B gene, Virtual Transcript, partial sequence, genomic survey sequence," Dec. 13, 2003, 2 Pages.
Database Geneseq Accession No. AAW86245, "Mouse ActRIIB4 receptor protein," Feb. 16, 1999, 1 Page.
Database Geneseq Accession No. AD043580, "Amino acid sequence of ActRIIB," Jul. 29, 2004, 2 Pages.
Database WPI Week 198933 Derwent Publications Ltd., London, GB; AN 1989-237375 XP002471408 & JP 01 171495 A (Ajinomoto KK) Jul. 6, 1989 (Jul. 6, 1989).
De Kretser DM, et al., "Activin A and follistatin: their role in the acute phase reaction and inflammation," Journal of Endocrinology. 1999, vol. 161, pp. 195-198.
Decision of Rejection for Japanese Patent Application No. 2012-171705, dated Aug. 26, 2015, 5 Pages.
Decision of Rejection for Japanese Patent Application No. 2013-030740, dated Jan. 6, 2016, 7 Pages.
Decision on Examination for Taiwan Patent Application No. 097107642, dated Aug. 29, 2012, 4 Pages.
Dennler, et al., "Direct binding of Smad3 and Smad4 to critical TGF.beta.-inducible elements in the promoter of human plasminogen activator inhibitor-type 1 gene," The EMBO Journal, 17(11):3091-3100, 1998.

(56) References Cited

OTHER PUBLICATIONS

Derynck, R., et al., "Smads: Transcriptional Activators of TGF-β Responses," Cell, Dec. 11, 1998, vol. 95, pp. 737-740.
Do, TV, "The role of activin A and Akt/GSK signaling in ovarian tumor biology," Endocrinology. 2008, vol. 149, pp. 3809-3816.
Doherty, TJ, "Aging and Sarcopenia," J Appl Physiol, 2003, 95:1717-1727.
Donaldson et al., "Activin and Inhibin Binding to the Soluble Extracellular Domain of Activin Receptor II," Endocrinology, 140(4):1760-1766, 1999.
Draper, L., et al., "The Unterine Myometrium Is a Target for Increased Levels of Activin A During Pregnancy," Endocrinology, 1997, vol. 137, No. 7, pp. 3042-3046.
Durocher, et al., "High-level and high-throughput recombinant protein production by transient transfection of suspension-growing human 293-EBNA1 cells," Nucleic Acids Research, 30(2e9) 2002, 9 Pages.
Dvorak, H.F., et al., "Tumor microenvironment and progression," Journal of Surgical Oncology, 2011, vol. 103, pp. 468-474.
Ebi, Swissprot Accession No. 095390, GDF11.sub.—Human, Growth/differentiation factor 11, 2 pages., [online] [retrieved on Sep. 9, 2010] Retrieved from the internet <URL:http://www.ebi.ac.uk/uniprot/unisave/?help=O&session=/ebi/exterv/-old-work/SESSION 14 . . . >.
Ellis, L.M., et al., "VEGF-targeted therapy: mechanisms of antitumour activity," Nature Reviews Cancer, 2008, vol. 8, pp. 579-591.
Eppstein, et al., "Biological activity of liposome-encapsulated murine interferon .gamma. is mediated by a cell membrane receptor," Proc. Natl. Acad. Sci. USA, 82:3688-3692, 1985.
Ethier, J-F., et al., "Bovine Activin Receptor Type IIB Messenger Ribonucleic Acid Displays Alternative Splicing Involving a Sequence Homologous to Src-Homology 3 domain Binding Sites," Endocrinology, Jun. 1997, vol. 138, No. 6, pp. 2425-2434.
European Examination Report for European Application No. 12154124. 7, dated Oct. 16, 2014, 4 pages.
Examination Report No. 1 for Australian Patent Application No. 2009320364, dated Nov. 30, 2011, 2 pages.
Examination Report for Australian Patent Application No. 2012364736, dated Oct. 19, 2016, 3 Pages.
Examination Report for Australian Patent Application No. 2013216639, dated Apr. 30, 2015, 4 Pages.
Examination Report No. 2 for Australian Patent Application No. 2014210609, dated May 23, 2016, 2 Pages.
Examination Report for Australian Patent Application No. 2014210609, dated Sep. 23, 2015, 2 Pages.
Examination Report No. 2 for Australian Patent Application No. 2016210719, dated Mar. 23, 2017, 2 Pages.
Examination Report No. 1 for Australian Patent Application No. 2016219676, dated Feb. 23, 2017, 2 Pages.
Examination Report for Gulf Cooperation Council Application No. GCC/P/2008/10291, dated Sep. 7, 2012, 6 pages.
Examination Report for Malaysia Patent Application No. PI20093636, dated Dec. 31, 2013, 3 Pages.
Examination Report from the Intellectual Property Office for Taiwan Patent Application No. 098140431, dated Jun. 18, 2012, 11 pages.
Examiner's First Report for Canadian Patent Application No. 2,627,200, dated Jun. 7, 2010, 3 pages.
Examiner's Second Report for Canadian Patent Application No. 2,627,200, dated Nov. 2, 2011, 2 pages.
Examiner's Third Report for Canadian Patent Application No. 2,627,200, dated May 28, 2012, 1 page.
Extended European Search Report for European Patent Application No. 16194631.4, dated Jan. 26, 2017, 7 Pages.
Extended European Search Report for European Patent Application No. 16179980.4, dated Sep. 7, 2016, 7 Pages.
Extended European Search Report for European Patent Application No. 16178026.7, dated Jan. 23, 2017, 9 Pages.
Extended European Search Report for European Patent Application No. 12154124.7, dated May 8, 2013, 12 Pages.

Final Rejection Office Action for Japanese Patent Application No. 2009-552758, dated Aug. 1, 2013, 5 Pages.
First Examination Report for India Application No. 6356/DELNP/2009, dated Jan. 20, 2015, 3 pages.
First Examination Report for New Zealand Patent Application No. 604818, dated Jan. 8, 2013, 2 Pages.
First Examination Report for New Zealand Patent Application No. 627111, dated Jul. 24, 2014, 1 page.
First Examination Report for New Zealand Patent Application No. 626580, dated Mar. 18, 2015, 2 Pages.
First Examination Report for New Zealand Patent Application No. 720036, dated May 31, 2016, 3 Pages.
First Office Action for Chinese Patent Application No. 200980147945.3, dated Mar. 21, 2013, 13 Pages.
First Office Action for Eurasian Patent Application No. 2009708/28, dated Sep. 15, 2011, 2 Pages.
Fujii, Y., et al., "Regulation of prostate-specific antigen by activin A in prostate cancer LNCaP cells," Am. J. Physiol. Endocrinol. Metab., 2004, vol. 286, pp. E927-E931.
Funaba, et al., "Unique Recognition of Activin and Inhibin by Polyclonal Antibodies to Inhibin Subunits," J. Biochem. 119:953-960, 1996.
Gabizon A, et al., "Polyethylene glycol-coated (pegylated) liposomal doxorubicin: rationale for use in solid tumours," Drugs. 1997, vol. 54 (suppl 4), pp. 15-21.
Gaedeke, J., et al., "Glomerular activin A overexpression is linked to fibrosis in anti-Thy1 glomerulonephritis," Nephrol. Dial. Transplant, 2005, vol. 20, pp. 319-328.
Gamer, L., et al., "A Novel BMP Expressed in Developing Mouse Limb, Spinal Cord, and Tail Bud Is a Potent Mesoderm Inducer in Xenopus Embryos," Developmental Biology, 1999, vol. 208, No. 1, pp. 222-232.
Geisse, S., et al., "Eukaryotic Expression Systems: A Comparison," Protein Expression and Purification, Nov. 1996, pp. 271-282, vol. 8, Is. 3, Academic Press, Inc.
Gibbs, R., et al., "Evolutionary and Biomedical Insights from the Rhesus Macaque Genome," Science, Apr. 13, 2007, pp. 222-234, vol. 316.
Gluzman, et al., "SV40-Transformed Simian Cells Support the Replication of Early SV40 Mutants," Cell, 23:175-182, 1981.
Gonzalez-Cadavid, N., et al., "Organization of the human myostatin gene and expression in healthy men and HIV-infected men with muscle wasting," PNAS USA, 1998, vol. 95, pp. 14938-14943.
Gray, P., et al., "Identification of a Binding Site on the Type 11 Activin Receptor for Activin and Inhibin," J. Biol. Chem., Feb. 4, 2000, vol. 275, No. 5, pp. 3206-3212.
Groome, N., et al., "Preparation of monoclonal Antibodies to the Beta A Subunit of Ovarian Inhibin Using a Synthetic Peptide Immunogen," Hybridoma, 1991, vol. 10, No. 2, pp. 309-316.
Hamrick, M., et al., "Bone Mineral Content and Density in the Humerus of Adult Myostatin-Deficient Mice," Calcif Tissue Int, 2002, vol. 71, No. 1, pp. 63-68.
Harada, K., et al., "Serum Immunoreactive Activin A Levels in Normal Subjects and Patients with Various Diseases," Journal of Clinical Endocrinology and Metabolism, 1996, vol. 81, pp. 2125-2130.
Harrison, C.A., et al., "Antagonists of activin signaling: mechanisms and potential biological applications," Trends in Endocrinology and Metabolism, Mar. 2005, vol. 16, No. 2, pp. 73-78.
Harrison, et al., "An Activin Mutant with Disrupted ALK4 Binding Blocks Signaling via Type II Receptors," Journal of Biological Chemistry, 279(27):28036-28044, 2004.
Hilden, K., et al., "Expression of Type 11 Activin Receptor Genes During Differentiation of Human K562 Cells and cDNA Cloning of the Human Type IIB Activin Receptor," Blood, Apr. 15, 1994, pp. 2163-2170, vol. 83, No. 8.
Holzbaur, E.L., et al., Myostatin inhibition slows muscle atrophy in rodent models of amyotrophic lateral sclerosis, Neurobioloav of Disease, 2006, pp. 697-707, vol. 23.
Hopp, T., et al., "A Short Polypeptide Marker Sequence Useful for Recombinant Protein Identification and Purification," Bio Technology, 1998, vol. 6, pp. 1204-1210.

(56) References Cited

OTHER PUBLICATIONS

Hubner G, et al., "Activin: a novel player in tissue repair processes," Histology & Histopathology. 1999, vol. 14, pp. 295-304.
Intellectual Property Office of the Philippines, Notice of Allowance, Philippine Patent Application No. 1/2009/501698, dated Feb. 5, 2015, 1 page.
Invitation to Respond to Written Opinion, Singapore Patent Application No. 201103777-7, dated Aug. 1, 2012, 5 pages.
Ito, et al., "Presence of activin signal transduction in normal ovarian cells and epithelial ovarian carcinoma," British Journal of Cancer, 82(8): 1415-1420, 2000.
Jones KL, et al., "Activin A and follistatin in systemic inflammation," Molecular & Cellular Endocrinology. 2004, vol. 225, pp. 119-125.
Jones, R., "Activin A and Inhibin A Differentially Regulate Human Uterine Matrix Metalloproteinases: Potential Interactions during Decidualization and Trophoblast Invasion," Endocrinology, 2006, vol. 147, No. 2, pp. 724-732.
Kaufman, R., et al., "Transgenic Analysis of a 100-kb Human β-Globin Cluster-Containing DNA Fragment Propagated as a Bacterial Artificial Chromosome," Blood, Nov. 1, 1999, vol. 94, No. 9, pp. 3178-3184.
Kinglsey, D., et al., "The TGF-β superfamily: new members, new receptors, and new genetic tests of function in different organisms," Genes Dev., 1994, vol. 8, pp. 133-146.
Klimka, et al., "Human anti-CD30 recombinant antibodies by guided phage antibody selection using cell panning," British Journal of Cancer (2000) 83:252-260.
Konishi, I. "Gonadotropins and ovarian carcinogenesis: a new era of basic research and its clinical implications," Int J Gynecol Cancer, 2006, vol. 16, pp. 16-22.
Kostelny, et al., "Formation of a Bispecific Antibody by the Use of Leucine Zippers," Journal of Immunology, 148(5):1547-1553, 1992.
Kwak, K.S., et al., "Regulation of protein catabolism by muscle-specific and cytokine-inducible ubiquitin ligase E3alpha-11 during cancer cachexia," Cancer Res, 2004, vol. 64, pp. 8193-8198.
Lalani, R., et al., "Myostatin and insulin-like growth factor-I and -II expression in the muscle of rafts exposed to the microgravity environment of the NeuroLab space shuttle flight," Journal of Endocrinology, 2000, vol. 167, pp. 417-428.
Lambert-Messerlian, G.M., et al., "Secretion of Activin A in Recurrent Epithelial Ovarian Carcinoma," Gynecologic Oncology, 1999, vol. 74, pp. 93-97.
Lang, C., et al., "Regulation of myostatin by glucocorticoids after thermal injury," FASEB, 2001, vol. 1, No. 15, pp. 1807-1809.
Langer, R., "Controlled release of macromolecules," ChemTech, 12:98-105, 1982.
Langer, R., et al., "Biocompatibility of polymeric delivery systems for macromolecules," J. of Biomedical Materials Research, 15:267-277, 1981.
Lederman, S., et al., "A single amino acid substitution in a common African allele of the CD4 molecule ablates binding of the monoclonal antibody," OKT4. Mol Immunol. 28(11):1171-81, 1991.
Lee SJ, et al., "Regulation of muscle growth by multiple ligands signaling through activin type II receptors," Proc Nati Acad Sci USA. 2005, vol. 102, pp. 18117-18122.
Lee SJ, et al., "Regulation of myostatin activity and muscle growth," Proc Natl. Acad. Sci., USA. 2001, vol. 98, pp. 9306-9311.
Li et al., "Activin A Binds to Perlecan through Its Pro-region That Has Heparin/Heparan Sulfate Binding Activity," JBC, 285(47)36645-36655, 2010.
Ling, N., et al., "Pituitary FSH is released by a heterodimer of the β-subunits from the two forms of inhibin," Nature, 1986, vol. 321, pp. 779-782.
Longfellow, C., et al., "Thermodynamic and Spectroscopic Study of Bulge Loops in Oligoribonucleoptides," Biochemistry, 1990, vol. 29, pp. 278-285.
Luisi S, et al., "Expression and secretion of activin A: possible physiological and clinical implications," European Journal of Endocrinology. 2001, vol. 145, pp. 225-236.
MacCallum, et al., "Antibody-antigen interactions: contact analysis and binding site topography," J Mol Biol. Oct. 11, 1996, 262(5):732-45.
MacDonald N, et al., "Understanding and managing cancer cachexia," J Am Coll Surg. 2003, vol. 197, pp. 143-161.
Macias-Silva, et al., "MADR2 Is a Substrate of the TGF.beta. Receptor and Its Phosphorylation Is Required for Nuclear Accumulation and Signaling," Cell, 87:1215-1224, 1996.
Mason, A., et al., "Complementary DNA sequences of ovarian follicular fluid inhibin show precursor structure and homology with transforming growth factor-β," Nature, Dec. 1985, pp. 659-663, vol. 318.
Massague, J., "How Cells Read TGF-β Signals," Nature Rev: Molecular Cell Biology, 2000, pp. 169-178, vol. 1.
Mathews, L.S., "Activin Receptors and Cellular Signaling by the Receptor Serine Kinase Family," Endocrine Review, 1994, vol. 15, pp. 310-325.
Matzuk MM, et al., "Development of cancer cachexia-like syndrome and adrenal tumors in inhibin-deficient mice," Proc Nati Acad Sci USA. 1994, vol. 91, pp. 8817-8321.
Matzuk MM, et al., "α-inhibin is a tumour-suppressor gene with gonadal specificity in mice," Nature. 1992, vol. 360, pp. 313-319.
McMahan, et al., "A novel IL-1 receptor, cloned from B cells by mammalian expression, is expressed in many cell types," The EMBO Journal, 10(10):2821-2832, 1991.
McPherron, A., et al., "Regulation of anterior/posterior patterning of the axial skeleton by growth/differentiation factor 11," Natr Genet, 1999, vol. 22, No. 93, pp. 260-264.
McPherron, A., et al., "Regulation of skeletal muscle mass in mice by a new TGF-β superfamily member," Nature (London), May 1997, vol. 387, pp. 83-90.
McPherron, et al., "Double muscling in cattle due to mutations in the myostatin gene," Proc. Natl. Acad. Sci. USA, 94:12457-12461, 1997.
McPherron, et al., "The Transforming Growth Factor β Superfamily," in Growth Factors and Cytokines in Health and Disease, vol. 1B, D. LeRoith and C. Bondy, eds., (JAI Press Inc., Greenwich, CT, USA), pp. 357-393, 1996.
Mendez, et al., "Functional transplant of megabase human immunoglobulin loci recapitulates human antibody response in mice," Nature Genetics 15:146-156, 1997.
Menon, U., et al., "Serum inhibin, activin and follistatin in post-menopausal women with epithelial ovarian carcinoma," British Journal of Obstetrics and Gynecology, 2000, vol. 107, pp. 1069-1074.
Merrifield, B., "Solid Phase Synthesis," Science, 232:341-347, 1986.
Mikaelian, et al., "Modification of the Overlap Extension Method for Extensive Mutagenesis on the Same Template," Methods in Molecular Biology, 57:193-202, 1996.
Morley JE, et al., "Cachexia: pathophysiology and clinical relevance," Am J Clin Nutr. 2006, vol. 83, pp. 735-743.
Muscaritoli M, et al., "Prevention and treatment of cancer cachexia: new insights into an old problem," Eur J Cancer. 2006, vol. 42, pp. 31-41.
NCBI, "Activin receptor type-2B precursor [*Homo sapiens*]," GenBank accession No. NP 001097, 3 pages, [online] [retrieved on Mar. 20, 2013] Retrieved from the internet <URL:http://www.ncbi.nlm.nih.gov/protein/np.sub.--001097>.
NCBI, GenBank: AAN76043.1 "immunoglobulin gamma 2 heavy chain constant region, partial [*Homo sapiens*]," Mar. 21, 2005, 2 pages, can be retrieved at <URL: http://www.ncbi.nlm.nih.gov/protein/25987833/>.
NCBI, "Genbank Accession No. AAB86694, myostatin [*Homo sapiens*]," Nov. 20, 1997, 2 Pages, [online] [retrieved on Sep. 9, 2010] Retrieved from the internet URL:http://www.ncbi.nlm.nih.gov/protein/116734708>.
NCBI, "Genbank Accession No. NM 002192, *Homo sapiens* inhibin, beta A (INHBA), mRNA," Aug. 3, 2010, 4 pages., [online] [retrieved on Sep. 9, 2010] Retrieved from the internet URL:http://www.ncbi.nlm.nih.gov/nuccore/62953137>.
NCBI, "Genbank Accession No. NP 001097, activin receptor type-2B precursor [*Homo sapiens*]," Aug. 3, 2010, 3 pages., [online]

(56) References Cited

OTHER PUBLICATIONS

[retrieved on Sep. 9, 2010] Retrieved from the internet URL:http://www.ncbi.nlm.nih.gov/nuccore/116734708>.
NCBI, "Myostatin [*Homo sapiens*]," GenBank Accession No. AAB86694, Nov. 20, 1997, 2 pages, [online] [retrieved on Mar. 20, 2013] Retrieved from the internet <URL: http://www.ncbi.nlm.nih.gov/protein/aab86694>.
NCBI, "*Homo sapiens* inhibin, beta A (INHBA), mRNA," GenBank Accession No. NM_002192, Mar. 10, 2013, 4 pages [online] [retrieved on Mar. 20, 2013] Retrieved from the internet <URL:http://www.ncbi.nlm.nih.gov/nuccore/nm_002192>.
Ngo, J.T., et al., "Computational Complexity, Protein Structure Prediction, and the Levinthal Paradox," The Protein Folding Problem and Tertiary Structure Predict, pp. 492-495, 1994.
Notice of Final Rejection for Korean Patent Application No. 2009-7020320, dated Sep. 4, 2012, 2 Pages.
Notice of Preliminary Rejection Office Action Summary for Korean Patent Application No. 2012-7008467, dated Apr. 18, 2013, 3 pages (English Translation).
Notice of Reasons for Rejection for Japanese Patent Application No. 2009-527594, dated Nov. 21, 2012, 16 pages.
Notice of Reasons for Rejection for Japanese Patent Application No. 2014-136375, dated Feb. 15, 2016, 6 Pages.
Notice of Reasons for Rejection for Japanese Patent Application No. 2013-030740, dated Jun. 3, 2015, 8 Pages.
Notice of Reasons for Rejection for Japanese Patent Application No. 2012-171705, dated Oct. 31, 2016, 13 Pages.
Notification of Grounds for Rejection for Japanese Patent Application No. 2009-527594, dated Sep. 12, 2013, 6 Pages.
Notification of Reasons for Rejection for Japanese Patent Application No. 2008-539077, dated Dec. 19, 2012, 5 Pages.
Notification of Reasons for Rejection for Japanese Patent Application No. 2008-539077, dated Feb. 2, 2012, 3 pages.
Notification of Reexamination Board Opinion for Chinese Patent Application No. 200880007116.0, dated Apr. 3, 2015, 11 Pages.
O'Connor, A.E., et al., "Serum activin A and follistatin concentrations during human pregnancy: a cross-sectional and longitudinal study," Human Reproduction, 1999, vol. 14, No. 3, pp. 827-832.
Office Action for Argentine Published Patent Application No. 074397 A1, dated Jan. 9, 2017, 7 Pages.
Office Action for Argentine Published Patent Application No. 065611 A1, dated Mar. 10, 2017, 8 Pages (With English Summary).
Office Action for Canadian Patent Application No. 2,661,878, dated Jan. 25, 2017, 6 Pages.
Office Action for Canadian Patent Application No. 2,661,878, dated Jan. 10, 2014, 4 Pages.
Office Action for Canadian Patent Application No. 2,661,878, dated Nov. 10, 2015, 6 Pages.
Office Action for Canadian Patent Application No. 2,661,878, dated Oct. 28, 2014, 4 pages.
Office Action for Canadian Patent Application No. 2,679,841, dated Apr. 26, 2016, 4 Pages.
Office Action for Canadian Patent Application No. 2,679,841, dated Apr. 28, 2014, 2 Pages.
Office Action for Canadian Patent Application No. 2,679,841, dated Apr. 8, 2013, 2 Pages.
Office Action for Canadian Patent Application No. 2,743,850, dated Oct. 24, 2013, 2 Pages.
Office Action for Canadian Patent Application No. 2,743,850, dated Nov. 6, 2014, 3 pages.
Office Action for Canadian Patent Application No. 2,743,850, dated Oct. 19, 2015, 4 pages.
Office Action for Canadian Patent Application No. 2,743,850, dated Sep. 5, 2012, 4 pages.
Office Action for Canadian Patent Application No. 2,743,850, dated Sep. 9, 2016, 3 Pages.
Office Action for Chilean Patent Application No. 2015-03139, dated Apr. 12, 2017, 8 Pages (With Concise Explanation of Relevance).
Office Action for Chilean Patent Application No. 2015-02166, dated Feb. 13, 2017, 13 Pages.
Office Action for Chilean Patent Application No. 2014-01648, dated Feb. 15, 2017, 19 Pages.
Office Action for Chilean Patent Application No. 2014-01648, dated Feb. 9, 2016, 18 Pages.
Office Action for Chilean Patent Application No. 1239-2011, dated Apr. 27, 2014, 75 Pages.
Office Action for Chinese Patent Application No. 201410462932.8, dated Nov. 28, 2016, 6 pages, (With Concise Explanation of Relevance).
Office Action for Chinese Patent Application No. 2012800701034, dated Sep. 18, 2015, 12 Pages. (With Concise Explanation of Relevance).
Office Action for Chinese Patent Application No. 201280070103.4, dated Dec. 27, 2016, 11 Pages, (With Concise Explanation of Relevance).
Office Action for Chinese Patent Application No. 200880007116.0, dated Feb. 22, 2013, 13 Pages.
Office Action for Colombian Patent Application No. 14-143018, dated Apr. 6, 2016, 26 Pages.
Office Action for Colombian Patent Application No. 11-079.058, dated Oct. 31, 2016, 12 Pages.
Office Action for Colombian Patent Application No. 11-079.058, dated Apr. 12, 2016, 17 Pages.
Office Action for Colombian Patent Application No. 11.079.058, dated May 14, 2014, 12 Pages.
Office Action for Colombian Patent Application No. 11-7905 8-5, dated Nov. 27, 2012, 15 Pages.
Office Action for Colombian Patent Application No. 11-79058-8, dated Jun. 17, 2013, 11 Pages.
Office Action for Colombian Patent Application No. 1239-2011 dated Jun. 18, 2013, 34 Pages.
Office Action for Colombian Patent Application No. 14-143018, dated Dec. 16, 2016, 7 Pages.
Office Action for Colombian Patent Application No. NC2016/0005077, dated May 2, 2017, 3 Pages (With English Summary),.
Office Action for Costa Rica Application No. 11054, dated Jan. 26, 2015, 15 pages.
Office Action for Costa Rica Patent Application No. 11054, dated Sep. 17, 2015, 16 Pages. (With Concise Explanation of Relevance).
Office Action for Costa Rica Patent Application No. 11054, dated Sep. 24, 2014, 9 Pages.
Office Action for Egypt Patent Application No. PCT13142009, dated May 1, 2013, 11 Pages.
Office Action for Eurasian Patent Application No. 201491231, dated Apr. 20, 2016, 4 Pages.
Office Action for Eurasian Patent Application No. 201490822, dated Apr. 12, 2017, 2 Pages.
Office Action for Eurasian Patent Application No. 201490822, dated May 5, 2016, 2 Pages (With Concise Explanation of Relevance).
Office Action for Eurasian Patent Application No. 201491231, dated Nov. 25, 2016, 5 Pages.
Office Action for Eurasian Patent Application No. 201100832, dated Nov. 28, 2014, 3 pages.
Office Action for Eurasian Patent Application No. 201100832, dated Aug. 26, 2015, 2 Pages.
Office Action for Eurasian Patent Application No. 201100832/28 dated Feb. 27, 2014, 3 Pages.
Office Action for Israeli Patent Application No. 200605, dated Aug. 7, 2014, 4 Pages.
Office Action for Israeli Patent Application No. 212773, dated Jun. 28, 2015, 3 pages. (With Concise Explanation of Relevance).
Office Action for Israeli Patent Application No. 240139, dated Feb. 28, 2016, 3 Pages. (With Concise Explanation of Relevance).
Office Action for Israeli Patent Application No. 248128, dated Oct. 5, 2016, 3 Pages, (With Concise Explanation of Relevance).
Office Action for Japanese Patent Application No. 2009-552758, dated Feb. 20, 2013, 2 Pages.
Office Action for Japanese Patent Application No. 2011-538599 dated Apr. 17, 2014, 6 Pages.
Office Action for Japanese Patent Application No. 2012-171705 dated Apr. 2, 2014, 9 Pages.
Office Action for Japanese Patent Application No. 2012-171705, dated Feb. 4, 2015, 8 pages.

(56) References Cited

OTHER PUBLICATIONS

Office Action for Japanese Patent Application No. 2013-030740, dated Jul. 23, 2014, 12 Pages.
Office Action for Japanese Patent Application No. 2014-177598, dated Oct. 14, 2015, 6 Pages.
Office Action for Japanese Patent Application No. 2014-548827, dated Sep. 28, 2016, 7 Pages.
Office Action for Japanese Patent Application No. 2016-092915, dated Mar. 29, 2017, 10 Pages.
Office Action for Korean Patent Application No. 10-2012-7008467, dated Sep. 7, 2016, 6 Pages, (With Concise Explanation of Relevance).
Office Action for Korean Patent Application No. 10-2011-7014720, dated Dec. 18, 2015, 7 Pages. (With Concise Explanation of Relevance).
Office Action for Korean Patent Application No. 2012-7008467, dated Oct. 18, 2013, 4 Pages.
Office Action for Mexican Patent Application No. MX/a/2011/005505, dated May 28, 2013, 9 Pages.
Office Action for Mexican Patent Application No. MX/a/2012/008808, dated May 2, 2014, 10 Pages.
Office Action for Mexican Patent Application No. MX/a/2012/014888, dated Jun. 27, 2014, 4 Pages.
Office Action for Mexican Patent Application No. MX/a/2013/012260, dated Nov. 7, 2016, 4 Pages, (With Concise Explanation of Relevance).
Office Action for Mexican Patent Application No. MX/E/2015/011882, dated Aug. 30, 2016, 3 Pages, (With Concise Explanation of Relevance).
Office Action for New Zealand Patent Application No. 604818 dated Apr. 2, 2014, 2 Pages.
Office Action for Peruvian Patent Application No. 002108-2012/DIN, dated Mar. 3, 2017, 17 Pages.
Office Action for Peruvian Application No. 1077-2011, dated Nov. 20, 2014, 12 pages.
Office Action for Peruvian Patent Application No. 000436.2008, dated May 21, 2014, 58 Pages.
Office Action for Philippine Patent Application No. 1/2009/501698, dated Nov. 18, 2014, 1 page.
Office Action for Philippine Patent Application No. 1-2009-501698, dated Jul. 10, 2013, 2 Pages.
Office Action for Taiwan Patent Application No. 105129851, dated May 15, 2017, 7 Pages.
Office Action for Taiwan Patent Application No. 103117408, dated Mar. 11, 2016, 5 Pages.
Office Action for Taiwan Patent Application No. 097107642 dated Feb. 17, 2014, 3 Pages.
Office Action for Taiwan Patent Application No. 098140431, dated Apr. 25, 2013, 3 Pages.
Office Action for Thailand Patent Application No. 1501004361, dated May 1, 2017, 2 Pages.
Office Action for Ukrainian Patent Application No. a 2012 14279, dated Jan. 20, 2017, 11 Pages.
Office Action for Ukrainian Patent Application No. a 2014 07864, dated May 4, 2017, 9 Pages.
Office Action for U.S. Appl. No. 11/590,962 dated Apr. 29, 2009, 18 Pages.
Office Action for U.S. Appl. No. 11/590,962 dated Mar. 3, 2010, 16 Pages.
Office Action for U.S. Appl. No. 11/590,962 dated Sep. 29, 2010, 6 Pages.
Office Action for U.S. Appl. No. 13/074,877, dated Feb. 1, 2013, 12 Pages.
Office Action for U.S. Appl. No. 13/080,515, dated May 17, 2012, 5 Pages.
Office Action for U.S. Appl. No. 13/080,515, dated Sep. 15, 2011, 7 Pages.
Office Action for U.S. Appl. No. 13/080,515, dated Sep. 26, 2013, 5 Pages.
Office Action for U.S. Appl. No. 13/190,255, dated Feb. 7, 2012, 10 Pages.
Office Action for U.S. Appl. No. 13/190,255, dated May 24, 2012, 9 Pages.
Office Action for U.S. Appl. No. 13/775,756, dated Aug. 25, 2014, 9 Pages.
Office Action for U.S. Appl. No. 13/775,756, dated Jul. 29, 2015, 7 Pages.
Office Action for U.S. Appl. No. 13/932,421, dated Jul. 28, 2014, 7 Pages.
Office Action for U.S. Appl. No. 14/085,056, dated Jul. 17, 2015, 8 Pages.
Office Action for U.S. Appl. No. 14/171,670, dated May 18, 2016, 22 Pages.
Office Action for U.S. Appl. No. 14/204,460, dated Dec. 4, 2015, 7 pages.
Office Action for U.S. Appl. No. 14/204,460, dated Jul. 22, 2015, 16 Pages.
Office Action for U.S. Appl. No. 14/260,856, dated May 9, 2016, 17 Pages.
Office Action for U.S. Appl. No. 14/366,978, dated Mar. 14, 2016, 6 Pages.
Office Action for U.S. Appl. No. 14/626,457, dated May 19, 2016, 7 Pages.
Office Action for U.S. Appl. No. 14/626,457, dated Dec. 31, 2015, 9 Pages.
Office Action for U.S. Appl. No. 15/014,889, dated Jun. 15, 2017, 11 Pages.
Office Action for U.S. Appl. No. 15/171,944, dated Nov. 9, 2016, 8 Pages.
Office Action for Vietnamese Patent Application No. 1-2014-02367, dated Nov. 17, 2014, 2 pages.
Office Action for Vietnamese Patent Application No. 1-2011-01521, dated Jul. 27, 2015, 2 Pages.
Office Action for Vietnamese Patent Application No. 1-2015-03103, dated Feb. 26, 2016, 2 Pages.
Office Action issued by Intellectual Property Office of the Philippines, Patent Application No. 1-2009-501698, dated Oct. 25, 2012, 2 Pages.
Oh, S., et al., "Activin type IIA and IIB receptors mediate Gdf1 1 signaling in axial vertebral patterning," Genes & Development, 2002, vol. 16, pp. 2749-2754.
Oh, S., et al., "The signaling pathway mediated by the type IIB activin receptor controls axial patterning and laternal asymmetry in the mouse," Genes Dev, 1997, vol. 11, pp. 1812-1826.
Opposition by AG Pharmaceutical Laboratories Industrial Association against Amgen Patent Application No. 1239-2011 in Chile, papers stamped by the Institution Nacional de Propiedad Industrial on Nov. 17, 2011 (Spanish with English translation), 34 Pages.
Otani, T., et al., "Production of Activin A and Hyperplasia and Adenocarcinoma of the Human Endometrium," Gynecologic Oncology, 2001, vol. 83, pp. 31-38.
Padlan, E., "Anatomy of the antibody molecule," Mol Immunol. Feb. 1994; 31(3):169-217.
Park, et al., "Rationally designed anti-HER2/neu peptide mimetic disables P185HER2/neutyrosine kinases in vitro and in vivo," (2000) Nature Biotech, 18:194-198.
Partial European Search Report for European Patent Application No. 12154124, dated Jan. 21, 2013, 5 pages.
Partial International Search Report, PCT/US2008/003119, dated Mar. 13, 2009, 9 pages.
Patent Examination Report No. 1 for Australian Patent Application No. 2011237541, dated Aug. 10, 2012, 3 pages.
Patent Examination Report No. 1 for Australian Patent Application No. 2012265564, dated Jun. 19, 2015, 6 Pages.
Patent Examination Report No. 2 for Australian Patent Application No. 2011237541, dated Oct. 22, 2012, 2 pages.
Patent Examination Report No. 2 for Australian Patent Application No. 2013216639, dated Feb. 16, 2016, 2 Pages.
Paul, "Fundamental Immunology," 3rd Edition, 1993, pp. 292-295.
Payne, S.J.L., et al., "Influence of the tumor microenvironment on angiogenesis," Future Oncology, 2011, vol. 7, pp. 395-408.

(56) References Cited

OTHER PUBLICATIONS

PCT International Search Report and Written Opinion for PCT/US2007/077923, dated Jun. 9, 2008, 16 Pages.
PCT International Search Report and Written Opinion for PCT/US2012/070571, dated Mar. 19, 2013, 12 Pages.
PCT International Search Report and Written Opinion for PCT/US2014/014490, dated Jun. 27, 2014, 20 Pages.
PCT International Search Report and Written Opinion, PCT/US2009/006252, dated Jun. 17, 2010, 15 pages.
PCT International Search Report and Written Opinion, PCT/US2006/043044, dated Mar. 15, 2007, 11 Pages.
PCT International Search Report, PCT/US2008/003119, dated May 12, 2009.
PCT Search Report and Written Opinion for PCT/US2008/003119, dated Sep. 6, 2009, 16 Pages.
Petraglia, F., et al., "Expression and Secretion of Inhibin and Activin in Normal and Neoplastic Uterine Tissues. High Levels of Serum Activin A in Women with Endometrial and Vercial Carcinoma," Journal of Clinical Endocrinology and Metabolism, 1998, vol. 83, pp. 1194-1200.
Phillips, A., "The challenge of gene therapy and DNA delivery," Journal of Pharmacy and Pharmacology, Mar. 6, 2001, vol. 53, pp. 1169-1174.
Portolano, S. et al., Lack of promiscuity in autoantigen-specific H and L chain combinations as revealed by human H and L chain "roulette", J. Immunology 150(3):880-887, 1993.
Provencher DM, et al., "Characterization of four novel epithelial ovarian cancer cell lines," In Vitro Cellular & Developmental Biology Animal, 2000, vol. 36, pp. 357-361.
R&D Systems, "Human/Mouse/Rat Activin A 13A subunit Antibody," R&D Systems, Mar. 13, 2015, 2 Pages, Can be retrieved at <URL:http://www.rndsystems.com/pdf/mab3381.pdf>.
R&D Systems, Inc., "Monoclonal Anti-humon/mouse/rat Activin A Antibody" Oct. 12, 2004, 1 page, can be retrieved at <URL:http://www.rndsystems.com/pdf/mab3381.pdf>.
Rabinovici, P. C., et al., "Localization and regulation of the activin-A dimer in human placental cells," Journal of Clinical Endocrinology and Metabolism, vol. 75, No. 2, pp. 571-576, 1992.
Rasmussen, et al., "Isolation, characterization and recombinant protein expression in Veggie-CHO: A serum-free CHO host cell line," Cytotechnology, 28:31-42, 1998.
Reis, F., et al., "Serum and Tissue Expression of Activin A in Postmenopausal Women with Breast Cancer," Journal of Clinical Endocrinology and Metabolism, 2002, vol. 87, pp. 2277-2282.
Risbridger, G.P., et al., "The contribution of inhibins and activins to malignant prostate disease," Molecular and Cellular Endocrinology, 2001, vol. 180, pp. 149-153.
Robertson, D.M., et al., "Inhibin/activin and ovarian cancer," Endocrine-Related Cancer, 2004, pp. 35-49, vol. 11.
Rosenzweig, B.L., et al., "Cloning and characterization of a human type II receptor for bone morphogenetic proteins," Proc. Natl. Acad. Sci. 1995, pp. 7632-7636, vol. 92.
Roth SM, et al., "Myostatin. A therapeutic target for skeletal muscle wasting," Curr Opin Clin Nutr Metab Care. 2004, vol. 7, pp. 259-263.
Roubenoff R, et al., "Standardization of nomenclature of body composition in weight loss," Am J Clin Nutr. 1997, vol. 66, pp. 192-196.
Roubenoff R., "Origins and clinical relevance of sarcopenia," Can. J Appl Phys. 2001, vol. 26, pp. 78-89.
Rudikoff, et al., "Single amino acid substitution altering antigen-binding specificity," Proc. Natl. Acad. Sci., Mar. 1982, pp. 1979-1983, vol. 79, No. 6.
Schneyer, et al., "Characterization of unique binding kinetics of follistatin and activin or inhibin in serum," Endocrinology, Aug. 1994, 135(2):667-74.
Search Report for Gulf Cooperation Council Application No. GCC/P/2008/10291, dated Aug. 10, 2011, 11 Pages.
Second Office Action for Chinese Patent Application No. 200980147945.3, dated Nov. 29, 2013, 9 Pages.
Second Office Action for Eurasian Patent Application No. 200970810/28, dated Nov. 21, 2012, 2 Pages.
Sharma, M., et al., "Myostatin, a Transforming Growth Factor-β Superfamily Member, Is Expressed in Heart Muscle and Is Upregulated in Cardiomyocytes After Infarct," Journal of Cell Physiology, 1999, vol. 180, No. 1, pp. 1-9.
Shou, W., et al., "Role of Androgens in Testicular Tumor Development in Inhibin-Deficient Mice," Endocrinology, 1997, vol. 138 No. 11 pp. 5000-5005.
Sidman, et al., "Controlled Release of Macromolecules and Pharmaceuticals from Synthetic Polypeptides Based on Glutamic Acid," Biopolymers, 22:547-556, 1983.
Songsivilai, et al., "Bispecific antibody: a tool for diagnosis and treatment of disease," Clin. Exp. Immunology, 79:315-321, 1990.
Steller, M., et al., "Inhibin Resistance is Associated with Aggressive Tumorigenicity of Ovarian Cancer Cells," Mol. Cancer Res., 2005, vol. 3, No. 1, pp. 50-61.
Strassmann, G., et al., "Suramin interferes with interleukin-6 receptor binding in vitro and inhibits colon-26-mediated experimental cancer cachexia in vivo," J Clin Invest, vol. 92, 1993, pp. 2152-2159.
Substantive Examination Report for Malaysian Patent Application No. PI 2011002346, dated May 15, 2015, 4 Pages.
Summons to attend oral proceedings pursuant to Rule 115(1) EPC for European Patent Application No. 12154124.7, Jul. 27, 2015, 5 Pages.
Supplementary European Search Report for European Applicaiton No. 14746114, dated Aug. 9, 2016, 19 Pages.
Tam, et al., "S.sub.N2 Deprotection of Synthetic Peptides with a Low Concentration of HF in Dimethyl Sulfide: Evidence and Application in Peptide Synthesis," J. American Chemical Society, 105:6442-6455, 1983.
Tanaka, T., et al., "Expression and function of activin receptors in human endometrial adenocarcinoma cells," International J. of Oncology, 2003, vol. 23, pp. 657-663.
Thomas, T.Z., et al., "Expression and Localization of Activin Subunits and Follostatins in Tissues from Men with High Grade Prostate Cancer," Journal of Clinical Endocrinology and Metabolism, 1997, vol. 82, No. 11, pp. 3851-3858.
Thompson et al., "Structures of an ActRIIB:activin A complex reveal a novel binding mode for TGF-.about.liqand:receptor interactions," The EMBO Journal 22(7): 1555-1566, 2003.
Tobin, J.F., et al., "Myostatin, a negative regulator of muscle mass: implications for muscle degenerative diseases," Current Opinion in Pharmacology, Elsevier Science Publishers, Jun. 2005, vol. 5, No. 3, pp. 328-332.
Tomayko MM, et al., "Determination of subcutaneous tumor size in athymic (nude) mice," Cancer Chemother Pharmacol. 1989, vol. 24, pp. 148-154.
Tournier, I., et al., "Germline Mutations of Inhibins in Early-Onset Ovarian Epithelial Tumors," Human Mutation, Dec. 2, 2013, pp. 294-297, vol. 35, No. 3.
Translation of Office Action for Ukrainian Patent Application No. a 2011 07872, dated Oct. 25, 2012, 2 Pages.
Tsai, C.-L., et al., "Secreted Stress-Induced Phosphoprotein 1 Activates the ALK2-SMAD Signaling Pathways and Promotes Cell Proliferation of Ovarian Cancer Cells," Cell Reports, Aug. 2012, pp. 283-293, vol. 2, No. 2.
Urlaub, et al., "Isolation of Chinese hamster cell mutants deficient in dihydrofolate reductase activity," Proc. Natl. Acad. Sci. USA, 77(7):4216-4220, 1980.
Vajdos, et al., "Comprehensive functional maps of the antigen-binding site of an anti-ErbB2 antibody obtained with shotgun scanning mutagenesis," J. Mol. Biol. Jul. 5, 2002, 320(2):415-28 at 416.
Vale, W., et al., "Chemical and Biological Characterization of the Inhibin Family of Protein Hormones," Recent Progress in Hormone Research, 1988, vol. 44, pp. 1-34.
Vale, W., et al., "Purification and characterization of an FSH releasing protein from porcine ovarian follicular fluid," Nature, Jun. 1986, vol. 321, 776-779.

(56) References Cited

OTHER PUBLICATIONS

Van Regenmortel, MHV, "Mapping Epitope Structure and Activity: From One-Dimensional Prediction to Four-Dimensional Description of Antigenic Specificity Methods," 9(3):465-72, 1996.

Wang, A., et al., "Rapid analysis of gene expression (RAGE) facilitates universal expression profiling," Nucl. Acids Res., 1999, vol. 27, pp. 4609-4618.

Wells, J., "Additivity of Mutational Effects in Proteins," Biochemistry, Sep. 18, 1990, vol. 29, pp. 8509-8517.

Welt, C., et al., "Presence of Activin, Inhibin, and Follistatin in Epithelial Ovarian Carcinoma," Journal of Clinical Endocrinology and Metabolism, 1997, vol. 82, No. 11, pp. 3720-3727.

Wigley, P., et al., "Site-specific Transgene Insertion: an Approach" Reprod Fertil. Dev., 1994, vol. 6, pp. 585-588.

Wildi, S. et al., "Overexpression of activin A in stage IV colorectal cancer," Gut, vol. 49, pp. 409-417, 2001.

Yamashita, S., et al., "Activin A Is a Potent Activator of Renal Interstitial Fibroblast," J. Am Soc Nephrol 15:91-101, 2004.

Yarasheski, K.E., et al., "Serum myostatin-immunoreactive protein is increased in 60-92 year old women and men with muscle wasting," Journal of Nutrition, Health and Aging, 2002, vol. 6, No. 5, pp. 343-348.

Yen, et al., "Obesity, diabetes, and neoplasia in yellow A.sup.vy /- mice: ectopic expression of the agouti gene," FASEBJ. 8:479-488, 1994.

Yndestad, A., et al., "Elevated Levels of Activin A in Heart Failure Potential Role in Myocardial Remodeling," Circulation, 2004, vol. 109, pp. 1379-1385.

Yoshinaga K, et al., "Clinical significance of the expression of activin A in esophageal carcinoma," Int J Oncol 2003, vol. 22, pp. 75-80.

Zabetakis, D., et al., "Contributions of the Complementarity Determining Regions to the Thermal Stability of a Single-Domain Antibody," PLOS One, Oct. 15, 2013, pp. 1-7, vol. 8, Article No. e77678.

Zachwieja, J., et al., "Plasma myostatin-immunoreactive protein is increased after prolonged bed rest with low-dose T3 Administration," Journal of Gravitational Physiology, Oct. 1999, vol. 6 No. 2, pp. 11-15.

Zhang, Z., et al., "Regulation of Growth and Prostatic Marker Expression by Activin A in an Androgen-Sensitive Prostate Cancer Cell Line LNCAP," Biochemical and Biophysical Research Communications, 1997, vol. 234, pp. 362-365.

Zheng, W., et al., "Tumor Stroma as the main Source of Inhibin Production in Ovarian Epithelial Tumors," AJRI, 2000, vol. 44, pp. 104-113.

Zhou X, et al., "Reversal of cancer cachexia and muscle wasting by ActRIIB antagonism leads to prolonged survival," Cell, 2010, vol. 142, pp. 531-543.

Zimmers, T., et al., "Induction of Cachexia in Mice by Systemically Administered Myostatin," Science, 2002, vol. 296, pp. 1486-1488.

\* cited by examiner

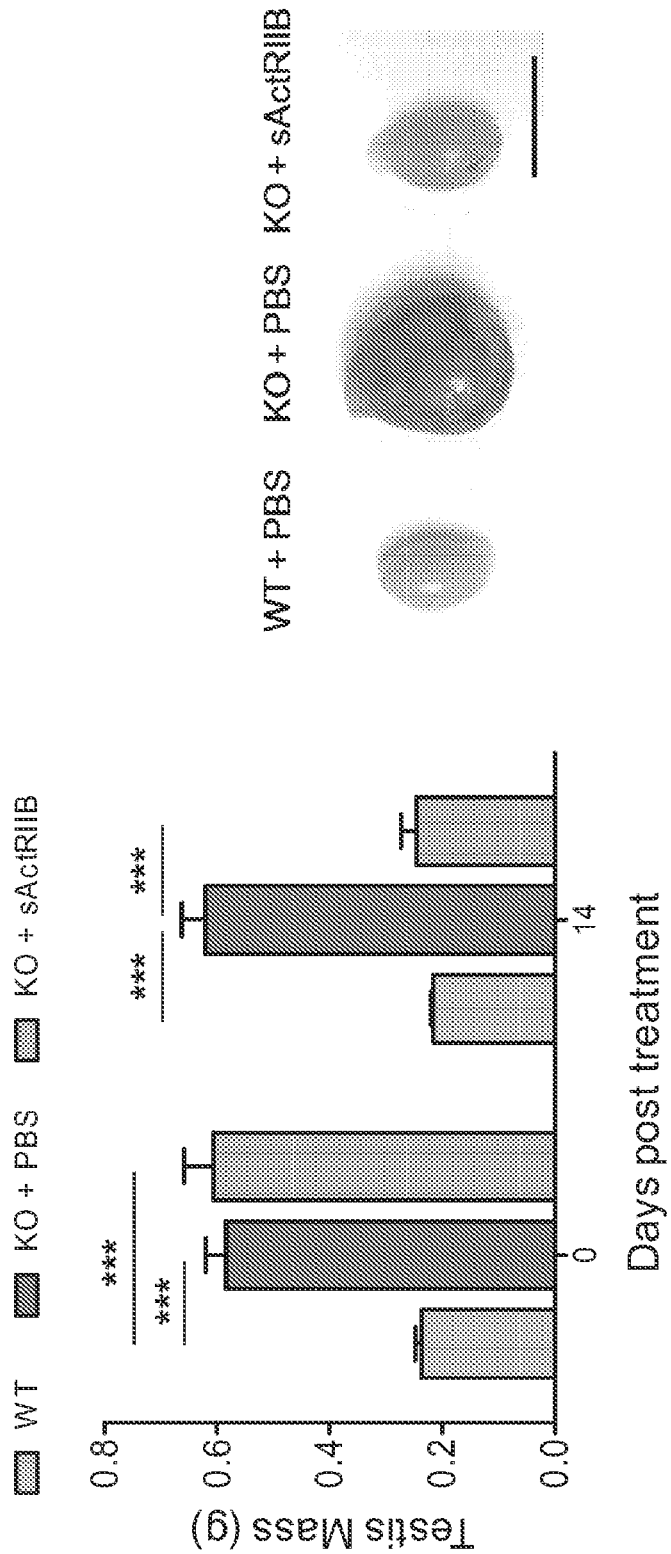

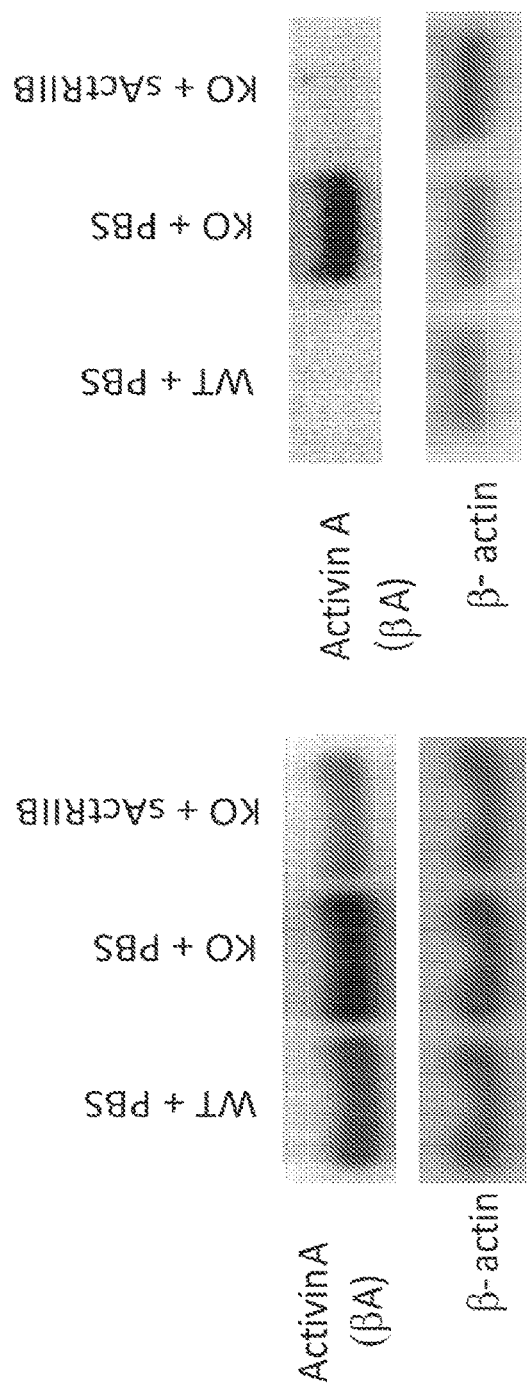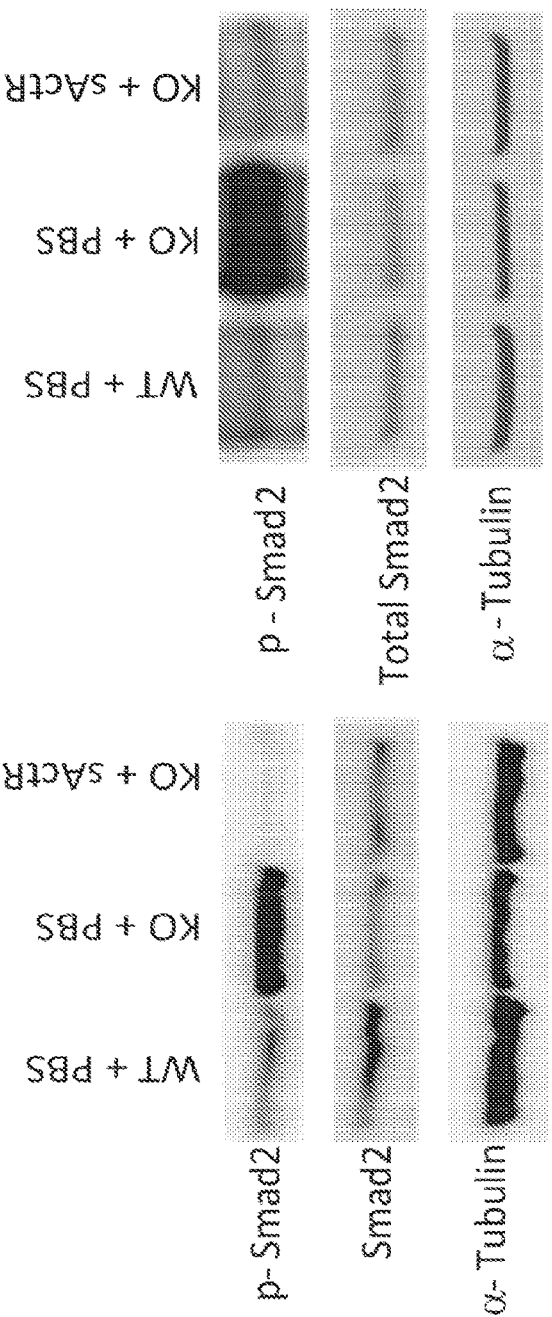
FIG. 5A
FIG. 5B

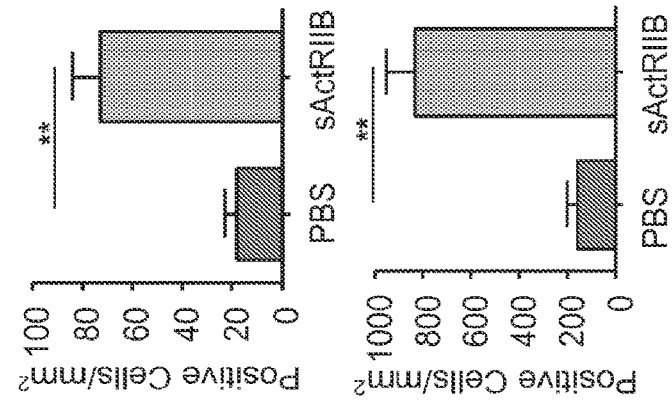
FIG. 15B
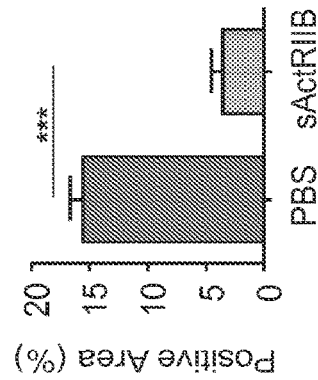
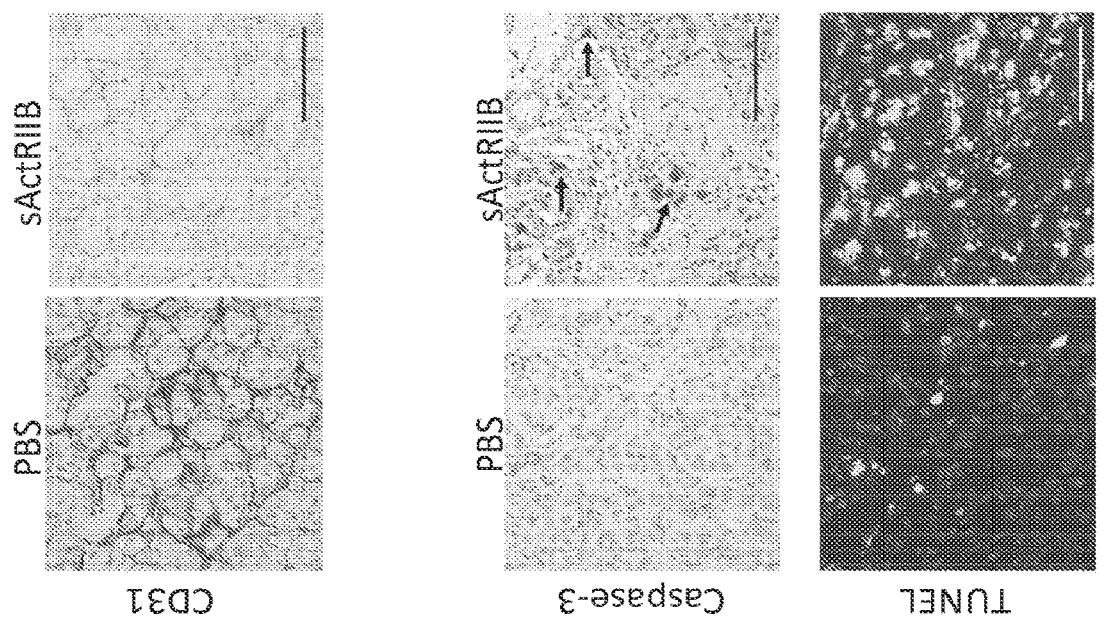
FIG. 15C

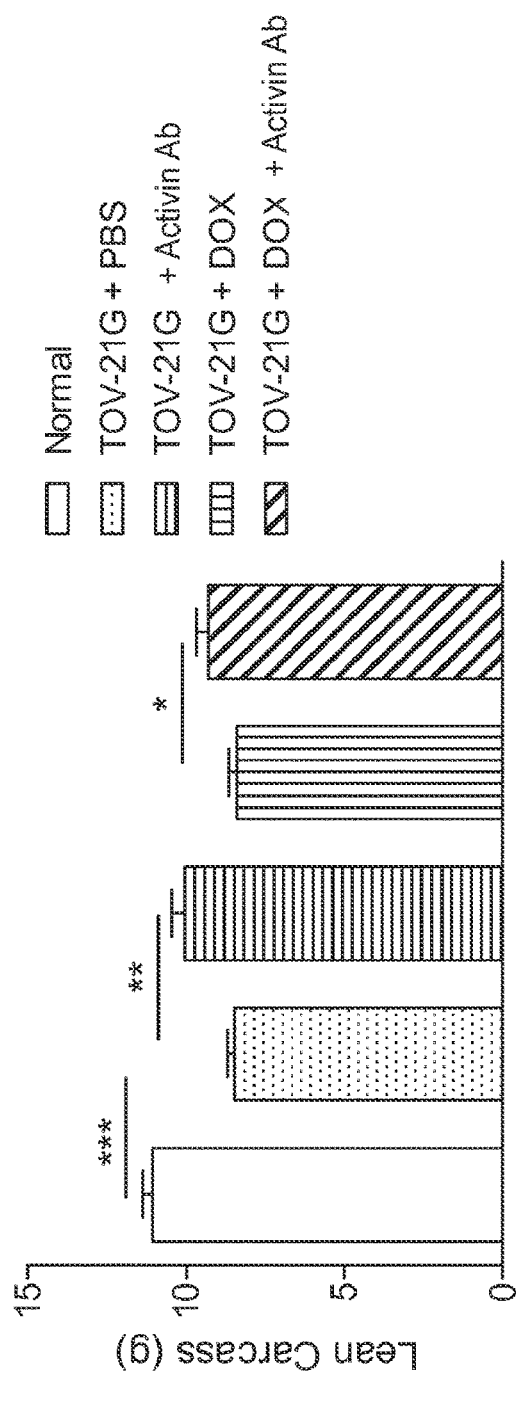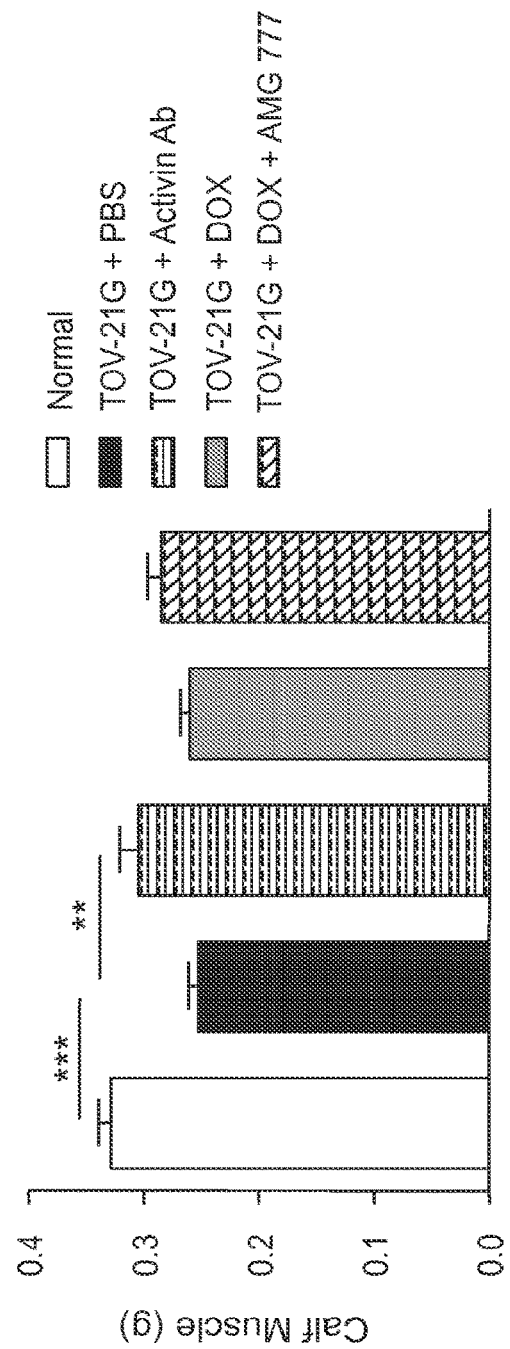
FIG. 38

SEQUENCE LISTING

```
<160> NUMBER OF SEQ ID NOS: 312

<210> SEQ ID NO 1
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 1 atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15
```

| | | | | | | | | | | | | | | | | |
|---|---|---|---|---|---|---|---|---|---|---|---|---|---|---|---|---|
| gcc | ggc | tct | ggg | cgt | ggg | gag | gct | gag | aca | cgg | gag | tgc | atc | tac | tac | 96 |
| Ala | Gly | Ser | Gly | Arg | Gly | Glu | Ala | Glu | Thr | Arg | Glu | Cys | Ile | Tyr | Tyr | |
| | | | 20 | | | | 25 | | | | | 30 | | | | |
| aac | gcc | aac | tgg | gag | ctg | gag | cgc | acc | aac | cag | agc | ggc | ctg | gag | cgc | 144 |
| Asn | Ala | Asn | Trp | Glu | Leu | Glu | Arg | Thr | Asn | Gln | Ser | Gly | Leu | Glu | Arg | |
| | | 35 | | | | | 40 | | | | | 45 | | | | |
| tgc | gaa | ggc | gag | cag | gac | aag | cgg | ctg | cac | tgc | tac | gcc | tcc | tgg | cgc | 192 |
| Cys | Glu | Gly | Glu | Gln | Asp | Lys | Arg | Leu | His | Cys | Tyr | Ala | Ser | Trp | Arg | |
| 50 | | | | | 55 | | | | | 60 | | | | | | |
| aac | agc | tct | ggc | acc | atc | gag | ctc | gtg | aag | aag | ggc | tgc | tgg | cta | gat | 240 |
| Asn | Ser | Ser | Gly | Thr | Ile | Glu | Leu | Val | Lys | Lys | Gly | Cys | Trp | Leu | Asp | |
| 65 | | | | 70 | | | | | 75 | | | | | 80 | | |
| gac | ttc | aac | tgc | tac | gat | agg | cag | gag | tgt | gtg | gcc | act | gag | gag | aac | 288 |
| Asp | Phe | Asn | Cys | Tyr | Asp | Arg | Gln | Glu | Cys | Val | Ala | Thr | Glu | Glu | Asn | |
| | | | | 85 | | | | 90 | | | | | 95 | | | |
| ccc | cag | gtg | tac | ttc | tgc | tgc | tgt | gaa | ggc | aac | ttc | tgc | aac | gag | cgc | 336 |
| Pro | Gln | Val | Tyr | Phe | Cys | Cys | Cys | Glu | Gly | Asn | Phe | Cys | Asn | Glu | Arg | |
| | | | 100 | | | | | 105 | | | | | 110 | | | |
| ttc | act | cat | ttg | cca | gag | gct | ggg | ggc | ccg | gaa | gtc | acg | tac | gag | cca | 384 |
| Phe | Thr | His | Leu | Pro | Glu | Ala | Gly | Gly | Pro | Glu | Val | Thr | Tyr | Glu | Pro | |
| | | | 115 | | | | | 120 | | | | | 125 | | | |
| ccc | ccg | aca | gcc | ccc | acc | | | | | | | | | | | 402 |
| Pro | Pro | Thr | Ala | Pro | Thr | | | | | | | | | | | |
| | | | 130 | | | | | | | | | | | | | |

<210> SEQ ID NO 2
<211> LENGTH: 134
<212> TYPE: PRT
<213> ORGANISM: Homo sapiens

<400> SEQUENCE: 2

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr
    130

<210> SEQ ID NO 3
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 3 atg gag ttt ggg ctg agc tgg gtt ttc ctc gtt gct ctt tta aga ggt    48

```
Met Glu Phe Gly Leu Ser Trp Val Phe Leu Val Ala Leu Leu Arg Gly
1               5                   10                  15 gtc cag tgt gag aca cgg tgg tgc atc tac tac aac gcc aac tgg gag    96
Val Gln Cys Glu Thr Arg Trp Cys Ile Tyr Tyr Asn Ala Asn Trp Glu
        20                  25                  30 ctg gag cgc acc aac cag acc ggc ctg gag cgc tgc gaa ggc gag cag   144
Leu Glu Arg Thr Asn Gln Thr Gly Leu Glu Arg Cys Glu Gly Glu Gln
            35                  40                  45 gac aag cgg ctg cac tgc tac gcc tcc tgg cgc aac agc tct ggc acc   192
Asp Lys Arg Leu His Cys Tyr Ala Ser Trp Arg Asn Ser Ser Gly Thr
50                  55                  60 atc gag ctc gtg aag aag ggc tgc tgg cta gat gac ttc aac tgc tac   240
Ile Glu Leu Val Lys Lys Gly Cys Trp Leu Asp Asp Phe Asn Cys Tyr
65                  70                  75                  80 gat agg cag gag tgt gtg gcc act gag gag aac ccc cag gtg tac ttc   288
Asp Arg Gln Glu Cys Val Ala Thr Glu Glu Asn Pro Gln Val Tyr Phe
                85                  90                  95 tgc tgc tgt gag ggc aac ttc tgc aac gag cgc ttc act cat ttg cca   336
Cys Cys Cys Glu Gly Asn Phe Cys Asn Glu Arg Phe Thr His Leu Pro
            100                 105                 110 gag gct ggg ggc ccg gaa gtc acg tac gag cca ccc ccg aca gcc ccc   384
Glu Ala Gly Gly Pro Glu Val Thr Tyr Glu Pro Pro Pro Thr Ala Pro
        115                 120                 125 acc                                                                387
Thr

<210> SEQ ID NO 4
<211> LENGTH: 129
<212> TYPE: PRT
<213> ORGANISM: Homo sapiens

<400> SEQUENCE: 4

Met Glu Phe Gly Leu Ser Trp Val Phe Leu Val Ala Leu Leu Arg Gly
1               5                   10                  15

Val Gln Cys Glu Thr Arg Trp Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
    50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Pro Thr Ala Pro
        115                 120                 125

Thr

<210> SEQ ID NO 5
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 5
```

```
gag aca cgg tgg tgc atc tac tac aac gcc aac tgg gag ctg gag cgc     48
Glu Thr Arg Trp Cys Ile Tyr Tyr Asn Ala Asn Trp Glu Leu Glu Arg
1               5                   10                  15 acc aac cag acc ggc ctg gag cgc tgc gaa ggc gag cag gac aag cgg     96
Thr Asn Gln Thr Gly Leu Glu Arg Cys Glu Gly Glu Gln Asp Lys Arg
            20                  25                  30 ctg cac tgc tac gcc tcc tgg cgc aac agc tct ggc acc atc gag ctc    144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag    192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgt        240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg    288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc            330
Gly Pro Glu Val Thr Tyr Glu Pro Pro Pro Thr Ala Pro Thr
            100                 105                 110

<210> SEQ ID NO 6
<211> LENGTH: 110
<212> TYPE: PRT
<213> ORGANISM: Homo sapiens

<400> SEQUENCE: 6

Glu Thr Arg Trp Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 7
<211> LENGTH: 1071
<212> TYPE: DNA
<213> ORGANISM: Homo sapiens
<220> FEATURE:
<221> NAME/KEY: CDS
<222> LOCATION: (1)..(1071)

<400> SEQUENCE: 7 atg gag ttt ggg ctg agc tgg gtt ttc ctc gtt gct ctt tta aga ggt     48
Met Glu Phe Gly Leu Ser Trp Val Phe Leu Val Ala Leu Leu Arg Gly
1               5                   10                  15 gtc cag tgt gag aca cgg tgg tgc atc tac tac aac gcc aac tgg gag     96
Val Gln Cys Glu Thr Arg Trp Cys Ile Tyr Tyr Asn Ala Asn Trp Glu
            20                  25                  30 ctg gag cgc acc aac cag acc ggc ctg gag cgc tgc gaa ggc gag cag    144
Leu Glu Arg Thr Asn Gln Thr Gly Leu Glu Arg Cys Glu Gly Glu Gln
        35                  40                  45
```

```
gac aag cgg ctg cac tgc tac gcc tcc tgg cgc aac agc tct ggc acc      192
Asp Lys Arg Leu His Cys Tyr Ala Ser Trp Arg Asn Ser Ser Gly Thr
 50                  55                  60 atc gag ctc gtg aag aag ggc tgc tgg cta gat gac ttc aac tgc tac      240
Ile Glu Leu Val Lys Lys Gly Cys Trp Leu Asp Asp Phe Asn Cys Tyr
 65                  70                  75                  80 gat agg cag gag tgt gtg gcc act gag gag aac ccc cag gtg tac ttc      288
Asp Arg Gln Glu Cys Val Ala Thr Glu Glu Asn Pro Gln Val Tyr Phe
                 85                  90                  95 tgc tgc tgt gag ggc aac ttc tgc aac gag cgc ttc act cat ttg cca      336
Cys Cys Cys Glu Gly Asn Phe Cys Asn Glu Arg Phe Thr His Leu Pro
            100                 105                 110 gag gct ggg ggc ccg gaa gtc acg tac gag cca ccc cca aca gcc ccc      384
Glu Ala Gly Gly Pro Glu Val Thr Tyr Glu Pro Pro Pro Thr Ala Pro
        115                 120                 125 acc gga ggg gga gga tct gtc gag tgc cca ccg tgc cca gca cca cct      432
Thr Gly Gly Gly Gly Ser Val Glu Cys Pro Pro Cys Pro Ala Pro Pro
130                 135                 140 gtg gca gga ccg tca gtc ttc ctc ttc ccc cca aaa ccc aag gac acc      480
Val Ala Gly Pro Ser Val Phe Leu Phe Pro Pro Lys Pro Lys Asp Thr
145                 150                 155                 160 ctc atg atc tcc cgg acc cct gag gtc acg tgc gtg gtg gtg gac gtg      528
Leu Met Ile Ser Arg Thr Pro Glu Val Thr Cys Val Val Val Asp Val
                165                 170                 175 agc cac gaa gac ccc gag gtc cag ttc aac tgg tac gtg gac ggc gtg      576
Ser His Glu Asp Pro Glu Val Gln Phe Asn Trp Tyr Val Asp Gly Val
            180                 185                 190 gag gtg cat aat gcc aag aca aag cca cgg gag gag cag ttc aac agc      624
Glu Val His Asn Ala Lys Thr Lys Pro Arg Glu Glu Gln Phe Asn Ser
        195                 200                 205 acg ttc cgt gtg gtc agc gtc ctc acc gtt gtg cac cag gac tgg ctg      672
Thr Phe Arg Val Val Ser Val Leu Thr Val Val His Gln Asp Trp Leu
210                 215                 220 aac ggc aag gag tac aag tgc aag gtc tcc aac aaa ggc ctc cca gcc      720
Asn Gly Lys Glu Tyr Lys Cys Lys Val Ser Asn Lys Gly Leu Pro Ala
225                 230                 235                 240 ccc atc gag aaa acc atc tcc aaa acc aaa ggg cag ccc cga gaa cca      768
Pro Ile Glu Lys Thr Ile Ser Lys Thr Lys Gly Gln Pro Arg Glu Pro
                245                 250                 255 cag gtg tac acc ctg ccc cca tcc cgg gag gag atg acc aag aac cag      816
Gln Val Tyr Thr Leu Pro Pro Ser Arg Glu Glu Met Thr Lys Asn Gln
            260                 265                 270 gtc agc ctg acc tgc ctg gtc aaa ggc ttc tat ccc agc gac atc gcc      864
Val Ser Leu Thr Cys Leu Val Lys Gly Phe Tyr Pro Ser Asp Ile Ala
        275                 280                 285 gtg gag tgg gag agc aat ggg cag ccg gag aac aac tac aag acc aca      912
Val Glu Trp Glu Ser Asn Gly Gln Pro Glu Asn Asn Tyr Lys Thr Thr
290                 295                 300 cct ccc atg ctg gac tcc gac ggc tcc ttc ttc ctc tac agc aag ctc      960
Pro Pro Met Leu Asp Ser Asp Gly Ser Phe Phe Leu Tyr Ser Lys Leu
305                 310                 315                 320 acc gtg gac aag agc agg tgg cag cag ggg aac gtc ttc tca tgc tcc     1008
Thr Val Asp Lys Ser Arg Trp Gln Gln Gly Asn Val Phe Ser Cys Ser
                325                 330                 335 gtg atg cat gag gct ctg cac aac cac tac acg cag aag agc ctc tcc     1056
Val Met His Glu Ala Leu His Asn His Tyr Thr Gln Lys Ser Leu Ser
            340                 345                 350 ctg tct ccg ggt aaa                                                  1071
Leu Ser Pro Gly Lys
```

```
                355

<210> SEQ ID NO 8
<211> LENGTH: 357
<212> TYPE: PRT
<213> ORGANISM: Homo sapiens

<400> SEQUENCE: 8

Met Glu Phe Gly Leu Ser Trp Val Phe Leu Val Ala Leu Leu Arg Gly
1               5                   10                  15

Val Gln Cys Glu Thr Arg Trp Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Thr Ala Pro
        115                 120                 125

Thr Gly Gly Gly Gly Ser Val Glu Cys Pro Pro Cys Pro Ala Pro Pro
130                 135                 140

Val Ala Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Gln Phe Asn Trp Tyr Val Asp Gly Val
            180                 185                 190

Glu Val His Asn Ala Lys Thr Lys Pro Arg Glu Glu Gln Phe Asn Ser
        195                 200                 205

Thr Phe Arg Val Val Ser Val Leu Thr Val Val His Gln Asp Trp Leu
210                 215                 220

Asn Gly Lys Glu Tyr Lys Cys Lys Val Ser Asn Lys Gly Leu Pro Ala
225                 230                 235                 240

Pro Ile Glu Lys Thr Ile Ser Lys Thr Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355
```

<210> SEQ ID NO 9
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 9

```
gag aca cgg tgg tgc atc tac tac aac gcc aac tgg gag ctg gag cgc      48
Glu Thr Arg Trp Cys Ile Tyr Tyr Asn Ala Asn Trp Glu Leu Glu Arg
1               5                   10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
            20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag     192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt     240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg     288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga ggg     336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga     384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc     432
Pro Ser Val Phe Leu Phe Pro Pro Lys Pro Lys Asp Thr Leu Met Ile
    130                 135                 140 tcc cgg acc cct gag gtc acg tgc gtg gtg gtg gac gtg agc cac gaa     480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat     528
Asp Pro Glu Val Gln Phe Asn Trp Tyr Val Asp Gly Val Glu Val His
                165                 170                 175 aat gcc aag aca aag cca cgg gag gag cag ttc aac agc acg ttc cgt     576
Asn Ala Lys Thr Lys Pro Arg Glu Glu Gln Phe Asn Ser Thr Phe Arg
            180                 185                 190 gtg gtc agc gtc ctc acc gtt gtg cac cag gac tgg ctg aac ggc aag     624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag     672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac     720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg     768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg     816
Thr Cys Leu Val Lys Gly Phe Tyr Pro Ser Asp Ile Ala Val Glu Trp
            260                 265                 270
```

```
gag agc aat ggg cag ccg gag aac aac tac aag acc aca cct ccc atg      864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac      912
Leu Asp Ser Asp Gly Ser Phe Phe Leu Tyr Ser Lys Leu Thr Val Asp
290                 295                 300 aag agc agg tgg cag cag ggg aac gtc ttc tca tgc tcc gtg atg cat      960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg     1008
Glu Ala Leu His Asn His Tyr Thr Gln Lys Ser Leu Ser Leu Ser Pro
                325                 330                 335 ggt aaa                                                              1014
Gly Lys <210> SEQ ID NO 10
<211> LENGTH: 338
<212> TYPE: PRT
<213> ORGANISM: Homo sapiens

<400> SEQUENCE: 10

Glu Thr Arg Trp Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Pro Val Ala Gly
        115                 120                 125

Pro Ser Val Phe Leu Phe Pro Pro Lys Pro Lys Asp Thr Leu Met Ile
    130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
```

```
                275                 280                 285
Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 11
<211> LENGTH: 387
<212> TYPE: DNA
<213> ORGANISM: Homo sapiens
<220> FEATURE:
<221> NAME/KEY: CDS
<222> LOCATION: (1)..(387)

<400> SEQUENCE: 11 atg gag ttt ggg ctg agc tgg gtt ttc ctc gtt gct ctt tta aga ggt    48
Met Glu Phe Gly Leu Ser Trp Val Phe Leu Val Ala Leu Leu Arg Gly
1               5                   10                  15 gtc cag tgt gag aca cgg tac tgc atc tac tac aac gcc aac tgg gag    96
Val Gln Cys Glu Thr Arg Tyr Cys Ile Tyr Tyr Asn Ala Asn Trp Glu
            20                  25                  30 ctg gag cgc acc aac cag acc ggc ctg gag cgc tgc gaa ggc gag cag   144
Leu Glu Arg Thr Asn Gln Thr Gly Leu Glu Arg Cys Glu Gly Glu Gln
        35                  40                  45 gac aag cgg ctg cac tgc tac gcc tcc tgg cgc aac agc tct ggc acc   192
Asp Lys Arg Leu His Cys Tyr Ala Ser Trp Arg Asn Ser Ser Gly Thr
    50                  55                  60 atc gag ctc gtg aag aag ggc tgc tgg cta gat gac ttc aac tgc tac   240
Ile Glu Leu Val Lys Lys Gly Cys Trp Leu Asp Asp Phe Asn Cys Tyr
65                  70                  75                  80 gat agg cag gag tgt gtg gcc act gag gag aac ccc cag gtg tac ttc   288
Asp Arg Gln Glu Cys Val Ala Thr Glu Glu Asn Pro Gln Val Tyr Phe
                85                  90                  95 tgc tgc tgt gag ggc aac ttc tgc aac gag cgc ttc act cat ttg cca   336
Cys Cys Cys Glu Gly Asn Phe Cys Asn Glu Arg Phe Thr His Leu Pro
            100                 105                 110 gag gct ggg ggc ccg gaa gtc acg tac gag cca ccc ccg aca gcc ccc   384
Glu Ala Gly Gly Pro Glu Val Thr Tyr Glu Pro Pro Pro Thr Ala Pro
        115                 120                 125 acc                                                               387
Thr

<210> SEQ ID NO 12
<211> LENGTH: 129
<212> TYPE: PRT
<213> ORGANISM: Homo sapiens

<400> SEQUENCE: 12

Met Glu Phe Gly Leu Ser Trp Val Phe Leu Val Ala Leu Leu Arg Gly
1               5                   10                  15

Val Gln Cys Glu Thr Arg Tyr Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
    50                  55                  60
```

```
Ile Glu Leu Val Lys Lys Gly Cys Trp Leu Asp Asp Phe Asn Cys Tyr
 65                  70                  75                  80

Asp Arg Gln Glu Cys Val Ala Thr Glu Glu Asn Pro Gln Val Tyr Phe
                 85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Thr Ala Pro
        115                 120                 125

Thr
```

```
<210> SEQ ID NO 13
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 13 gag aca cgg tac tgc atc tac tac aac gcc aac tgg gag ctg gag cgc      48
Glu Thr Arg Tyr Cys Ile Tyr Tyr Asn Ala Asn Trp Glu Leu Glu Arg
 1               5                  10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
             20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
         35                  40                  45 gtg aag aag ggc tgc tgg cta gat gac ttc aac tgc tac gat agg cag     192
Val Lys Lys Gly Cys Trp Leu Asp Asp Phe Asn Cys Tyr Asp Arg Gln
     50                  55                  60 gag tgt gtg gcc act gag gag aac ccc cag gtg tac ttc tgc tgt         240
Glu Cys Val Ala Thr Glu Glu Asn Pro Gln Val Tyr Phe Cys Cys Cys
 65                  70                  75                  80 gag ggc aac ttc tgc aac gag cgc ttc act cat ttg cca gag gct ggg     288
Glu Gly Asn Phe Cys Asn Glu Arg Phe Thr His Leu Pro Glu Ala Gly
                 85                  90                  95 ggc ccg gaa gtc acg tac gag cca ccc ccg aca gcc ccc acc                330
Gly Pro Glu Val Thr Tyr Glu Pro Pro Thr Ala Pro Thr
            100                 105                 110
```

```
<210> SEQ ID NO 14
<211> LENGTH: 110
<212> TYPE: PRT
<213> ORGANISM: Homo sapiens

<400> SEQUENCE: 14

Glu Thr Arg Tyr Cys Ile Tyr Tyr Asn Ala Asn Trp Glu Leu Glu Arg
 1               5                  10                  15

Thr Asn Gln Thr Gly Leu Glu Arg Cys Glu Gly Glu Gln Asp Lys Arg
             20                  25                  30

Leu His Cys Tyr Ala Ser Trp Arg Asn Ser Ser Gly Thr Ile Glu Leu
         35                  40                  45

Val Lys Lys Gly Cys Trp Leu Asp Asp Phe Asn Cys Tyr Asp Arg Gln
     50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95
```

<210> SEQ ID NO 15
<211> LENGTH: 1071
<212> TYPE: DNA
<213> ORGANISM: Homo sapiens
<220> FEATURE:
<221> NAME/KEY: CDS
<222> LOCATION: (1)..(1071)

<400> SEQUENCE: 15

| | | | | | | | | | | | | | | | | |
|---|---|---|---|---|---|---|---|---|---|---|---|---|---|---|---|---|
| atg | gag | ttt | ggg | ctg | agc | tgg | gtt | ttc | ctc | gtt | gct | ctt | tta | aga | ggt | 48 |
| Met | Glu | Phe | Gly | Leu | Ser | Trp | Val | Phe | Leu | Val | Ala | Leu | Leu | Arg | Gly | |
| 1 | | | | 5 | | | | | 10 | | | | | 15 | | |
| gtc | cag | tgt | gag | aca | cgg | tac | tgc | atc | tac | tac | aac | gcc | aac | tgg | gag | 96 |
| Val | Gln | Cys | Glu | Thr | Arg | Tyr | Cys | Ile | Tyr | Tyr | Asn | Ala | Asn | Trp | Glu | |
| | | 20 | | | | | 25 | | | | | 30 | | | | |
| ctg | gag | cgc | acc | aac | cag | acc | ggc | ctg | gag | cgc | tgc | gaa | ggc | gag | cag | 144 |
| Leu | Glu | Arg | Thr | Asn | Gln | Thr | Gly | Leu | Glu | Arg | Cys | Glu | Gly | Glu | Gln | |
| | 35 | | | | | 40 | | | | | 45 | | | | | |
| gac | aag | cgg | ctg | cac | tgc | tac | gcc | tcc | tgg | cgc | aac | agc | tct | ggc | acc | 192 |
| Asp | Lys | Arg | Leu | His | Cys | Tyr | Ala | Ser | Trp | Arg | Asn | Ser | Ser | Gly | Thr | |
| 50 | | | | | 55 | | | | | 60 | | | | | | |
| atc | gag | ctc | gtg | aag | aag | ggc | tgc | tgg | cta | gat | gac | ttc | aac | tgc | tac | 240 |
| Ile | Glu | Leu | Val | Lys | Lys | Gly | Cys | Trp | Leu | Asp | Asp | Phe | Asn | Cys | Tyr | |
| 65 | | | | | 70 | | | | | 75 | | | | | 80 | |
| gat | agg | cag | gag | tgt | gtg | gcc | act | gag | gag | aac | ccc | cag | gtg | tac | ttc | 288 |
| Asp | Arg | Gln | Glu | Cys | Val | Ala | Thr | Glu | Glu | Asn | Pro | Gln | Val | Tyr | Phe | |
| | | | | 85 | | | | | 90 | | | | | 95 | | |
| tgc | tgc | tgt | gag | ggc | aac | ttc | tgc | aac | gag | cgc | ttc | act | cat | ttg | cca | 336 |
| Cys | Cys | Cys | Glu | Gly | Asn | Phe | Cys | Asn | Glu | Arg | Phe | Thr | His | Leu | Pro | |
| | | | 100 | | | | | 105 | | | | | 110 | | | |
| gag | gct | ggg | ggc | ccg | gaa | gtc | acg | tac | gag | cca | ccc | cga | aca | gcc | ccc | 384 |
| Glu | Ala | Gly | Gly | Pro | Glu | Val | Thr | Tyr | Glu | Pro | Pro | Thr | Ala | Pro | |
| | | 115 | | | | | 120 | | | | | 125 | | | | |
| acc | gga | ggg | gga | gga | tct | gtc | gag | tgc | cca | ccg | tgc | cca | gca | cca | cct | 432 |
| Thr | Gly | Gly | Gly | Gly | Ser | Val | Glu | Cys | Pro | Pro | Cys | Pro | Ala | Pro | Pro | |
| | 130 | | | | | 135 | | | | | 140 | | | | | |
| gtg | gca | gga | ccg | tca | gtc | ttc | ctc | ttc | ccc | cca | aaa | ccc | aag | gac | acc | 480 |
| Val | Ala | Gly | Pro | Ser | Val | Phe | Leu | Phe | Pro | Pro | Lys | Pro | Lys | Asp | Thr | |
| 145 | | | | | 150 | | | | | 155 | | | | | 160 | |
| ctc | atg | atc | tcc | cgg | acc | cct | gag | gtc | acg | tgc | gtg | gtg | gtg | gac | gtg | 528 |
| Leu | Met | Ile | Ser | Arg | Thr | Pro | Glu | Val | Thr | Cys | Val | Val | Val | Asp | Val | |
| | | | | 165 | | | | | 170 | | | | | 175 | | |
| agc | cac | gaa | gac | ccc | gag | gtc | cag | ttc | aac | tgg | tac | gtg | gac | ggc | gtg | 576 |
| Ser | His | Glu | Asp | Pro | Glu | Val | Gln | Phe | Asn | Trp | Tyr | Val | Asp | Gly | Val | |
| | | | 180 | | | | | 185 | | | | | 190 | | | |
| gag | gtg | cat | aat | gcc | aag | aca | aag | cca | cgg | gag | gag | cag | ttc | aac | agc | 624 |
| Glu | Val | His | Asn | Ala | Lys | Thr | Lys | Pro | Arg | Glu | Glu | Gln | Phe | Asn | Ser | |
| | | 195 | | | | | 200 | | | | | 205 | | | | |
| acg | ttc | cgt | gtg | gtc | agc | gtc | ctc | acc | gtt | gtg | cac | cag | gac | tgg | ctg | 672 |
| Thr | Phe | Arg | Val | Val | Ser | Val | Leu | Thr | Val | Val | His | Gln | Asp | Trp | Leu | |
| | 210 | | | | | 215 | | | | | 220 | | | | | |
| aac | ggc | aag | gag | tac | aag | tgc | aag | gtc | tcc | aac | aaa | ggc | ctc | cca | gcc | 720 |
| Asn | Gly | Lys | Glu | Tyr | Lys | Cys | Lys | Val | Ser | Asn | Lys | Gly | Leu | Pro | Ala | |
| 225 | | | | | 230 | | | | | 235 | | | | | 240 | |
| ccc | atc | gag | aaa | acc | atc | tcc | aaa | acc | aaa | ggg | cag | ccc | cga | gaa | cca | 768 |
| Pro | Ile | Glu | Lys | Thr | Ile | Ser | Lys | Thr | Lys | Gly | Gln | Pro | Arg | Glu | Pro | |
| | | | | 245 | | | | | 250 | | | | | 255 | | |
| cag | gtg | tac | acc | ctg | ccc | cca | tcc | cgg | gag | gag | atg | acc | aag | aac | cag | 816 |

```
                Gln Val Tyr Thr Leu Pro Pro Ser Arg Glu Met Thr Lys Asn Gln
                            260                 265                 270 gtc agc ctg acc tgc ctg gtc aaa ggc ttc tat ccc agc gac atc gcc      864
Val Ser Leu Thr Cys Leu Val Lys Gly Phe Tyr Pro Ser Asp Ile Ala
            275                 280                 285 gtg gag tgg gag agc aat ggg cag ccg gag aac aac tac aag acc aca      912
Val Glu Trp Glu Ser Asn Gly Gln Pro Glu Asn Asn Tyr Lys Thr Thr
        290                 295                 300 cct ccc atg ctg gac tcc gac ggc tcc ttc ttc ctc tac agc aag ctc      960
Pro Pro Met Leu Asp Ser Asp Gly Ser Phe Phe Leu Tyr Ser Lys Leu
305                 310                 315                 320 acc gtg gac aag agc agg tgg cag cag ggg aac gtc ttc tca tgc tcc     1008
Thr Val Asp Lys Ser Arg Trp Gln Gln Gly Asn Val Phe Ser Cys Ser
                325                 330                 335 gtg atg cat gag gct ctg cac aac cac tac acg cag aag agc ctc tcc     1056
Val Met His Glu Ala Leu His Asn His Tyr Thr Gln Lys Ser Leu Ser
            340                 345                 350 ctg tct ccg ggt aaa                                                  1071
Leu Ser Pro Gly Lys
            355

<210> SEQ ID NO 16
<211> LENGTH: 357
<212> TYPE: PRT
<213> ORGANISM: Homo sapiens

<400> SEQUENCE: 16

Met Glu Phe Gly Leu Ser Trp Val Phe Leu Val Ala Leu Leu Arg Gly
1               5                   10                  15

Val Gln Cys Glu Thr Arg Tyr Cys Ile Tyr Tyr Asn Ala Asn Trp Glu
            20                  25                  30

Leu Glu Arg Thr Asn Gln Thr Gly Leu Glu Arg Cys Glu Gly Glu Gln
        35                  40                  45

Asp Lys Arg Leu His Cys Tyr Ala Ser Trp Arg Asn Ser Ser Gly Thr
    50                  55                  60

Ile Glu Leu Val Lys Lys Gly Cys Trp Leu Asp Asp Phe Asn Cys Tyr
65                  70                  75                  80

Asp Arg Gln Glu Cys Val Ala Thr Glu Glu Asn Pro Gln Val Tyr Phe
                85                  90                  95

Cys Cys Cys Glu Gly Asn Phe Cys Asn Glu Arg Phe Thr His Leu Pro
            100                 105                 110

Glu Ala Gly Gly Pro Glu Val Thr Tyr Glu Pro Pro Pro Thr Ala Pro
        115                 120                 125

Thr Gly Gly Gly Gly Ser Val Glu Cys Pro Pro Cys Pro Ala Pro Pro
    130                 135                 140

Val Ala Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Gln Phe Asn Trp Tyr Val Asp Gly Val
            180                 185                 190

Glu Val His Asn Ala Lys Thr Lys Pro Arg Glu Glu Gln Phe Asn Ser
        195                 200                 205

Thr Phe Arg Val Val Ser Val Leu Thr Val Val His Gln Asp Trp Leu
    210                 215                 220

Asn Gly Lys Glu Tyr Lys Cys Lys Val Ser Asn Lys Gly Leu Pro Ala
225                 230                 235                 240
```

```
Pro Ile Glu Lys Thr Ile Ser Lys Thr Lys Gly Gln Pro Arg Glu Pro
                245                 250                 255

Gln Val Tyr Thr Leu Pro Pro Ser Arg Glu Glu Met Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Met Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 17
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 17 gag aca cgg tac tgc atc tac tac aac gcc aac tgg gag ctg gag cgc      48
Glu Thr Arg Tyr Cys Ile Tyr Tyr Asn Ala Asn Trp Glu Leu Glu Arg
1               5                   10                  15 acc aac cag acc ggc ctg gag cgc tgc gaa ggc gag cag gac aag cgg      96
Thr Asn Gln Thr Gly Leu Glu Arg Cys Glu Gly Glu Gln Asp Lys Arg
            20                  25                  30 ctg cac tgc tac gcc tcc tgg cgc aac agc tct ggc acc atc gag ctc     144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag     192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt     240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg     288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga ggg     336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga     384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc     432
Pro Ser Val Phe Leu Phe Pro Pro Lys Pro Lys Asp Thr Leu Met Ile
    130                 135                 140 tcc cgg acc cct gag gtc acg tgc gtg gtg gtg gac gtg agc cac gaa     480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat     528
Asp Pro Glu Val Gln Phe Asn Trp Tyr Val Asp Gly Val Glu Val His
                165                 170                 175
```

```
aat gcc aag aca aag cca cgg gag gag cag ttc aac agc acg ttc cgt     576
Asn Ala Lys Thr Lys Pro Arg Glu Glu Gln Phe Asn Ser Thr Phe Arg
        180                 185                 190 gtg gtc agc gtc ctc acc gtt gtg cac cag gac tgg ctg aac ggc aag     624
Val Val Ser Val Leu Thr Val Val His Gln Asp Trp Leu Asn Gly Lys
            195                 200                 205 gag tac aag tgc aag gtc tcc aac aaa ggc ctc cca gcc ccc atc gag     672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac     720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg     768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg     816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg     864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac     912
Leu Asp Ser Asp Gly Ser Phe Phe Leu Tyr Ser Lys Leu Thr Val Asp
    290                 295                 300 aag agc agg tgg cag cag ggg aac gtc ttc tca tgc tcc gtg atg cat     960
Lys Ser Arg Trp Gln Gln Gly Asn Val Phe Ser Cys Ser Val Met His
305                 310                 315                 320 gag gct ctg cac aac cac tac acg cag aag agc ctc tcc ctg tct ccg    1008
Glu Ala Leu His Asn His Tyr Thr Gln Lys Ser Leu Ser Leu Ser Pro
                325                 330                 335 ggt aaa                                                            1014
Gly Lys

<210> SEQ ID NO 18
<211> LENGTH: 338
<212> TYPE: PRT
<213> ORGANISM: Homo sapiens

<400> SEQUENCE: 18

Glu Thr Arg Tyr Cys Ile Tyr Tyr Asn Ala Asn Trp Glu Leu Glu Arg
1               5                   10                  15

Thr Asn Gln Thr Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Val Ala Gly
        115                 120                 125

Pro Ser Val Phe Leu Phe Pro Pro Lys Pro Lys Asp Thr Leu Met Ile
    130                 135                 140
```

```
Ser Arg Thr Pro Glu Val Thr Cys Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
    210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 19
<211> LENGTH: 110
<212> TYPE: PRT
<213> ORGANISM: Homo sapiens

<400> SEQUENCE: 19

Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110

<210> SEQ ID NO 20
<211> LENGTH: 1014
<212> TYPE: DNA
<213> ORGANISM: Homo sapiens
<220> FEATURE:
<221> NAME/KEY: CDS
<222> LOCATION: (1)..(1014)

<400> SEQUENCE: 20 gag aca cgg tgg tgc atc tac tac aac gcc aac tgg gag ctg gag cgc    48
```

```
Glu Thr Arg Trp Cys Ile Tyr Tyr Asn Ala Asn Trp Glu Leu Glu Arg
1               5                   10                  15 acc aac cag agc ggc ctg gag cgc tgc gaa ggc gag cag gac aag cgg        96
Thr Asn Gln Ser Gly Leu Glu Arg Cys Glu Gly Glu Gln Asp Lys Arg
            20                  25                  30 ctg cac tgc tac gcc tcc tgg cgc aac agc tct ggc acc atc gag ctc       144
Leu His Cys Tyr Ala Ser Trp Arg Asn Ser Ser Gly Thr Ile Glu Leu
        35                  40                  45 gtg aag aag ggc tgc tgg cta gat gac ttc aac tgc tac gat agg cag       192
Val Lys Lys Gly Cys Trp Leu Asp Asp Phe Asn Cys Tyr Asp Arg Gln
    50                  55                  60 gag tgt gtg gcc act gag gag aac ccc cag gtg tac ttc tgc tgc tgt       240
Glu Cys Val Ala Thr Glu Glu Asn Pro Gln Val Tyr Phe Cys Cys Cys
65                  70                  75                  80 gag ggc aac ttc tgc aac gag cgc ttc act cat ttg cca gag gct ggg       288
Glu Gly Asn Phe Cys Asn Glu Arg Phe Thr His Leu Pro Glu Ala Gly
                85                  90                  95 ggc ccg gaa gtc acg tac gag cca ccc ccg aca gcc ccc acc gga gga       336
Gly Pro Glu Val Thr Tyr Glu Pro Pro Pro Thr Ala Pro Thr Gly Gly
            100                 105                 110 gga gga tct gtc gag tgc cca ccg tgc cca gca cca cct gtg gca gga       384
Gly Gly Ser Val Glu Cys Pro Pro Cys Pro Ala Pro Pro Val Ala Gly
        115                 120                 125 ccg tca gtc ttc ctc ttc ccc cca aaa ccc aag gac acc ctc atg atc       432
Pro Ser Val Phe Leu Phe Pro Pro Lys Pro Lys Asp Thr Leu Met Ile
    130                 135                 140 tcc cgg acc cct gag gtc acg tgc gtg gtg gtg gac gtg agc cac gaa       480
Ser Arg Thr Pro Glu Val Thr Cys Val Val Val Asp Val Ser His Glu
145                 150                 155                 160 gac ccc gag gtc cag ttc aac tgg tac gtg gac ggc gtg gag gtg cat       528
Asp Pro Glu Val Gln Phe Asn Trp Tyr Val Asp Gly Val Glu Val His
                165                 170                 175 aat gcc aag aca aag cca cgg gag gag cag ttc aac agc acg ttc cgt       576
Asn Ala Lys Thr Lys Pro Arg Glu Glu Gln Phe Asn Ser Thr Phe Arg
            180                 185                 190 gtg gtc agc gtc ctc acc gtt gtg cac cag gac tgg ctg aac ggc aag       624
Val Val Ser Val Leu Thr Val Val His Gln Asp Trp Leu Asn Gly Lys
        195                 200                 205 gag tac aag tgc aag gtc tcc aac aaa ggc ctc cca gcc ccc atc gag       672
Glu Tyr Lys Cys Lys Val Ser Asn Lys Gly Leu Pro Ala Pro Ile Glu
    210                 215                 220 aaa acc atc tcc aaa acc aaa ggg cag ccc cga gaa cca cag gtg tac       720
Lys Thr Ile Ser Lys Thr Lys Gly Gln Pro Arg Glu Pro Gln Val Tyr
225                 230                 235                 240 acc ctg ccc cca tcc cgg gag gag atg acc aag aac cag gtc agc ctg       768
Thr Leu Pro Pro Ser Arg Glu Glu Met Thr Lys Asn Gln Val Ser Leu
                245                 250                 255 acc tgc ctg gtc aaa ggc ttc tat ccc agc gac atc gcc gtg gag tgg       816
Thr Cys Leu Val Lys Gly Phe Tyr Pro Ser Asp Ile Ala Val Glu Trp
            260                 265                 270 gag agc aat ggg cag ccg gag aac aac tac aag acc aca cct ccc atg       864
Glu Ser Asn Gly Gln Pro Glu Asn Asn Tyr Lys Thr Thr Pro Pro Met
        275                 280                 285 ctg gac tcc gac ggc tcc ttc ttc ctc tac agc aag ctc acc gtg gac       912
Leu Asp Ser Asp Gly Ser Phe Phe Leu Tyr Ser Lys Leu Thr Val Asp
    290                 295                 300 aag agc agg tgg cag cag ggg aac gtc ttc tca tgc tcc gtg atg cat       960
Lys Ser Arg Trp Gln Gln Gly Asn Val Phe Ser Cys Ser Val Met His
305                 310                 315                 320
```

| | | | | | | | | | | | | |
|---|---|---|---|---|---|---|---|---|---|---|---|---|
| gag | gct | ctg | cac | aac | cac | tac | acg | cag | aag | agc | ctc | tcc | ctg | tct | ccg | 1008 |
| Glu | Ala | Leu | His | Asn | His | Tyr | Thr | Gln | Lys | Ser | Leu | Ser | Leu | Ser | Pro | |
| 325 | | | | | | 330 | | | | | | 335 | | | | |

| | |
|---|---|
| ggt aaa | 1014 |
| Gly Lys | |

<210> SEQ ID NO 21
<211> LENGTH: 338
<212> TYPE: PRT
<213> ORGANISM: Homo sapiens

<400> SEQUENCE: 21

Glu Thr Arg Trp Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Ala Pro Thr Gly Gly
            100                 105                 110

Gly Gly Ser Val Glu Cys Pro Pro Cys Pro Ala Pro Val Ala Gly
        115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Val Asp Val Ser His Glu
145                 150                 155                 160

Asp Pro Glu Val Gln Phe Asn Trp Tyr Val Asp Gly Val Glu Val His
                165                 170                 175

Asn Ala Lys Thr Lys Pro Arg Glu Glu Gln Phe Asn Ser Thr Phe Arg
            180                 185                 190

Val Val Ser Val Leu Thr Val Val His Gln Asp Trp Leu Asn Gly Lys
        195                 200                 205

Glu Tyr Lys Cys Lys Val Ser Asn Lys Gly Leu Pro Ala Pro Ile Glu
210                 215                 220

Lys Thr Ile Ser Lys Thr Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Met
        275                 280                 285

Leu Asp Ser Asp Gly Ser Phe Phe Leu Tyr Ser Lys Leu Thr Val Asp
290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 22
<211> LENGTH: 216
<212> TYPE: PRT
<213> ORGANISM: Homo sapiens

<400> SEQUENCE: 22

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 23
<211> LENGTH: 217
<212> TYPE: PRT
<213> ORGANISM: Homo sapiens

<400> SEQUENCE: 23

Ala Pro Glu Leu Leu Gly Gly Pro Ser Val Phe Leu Phe Pro Pro Lys
1               5                   10                  15

Pro Lys Asp Ile Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Gly Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 24
<211> LENGTH: 217
<212> TYPE: PRT
<213> ORGANISM: Homo sapiens

<400> SEQUENCE: 24

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
                180                 185                 190

Phe Ser Cys Ser Val Met His Glu Ala Leu His Asn His Tyr Thr Gln
            195                 200                 205

Lys Ser Leu Ser Leu Ser Leu Gly Lys
    210                 215

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
``` linker peptide

<400> SEQUENCE: 25

Gly Gly Gly Gly Ser
1               5

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(36)

<400> SEQUENCE: 26 gga ggg gga gga tct gtc gag tgc cca ccg tgc cca        36
Gly Gly Gly Gly Ser Val Glu Cys Pro Pro Cys Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 27

Gly Gly Gly Gly Ser Val Glu Cys Pro Pro Cys Pro
1               5                   10

<210> SEQ ID NO 28
<211> LENGTH: 12
<212> TYPE: PRT
<213> ORGANISM: Homo sapiens

<400> SEQUENCE: 28

Glu Arg Lys Cys Cys Val Glu Cys Pro Pro Cys Pro
1               5                   10

<210> SEQ ID NO 29
<211> LENGTH: 15
<212> TYPE: PRT
<213> ORGANISM: Homo sapiens

<400> SEQUENCE: 29

Glu Pro Lys Ser Cys Asp Lys Thr His Thr Cys Pro Pro Cys Pro
1               5                   10                  15

<210> SEQ ID NO 30
<211> LENGTH: 12
<212> TYPE: PRT
<213> ORGANISM: Homo sapiens

<400> SEQUENCE: 30

Glu Ser Lys Thr Gly Pro Pro Cys Pro Ser Cys Pro
1               5                   10

<210> SEQ ID NO 31
<211> LENGTH: 18
<212> TYPE: PRT
<213> ORGANISM: Homo sapiens

<400> SEQUENCE: 31

Met Thr Ala Pro Trp Val Ala Leu Ala Leu Leu Trp Gly Ser Leu Trp
1               5                   10                  15

Pro Gly

<210> SEQ ID NO 32
<211> LENGTH: 18
<212> TYPE: PRT
<213> ORGANISM: Homo sapiens

<400> SEQUENCE: 32

Met Thr Ala Pro Trp Val Ala Leu Ala Leu Leu Trp Gly Ser Leu Cys
1               5                   10                  15

Ala Gly

<210> SEQ ID NO 33
<211> LENGTH: 512
<212> TYPE: PRT
<213> ORGANISM: Homo sapiens

<400> SEQUENCE: 33

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys

```
                   275                 280                 285
His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 34
<211> LENGTH: 426
<212> TYPE: PRT
<213> ORGANISM: Homo sapiens

<400> SEQUENCE: 34

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
        50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140
```

-continued

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Glu Gly Lys Lys Lys
            260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
        370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 35
<211> LENGTH: 375
<212> TYPE: PRT
<213> ORGANISM: Homo sapiens

<400> SEQUENCE: 35

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

```
Gln Arg Asp Asp Ser Asp Gly Ser Leu Glu Asp Asp Tyr His
            100                 105                 110

Ala Thr Thr Glu Thr Ile Ile Thr Met Pro Thr Glu Ser Asp Phe Leu
            115                 120                 125

Met Gln Val Asp Gly Lys Pro Lys Cys Cys Phe Phe Lys Phe Ser Ser
130                 135                 140

Lys Ile Gln Tyr Asn Lys Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
                195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
                275                 280                 285

Asp Phe Glu Ala Phe Gly Trp Asp Trp Ile Ile Ala Pro Lys Arg Tyr
                290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
370                 375

<210> SEQ ID NO 36
<211> LENGTH: 217
<212> TYPE: PRT
<213> ORGANISM: Homo sapiens

<400> SEQUENCE: 36

Ala Pro Glu Leu Leu Gly Gly Pro Ser Val Phe Leu Phe Pro Pro Lys
1               5                   10                  15

Pro Lys Asp Ile Leu Met Ile Ser Arg Thr Pro Glu Val Thr Cys Val
                20                  25                  30

Val Val Asp Val Ser His Glu Asp Pro Glu Val Lys Phe Asn Trp Tyr
                35                  40                  45

Val Gly Gly Val Glu Val His Asn Ala Lys Thr Lys Pro Arg Glu Glu
            50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                    85                  90                  95
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(48)

<400> SEQUENCE: 37 gga ggg gga gga tct gag cgc aaa tgt tgt gtc gag tgc cca ccg tgc    48
Gly Gly Gly Gly Ser Glu Arg Lys Cys Cys Val Glu Cys Pro Pro Cys
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 38

Gly Gly Gly Gly Ser Glu Arg Lys Cys Cys Val Glu Cys Pro Pro Cys
1               5                   10                  15

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(42)

<400> SEQUENCE: 39 gga ggg gga gga tct ggt gga ggt ggt tca ggt cca ccg tgc              42
Gly Gly Gly Gly Ser Gly Gly Gly Gly Ser Gly Pro Pro Cys
1               5                   10

<210> SEQ ID NO 40
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      hinge linker eptide

<400> SEQUENCE: 40

Gly Gly Gly Gly Ser Gly Gly Gly Gly Ser Gly Pro Pro Cys
1               5                   10

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(42)

<400> SEQUENCE: 41 gga ggg gga gga tct ggt gga ggt ggt tca ggt cca ccg gga         42
Gly Gly Gly Gly Ser Gly Gly Gly Gly Ser Gly Pro Pro Gly
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 42

Gly Gly Gly Gly Ser Gly Gly Gly Gly Ser Gly Pro Pro Gly
1               5                   10

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence: Synthetic
      hinge linker oligonucleotide
<220> FEATURE:
<221> NAME/KEY: CDS
<222> LOCATION: (1)..(54)

<400> SEQUENCE: 43 gga ggg gga gga tct gag cgc aaa tgt cca cct tgt gtc gag tgc cca     48
Gly Gly Gly Gly Ser Glu Arg Lys Cys Pro Pro Cys Val Glu Cys Pro
1               5                   10                  15 ccg tgc                                                             54
Pro Cys

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 44

Gly Gly Gly Gly Ser Glu Arg Lys Cys Pro Pro Cys Val Glu Cys Pro
1               5                   10                  15

Pro Cys
```

```
<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 45

Gly Pro Ala Ser Gly Gly Pro Ala Ser Gly Pro Pro Cys Pro
1               5                   10

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 46

Gly Pro Ala Ser Gly Gly Pro Ala Ser Gly Cys Pro Pro Cys Val Glu
1               5                   10                  15

Cys Pro Pro Cys Pro
            20

<210> SEQ ID NO 47
<211> LENGTH: 217
<212> TYPE: PRT
<213> ORGANISM: Homo sapiens

<400> SEQUENCE: 47

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Lys
    210             215
```

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 48

```
Gly Gly Gly Gly Ser Val Asp Lys Thr His Thr Cys Pro Pro Cys Pro
1               5                   10                  15
```

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 49

```
Gly Gly Gly Gly Ser Val Asp Lys Thr His Thr Gly Pro Pro Cys Pro
1               5                   10                  15
```

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      hinge linker peptide

<400> SEQUENCE: 50

```
Gly Gly Gly Gly Ser Gly Gly Gly Ser Val Asp Lys Thr His Thr
1               5                   10                  15

Gly Pro Pro Cys Pro
            20
```

<210> SEQ ID NO 51
<211> LENGTH: 48
<212> TYPE: DNA
<213> ORGANISM: Homo sapiens

<400> SEQUENCE: 51
aggtctagtc agagcctcct gcatagtact ggatacaact atttggat          48

<210> SEQ ID NO 52
<211> LENGTH: 21
<212> TYPE: DNA
<213> ORGANISM: Homo sapiens

<400> SEQUENCE: 52
ttgggttctt ttcgggcctc c                                       21

<210> SEQ ID NO 53
<211> LENGTH: 26
<212> TYPE: DNA
<213> ORGANISM: Homo sapiens

<400> SEQUENCE: 53
atgcaagctc tccaaactcc gtgcag                                  26

<210> SEQ ID NO 54
<211> LENGTH: 30
<212> TYPE: DNA
<213> ORGANISM: Homo sapiens

<400> SEQUENCE: 54
ggatacacct tcaccggcta ctatatccac                              30

<210> SEQ ID NO 55
<211> LENGTH: 51
<212> TYPE: DNA
<213> ORGANISM: Homo sapiens

<400> SEQUENCE: 55
tggatcaacc ctaacagtgg tggcacaaac tatgcacaga gtttcaggg c        51

<210> SEQ ID NO 56
<211> LENGTH: 36
<212> TYPE: DNA
<213> ORGANISM: Homo sapiens

<400> SEQUENCE: 56
gattcggggt atagcagcag ctggcacttt gactac                       36

<210> SEQ ID NO 57
<211> LENGTH: 112
<212> TYPE: PRT
<213> ORGANISM: Homo sapiens

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Phe Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Cys Ser Phe Gly Gln Gly Thr Lys Leu Glu Ile Lys
            100                 105                 110

<210> SEQ ID NO 58
<211> LENGTH: 121
<212> TYPE: PRT
<213> ORGANISM: Homo sapiens

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr

```
            65                  70                  75                  80
Met Glu Leu Ser Arg Leu Arg Ser Asp Thr Ala Val Tyr Phe Cys
                    85                  90                  95
Ala Arg Asp Ser Gly Tyr Ser Ser Trp His Phe Asp Tyr Trp Gly
                100                 105                 110
Gln Gly Thr Leu Val Thr Val Ser Ser
            115                 120
```

<210> SEQ ID NO 59
<211> LENGTH: 11
<212> TYPE: PRT
<213> ORGANISM: Homo sapiens

<400> SEQUENCE: 59

```
Ser Gly Asp Lys Leu Gly Asp Lys Tyr Ala Cys
1               5                   10
```

<210> SEQ ID NO 60
<211> LENGTH: 7
<212> TYPE: PRT
<213> ORGANISM: Homo sapiens

<400> SEQUENCE: 60

```
Gln Asp Ser Lys Arg Pro Ser
1               5
```

<210> SEQ ID NO 61
<211> LENGTH: 9
<212> TYPE: PRT
<213> ORGANISM: Homo sapiens

<400> SEQUENCE: 61

```
Gln Ala Trp Asp Ser Ser Thr Ala Val
1               5
```

<210> SEQ ID NO 62
<211> LENGTH: 10
<212> TYPE: PRT
<213> ORGANISM: Homo sapiens

<400> SEQUENCE: 62

```
Gly Tyr Thr Phe Thr Ser Tyr Gly Leu Ser
1               5                   10
```

<210> SEQ ID NO 63
<211> LENGTH: 17
<212> TYPE: PRT
<213> ORGANISM: Homo sapiens

<400> SEQUENCE: 63

```
Trp Ile Ile Pro Tyr Asn Gly Asn Thr Asn Ser Ala Gln Lys Leu Gln
1               5                   10                  15

Gly
```

<210> SEQ ID NO 64
<211> LENGTH: 13
<212> TYPE: PRT
<213> ORGANISM: Homo sapiens

<400> SEQUENCE: 64

```
Asp Arg Asp Tyr Gly Val Asn Tyr Asp Ala Phe Asp Ile
1               5                   10
```

<210> SEQ ID NO 65
<211> LENGTH: 339
<212> TYPE: DNA
<213> ORGANISM: Homo sapiens

<400> SEQUENCE: 65

```
gacatcgtga tgacccagtc tccagactcc ctggctgtgt ctctgggcga gagggccacc      60
atcacctgca gtccagcca gagtatttta tacagttcca acaataagaa gtatctagtt      120
tggtaccagc agaaaccagg acagcctcct aagctgatca tttactggac atctatgcgg     180
gaatccgggg tccctgaccg attcagtggc agcgggtctg ggacagattt cactctcacc     240
atcaacagcc tgcaggctga agatgtggca gtttattact gtcagcaata ttatagtact     300
ccgtggacgt tcggccaagg gaccaaggtg gaaatcaaa                            339
```

<210> SEQ ID NO 66
<211> LENGTH: 488
<212> TYPE: DNA
<213> ORGANISM: Homo sapiens

<400> SEQUENCE: 66

```
caggtgcagc tgcaggagtc gggcccagga ctggtgaagc cttcggagac cctgtccctc      60
acctgcactg tctctggtgg ctccatcaat agtttctact ggagctggat ccggcagccc     120
ccagggaagg gactggagtg gattgggtat atctattaca gtgggagcac caactacaat     180
ccctccctca gagtcgagt caccatatca gtagacacgt ccaagaccca gttctccctg      240
aagctgagct ctgtgaccgc tgcggacacg gccgtgtatt actgtgcgag agacagtata     300
gcagcccct ttgactactg gggccaggga accctggtca ccgtctcctc agcttccacc      360
aagggcccat ccgtcttccc cctggcgccc tgctccagga gcacctccga gagcacagcc     420
gccctgggct gcctggtcaa ggactacttc cccgaaccgg tgacggtgtc gtggaactca     480
tgcgccct                                                             488
```

<210> SEQ ID NO 67
<211> LENGTH: 51
<212> TYPE: DNA
<213> ORGANISM: Homo sapiens

<400> SEQUENCE: 67

```
aagtccagcc agagtatttt atacagttcc aacaataaga agtatctagt t               51
```

<210> SEQ ID NO 68
<211> LENGTH: 21
<212> TYPE: DNA
<213> ORGANISM: Homo sapiens

<400> SEQUENCE: 68

```
tggacatcta tgcgggaatc c                                               21
```

<210> SEQ ID NO 69
<211> LENGTH: 27
<212> TYPE: DNA
<213> ORGANISM: Homo sapiens

<400> SEQUENCE: 69

```
cagcaatatt atagtactcc gtggacg                                         27
```

<210> SEQ ID NO 70
<211> LENGTH: 30

-continued

<212> TYPE: DNA
<213> ORGANISM: Homo sapiens

<400> SEQUENCE: 70
ggtggctcca tcaatagttt ctactggagc                                    30

<210> SEQ ID NO 71
<211> LENGTH: 48
<212> TYPE: DNA
<213> ORGANISM: Homo sapiens

<400> SEQUENCE: 71
tatatctatt acagtgggag caccaactac aatccctccc tcaagagt                48

<210> SEQ ID NO 72
<211> LENGTH: 27
<212> TYPE: DNA
<213> ORGANISM: Homo sapiens

<400> SEQUENCE: 72
gacagtatag cagccccctt tgactac                                       27

<210> SEQ ID NO 73
<211> LENGTH: 113
<212> TYPE: PRT
<213> ORGANISM: Homo sapiens

<400> SEQUENCE: 73

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Ile Leu Tyr Ser
            20                  25                  30

Ser Asn Asn Lys Lys Tyr Leu Val Trp Tyr Gln Lys Pro Gly Gln
        35                  40                  45

Pro Pro Lys Leu Ile Ile Tyr Trp Thr Ser Met Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 74
<211> LENGTH: 117
<212> TYPE: PRT
<213> ORGANISM: Homo sapiens

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Phe
            20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Thr Gln Phe Ser Leu

```
                65                  70                  75                  80
Lys Leu Ser Ser Val Thr Ala Ala Asp Thr Ala Val Tyr Tyr Cys Ala
                    85                  90                  95
Arg Asp Ser Ile Ala Ala Pro Phe Asp Tyr Trp Gly Gln Gly Thr Leu
                100                 105                 110
Val Thr Val Ser Ser
            115

<210> SEQ ID NO 75
<211> LENGTH: 17
<212> TYPE: PRT
<213> ORGANISM: Homo sapiens

<400> SEQUENCE: 75

Lys Ser Ser Gln Ser Ile Leu Tyr Ser Ser Asn Asn Lys Lys Tyr Leu
1               5                   10                  15
Val

<210> SEQ ID NO 76
<211> LENGTH: 7
<212> TYPE: PRT
<213> ORGANISM: Homo sapiens

<400> SEQUENCE: 76

Trp Thr Ser Met Arg Glu Ser
1               5

<210> SEQ ID NO 77
<211> LENGTH: 9
<212> TYPE: PRT
<213> ORGANISM: Homo sapiens

<400> SEQUENCE: 77

Gln Gln Tyr Tyr Ser Thr Pro Trp Thr
1               5

<210> SEQ ID NO 78
<211> LENGTH: 10
<212> TYPE: PRT
<213> ORGANISM: Homo sapiens

<400> SEQUENCE: 78

Gly Gly Ser Ile Asn Ser Phe Tyr Trp Ser
1               5                   10

<210> SEQ ID NO 79
<211> LENGTH: 16
<212> TYPE: PRT
<213> ORGANISM: Homo sapiens

<400> SEQUENCE: 79

Tyr Ile Tyr Tyr Ser Gly Ser Thr Asn Tyr Asn Pro Ser Leu Lys Ser
1               5                   10                  15

<210> SEQ ID NO 80
<211> LENGTH: 9
<212> TYPE: PRT
<213> ORGANISM: Homo sapiens

<400> SEQUENCE: 80

Asp Ser Ile Ala Ala Pro Phe Asp Tyr
1               5
```

<210> SEQ ID NO 81
<211> LENGTH: 321
<212> TYPE: DNA
<213> ORGANISM: Homo sapiens

<400> SEQUENCE: 81

```
gacatccaga tgacccagtc tccatcctcc ctgtctgcat ctgtaggaga cagagtcacc      60
atcacttgcc gggcaagtca gagcattagc aactatttaa attggtatca gcagagacca     120
gggaaagccc ctaagctcct gatctatgct acatccagtt tgcaaagtgg ggtcccatca     180
aggttcagtg gcagtggatc tgggacagat ttcactctca ccatcagcag tctgcaacct     240
gaagattttg taagttacta ctgtcaacag agttacagta tttcgcccac tttcggcggc     300
gggaccaagg tggagaacaa a                                               321
```

<210> SEQ ID NO 82
<211> LENGTH: 357
<212> TYPE: DNA
<213> ORGANISM: Homo sapiens

<400> SEQUENCE: 82

```
caggtgcagc tacagcagtg gggcgcagga ctgttgaagc cttcggagac cctgtccctc      60
acctgcgctg tctatggtgg gtccttcagt gcttactact ggagctggat ccgccagccc     120
ccagggaagg gactggagtg gattgggaa  atcaatcata gtggaggcac caactacaac     180
ccgtccctca agagtcgagt caccatatca gtagacacgt ccaagaacca gttctccctg     240
aagctgagct ctgtgaccgc cgcggacacg gctgtgtatt actgtgcgag agtacagtgg     300
ctcgaactgg cctactttga ctactggggc cagggaaccc tggtcaccgt ctcctca       357
```

<210> SEQ ID NO 83
<211> LENGTH: 33
<212> TYPE: DNA
<213> ORGANISM: Homo sapiens

<400> SEQUENCE: 83

```
cgggcaagtc agagcattag caactattta aat                                   33
```

<210> SEQ ID NO 84
<211> LENGTH: 106
<212> TYPE: PRT
<213> ORGANISM: Homo sapiens

<400> SEQUENCE: 84

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 85
<211> LENGTH: 27
<212> TYPE: DNA
<213> ORGANISM: Homo sapiens

<400> SEQUENCE: 85
caacagagtt acagtatttc gcccact            27

<210> SEQ ID NO 86
<211> LENGTH: 30
<212> TYPE: DNA
<213> ORGANISM: Homo sapiens

<400> SEQUENCE: 86
ggtgggtcct tcagtgctta ctactggagc         30

<210> SEQ ID NO 87
<211> LENGTH: 48
<212> TYPE: DNA
<213> ORGANISM: Homo sapiens

<400> SEQUENCE: 87
gaaatcaatc atagtggagg caccaactac aacccgtccc tcaagagt    48

<210> SEQ ID NO 88
<211> LENGTH: 33
<212> TYPE: DNA
<213> ORGANISM: Homo sapiens

<400> SEQUENCE: 88
gtacagtggc tcgaactggc ctactttgac tac      33

<210> SEQ ID NO 89
<211> LENGTH: 107
<212> TYPE: PRT
<213> ORGANISM: Homo sapiens

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Arg Pro Gly Lys Ala Pro Lys Leu Leu Ile
            35                  40                  45

Tyr Ala Thr Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Val Ser Tyr Tyr Cys Gln Gln Ser Tyr Ser Ile Ser Pro
                85                  90                  95

Thr Phe Gly Gly Gly Thr Lys Val Glu Asn Lys
            100                 105

<210> SEQ ID NO 90
<211> LENGTH: 119
<212> TYPE: PRT
<213> ORGANISM: Homo sapiens

<400> SEQUENCE: 90

Gln Val Gln Leu Gln Gln Trp Gly Ala Gly Leu Leu Lys Pro Ser Glu
1               5                   10                  15

-continued

```
Thr Leu Ser Leu Thr Cys Ala Val Tyr Gly Gly Ser Phe Ser Ala Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Gly Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Val Gln Trp Leu Glu Leu Ala Tyr Phe Asp Tyr Trp Gly Gln Gly
            100                 105                 110

Thr Leu Val Thr Val Ser Ser
            115
```

<210> SEQ ID NO 91
<211> LENGTH: 11
<212> TYPE: PRT
<213> ORGANISM: Homo sapiens

<400> SEQUENCE: 91

```
Arg Ala Ser Gln Ser Ile Ser Asn Tyr Leu Asn
 1               5                  10
```

<210> SEQ ID NO 92
<211> LENGTH: 7
<212> TYPE: PRT
<213> ORGANISM: Homo sapiens

<400> SEQUENCE: 92

```
Ala Thr Ser Ser Leu Gln Ser
 1               5
```

<210> SEQ ID NO 93
<211> LENGTH: 9
<212> TYPE: PRT
<213> ORGANISM: Homo sapiens

<400> SEQUENCE: 93

```
Gln Gln Ser Tyr Ser Ile Ser Pro Thr
 1               5
```

<210> SEQ ID NO 94
<211> LENGTH: 10
<212> TYPE: PRT
<213> ORGANISM: Homo sapiens

<400> SEQUENCE: 94

```
Gly Gly Ser Phe Ser Ala Tyr Tyr Trp Ser
 1               5                  10
```

<210> SEQ ID NO 95
<211> LENGTH: 16
<212> TYPE: PRT
<213> ORGANISM: Homo sapiens

<400> SEQUENCE: 95

```
Glu Ile Asn His Ser Gly Gly Thr Asn Tyr Asn Pro Ser Leu Lys Ser
 1               5                  10                  15
```

<210> SEQ ID NO 96

```
<211> LENGTH: 11
<212> TYPE: PRT
<213> ORGANISM: Homo sapiens

<400> SEQUENCE: 96

Val Gln Trp Leu Glu Leu Ala Tyr Phe Asp Tyr
1               5                   10

<210> SEQ ID NO 97
<211> LENGTH: 321
<212> TYPE: DNA
<213> ORGANISM: Homo sapiens

<400> SEQUENCE: 97
gacatccaga tgacccagtc tccatcctcc ctgtctgcat ctgtaggaga cagagtcacc      60
atcacttgcc gggcaggtca gggcattaga aatgatttag tctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacaa cataatactt acccattcac tttcggccct     300
gggaccaaag tggatatcaa a                                               321

<210> SEQ ID NO 98
<211> LENGTH: 363
<212> TYPE: DNA
<213> ORGANISM: Homo sapiens

<400> SEQUENCE: 98
caggtgcagc tggtggactc tgggggaggc gtggtccagc ctgggaggtc cctgagactc      60
tcctgtgcag cgtctggatt caccttcatt agctatggca tgcactgggt ccgccaggct     120
ccaggcaagg gctggagtg gtggcagtt atctggtatg atggaagtac tgaatactat      180
gcagactccg tgaagggccg attcaccatc tccagagaca attccaagaa cacgctgtat     240
ctgcaaatga acagcctgag agccgaggac acggctgtgt attactgtgc gagagagagg     300
cagtggctct accactacgg tatggacgtc tggggccaag ggaccacggt caccgtctcc     360
tca                                                                  363

<210> SEQ ID NO 99
<211> LENGTH: 33
<212> TYPE: DNA
<213> ORGANISM: Homo sapiens

<400> SEQUENCE: 99
cgggcaggtc agggcattag aaatgattta gtc                                  33

<210> SEQ ID NO 100
<211> LENGTH: 107
<212> TYPE: PRT
<213> ORGANISM: Homo sapiens

<400> SEQUENCE: 100

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
```

```
                50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 101
<211> LENGTH: 27
<212> TYPE: DNA
<213> ORGANISM: Homo sapiens

<400> SEQUENCE: 101
ctacaacata atacttaccc attcact                                         27

<210> SEQ ID NO 102
<211> LENGTH: 30
<212> TYPE: DNA
<213> ORGANISM: Homo sapiens

<400> SEQUENCE: 102
ggattcacct tcattagcta tggcatgcac                                      30

<210> SEQ ID NO 103
<211> LENGTH: 51
<212> TYPE: DNA
<213> ORGANISM: Homo sapiens

<400> SEQUENCE: 103
gttatctggt atgatggaag tactgaatac tatgcagact ccgtgaaggg c              51

<210> SEQ ID NO 104
<211> LENGTH: 36
<212> TYPE: DNA
<213> ORGANISM: Homo sapiens

<400> SEQUENCE: 104
gagaggcagt ggctctacca ctacggtatg gacgtc                               36

<210> SEQ ID NO 105
<211> LENGTH: 107
<212> TYPE: PRT
<213> ORGANISM: Homo sapiens

<400> SEQUENCE: 105

```
Asp Ile Gln Met Thr Gln Ser Pro Ser Ser Leu Ser Ala Ser Val Gly
 1               5                  10                  15

Asp Arg Val Thr Ile Thr Cys Arg Ala Gly Gln Gly Ile Arg Asn Asp
                20                  25                  30

Leu Val Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Thr Tyr Pro Phe
                 85                  90                  95

Thr Phe Gly Pro Gly Thr Lys Val Asp Ile Lys
            100                 105
```

<210> SEQ ID NO 106
<211> LENGTH: 121
<212> TYPE: PRT
<213> ORGANISM: Homo sapiens

<400> SEQUENCE: 106

Gln Val Gln Leu Val Asp Ser Gly Gly Val Val Gln Pro Gly Arg
1               5                   10                  15

Ser Leu Arg Leu Ser Cys Ala Ala Ser Gly Phe Thr Phe Ile Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Thr Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gln Trp Leu Tyr His Tyr Gly Met Asp Val Trp Gly
            100                 105                 110

Gln Gly Thr Thr Val Thr Val Ser Ser
        115                 120

<210> SEQ ID NO 107
<211> LENGTH: 11
<212> TYPE: PRT
<213> ORGANISM: Homo sapiens

<400> SEQUENCE: 107

Arg Ala Gly Gln Gly Ile Arg Asn Asp Leu Val
1               5                   10

<210> SEQ ID NO 108
<211> LENGTH: 107
<212> TYPE: PRT
<213> ORGANISM: Homo sapiens

<400> SEQUENCE: 108

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 109
<211> LENGTH: 9
<212> TYPE: PRT
<213> ORGANISM: Homo sapiens

<400> SEQUENCE: 109

Leu Gln His Asn Thr Tyr Pro Phe Thr
1               5

<210> SEQ ID NO 110
<211> LENGTH: 10
<212> TYPE: PRT
<213> ORGANISM: Homo sapiens

<400> SEQUENCE: 110

Gly Phe Thr Phe Ile Ser Tyr Gly Met His
1               5                   10

<210> SEQ ID NO 111
<211> LENGTH: 17
<212> TYPE: PRT
<213> ORGANISM: Homo sapiens

<400> SEQUENCE: 111

Val Ile Trp Tyr Asp Gly Ser Thr Glu Tyr Tyr Ala Asp Ser Val Lys
1               5                   10                  15

Gly

<210> SEQ ID NO 112
<211> LENGTH: 12
<212> TYPE: PRT
<213> ORGANISM: Homo sapiens

<400> SEQUENCE: 112

Glu Arg Gln Trp Leu Tyr His Tyr Gly Met Asp Val
1               5                   10

<210> SEQ ID NO 113
<211> LENGTH: 339
<212> TYPE: DNA
<213> ORGANISM: Homo sapiens

<400> SEQUENCE: 113

| | | | | | |
|---|---|---|---|---|---|
| gacatcgtga | tgacccagtc | tccagactcc | ctggctgtgt | ctctgggcga | gagggccacc | 60 |
| atcacctgca | agtccagcca | gagtatttta | tacagctcca | acaataagaa | gtatctagtt | 120 |
| tggtaccagc | agaaaccagg | acagcctcct | aagttgatca | tttactggac | atctatgcgg | 180 |
| gaatccgggg | tccctgaccg | attcagtggc | agcgggtctg | ggacagattt | cactctcacc | 240 |
| atcagcagcc | tgcaggctga | agatgtggca | gtttattact | gtcagcaata | ttatagtact | 300 |
| ccgtggacgt | tcggccaagg | gaccaaggtg | gaaatcaaa | | | 339 |

<210> SEQ ID NO 114
<211> LENGTH: 351
<212> TYPE: DNA
<213> ORGANISM: Homo sapiens

<400> SEQUENCE: 114

| | | | | | |
|---|---|---|---|---|---|
| caggtgcagc | tgcaggagtc | gggcccagga | ctggtgaagc | cctcggagac | cctgtccctc | 60 |
| acctgcactg | tctctggtgg | ctccatcaat | agtttctact | ggagctggat | ccggcagccc | 120 |
| ccagggaagg | gactggagtg | gattgggtat | atctattaca | gtgggagcac | caactacaat | 180 |
| ccctccctca | agaggcgagt | caccatatca | gtagacacgt | ccaagaccca | gttctccctg | 240 |
| aagctgagct | ctgtgaccgc | tgcggacacg | gccgtgtatt | actgtgcgag | agacagtata | 300 |
| gcagccccct | ttgactactg | gggccaggga | accctggtca | ccgtctcctc | a | 351 |

```
<210> SEQ ID NO 115
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (6)..(6)
<223> OTHER INFORMATION: Leu or Ile
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Gly or Asn
<220> FEATURE:
<221> NAME/KEY: MOD_RES
<222> LOCATION: (12)..(12)
<223> OTHER INFORMATION: Tyr or Asn
<220> FEATURE:
<221> NAME/KEY: MOD_RES
<222> LOCATION: (13)..(13)
<223> OTHER INFORMATION: Asn or Lys
<220> FEATURE:
<221> NAME/KEY: MOD_RES
<222> LOCATION: (14)..(14)
<223> OTHER INFORMATION: May or may not be present
<220> FEATURE:
<221> NAME/KEY: MOD_RES
<222> LOCATION: (17)..(17)
<223> OTHER INFORMATION: Asp or Val

<400> SEQUENCE: 115

Xaa Ser Ser Gln Ser Xaa Leu Xaa Ser Xaa Xaa Xaa Xaa Lys Tyr Leu
1               5                   10                  15

Xaa

<210> SEQ ID NO 116
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Ser or Gly
<220> FEATURE:
<221> NAME/KEY: MOD_RES
<222> LOCATION: (5)..(5)
<223> OTHER INFORMATION: Ser or Gly
<220> FEATURE:
<221> NAME/KEY: MOD_RES
<222> LOCATION: (7)..(7)
<223> OTHER INFORMATION: Ser or Arg
<220> FEATURE:
<221> NAME/KEY: MOD_RES
<222> LOCATION: (9)..(9)
<223> OTHER INFORMATION: Tyr, Asp or Asn
<220> FEATURE:
<221> NAME/KEY: MOD_RES
<222> LOCATION: (11)..(11)
<223> OTHER INFORMATION: Asp, Val or Gly

<400> SEQUENCE: 116

Arg Ala Xaa Gln Xaa Ile Xaa Asn Xaa Leu Xaa
```

```
<210> SEQ ID NO 117
<211> LENGTH: 27
<212> TYPE: DNA
<213> ORGANISM: Homo sapiens

<400> SEQUENCE: 117
cagcaatatt atagtactcc gtggacg                                27

<210> SEQ ID NO 118
<211> LENGTH: 30
<212> TYPE: DNA
<213> ORGANISM: Homo sapiens

<400> SEQUENCE: 118
ggtggctcca tcaatagttt ctactggagc                             30

<210> SEQ ID NO 119
<211> LENGTH: 48
<212> TYPE: DNA
<213> ORGANISM: Homo sapiens

<400> SEQUENCE: 119
tatatctatt acagtgggag caccaactac aatccctccc tcaagagg         48

<210> SEQ ID NO 120
<211> LENGTH: 27
<212> TYPE: DNA
<213> ORGANISM: Homo sapiens

<400> SEQUENCE: 120
gacagtatag cagccccctt tgactac                                27

<210> SEQ ID NO 121
<211> LENGTH: 113
<212> TYPE: PRT
<213> ORGANISM: Homo sapiens

<400> SEQUENCE: 121
```

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Ile Leu Tyr Ser
            20                  25                  30

Ser Asn Asn Lys Lys Tyr Leu Val Trp Tyr Gln Gln Lys Pro Gly Gln
        35                  40                  45

Pro Pro Lys Leu Ile Ile Tyr Trp Thr Ser Met Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

```
<210> SEQ ID NO 122
<211> LENGTH: 117
<212> TYPE: PRT
<213> ORGANISM: Homo sapiens
```

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Arg Arg Val Thr Ile Ser Val Asp Thr Ser Lys Thr Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ile Ala Ala Pro Phe Asp Tyr Trp Gly Gln Gly Thr Leu
            100                 105                 110

Val Thr Val Ser Ser
        115

<210> SEQ ID NO 123
<211> LENGTH: 11
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (5)..(5)
<223> OTHER INFORMATION: Trp or Leu
<220> FEATURE:
<221> NAME/KEY: MOD_RES
<222> LOCATION: (7)..(7)
<223> OTHER INFORMATION: Glu or Asp
<220> FEATURE:
<221> NAME/KEY: MOD_RES
<222> LOCATION: (9)..(9)
<223> OTHER INFORMATION: Tyr or Phe
<220> FEATURE:
<221> NAME/KEY: MOD_RES
<222> LOCATION: (10)..(10)
<223> OTHER INFORMATION: Ala or Val
<220> FEATURE:
<221> NAME/KEY: MOD_RES
<222> LOCATION: (11)..(11)
<223> OTHER INFORMATION: Cys or Phe

<400> SEQUENCE: 123

Ser Gly Xaa Lys Xaa Gly Xaa Lys Xaa Xaa Xaa
1               5                   10

<210> SEQ ID NO 124
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ala, Trp or Leu
<220> FEATURE:
<221> NAME/KEY: MOD_RES
<222> LOCATION: (2)..(2)
<223> OTHER INFORMATION: Thr, Ala or Gly
<220> FEATURE:
<221> NAME/KEY: MOD_RES
<222> LOCATION: (4)..(4)
<223> OTHER INFORMATION: Ser, Met or Phe
<220> FEATURE:

```
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Gln, Glu or Ala

<400> SEQUENCE: 124

Xaa Xaa Ser Xaa Xaa Xaa Ser
1               5

<210> SEQ ID NO 125
<211> LENGTH: 9
<212> TYPE: PRT
<213> ORGANISM: Homo sapiens

<400> SEQUENCE: 125

Gln Gln Tyr Tyr Ser Thr Pro Trp Thr
1               5

<210> SEQ ID NO 126
<211> LENGTH: 10
<212> TYPE: PRT
<213> ORGANISM: Homo sapiens

<400> SEQUENCE: 126

Gly Gly Ser Ile Asn Ser Phe Tyr Trp Ser
1               5                   10

<210> SEQ ID NO 127
<211> LENGTH: 16
<212> TYPE: PRT
<213> ORGANISM: Homo sapiens

<400> SEQUENCE: 127

Tyr Ile Tyr Tyr Ser Gly Ser Thr Asn Tyr Asn Pro Ser Leu Lys Arg
1               5                   10                  15

<210> SEQ ID NO 128
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Gln, Leu or His
<220> FEATURE:
<221> NAME/KEY: MOD_RES
<222> LOCATION: (3)..(3)
<223> OTHER INFORMATION: Thr, Asn or Ser

<400> SEQUENCE: 128

Xaa Asp Xaa Lys Arg Pro Ser
1               5

<210> SEQ ID NO 129
<211> LENGTH: 321
<212> TYPE: DNA
<213> ORGANISM: Homo sapiens

<400> SEQUENCE: 129
gacatccaga tgacccagtc tccatcctcc ctgtctgcat ctgtaggaga cagagtcacc      60
atcacttgcc gggcaagtca gggcattaga aataatttag gctggtatca gcagaaacca     120
gggaaagccc ctaagcgcct gatttatgct gcatccagtt tgcaaagtgg ggtcccatca     180
```

```
aggttcagcg gcagtggatc tgggacagaa ttcactctca caatcagcag cctgcagcct      240
gaagatttta caacttatta ctgtctacag cataatagtt acccgtggac gttcggccaa      300
gggaccaagg tggaaatcaa a                                                321
```

```
<210> SEQ ID NO 130
<211> LENGTH: 372
<212> TYPE: DNA
<213> ORGANISM: Homo sapiens

<400> SEQUENCE: 130
caggtgcagc tggtggagtc tgggggaggc gtggtccagc ctgggaggtc cctgagactc       60
tcctgtgcag cgtctggatt caccttcagt agttacggca tgcactgggt ccgccaggct      120
ccaggcaagg ggctggagtg ggtggcagtt atatggtatg atggaagtaa taaataccat      180
gcagactccg tgaagggccg attcaccatc tccagagaca attccaagaa cacgctgtat      240
ctgcaagtga acagcctgag agccgaggac acggctgtgt attactgtgt gagaagtcgg      300
aactggaact acgacaacta ctactacggt ctggacgtct ggggccaagg gaccacggtc      360
accgtctcct ca                                                          372
```

```
<210> SEQ ID NO 131
<211> LENGTH: 9
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (7)..(7)
<223> OTHER INFORMATION: Pro or Thr
<220> FEATURE:
<221> NAME/KEY: MOD_RES
<222> LOCATION: (8)..(8)
<223> OTHER INFORMATION: Phe or Trp

<400> SEQUENCE: 131

Leu Gln His Asn Xaa Tyr Xaa Xaa Thr
1               5
```

```
<210> SEQ ID NO 132
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Met, Gln or Arg
<220> FEATURE:
<221> NAME/KEY: MOD_RES
<222> LOCATION: (3)..(3)
<223> OTHER INFORMATION: Ala, Tyr, Gln or Ser
<220> FEATURE:
<221> NAME/KEY: MOD_RES
<222> LOCATION: (4)..(4)
<223> OTHER INFORMATION: Leu, Tyr or Asn
<220> FEATURE:
<221> NAME/KEY: MOD_RES
<222> LOCATION: (5)..(5)
<223> OTHER INFORMATION: Gln, Ser or Thr
<220> FEATURE:
<221> NAME/KEY: MOD_RES
<222> LOCATION: (6)..(6)
<223> OTHER INFORMATION: Thr, Tyr or Ile
<220> FEATURE:
<221> NAME/KEY: MOD_RES
<222> LOCATION: (7)..(7)
```

```
<223> OTHER INFORMATION: Pro or Ser
<220> FEATURE:
<221> NAME/KEY: MOD_RES
<222> LOCATION: (8)..(8)
<223> OTHER INFORMATION: Cys, Trp, Leu or Pro
<220> FEATURE:
<221> NAME/KEY: MOD_RES
<222> LOCATION: (9)..(9)
<223> OTHER INFORMATION: Ser or Thr

<400> SEQUENCE: 132

Xaa Gln Xaa Xaa Xaa Xaa Xaa Xaa Xaa
1               5

<210> SEQ ID NO 133
<211> LENGTH: 27
<212> TYPE: DNA
<213> ORGANISM: Homo sapiens

<400> SEQUENCE: 133
ctacagcata atagttaccc gtggacg                                        27

<210> SEQ ID NO 134
<211> LENGTH: 11
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Ile or Phe
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Phe or Tyr

<400> SEQUENCE: 134

Gly Gly Ser Xaa Xaa Xaa Xaa Xaa Xaa Tyr Trp
1               5                   10

<210> SEQ ID NO 135
<211> LENGTH: 51
<212> TYPE: DNA
<213> ORGANISM: Homo sapiens

<400> SEQUENCE: 135
gttatatggt atgatggaag taataaatac catgcagact ccgtgaaggg c             51

<210> SEQ ID NO 136
<211> LENGTH: 45
<212> TYPE: DNA
<213> ORGANISM: Homo sapiens

<400> SEQUENCE: 136
agtcggaact ggaactacga caactactac tacggtctgg acgtc                    45
```

<210> SEQ ID NO 137
<211> LENGTH: 107
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 138
<211> LENGTH: 124
<212> TYPE: PRT
<213> ORGANISM: Homo sapiens

<400> SEQUENCE: 138

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Val Arg Ser Arg Asn Trp Asn Tyr Asp Asn Tyr Tyr Tyr Gly Leu Asp
            100                 105                 110

Val Trp Gly Gln Gly Thr Thr Val Thr Val Ser Ser
        115                 120

<210> SEQ ID NO 139
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (3)..(3)
<223> OTHER INFORMATION: Tyr or Ser
<220> FEATURE:
<221> NAME/KEY: MOD_RES
<222> LOCATION: (5)..(5)
<223> OTHER INFORMATION: Thr, Ser or Ile

```
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (8)..(8)
<223> OTHER INFORMATION: Tyr, Gly or Trp
<220> FEATURE:
<221> NAME/KEY: MOD_RES
<222> LOCATION: (9)..(9)
<223> OTHER INFORMATION: Ile or Met
<220> FEATURE:
<221> NAME/KEY: MOD_RES
<222> LOCATION: (10)..(10)
<223> OTHER INFORMATION: His or Gly

<400> SEQUENCE: 139

Gly Xaa Xaa Phe Xaa Xaa Tyr Xaa Xaa Xaa
1               5                   10

<210> SEQ ID NO 140
<211> LENGTH: 10
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (5)..(5)
<223> OTHER INFORMATION: Thr or Ser
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (8)..(8)
<223> OTHER INFORMATION: Gly or Trp
<220> FEATURE:
<221> NAME/KEY: MOD_RES
<222> LOCATION: (9)..(9)
<223> OTHER INFORMATION: Leu, Met or Ile
<220> FEATURE:
<221> NAME/KEY: MOD_RES
<222> LOCATION: (10)..(10)
<223> OTHER INFORMATION: Ser or His

<400> SEQUENCE: 140

Gly Xaa Thr Phe Xaa Xaa Tyr Xaa Xaa Xaa
1               5                   10

<210> SEQ ID NO 141
<211> LENGTH: 9
<212> TYPE: PRT
<213> ORGANISM: Homo sapiens

<400> SEQUENCE: 141

Leu Gln His Asn Ser Tyr Pro Trp Thr
1               5

<210> SEQ ID NO 142
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Tyr or Glu
<220> FEATURE:
<221> NAME/KEY: MOD_RES
```

```
<222> LOCATION: (3)..(3)
<223> OTHER INFORMATION: Ser, Tyr or Asn
<220> FEATURE:
<221> NAME/KEY: MOD_RES
<222> LOCATION: (4)..(4)
<223> OTHER INFORMATION: Tyr or His
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (9)..(9)
<223> OTHER INFORMATION: Tyr or Asn
<220> FEATURE:
<221> NAME/KEY: MOD_RES
<222> LOCATION: (16)..(16)
<223> OTHER INFORMATION: Ser or Arg

<400> SEQUENCE: 142

Xaa Ile Xaa Xaa Ser Gly Xaa Thr Xaa Tyr Asn Pro Ser Leu Lys Xaa
1               5                   10                  15

<210> SEQ ID NO 143
<211> LENGTH: 17
<212> TYPE: PRT
<213> ORGANISM: Homo sapiens

<400> SEQUENCE: 143

Val Ile Trp Tyr Asp Gly Ser Asn Lys Tyr His Ala Asp Ser Val Lys
1               5                   10                  15

Gly

<210> SEQ ID NO 144
<211> LENGTH: 15
<212> TYPE: PRT
<213> ORGANISM: Homo sapiens

<400> SEQUENCE: 144

Ser Arg Asn Trp Asn Tyr Asp Asn Tyr Tyr Gly Leu Asp Val
1               5                   10                  15

<210> SEQ ID NO 145
<211> LENGTH: 315
<212> TYPE: DNA
<213> ORGANISM: Homo sapiens

<400> SEQUENCE: 145
tcctatgagc tgactcagcc accctcagtg tccgtgtccc caggacagac agccagcatc      60
acctgctctg gagaaaaatg gggagagaaa tatgcttgtt ggtatcagca gaagccaggc     120
cagtcccctg tgctggtcat ctatcaagat accaagcggc cctccgggat ccctgagcga     180
ttctctggct ccatttctgg gaacacagcc actctgacca tcagcgggac ccaggctatg     240
gatgaggctg actattattg tcaggcgtgg gacaggagca ctgtattcgg cggagggacc     300
aagctgaccg tccta                                                      315

<210> SEQ ID NO 146
<211> LENGTH: 348
<212> TYPE: DNA
<213> ORGANISM: Homo sapiens

<400> SEQUENCE: 146
gaggtgcagc tggtgcagtc tggagcagag gtgaaaaagc ccggggagtc tctgaagatc      60
tcctgtcagg gttctggata cagctttacc agctactgga tcggctgggt gcgccagatg     120
```

```
cccgggaaag gcctggagtg gatggggatc atctatcctg gtgactctga taccagatac    180
agcccgtcct tccaaggcca ggtcaccatc tcagccgaca gtccatcag caccgcctac    240 ctgcagtgga gcagcctgaa ggcctcggac accgccatgt attactgtgc gagacaagga   300
ctggggtttg actactgggg ccagggaacc ctggtcaccg tctcctca                348
```

```
<210> SEQ ID NO 147
<211> LENGTH: 33
<212> TYPE: DNA
<213> ORGANISM: Homo sapiens

<400> SEQUENCE: 147
tctggagaaa aatggggaga gaaatatgct tgt                                 33

<210> SEQ ID NO 148
<211> LENGTH: 21
<212> TYPE: DNA
<213> ORGANISM: Homo sapiens

<400> SEQUENCE: 148
caagatacca agcggccctc c                                              21

<210> SEQ ID NO 149
<211> LENGTH: 24
<212> TYPE: DNA
<213> ORGANISM: Homo sapiens

<400> SEQUENCE: 149
caggcgtggg acaggagcac tgta                                           24

<210> SEQ ID NO 150
<211> LENGTH: 30
<212> TYPE: DNA
<213> ORGANISM: Homo sapiens

<400> SEQUENCE: 150
ggatacagct ttaccagcta ctggatcggc                                     30

<210> SEQ ID NO 151
<211> LENGTH: 51
<212> TYPE: DNA
<213> ORGANISM: Homo sapiens

<400> SEQUENCE: 151
atcatctatc ctggtgactc tgataccaga tacagcccgt ccttccaagg c             51

<210> SEQ ID NO 152
<211> LENGTH: 21
<212> TYPE: DNA
<213> ORGANISM: Homo sapiens

<400> SEQUENCE: 152
caaggactgg ggtttgacta c                                              21

<210> SEQ ID NO 153
<211> LENGTH: 105
<212> TYPE: PRT
<213> ORGANISM: Homo sapiens

<400> SEQUENCE: 153

Ser Tyr Glu Leu Thr Gln Pro Pro Ser Val Ser Val Ser Pro Gly Gln
1               5                   10                  15
```

Thr Ala Ser Ile Thr Cys Ser Gly Glu Lys Trp Gly Glu Lys Tyr Ala
            20                  25                  30

Cys Trp Tyr Gln Gln Lys Pro Gly Gln Ser Pro Val Leu Val Ile Tyr
        35                  40                  45

Gln Asp Thr Lys Arg Pro Ser Gly Ile Pro Glu Arg Phe Ser Gly Ser
50                  55                  60

Ile Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Arg Ser Thr Val Phe
                85                  90                  95

Gly Gly Gly Thr Lys Leu Thr Val Leu
            100                 105

<210> SEQ ID NO 154
<211> LENGTH: 116
<212> TYPE: PRT
<213> ORGANISM: Homo sapiens

<400> SEQUENCE: 154

Glu Val Gln Leu Val Gln Ser Gly Ala Glu Val Lys Lys Pro Gly Glu
1               5                   10                  15

Ser Leu Lys Ile Ser Cys Gln Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Leu Gly Phe Asp Tyr Trp Gly Gln Gly Thr Leu Val
            100                 105                 110

Thr Val Ser Ser
        115

<210> SEQ ID NO 155
<211> LENGTH: 11
<212> TYPE: PRT
<213> ORGANISM: Homo sapiens

<400> SEQUENCE: 155

Ser Gly Glu Lys Trp Gly Glu Lys Tyr Ala Cys
1               5                   10

<210> SEQ ID NO 156
<211> LENGTH: 7
<212> TYPE: PRT
<213> ORGANISM: Homo sapiens

<400> SEQUENCE: 156

Gln Asp Thr Lys Arg Pro Ser
1               5

<210> SEQ ID NO 157
<211> LENGTH: 8
<212> TYPE: PRT
<213> ORGANISM: Homo sapiens

<400> SEQUENCE: 157

Gln Ala Trp Asp Arg Ser Thr Val
1               5

<210> SEQ ID NO 158
<211> LENGTH: 10
<212> TYPE: PRT
<213> ORGANISM: Homo sapiens

<400> SEQUENCE: 158

Gly Tyr Ser Phe Thr Ser Tyr Trp Ile Gly
1               5                   10

<210> SEQ ID NO 159
<211> LENGTH: 17
<212> TYPE: PRT
<213> ORGANISM: Homo sapiens

<400> SEQUENCE: 159

Ile Ile Tyr Pro Gly Asp Ser Asp Thr Arg Tyr Ser Pro Ser Phe Gln
1               5                   10                  15

Gly

<210> SEQ ID NO 160
<211> LENGTH: 7
<212> TYPE: PRT
<213> ORGANISM: Homo sapiens

<400> SEQUENCE: 160

Gln Gly Leu Gly Phe Asp Tyr
1               5

<210> SEQ ID NO 161
<211> LENGTH: 318
<212> TYPE: DNA
<213> ORGANISM: Homo sapiens

<400> SEQUENCE: 161
tcctatgagc tgactcagcc accctcagtg tccgtgtccc caggacagac agccagcatc     60
acctgctctg gagataaaat tggggataaa tttgctttct ggtatcagct gaagccaggc    120
cagtcccctg tgctggtcat ctatcaagat aacaagcggc cctcaggtat ccctgagcga    180
ttctctggct ccaactctgg gaacacagcc actctgacca tcagcgggac ccaggctatg    240
gatgcggctg acttttactg tcaggcgtgg gacagcagca ctgtggtatt cggcggaggg    300
accaagctga ccgtccta                                                  318

<210> SEQ ID NO 162
<211> LENGTH: 363
<212> TYPE: DNA
<213> ORGANISM: Homo sapiens

<400> SEQUENCE: 162
caggtgcagc tgcaggagtc gggcccagga ctggtgaagc cttcacagac cctgtccctc     60
acctgcactg tctctggtgg ctccatcagc agtggtggtt actactggag ctggatccgc    120
cagcacccag ggaagggcct ggagtggatt gggtacatct cttacagtgg gagcacctac    180
tacaacccgt ccctcaagag tcgagttacc atatcagttg acacgtctaa gaaccagttc    240
tccctgaagc tgaactctgt gactgccgcg gacacggccg tgtattactg tgcgcgcgct    300
tacggtgact atcgcggctg gttcgacccc tggggccagg aaccctggt caccgtctcc    360

-continued tca                                                                     363

<210> SEQ ID NO 163
<211> LENGTH: 33
<212> TYPE: DNA
<213> ORGANISM: Homo sapiens

<400> SEQUENCE: 163
tctggagata aattggggga taaatttgct ttc                                      33

<210> SEQ ID NO 164
<211> LENGTH: 21
<212> TYPE: DNA
<213> ORGANISM: Homo sapiens

<400> SEQUENCE: 164
caagataaca agcggccctc a                                                   21

<210> SEQ ID NO 165
<211> LENGTH: 27
<212> TYPE: DNA
<213> ORGANISM: Homo sapiens

<400> SEQUENCE: 165
caggcgtggg acagcagcac tgtggta                                             27

<210> SEQ ID NO 166
<211> LENGTH: 36
<212> TYPE: DNA
<213> ORGANISM: Homo sapiens

<400> SEQUENCE: 166
ggtggctcca tcagcagtgg tggttactac tggagc                                   36

<210> SEQ ID NO 167
<211> LENGTH: 48
<212> TYPE: DNA
<213> ORGANISM: Homo sapiens

<400> SEQUENCE: 167
tacatctctt acagtgggag cacctactac aacccgtccc tcaagagt                      48

<210> SEQ ID NO 168
<211> LENGTH: 33
<212> TYPE: DNA
<213> ORGANISM: Homo sapiens

<400> SEQUENCE: 168
gcttacggtg actatcgcgg ctggttcgac ccc                                      33

<210> SEQ ID NO 169
<211> LENGTH: 106
<212> TYPE: PRT
<213> ORGANISM: Homo sapiens

<400> SEQUENCE: 169

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Phe Trp Tyr Gln Leu Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Met
 65                  70                  75                  80

Asp Ala Ala Asp Phe Tyr Cys Gln Ala Trp Asp Ser Ser Thr Val Val
                 85                  90                  95

Phe Gly Gly Gly Thr Lys Leu Thr Val Leu
            100                 105

<210> SEQ ID NO 170
<211> LENGTH: 121
<212> TYPE: PRT
<213> ORGANISM: Homo sapiens

<400> SEQUENCE: 170

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Arg Ala Tyr Gly Asp Tyr Arg Gly Trp Phe Asp Pro Trp Gly
            100                 105                 110

Gln Gly Thr Leu Val Thr Val Ser Ser
            115                 120

<210> SEQ ID NO 171
<211> LENGTH: 11
<212> TYPE: PRT
<213> ORGANISM: Homo sapiens

<400> SEQUENCE: 171

Ser Gly Asp Lys Leu Gly Asp Lys Phe Ala Phe
 1               5                  10

<210> SEQ ID NO 172
<211> LENGTH: 7
<212> TYPE: PRT
<213> ORGANISM: Homo sapiens

<400> SEQUENCE: 172

Gln Asp Asn Lys Arg Pro Ser
 1               5

<210> SEQ ID NO 173
<211> LENGTH: 9
<212> TYPE: PRT
<213> ORGANISM: Homo sapiens

<400> SEQUENCE: 173

Gln Ala Trp Asp Ser Ser Thr Val Val
 1               5

<210> SEQ ID NO 174
<211> LENGTH: 12
<212> TYPE: PRT
<213> ORGANISM: Homo sapiens

<400> SEQUENCE: 174

Gly Gly Ser Ile Ser Ser Gly Gly Tyr Tyr Trp Ser
1               5                   10

<210> SEQ ID NO 175
<211> LENGTH: 16
<212> TYPE: PRT
<213> ORGANISM: Homo sapiens

<400> SEQUENCE: 175

Tyr Ile Ser Tyr Ser Gly Ser Thr Tyr Tyr Asn Pro Ser Leu Lys Ser
1               5                   10                  15

<210> SEQ ID NO 176
<211> LENGTH: 11
<212> TYPE: PRT
<213> ORGANISM: Homo sapiens

<400> SEQUENCE: 176

Ala Tyr Gly Asp Tyr Arg Gly Trp Phe Asp Pro
1               5                   10

<210> SEQ ID NO 177
<211> LENGTH: 321
<212> TYPE: DNA
<213> ORGANISM: Homo sapiens

<400> SEQUENCE: 177
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattgtg caacttatta ttgtctacag cataatagtt atacgtggac gttcggccaa    300
gggaccaagg tggaaatcaa a                                              321

<210> SEQ ID NO 178
<211> LENGTH: 372
<212> TYPE: DNA
<213> ORGANISM: Homo sapiens

<400> SEQUENCE: 178
caggtgcagc tggtggagtc tgggggaggc gtggtccagc ctgggaggtc cctgagactc      60
tcctgtgtag cgtctggatt caccttcagt gcctatggca tgcactgggt ccgccaggct    120
ccaggcaagg gctggagtg gtggcagtt atatggtatg atggaagtaa taaatactat     180
gcagactccg tgaagggccg attcatcatc tccagagaca attccaagaa cacgctgtat    240
ctgcaaatga acagcctgag agccgaggac acggctgtgt attactgtgc gagaagtcgg    300
aactggaact acgactccta ccaatacggt ttggacgtct ggggccaagg gaccacggtc    360
accgtctcct ca                                                        372

<210> SEQ ID NO 179
<211> LENGTH: 17
<212> TYPE: PRT
<213> ORGANISM: Homo sapiens

```
<220> FEATURE:
<221> NAME/KEY: MOD_RES
<222> LOCATION: (1)..(1)
<223> OTHER INFORMATION: Asn or Val
<220> FEATURE:
<221> NAME/KEY: MOD_RES
<222> LOCATION: (3)..(3)
<223> OTHER INFORMATION: Trp or Lys
<220> FEATURE:
<221> NAME/KEY: MOD_RES
<222> LOCATION: (4)..(4)
<223> OTHER INFORMATION: Tyr or Gln
<220> FEATURE:
<221> NAME/KEY: MOD_RES
<222> LOCATION: (8)..(8)
<223> OTHER INFORMATION: Asn, Glu or Ser
<220> FEATURE:
<221> NAME/KEY: MOD_RES
<222> LOCATION: (9)..(9)
<223> OTHER INFORMATION: Lys or Glu
<220> FEATURE:
<221> NAME/KEY: MOD_RES
<222> LOCATION: (11)..(11)
<223> OTHER INFORMATION: His or Tyr
<220> FEATURE:
<221> NAME/KEY: MOD_RES
<222> LOCATION: (12)..(12)
<223> OTHER INFORMATION: Ala or Val

<400> SEQUENCE: 179

Xaa Ile Xaa Xaa Asp Gly Ser Xaa Xaa Tyr Xaa Xaa Asp Ser Val Lys
1               5                   10                  15

Gly

<210> SEQ ID NO 180
<211> LENGTH: 17
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Trp or Ile
<220> FEATURE:
<221> NAME/KEY: MOD_RES
<222> LOCATION: (3)..(3)
<223> OTHER INFORMATION: Asn, Ile, Ser or Tyr
<220> FEATURE:
<221> NAME/KEY: MOD_RES
<222> LOCATION: (4)..(4)
<223> OTHER INFORMATION: Pro or Ala
<220> FEATURE:
<221> NAME/KEY: MOD_RES
<222> LOCATION: (5)..(5)
<223> OTHER INFORMATION: Asn, Tyr or Gly
<220> FEATURE:
<221> NAME/KEY: MOD_RES
<222> LOCATION: (6)..(6)
<223> OTHER INFORMATION: Ser, Asn or Asp
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Gly, Asn or Asp
<220> FEATURE:
<221> NAME/KEY: MOD_RES
<222> LOCATION: (10)..(10)
<223> OTHER INFORMATION: Asn or Arg
<220> FEATURE:
<221> NAME/KEY: MOD_RES
<222> LOCATION: (11)..(11)
<223> OTHER INFORMATION: Tyr or Ser
<220> FEATURE:
<221> NAME/KEY: MOD_RES
```

```
<222> LOCATION: (12)..(12)
<223> OTHER INFORMATION: Ala or Ser
<220> FEATURE:
<221> NAME/KEY: MOD_RES
<222> LOCATION: (13)..(13)
<223> OTHER INFORMATION: Gln or Pro
<220> FEATURE:
<221> NAME/KEY: MOD_RES
<222> LOCATION: (14)..(14)
<223> OTHER INFORMATION: Lys or Ser
<220> FEATURE:
<221> NAME/KEY: MOD_RES
<222> LOCATION: (15)..(15)
<223> OTHER INFORMATION: Phe or Leu

<400> SEQUENCE: 180

Xaa Ile Xaa Xaa Xaa Xaa Xaa Xaa Thr Xaa Xaa Xaa Xaa Xaa Xaa Gln
1               5                   10                  15

Gly

<210> SEQ ID NO 181
<211> LENGTH: 27
<212> TYPE: DNA
<213> ORGANISM: Homo sapiens

<400> SEQUENCE: 181
ctacagcata atagttatac gtggacg                                            27

<210> SEQ ID NO 182
<211> LENGTH: 30
<212> TYPE: DNA
<213> ORGANISM: Homo sapiens

<400> SEQUENCE: 182
ggattcacct tcagtgccta tggcatgcac                                         30

<210> SEQ ID NO 183
<211> LENGTH: 51
<212> TYPE: DNA
<213> ORGANISM: Homo sapiens

<400> SEQUENCE: 183
gttatatggt atgatggaag taataaatac tatgcagact ccgtgaaggg c                 51

<210> SEQ ID NO 184
<211> LENGTH: 45
<212> TYPE: DNA
<213> ORGANISM: Homo sapiens

<400> SEQUENCE: 184
agtcggaact ggaactacga ctcctaccaa tacggtttgg acgtc                        45

<210> SEQ ID NO 185
<211> LENGTH: 107
<212> TYPE: PRT
<213> ORGANISM: Homo sapiens

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Cys Ala Thr Tyr Tyr Cys Leu Gln His Asn Ser Tyr Thr Trp
                 85                  90                  95

Thr Phe Gly Gln Gly Thr Lys Val Glu Ile Lys
                100                 105

<210> SEQ ID NO 186
<211> LENGTH: 124
<212> TYPE: PRT
<213> ORGANISM: Homo sapiens

<400> SEQUENCE: 186

Gln Val Gln Leu Val Glu Ser Gly Gly Gly Val Val Gln Pro Gly Arg
 1               5                  10                  15

Ser Leu Arg Leu Ser Cys Val Ala Ser Gly Phe Thr Phe Ser Ala Tyr
                20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
         50                  55                  60

Lys Gly Arg Phe Ile Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Arg Asn Trp Asn Tyr Asp Ser Tyr Gln Tyr Gly Leu Asp
                100                 105                 110

Val Trp Gly Gln Gly Thr Thr Val Thr Val Ser Ser
            115                 120

<210> SEQ ID NO 187
<211> LENGTH: 11
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: Asp, Trp or absent
<220> FEATURE:
<221> NAME/KEY: MOD_RES
<222> LOCATION: (4)..(4)
<223> OTHER INFORMATION: Ser, Leu or absent
<220> FEATURE:
<221> NAME/KEY: MOD_RES
<222> LOCATION: (5)..(5)
<223> OTHER INFORMATION: Ile, Glu or Gln
<220> FEATURE:
<221> NAME/KEY: MOD_RES
<222> LOCATION: (6)..(6)
<223> OTHER INFORMATION: Ala, Leu or Gly
<220> FEATURE:
<221> NAME/KEY: MOD_RES
<222> LOCATION: (7)..(7)
<223> OTHER INFORMATION: Ala or Leu
<220> FEATURE:
<221> NAME/KEY: MOD_RES
<222> LOCATION: (8)..(8)
<223> OTHER INFORMATION: Pro, Tyr or Gly

<400> SEQUENCE: 187

```
Val Gln Xaa Xaa Xaa Xaa Xaa Xaa Phe Asp Tyr
1               5                   10

<210> SEQ ID NO 188
<211> LENGTH: 13
<212> TYPE: PRT
<213> ORGANISM: Homo sapiens
<220> FEATURE:
<221> NAME/KEY: MOD_RES
<222> LOCATION: (1)..(2)
<223> OTHER INFORMATION: May or may not be present
<220> FEATURE:
<221> NAME/KEY: MOD_RES
<222> LOCATION: (3)..(3)
<223> OTHER INFORMATION: Asp or Ala
<220> FEATURE:
<221> NAME/KEY: MOD_RES
<222> LOCATION: (5)..(5)
<223> OTHER INFORMATION: Tyr or Gly
<220> FEATURE:
<221> NAME/KEY: MOD_RES
<222> LOCATION: (7)..(7)
<223> OTHER INFORMATION: Ser or Tyr
<220> FEATURE:
<221> NAME/KEY: MOD_RES
<222> LOCATION: (8)..(8)
<223> OTHER INFORMATION: Ser or Arg
<220> FEATURE:
<221> NAME/KEY: MOD_RES
<222> LOCATION: (11)..(11)
<223> OTHER INFORMATION: May or may not be present
<220> FEATURE:
<221> NAME/KEY: MOD_RES
<222> LOCATION: (12)..(12)
<223> OTHER INFORMATION: Gly or Asp
<220> FEATURE:
<221> NAME/KEY: MOD_RES
<222> LOCATION: (13)..(13)
<223> OTHER INFORMATION: His or Pro

<400> SEQUENCE: 188

Asp Gln Xaa Tyr Xaa Asp Xaa Xaa Gly Trp Phe Xaa Xaa
1               5                   10

<210> SEQ ID NO 189
<211> LENGTH: 9
<212> TYPE: PRT
<213> ORGANISM: Homo sapiens

<400> SEQUENCE: 189

Leu Gln His Asn Ser Tyr Thr Trp Thr
1               5

<210> SEQ ID NO 190
<211> LENGTH: 10
<212> TYPE: PRT
<213> ORGANISM: Homo sapiens

<400> SEQUENCE: 190

Gly Phe Thr Phe Ser Ala Tyr Gly Met His
1               5                   10

<210> SEQ ID NO 191
<211> LENGTH: 17
<212> TYPE: PRT
<213> ORGANISM: Homo sapiens

<400> SEQUENCE: 191

Val Ile Trp Tyr Asp Gly Ser Asn Lys Tyr Tyr Ala Asp Ser Val Lys
1               5                   10                  15
```

Gly

<210> SEQ ID NO 192
<211> LENGTH: 15
<212> TYPE: PRT
<213> ORGANISM: Homo sapiens

<400> SEQUENCE: 192

Ser Arg Asn Trp Asn Tyr Asp Ser Tyr Gln Tyr Gly Leu Asp Val
1               5                   10                  15

<210> SEQ ID NO 193
<211> LENGTH: 315
<212> TYPE: DNA
<213> ORGANISM: Homo sapiens

<400> SEQUENCE: 193
tcctatgagc tgactcagcc accctcagtg tccgtgtccc caggacagac agccagcatc     60
acctgctctg gagataaatt ggggataaaa tatgtttgtt ggtatcagca gaagccaggc    120
cagtcccctg aactggtcat ctatctagat aacaagcggc cctcagggat ccctgagcga    180
ttctctggct ccaactctgg gaacacagcc actctgacca tcagcgggac ccaggctatg    240
gatgaggctg actattactg tcaggcgtgg gacagcagca cggtattcgg cggagggacc    300
aaactgaccg tcctg                                                     315

<210> SEQ ID NO 194
<211> LENGTH: 363
<212> TYPE: DNA
<213> ORGANISM: Homo sapiens

<400> SEQUENCE: 194
caggttcagc tggtgcagtc tggagctgag gtgaagaagc ctggggcctc agtgaaggtc     60
tcctgcaagg cttctggtta ccctttacc agctatggta tcagctgggt gcgacaggcc    120
cctggacaag gcttgagag gatgggatgg atcagcgctt acaatggtaa cacaaactat    180
gcacagaagt tccagggcag agtcaccatg accacagaca catcaacgac cacagcctac    240
atggagctga ggagcctgag atctgacgac acggccgtgt attactgtgc gagagatcaa    300
gattactatg atagtagtgg ttggggccac tggggccagg gaaccctggt caccgtctcc    360
tca                                                                  363

<210> SEQ ID NO 195
<211> LENGTH: 33
<212> TYPE: DNA
<213> ORGANISM: Homo sapiens

<400> SEQUENCE: 195
tctggagata aattggggga taaatatgtt tgt                                  33

<210> SEQ ID NO 196
<211> LENGTH: 21
<212> TYPE: DNA
<213> ORGANISM: Homo sapiens

<400> SEQUENCE: 196
ctagataaca agcggccctc a                                               21

<210> SEQ ID NO 197
<211> LENGTH: 24

```
<212> TYPE: DNA
<213> ORGANISM: Homo sapiens

<400> SEQUENCE: 197
caggcgtggg acagcagcac ggta                                          24

<210> SEQ ID NO 198
<211> LENGTH: 30
<212> TYPE: DNA
<213> ORGANISM: Homo sapiens

<400> SEQUENCE: 198
ggttacacct ttaccagcta tggtatcagc                                    30

<210> SEQ ID NO 199
<211> LENGTH: 51
<212> TYPE: DNA
<213> ORGANISM: Homo sapiens

<400> SEQUENCE: 199
tggatcagcg cttacaatgg taacacaaac tatgcacaga agttccaggg c             51

<210> SEQ ID NO 200
<211> LENGTH: 36
<212> TYPE: DNA
<213> ORGANISM: Homo sapiens

<400> SEQUENCE: 200
gatcaagatt actatgatag tagtggttgg ggccac                             36

<210> SEQ ID NO 201
<211> LENGTH: 105
<212> TYPE: PRT
<213> ORGANISM: Homo sapiens

<400> SEQUENCE: 201
```

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Gln Ser Pro Glu Leu Val Ile Tyr
        35                  40                  45

Leu Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Val Phe
                85                  90                  95

Gly Gly Gly Thr Lys Leu Thr Val Leu
            100                 105

```
<210> SEQ ID NO 202
<211> LENGTH: 121
<212> TYPE: PRT
<213> ORGANISM: Homo sapiens

<400> SEQUENCE: 202
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Gly Ile Ser Trp Val Arg Gln Ala Pro Gly Gln Gly Leu Glu Arg Met
            35                  40                  45

Gly Trp Ile Ser Ala Tyr Asn Gly Asn Thr Asn Tyr Ala Gln Lys Phe
        50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Thr Ala Val Tyr Tyr Cys
                85                  90                  95

Ala Arg Asp Gln Asp Tyr Tyr Asp Ser Ser Gly Trp Gly His Trp Gly
                100                 105                 110

Gln Gly Thr Leu Val Thr Val Ser Ser
        115                 120
```

<210> SEQ ID NO 203
<211> LENGTH: 11
<212> TYPE: PRT
<213> ORGANISM: Homo sapiens

<400> SEQUENCE: 203

```
Ser Gly Asp Lys Leu Gly Asp Lys Tyr Val Cys
1               5                   10
```

<210> SEQ ID NO 204
<211> LENGTH: 7
<212> TYPE: PRT
<213> ORGANISM: Homo sapiens

<400> SEQUENCE: 204

```
Leu Asp Asn Lys Arg Pro Ser
1               5
```

<210> SEQ ID NO 205
<211> LENGTH: 8
<212> TYPE: PRT
<213> ORGANISM: Homo sapiens

<400> SEQUENCE: 205

```
Gln Ala Trp Asp Ser Ser Thr Val
1               5
```

<210> SEQ ID NO 206
<211> LENGTH: 10
<212> TYPE: PRT
<213> ORGANISM: Homo sapiens

<400> SEQUENCE: 206

```
Gly Tyr Thr Phe Thr Ser Tyr Gly Ile Ser
1               5                   10
```

<210> SEQ ID NO 207
<211> LENGTH: 17
<212> TYPE: PRT
<213> ORGANISM: Homo sapiens

<400> SEQUENCE: 207

```
Trp Ile Ser Ala Tyr Asn Gly Asn Thr Asn Tyr Ala Gln Lys Phe Gln
1               5                   10                  15

Gly
```

<210> SEQ ID NO 208
<211> LENGTH: 12

<212> TYPE: PRT
<213> ORGANISM: Homo sapiens

<400> SEQUENCE: 208

Asp Gln Asp Tyr Tyr Asp Ser Ser Gly Trp Gly His
1               5                   10

<210> SEQ ID NO 209
<211> LENGTH: 316
<212> TYPE: DNA
<213> ORGANISM: Homo sapiens

<400> SEQUENCE: 209
tcctatgagc tgactcagcc accctcagtg tccgtgtccc caggacagac agcctccatc      60
acctgctctg gagataaatt gggggataaa tatgctttct ggtatcagca gaagccaggc     120
cagtcccctg tgctggtctt ctatcatgat accaagcggc cctcagggat ccctgagcga     180
ttctctggct ccaactctgg gaacacagcc actctgacca tcagcgggac ccaggctatg     240
gatgaggctg actatcactg tcaggcgtgg gacagcagca cggtcttcgg cggagggacc     300
aagctgaccg tcctac                                                    316

<210> SEQ ID NO 210
<211> LENGTH: 363
<212> TYPE: DNA
<213> ORGANISM: Homo sapiens

<400> SEQUENCE: 210
caggttcagc tggtgcaatc tggagctgag gtgaagaagc ctggggcctc agtgaaggtc      60
tcctgcaaga cttctggtta cacctttacc agctatggta tcagctgggt gcgacaggcc     120
cctggacaag gcttgagtg gatgggatgg atcagccctt acaatggtaa cacaaactat      180
gcacagaagt tccagggcag agtcaccatg accacagaca atccacgag cacagcctac     240 atggagctga ggagcctgcg atctgacgac acggccgtgt attactgtgc gagagatcaa     300
gattactatg atagtagtgg ttgggacccc tggggccagg gaaccctggt caccgtctcc     360
tcg                                                                  363

<210> SEQ ID NO 211
<211> LENGTH: 33
<212> TYPE: DNA
<213> ORGANISM: Homo sapiens

<400> SEQUENCE: 211
tctggagata aattggggga taaatatgct ttc                                  33

<210> SEQ ID NO 212
<211> LENGTH: 21
<212> TYPE: DNA
<213> ORGANISM: Homo sapiens

<400> SEQUENCE: 212
catgatacca agcggccctc a                                               21

<210> SEQ ID NO 213
<211> LENGTH: 360
<212> TYPE: DNA
<213> ORGANISM: Artificial Sequence
<220> FEATURE:
<223> OTHER INFORMATION: Description of Artificial Sequence: Synthetic
      activin A/B chimera polynucleotide

```
<400> SEQUENCE: 213
ggtctagagt gtgatggcaa ggtcaacatc tgctgtaaga aacagttctt tgtcagtttc      60
aaggacatcg gctggaatga ctggatcatt gctccctctg gctatcatgc caactactgc     120
gagggtgagt gcccgagcca tatagcaggc acgtccgggt caagcttgtc cttccactca     180
acagtcatca accactaccg catgcgggc catagcccct tgccaacct caaatcatgc      240 tgtattccca ccaagctgag caccatgtcc atgttgtact ttgatgatga gtacaacatc     300
gtcaaaaggg acgttccgaa catgatcgtg gaggagtgtg ggtgctcatg agcggccgct     360

<210> SEQ ID NO 214
<211> LENGTH: 326
<212> TYPE: PRT
<213> ORGANISM: Homo sapiens

<400> SEQUENCE: 214

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 215
<211> LENGTH: 326
<212> TYPE: PRT
<213> ORGANISM: Homo sapiens

<400> SEQUENCE: 215

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 216
```

<211> LENGTH: 36
<212> TYPE: DNA
<213> ORGANISM: Homo sapiens

<400> SEQUENCE: 216
gatcaagatt actatgatag tagtggttgg gacccc        36

<210> SEQ ID NO 217
<211> LENGTH: 105
<212> TYPE: PRT
<213> ORGANISM: Homo sapiens

<400> SEQUENCE: 217

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Phe Trp Tyr Gln Gln Lys Pro Gly Gln Ser Pro Val Leu Val Phe Tyr
        35                  40                  45

His Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr His Cys Gln Ala Trp Asp Ser Ser Thr Val Phe
                85                  90                  95

Gly Gly Gly Thr Lys Leu Thr Val Leu
            100                 105

<210> SEQ ID NO 218
<211> LENGTH: 121
<212> TYPE: PRT
<213> ORGANISM: Homo sapiens

<400> SEQUENCE: 218

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Lys Phe
    50                  55                  60

Gln Gly Arg Val Thr Met Thr Thr Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gln Asp Tyr Tyr Asp Ser Ser Gly Trp Asp Pro Trp Gly
            100                 105                 110

Gln Gly Thr Leu Val Thr Val Ser Ser
        115                 120

<210> SEQ ID NO 219
<211> LENGTH: 11
<212> TYPE: PRT
<213> ORGANISM: Homo sapiens

<400> SEQUENCE: 219

Ser Gly Asp Lys Leu Gly Asp Lys Tyr Ala Phe
1               5                   10

<210> SEQ ID NO 220
<211> LENGTH: 7
<212> TYPE: PRT
<213> ORGANISM: Homo sapiens

<400> SEQUENCE: 220

His Asp Thr Lys Arg Pro Ser
1               5

<210> SEQ ID NO 221
<211> LENGTH: 326
<212> TYPE: PRT
<213> ORGANISM: Homo sapiens

<400> SEQUENCE: 221

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 222
<211> LENGTH: 318
<212> TYPE: DNA
<213> ORGANISM: Homo sapiens

<400> SEQUENCE: 222
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tatctgagcc tgacgcctga gcagtggaag      240
tcccacagaa gctacagctg ccaggtcacg catgaaggga gcaccgtgga agacagtg       300 gccctacag aatgttca                                                    318

<210> SEQ ID NO 223
<211> LENGTH: 321
<212> TYPE: DNA
<213> ORGANISM: Homo sapiens

<400> SEQUENCE: 223
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 224
<211> LENGTH: 12
<212> TYPE: PRT
<213> ORGANISM: Homo sapiens

<400> SEQUENCE: 224

Asp Gln Asp Tyr Tyr Asp Ser Ser Gly Trp Asp Pro
1               5                   10

<210> SEQ ID NO 225
<211> LENGTH: 116
<212> TYPE: PRT
<213> ORGANISM: Homo sapiens

<400> SEQUENCE: 225

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp

```
                    85                  90                  95
Gly Gln Asn Ile Ile Lys Lys Asp Ile Gln Asn Met Ile Val Glu Glu
                100                 105                 110
Cys Gly Cys Ser
        115

<210> SEQ ID NO 226
<211> LENGTH: 8
<212> TYPE: PRT
<213> ORGANISM: Homo sapiens

<400> SEQUENCE: 226

Asp Tyr Lys Asp Asp Asp Asp Lys
1               5

<210> SEQ ID NO 227
<211> LENGTH: 636
<212> TYPE: DNA
<213> ORGANISM: Homo sapiens

<400> SEQUENCE: 227
tcctatgagg tgactcaggc accctcagtg tccgtgtccc caggacagac agccagcatc      60
acctgctctg gagataaatt gggggataaa tatgcttgtt ggtatcagca gaagccaggc     120
cagtcccctg tgctggtcat ctatcaagat agcaagcggc cctcagggat ccctgagcga     180
ttctctggct ccaactctgg aaacacagcc actctgacca tcagcgggac ccaggctatg     240
gatgaggctg actattactg tcaggcgtgg gacagcagca ctgcggtatt cggcggaggg     300
accaagctga ccgtcctagg tcagcccaag gctgccccct cggtcactct gttcccgccc     360
tcctctgagg agcttcaagc caacaaggcc acactggtgt gtctcataag tgacttctac     420
ccgggagccg tgacagtggc ctggaaggca gatagcagcc ccgtcaaggc gggagtggag     480
accaccacac cctccaaaca aagcaacaac aagtacgcgg ccagcagcta tctgagcctg     540
acgcctgagc agtggaagtc ccacagaagc tacagctgcc aggtcacgca tgaagggagc     600
accgtggaga agacagtggc ccctacagaa tgttca                               636

<210> SEQ ID NO 228
<211> LENGTH: 1344
<212> TYPE: DNA
<213> ORGANISM: Homo sapiens

<400> SEQUENCE: 228
caggttcagc tggtgcagtc tggagctgag gtgaagaagc ctggggcctc agtgaaggtc      60
tcctgcaagg cttctggtta cacctttacc agttatggtc tcagctgggt gcgacaggcc     120
cctggacaag gcttgagtg gatgggatgg atcatccctt acaatggtaa cacaaactct     180
gcacagaaac tccagggcag agtcaccatg accacagaca catccacgag cacagcctac     240
atggagctga ggagcctgag atctgacgac acggccgtgt atttctgtgc gagagacagg     300
gactacggtg tcaattatga tgcttttgat atctggggcc aagggacaat ggtcaccgtc     360
tcttcagcct ccaccaaggg cccatcggtc ttccccctgg cgccctgctc caggagcacc     420
tccgagagca cagcggccct gggctgcctg gtcaaggact acttccccga accggtgacg     480
gtgtcgtgga actcaggcgc tctgaccagc ggcgtgcaca ccttcccagc tgtcctacag     540
tcctcaggac tctactccct cagcagcgtg gtgaccgtgc cctccagcaa cttcggcacc     600
cagacctaca cctgcaacgt agatcacaag cccagcaaca ccaaggtgga caagacagtt     660
```

| | |
|---|---|
| gagcgcaaat gttgtgtcga gtgcccaccg tgcccagcac cacctgtggc aggaccgtca | 720 |
| gtcttcctct tcccccaaaa acccaaggac accctcatga tctcccggac ccctgaggtc | 780 |
| acgtgcgtgg tggtggacgt gagccacgaa gaccccgagg tccagttcaa ctggtacgtg | 840 |
| gacggcgtgg aggtgcataa tgccaagaca aagccacggg aggagcagtt caacagcacg | 900 |
| ttccgtgtgg tcagcgtcct caccgttgtg caccaggact ggctgaacgg caaggagtac | 960 |
| aagtgcaagg tctccaacaa aggcctccca gcccccatcg agaaaaccat ctccaaaacc | 1020 |
| aaagggcagc cccgagaacc acaggtgtac accctgcccc catcccggga ggagatgacc | 1080 |
| aagaaccagg tcagcctgac ctgcctggtc aaaggcttct accccagcga catcgccgtg | 1140 |
| gagtgggaga gcaatgggca gccggagaac aactacaaga ccacacctcc catgctggac | 1200 |
| tccgacggct ccttcttcct ctacagcaag ctcaccgtgg acaagagcag gtggcagcag | 1260 |
| gggaacgtct tctcatgctc cgtgatgcat gaggctctgc acaaccacta cacgcagaag | 1320 |
| agcctctccc tgtctccggg taaa | 1344 |

<210> SEQ ID NO 229
<211> LENGTH: 642
<212> TYPE: DNA
<213> ORGANISM: Homo sapiens

<400> SEQUENCE: 229

| | |
|---|---|
| gacatccaga tgacccagtc tccatcctcc ctgtctgcat ctgtaggaga cagagtcacc | 60 |
| atcacttgcc gggcaagtca gggcattaga aataatttag gctggtatca gcagaaacca | 120 |
| gggaaagccc ctaagcgcct gatttatgct gcatccagtt tgcaaagtgg ggtcccatca | 180 |
| aggttcagcg gcagtggatc tgggacagaa ttcactctca caatcagcag tctgcagcct | 240 |
| gaagatttta caacttatta ctgtctacag cataatagtt acccgtggac gttcggccaa | 300 |
| gggaccaagg tggaaatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag caccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gt | 642 |

<210> SEQ ID NO 230
<211> LENGTH: 1350
<212> TYPE: DNA
<213> ORGANISM: Homo sapiens

<400> SEQUENCE: 230

| | |
|---|---|
| caggtgcagc tggtggagtc tgggggaggc gtggtccagc ctgggaggtc cctgagactc | 60 |
| tcctgtgcag cgtctggatt cacccttcagt agttacggca tgcactgggt ccgccaggct | 120 |
| ccaggcaagg ggctggagtg ggtggcagtt atatggtatg atggaagtaa taaataccat | 180 |
| gcagactccg tgaagggccg attcaccatc tccagagaca attccaagaa cacgctgtat | 240 |
| ctgcaagtga acagcctgag agccgaggac acggctgtgt attactgtgt gagaagtcgg | 300 |
| aactggaact acgacaacta ctactacggt ctggacgtct ggggccaagg gaccacggtc | 360 |
| accgtctcct cagcctccac caagggccca tcggtcttcc cctggcgccc tgctccagg | 420 |
| agcacctccg agagcacagc ggccctgggc tgcctggtca aggactactt ccccgaaccg | 480 |
| gtgacggtgt cgtggaactc aggcgctctg accagcggcg tgcacacctt cccagctgtc | 540 |

-continued

```
ctacagtcct caggactcta ctccctcagc agcgtggtga ccgtgccctc cagcaacttc    600
ggcacccaga cctacacctg caacgtagat cacaagccca gcaacaccaa ggtggacaag    660
acagttgagc gcaaatgttg tgtcgagtgc ccaccgtgcc cagcaccacc tgtggcagga    720
ccgtcagtct tcctcttccc cccaaaaccc aaggacaccc tcatgatctc ccggacccct    780
gaggtcacgt gcgtggtggt ggacgtgagc cacgaagacc ccgaggtcca gttcaactgg    840
tacgtggacg gcgtggaggt gcataatgcc aagacaaagc cacgggagga gcagttcaac    900
agcacgttcc gtgtggtcag cgtcctcacc gttgtgcacc aggactggct gaacggcaag    960
gagtacaagt gcaaggtctc caacaaaggc ctcccagccc ccatcgagaa aaccatctcc   1020
aaaaccaaag ggcagccccg agaaccacag gtgtacaccc tgcccccatc ccgggaggag   1080
atgaccaaga accaggtcag cctgacctgc ctggtcaaag gcttctaccc cagcgacatc   1140
gccgtggagt gggagagcaa tgggcagccg gagaacaact acaagaccac acctcccatg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350

<210> SEQ ID NO 231
<211> LENGTH: 642
<212> TYPE: DNA
<213> ORGANISM: Homo sapiens

<400> SEQUENCE: 231
gacatccaga tgacccagtc tccatcctcc ctgtctgcat ctgtaggaga cagagtcacc     60
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtcgacag caaaatactt acccgctcac tttcggcgga    300
gggaccaagg tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 232
<211> LENGTH: 1347
<212> TYPE: DNA
<213> ORGANISM: Homo sapiens

<400> SEQUENCE: 232
gaggtgcagt tggtggagtc tgggggaggc ttggtccagc ctggggggtc cctgagactc     60
tcctgtgcag cctctggatt cacctttagt agttattgga tgagctgggt ccgccaggct    120
ccagggaagg ggctggagtg cgtggccaac ataaagcaag atggaagtga ggaatactat    180
gtggactctg tgaagggccg attcaccatc tccagagaca acgccaagaa ttcactgtat    240
ctgcaaatga acagcctgag agccgaggac acggctgtgt attactgtgc gagaggtagc    300
agcagctggt actactacaa ctacggtatg gacgtctggg gccaagggac cacggtcacc    360
```

```
gtctcctcag cctccaccaa gggcccatcg gtcttccccc tggcgccctg ctccaggagc    420
acctccgaga gcacagcggc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca acaccaaggt ggacaagaca    660
gttgagcgca aatgttgtgt cgagtgccca ccgtgcccag caccacctgt ggcaggaccg    720
tcagtcttcc tcttcccccc aaaacccaag gacaccctca tgatctcccg gacccctgag    780
gtcacgtgcg tggtggtgga cgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagccccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctaccccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                       1347
```

<210> SEQ ID NO 233
<211> LENGTH: 212
<212> TYPE: PRT
<213> ORGANISM: Homo sapiens
<400> SEQUENCE: 233

```
Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
```

Thr Glu Cys Ser
    210

<210> SEQ ID NO 234
<211> LENGTH: 448
<212> TYPE: PRT
<213> ORGANISM: Homo sapiens

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 235
<211> LENGTH: 214
<212> TYPE: PRT
<213> ORGANISM: Homo sapiens

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 236
<211> LENGTH: 450
<212> TYPE: PRT
<213> ORGANISM: Homo sapiens

<400> SEQUENCE: 236

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
            35                  40                  45
Ala Val Ile Trp Tyr Asp Gly Ser Asn Lys Tyr His Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Val Asn Ser Leu Arg Ala Glu Asp Thr Ala Val Tyr Tyr Cys
                85                  90                  95
Val Arg Ser Arg Asn Trp Asn Tyr Asp Asn Tyr Tyr Gly Leu Asp
               100                 105                 110
Val Trp Gly Gln Gly Thr Thr Val Thr Val Ser Ser Ala Ser Thr Lys
               115                 120                 125
Gly Pro Ser Val Phe Pro Leu Ala Pro Cys Ser Arg Ser Thr Ser Glu
           130                 135                 140
Ser Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Asn Phe Gly Thr Gln Thr Tyr Thr Cys Asn
                195                 200                 205
Val Asp His Lys Pro Ser Asn Thr Lys Val Asp Lys Thr Val Glu Arg
            210                 215                 220
Lys Cys Cys Val Glu Cys Pro Pro Cys Pro Ala Pro Pro Val Ala Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Phe Asn Ser Thr Phe Arg
 290                 295                 300
Val Val Ser Val Leu Thr Val Val His Gln Asp Trp Leu Asn Gly Lys
305                 310                 315                 320
Glu Tyr Lys Cys Lys Val Ser Asn Lys Gly Leu Pro Ala Pro Ile Glu
                325                 330                 335
Lys Thr Ile Ser Lys Thr Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Met
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
```

```
                      435                 440                 445

Gly Lys
    450

<210> SEQ ID NO 237
<211> LENGTH: 214
<212> TYPE: PRT
<213> ORGANISM: Homo sapiens

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Arg Gln Gln Asn Thr Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 238
<211> LENGTH: 449
<212> TYPE: PRT
<213> ORGANISM: Homo sapiens

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Cys Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
            85                  90                  95
Ala Arg Gly Ser Ser Trp Tyr Tyr Tyr Asn Tyr Gly Met Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
                195                 200                 205

Asp His Lys Pro Ser Asn Thr Lys Val Asp Lys Thr Val Glu Arg Lys
            210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Phe Arg Val
290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 239
<211> LENGTH: 321
<212> TYPE: DNA
<213> ORGANISM: Homo sapiens

<400> SEQUENCE: 239
cgaactgtgg ctgcaccatc tgtcttcatc ttcccgccat ctgatgagca gttgaaatct    60
```

```
ggaactgcct ctgttgtgtg cctgctgaat aacttctatc ccagagaggc caaagtacag        120
tggaaggtgg ataacgccct ccaatcgggt aactcccagg agagtgtcac agagcaggac        180
agcaaggaca gcacctacag cctcagcagc accctgacgc tgagcaaagc agactacgag        240
aaacacaaag tctacgcctg cgaagtcacc catcagggcc tgagctcgcc cgtcacaaag        300
agcttcaaca ggggagagtg t                                                  321

<210> SEQ ID NO 240
<211> LENGTH: 978
<212> TYPE: DNA
<213> ORGANISM: Homo sapiens

<400> SEQUENCE: 240
gcctccacca agggcccatc ggtcttcccc ctggcgccct gctccaggag cacctccgag         60
agcacagcgg ccctgggctg cctggtcaag gactacttcc ccgaaccggt gacggtgtcg        120
tggaactcag gcgctctgac cagcggcgtg cacaccttcc cagctgtcct acagtcctca        180
ggactctact ccctcagcag cgtggtgacc gtgccctcca gcaacttcgg cacccagacc        240
tacacctgca acgtagatca caagcccagc aacaccaagg tggacaagac agttgagcgc        300
aaatgttgtg tcgagtgccc accgtgccca gcaccacctg tggcaggacc gtcagtcttc        360
ctcttccccc caaaacccaa ggacaccctc atgatctccc ggacccctga ggtcacgtgc        420
gtggtggtgg acgtgagcca cgaagacccc gaggtccagt tcaactggta cgtggacggc        480
gtggaggtgc ataatgccaa gacaaagcca cgggaggagc agttcaacag cacgttccgt        540
gtggtcagcg tcctcaccgt tgtgcaccag gactggctga acggcaagga gtacaagtgc        600
aaggtctcca acaaaggcct cccagccccc atcgagaaaa ccatctccaa aaccaaaggg        660
cagccccgag aaccacaggt gtacaccctg cccccatccc gggaggagat gaccaagaac        720
caggtcagcc tgacctgcct ggtcaaaggc ttctacccca gcgacatcgc cgtggagtgg        780
gagagcaatg ggcagccgga gaacaactac aagaccacac ctcccatgct ggactccgac        840
ggctccttct cctctacagc aagctcaccg tggacaaga gcaggtggca gcagggggaac       900 gtcttctcat gctccgtgat gcatgaggct ctgcacaacc actacacgca gaagagcctc        960
tccctgtctc cgggtaaa                                                     978

<210> SEQ ID NO 241
<211> LENGTH: 978
<212> TYPE: DNA
<213> ORGANISM: Homo sapiens

<400> SEQUENCE: 241
gcctccacca agggcccatc ggtcttcccc ctggcgccct gctccaggag cacctccgag         60
agcacagcgg ccctgggctg cctggtcaag gactacttcc ccgaaccggt gacggtgtcg        120
tggaactcag gcgctctgac cagcggcgtg cacaccttcc cagctgtcct acagtcctca        180
ggactctact ccctcagcag cgtggtgacc gtgccctcca gcaacttcgg cacccagacc        240
tacacctgca acgtagatca caagcccagc aacaccaagg tggacaagac agttgagcgc        300
aaatgttgtg tcgagtgccc accgtgccca gcaccacctg tggcaggacc gtcagtcttc        360
ctcttccccc caaaacccaa ggacaccctc atgatctccc ggacccctga ggtcacgtgc        420
gtggtggtgg acgtgagcca cgaagacccc gaggtccagt tcaactggta cgtggacggc        480
gtggaggtgc ataatgccaa gacaaagcca cgggaggagc agttcaacag cacgttccgt        540
```

```
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac ctcccatgct ggactccgac      840
ggctccttct tcctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaa                                                    978

<210> SEQ ID NO 242
<211> LENGTH: 824
<212> TYPE: DNA
<213> ORGANISM: Homo sapiens

<400> SEQUENCE: 242
gcctccacca agggcccatc ggtcttcccc ctggcgccct gctccaggag cacctccgag       60
agcacagcgg ccctgggctg cctggtcaag gactacttcc ccgaaccggt gacggtgtcg      120
tggaactcag gcgctctgac cagcggcgtg cacaccttcc cagctgtcct acagtcctca      180
ggactctact ccctcagcag cgtggtgacc gtgccctcca gcaacttcgg cacccagacc      240
tacacctgca acgtagatca caagcccagc aacaccaagg tggacaagac agttgagcgc      300
aaatgttgtg tcgagtgccc accgtgccca gcaccacctg tggcaggacc gtcagtcttc      360
ctcttccccc caaaacccaa ggacaccctc atgatctccc ggacccctga ggtcacgtgc      420
gtggtggtgg acgtgagcca cgaagacccc gaggtccagt tcaactggta cgtggacggc      480
gtggaggtgc ataatgccaa gacaaagcca cgggaggagc agttcaacag cacgttccgt      540
gtggtcagcg tcctcaccgt tgtgcaccag gactggctga acggcaagga gtacaagtgc      600
aaggtctcca acaaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctacccca gcgacatcgc cgtggagtgg      780
gagagcaatg ggcagccgga gaacaactac aagaccacac tcc                       824

<210> SEQ ID NO 243
<211> LENGTH: 116
<212> TYPE: PRT
<213> ORGANISM: Artificial Sequence
<220> FEATURE:
<223> OTHER INFORMATION: Description of Artificial Sequence: Synthetic
      activin A/B chimera polypeptide

<400> SEQUENCE: 243

Gly Leu Glu Cys Asp Gly Lys Val Asn Ile Cys Cys Arg Gln Gln Phe
1               5                   10                  15

Phe Ile Asp Phe Arg Leu Ile Gly Trp Asn Asp Trp Ile Ile Ala Pro
            20                  25                  30

Thr Gly Tyr Tyr Gly Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Val Pro Thr Lys Leu Arg Pro Met Ser Met Leu Tyr Tyr Asp Asp
```

```
                    85                  90                  95

Gly Gln Asn Ile Ile Lys Lys Asp Ile Gln Asn Met Ile Val Glu Glu
            100                 105                 110

Cys Gly Cys Ser
        115

<210> SEQ ID NO 244
<211> LENGTH: 116
<212> TYPE: PRT
<213> ORGANISM: Artificial Sequence
<220> FEATURE:
<223> OTHER INFORMATION: Description of Artificial Sequence: Synthetic
      activin A/B chimera polypeptide

<400> SEQUENCE: 244

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile Ala Pro
            20                  25                  30

Ser Gly Tyr His Ala Asn Tyr Cys Glu Gly Glu Cys Pro Ser His Ile
        35                  40                  45

Ala Gly Thr Ser Gly Ser Ser Leu Ser Phe His Ser Thr Val Ile Asn
    50                  55                  60

His Tyr Arg Met Arg Gly His Ser Pro Phe Ala Asn Leu Lys Ser Cys
65                  70                  75                  80

Cys Ile Pro Thr Lys Leu Ser Thr Met Ser Met Leu Tyr Phe Asp Asp
                85                  90                  95

Glu Tyr Asn Ile Val Lys Arg Asp Val Pro Asn Met Ile Val Glu Glu
            100                 105                 110

Cys Gly Cys Ser
        115

<210> SEQ ID NO 245
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ctcgaggtcg actagaccac catgcccttg c                                    31

<210> SEQ ID NO 246
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
ccatcacact ctagaccccg ccgacgcc                                        28

<210> SEQ ID NO 247
<211> LENGTH: 360
<212> TYPE: DNA
<213> ORGANISM: Artificial Sequence
<220> FEATURE:
<223> OTHER INFORMATION: Description of Artificial Sequence: Synthetic
      activin A/B chimera polynucleotide

<400> SEQUENCE: 247
```

```
ggtctagagt gtgatggcaa ggtcaacatc tgctgtaggc aacagttctt tatcgatttc    60
aggctcatcg gctggaatga ctggatcatt gctcccactg gctattatgg caactactgc   120
gagggtgagt gcccgagcca tatagcaggc acgtccgggt caagcttgtc cttccactca   180
acagtcatca accactaccg catgcgggc catagcccct ttgccaacct caaatcatgc   240
tgtgtgccca ccaagctgag acccatgtcc atgttgtact atgatgatgg tcaaaacatc   300
atcaaaaagg acattcagaa catgatcgtg gaggagtgtg ggtgctcatg agcggccgct   360
```

```
<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      anti activin A antibody peptide
<220> FEATURE:
<221> NAME/KEY: MOD_RES
<222> LOCATION: (5)..(5)
<223> OTHER INFORMATION: Arg or Ser
<220> FEATURE:
<221> NAME/KEY: MOD_RES
<222> LOCATION: (8)..(8)
<223> OTHER INFORMATION: Val or Ala
<220> FEATURE:
<221> NAME/KEY: MOD_RES
<222> LOCATION: (9)..(9)
<223> OTHER INFORMATION: May or may not be present

<400> SEQUENCE: 248

Gln Ala Trp Asp Xaa Ser Thr Xaa Val
1               5
```

```
<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      anti activin A antibody peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Ser, Glu or absent
<220> FEATURE:
<221> NAME/KEY: MOD_RES
<222> LOCATION: (3)..(3)
<223> OTHER INFORMATION: Arg, Ser or absent
<220> FEATURE:
<221> NAME/KEY: MOD_RES
<222> LOCATION: (4)..(4)
<223> OTHER INFORMATION: Asp, Asn, Ser or Gln
<220> FEATURE:
<221> NAME/KEY: MOD_RES
<222> LOCATION: (5)..(5)
<223> OTHER INFORMATION: Ser, Arg or Trp
<220> FEATURE:
<221> NAME/KEY: MOD_RES
<222> LOCATION: (6)..(6)
<223> OTHER INFORMATION: Gly, Asp, Asn, Tyr or Leu
<220> FEATURE:
<221> NAME/KEY: MOD_RES
<222> LOCATION: (8)..(8)
<223> OTHER INFORMATION: Ser, Gly, Asp or absent
<220> FEATURE:
<221> NAME/KEY: MOD_RES
<222> LOCATION: (9)..(9)
<223> OTHER INFORMATION: Ser, Val, Asn or Tyr
```

```
<220> FEATURE:
<221> NAME/KEY: MOD_RES
<222> LOCATION: (10)..(10)
<223> OTHER INFORMATION: Ser, Asn, Tyr or His
<220> FEATURE:
<221> NAME/KEY: MOD_RES
<222> LOCATION: (11)..(11)
<223> OTHER INFORMATION: Trp, Tyr or Gln
<220> FEATURE:
<221> NAME/KEY: MOD_RES
<222> LOCATION: (12)..(12)
<223> OTHER INFORMATION: His, Asp, Tyr or absent
<220> FEATURE:
<221> NAME/KEY: MOD_RES
<222> LOCATION: (13)..(13)
<223> OTHER INFORMATION: Phe, Ala or Gly
<220> FEATURE:
<221> NAME/KEY: MOD_RES
<222> LOCATION: (14)..(14)
<223> OTHER INFORMATION: Asp, Phe, Leu or Met
<220> FEATURE:
<221> NAME/KEY: MOD_RES
<222> LOCATION: (15)..(15)
<223> OTHER INFORMATION: Tyr or Asp
<220> FEATURE:
<221> NAME/KEY: MOD_RES
<222> LOCATION: (16)..(16)
<223> OTHER INFORMATION: Ile, Val or absent

<400> SEQUENCE: 249

Gly Xaa Xaa Xaa Xaa Xaa Tyr Xaa Xaa Xaa Xaa Xaa Xaa Xaa Xaa
1               5                   10                  15

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      anti activin A antibody peptide
<220> FEATURE:
<221> NAME/KEY: MOD_RES
<222> LOCATION: (3)..(3)
<223> OTHER INFORMATION: Ser or Gly
<220> FEATURE:
<221> NAME/KEY: MOD_RES
<222> LOCATION: (7)..(7)
<223> OTHER INFORMATION: Ser or Arg
<220> FEATURE:
<221> NAME/KEY: MOD_RES
<222> LOCATION: (9)..(9)
<223> OTHER INFORMATION: Asp or Asn
<220> FEATURE:
<221> NAME/KEY: MOD_RES
<222> LOCATION: (11)..(11)
<223> OTHER INFORMATION: Val or Gly

<400> SEQUENCE: 250

Arg Ala Xaa Gln Gly Ile Xaa Asn Xaa Leu Xaa
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 251

Arg Ala Ser Gln Ser Ile Ser Asn Tyr Leu Asn Thr
1               5                   10
```

-continued

```
<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      anti activin A antibody peptide
<220> FEATURE:
<221> NAME/KEY: MOD_RES
<222> LOCATION: (4)..(4)
<223> OTHER INFORMATION: Ile or Phe
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (7)..(8)
<223> OTHER INFORMATION: May or may not be present
<220> FEATURE:
<221> NAME/KEY: MOD_RES
<222> LOCATION: (9)..(9)
<223> OTHER INFORMATION: Phe or Tyr

<400> SEQUENCE: 252

Gly Gly Ser Xaa Xaa Xaa Gly Gly Xaa Tyr Trp Ser
1               5                   10

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 253

Arg Ser Ser Gln Ser Leu Leu His Ser Thr Gly Tyr Asn Tyr Leu Asp
1               5                   10                  15

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 254

Leu Gly Ser Phe Arg Ala Ser
1               5

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 255

Met Gln Ala Leu Gln Thr Pro Cys Ser
1               5

<210> SEQ ID NO 256
<211> LENGTH: 10
<212> TYPE: PRT
```

<213> ORGANISM: Artificial Sequence
<220> FEATURE:
<223> OTHER INFORMATION: Description of Artificial Sequence: Synthetic
anti activin A antibody peptide

<400> SEQUENCE: 256

Gly Tyr Thr Phe Thr Gly Tyr Tyr Ile His
1 5 10

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
anti activin A antibody peptide
<220> FEATURE:
<221> NAME/KEY: MOD_RES
<222> LOCATION: (2)..(2)
<223> OTHER INFORMATION: Tyr or Phe
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (5)..(5)
<223> OTHER INFORMATION: Thr,Ser or Ile
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (8)..(8)
<223> OTHER INFORMATION: Tyr, Gly or Trp
<220> FEATURE:
<221> NAME/KEY: MOD_RES
<222> LOCATION: (9)..(9)
<223> OTHER INFORMATION: Ile or Met
<220> FEATURE:
<221> NAME/KEY: MOD_RES
<222> LOCATION: (10)..(10)
<223> OTHER INFORMATION: His or Gly

<400> SEQUENCE: 257

Gly Xaa Xaa Phe Xaa Xaa Tyr Xaa Xaa Xaa
1 5 10

<210> SEQ ID NO 258
<211> LENGTH: 17
<212> TYPE: PRT
<213> ORGANISM: Artificial Sequence
<220> FEATURE:
<223> OTHER INFORMATION: Description of Artificial Sequence: Synthetic
anti activin A antibody peptide

<400> SEQUENCE: 258

Trp Ile Asn Pro Asn Ser Gly Gly Thr Asn Tyr Ala Gln Lys Phe Gln
1 5 10 15

Gly

<210> SEQ ID NO 259
<211> LENGTH: 17
<212> TYPE: PRT
<213> ORGANISM: Artificial Sequence
<220> FEATURE:
<223> OTHER INFORMATION: Description of Artificial Sequence: Synthetic
anti activin A antibody peptide

<400> SEQUENCE: 259

```
Trp Ile Ser Pro Tyr Asn Gly Asn Thr Asn Tyr Ala Gln Lys Phe Gln
1               5                   10                  15

Gly

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 260

Asp Ser Gly Tyr Ser Ser Ser Trp His Phe Asp Tyr
1               5                   10

<210> SEQ ID NO 261
<211> LENGTH: 13
<212> TYPE: PRT
<213> ORGANISM: Artificial Sequence
<220> FEATURE:
<223> OTHER INFORMATION: Description of Artificial Sequence: Synthetic
      anti activin A antibody peptide

<400> SEQUENCE: 261

Gly Ser Ser Ser Trp Tyr Tyr Tyr Asn Gly Met Asp Val
1               5                   10

<210> SEQ ID NO 262
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide corresponding to amino acid residues
      1-30 of activin A

<400> SEQUENCE: 262

Gly Leu Glu Cys Asp Gly Lys Val Asn Ile Cys Cys Lys Lys Gln Phe
1               5                   10                  15

Phe Val Ser Phe Lys Asp Ile Gly Trp Asn Asp Trp Ile Ile
            20                  25                  30

<210> SEQ ID NO 263
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide corresponding to amino acid residues
      31-60 of activin A

<400> SEQUENCE: 263

Ala Pro Ser Gly Tyr His Ala Asn Tyr Cys Glu Gly Glu Cys Pro Ser
1               5                   10                  15

His Ile Ala Gly Thr Ser Gly Ser Ser Leu Ser Phe His Ser
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide corresponding to amino acid residues
      61-90 of activin A
```

<400> SEQUENCE: 264

Thr Val Ile Asn His Tyr Arg Met Arg Gly His Ser Pro Phe Ala Asn
1               5                   10                  15

Leu Lys Ser Cys Cys Val Pro Thr Lys Leu Arg Pro Met Ser
            20                  25                  30

<210> SEQ ID NO 265
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide corresponding to amino acid residues
      91-116 of activin A

<400> SEQUENCE: 265

Met Leu Tyr Tyr Asp Asp Gly Gln Asn Ile Ile Lys Lys Asp Ile Gln
1               5                   10                  15

Asn Met Ile Val Glu Glu Cys Gly Cys Ser
            20                  25

<210> SEQ ID NO 266
<211> LENGTH: 116
<212> TYPE: PRT
<213> ORGANISM: Artificial Sequence
<220> FEATURE:
<223> OTHER INFORMATION: Description of Artificial Sequence: Synthetic
      activin A 13/39B polypeptide

<400> SEQUENCE: 266

Gly Leu Glu Cys Asp Gly Lys Val Asn Ile Cys Cys Arg Gln Gln Phe
1 5 10 15

Phe Ile Asp Phe Arg Leu Ile Gly Trp Asn Asp Trp Ile Ile Ala Pro
20 25 30

Thr Gly Tyr Tyr Gly Asn Tyr Cys Glu Gly Glu Cys Pro Ser His Ile
35 40 45

Ala Gly Thr Ser Gly Ser Ser Leu Ser Phe His Ser Thr Val Ile Asn
50 55 60

His Tyr Arg Met Arg Gly His Ser Pro Phe Ala Asn Leu Lys Ser Cys
65 70 75 80

Cys Val Pro Thr Lys Leu Arg Pro Met Ser Met Leu Tyr Tyr Asp Asp
85 90 95

Gly Gln Asn Ile Ile Lys Lys Asp Ile Gln Asn Met Ile Val Glu Glu
100 105 110

Cys Gly Cys Ser
115

<210> SEQ ID NO 267
<211> LENGTH: 318
<212> TYPE: DNA
<213> ORGANISM: Homo sapiens

<400> SEQUENCE: 267
tcctatgagg tgactcaggc accctcagtg tccgtgtccc caggacagac agccagcatc 60
acctgctctg gagataaatt gggggataaa tatgcttgtt ggtatcagca gaagccaggc 120
cagtcccctg tgctggtcat ctatcaagat agcaagcggc cctcagggat ccctgagcga 180
ttctctggct ccaactctgg aaacacagcc actctgacca tcagcgggac ccaggctatg 240
gatgaggctg actattactg tcaggcgtgg gacagcagca ctgcggtatt cggcggaggg 300
accaagctga ccgtccta 318

<210> SEQ ID NO 268
<211> LENGTH: 366
<212> TYPE: DNA
<213> ORGANISM: Homo sapiens

<400> SEQUENCE: 268
caggttcagc tggtgcagtc tggagctgag gtgaagaagc ctggggcctc agtgaaggtc   60
tcctgcaagg cttctggtta cacctttacc agttatggtc tcagctgggt gcgacaggcc  120
cctggacaag gccttgagtg gatgggatgg atcatccctt acaatggtaa cacaaactct  180
gcacagaaac tccagggcag agtcaccatg accacagaca catccacgag cacagcctac  240
atggagctga ggagcctgag atctgacgac acggccgtgt atttctgtgc gagagacagg  300
gactacggtg tcaattatga tgcttttgat atctggggcc aagggacaat ggtcaccgtc  360
tcttca                                                              366

<210> SEQ ID NO 269
<211> LENGTH: 373
<212> TYPE: DNA
<213> ORGANISM: Homo sapiens

<400> SEQUENCE: 269
caggtgcagc tggtggagtc tgggggaggc gtggtccagc ctggggaggtc cctgagactc   60
tcctgtgcag cgtctggatt caccttcagt agttacggca tgcactgggt ccgccaggct  120
ccaggcaagg gctggagtg gtggcagtt atatggtatg atggaagtaa taaataccat  180
gcagactccg tgaagggccg attcaccatc tccagagaca attccaagaa cacgctgtat  240
ctgcaagtga acagcctgag agccgaggac acggctgtgt attactgtgt gagaagtcgg  300
aactggaact acgacaacta ctactacggt ctggacgtct ggggccaagg gaccacggtc  360
accgtctcct cag                                                      373

<210> SEQ ID NO 270
<211> LENGTH: 321
<212> TYPE: DNA
<213> ORGANISM: Homo sapiens

<400> SEQUENCE: 270
gacatccaga tgacccagtc tccatcctcc ctgtctgcat ctgtaggaga cagagtcacc   60
atcacttgcc gggcaagtca gggcattaga aataatttag gctggtatca gcagaaacca  120
gggaaagccc ctaagcgcct gatttatgct gcatccagtt tgcaaagtgg ggtcccatca  180
aggttcagcg gcagtggatc tgggacagaa ttcactctca caatcagcag tctgcagcct  240
gaagatttta caacttatta ctgtctacag cataatagtt acccgtggac gttcggccaa  300
gggaccaagg tggaaatcaa a                                             321

<210> SEQ ID NO 271
<211> LENGTH: 369
<212> TYPE: DNA
<213> ORGANISM: Homo sapiens

<400> SEQUENCE: 271
gaggtgcagt tggtggagtc tgggggaggc ttggtccagc ctgggggtc cctgagactc    60
tcctgtgcag cctctggatt cacctttagt agttattgga tgagctgggt ccgccaggct  120
ccagggaagg gctggagtg cgtggccaac ataaagcaag atggaagtga ggaatactat  180

```
gtggactctg tgaagggccg attcaccatc tccagagaca acgccaagaa ttcactgtat    240
ctgcaaatga acagcctgag agccgaggac acggctgtgt attactgtgc gagaggtagc    300
agcagctggt actactacaa ctacggtatg gacgtctggg gccaagggac cacggtcacc    360
gtctcctca                                                            369

<210> SEQ ID NO 272
<211> LENGTH: 321
<212> TYPE: DNA
<213> ORGANISM: Homo sapiens

<400> SEQUENCE: 272
gacatccaga tgacccagtc tccatcctcc ctgtctgcat ctgtaggaga cagagtcacc     60
atcacttgcc gggcaagtca gggcattaga aatgatttag ctggtatca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtcgacag caaaatactt acccgctcac tttcggcgga    300
gggaccaagg tggagatcaa a                                              321

<210> SEQ ID NO 273
<211> LENGTH: 363
<212> TYPE: DNA
<213> ORGANISM: Homo sapiens

<400> SEQUENCE: 273
caggtgcagc tggtgcagtc tggggctgag gtgaagaagc ctggggcctc agtgaaggtc     60
tcctgcaagg cttctggata caccttcacc ggctactata tccactgggt gcgacaggcc    120
cctggacaag gcttgagtg gatgggatgg atcaaccta acagtggtgg cacaaactat    180
gcacagaagt ttcagggcag ggtcaccatg accaggaca cgtccatcag cacagcctac    240
atggagctga gcaggctgag atctgacgac acggccgtgt atttctgtgc gagagattcg    300
gggtatagca gcagctggca ctttgactac tggggccagg gaaccctggt caccgtctcc    360
tca                                                                  363

<210> SEQ ID NO 274
<211> LENGTH: 336
<212> TYPE: DNA
<213> ORGANISM: Homo sapiens

<400> SEQUENCE: 274
gatattgtga tgactcagtc tccactctcc ctgcccgtca cccctggaga gccggcctcc     60
atctcctgca ggtctagtca gagcctcctg catagtactg gatacaacta tttggattgg    120
tacctgcaga agccagggca gtctccacag ctcctgatct atttgggttc ttttcgggcc    180
tccggggtcc ctgacaggtt cagtggcagt gggtcaggca cagatttac actgaaaatc    240 agcagagtgg aggctgagga tgttggggtt tattactgca tgcaagctct ccaaactccg    300
tgcagttttg gccaggggac caagctggag atcaag                              336

<210> SEQ ID NO 275
<211> LENGTH: 106
<212> TYPE: PRT
<213> ORGANISM: Homo sapiens

<400> SEQUENCE: 275
```

```
Ser Tyr Glu Val Thr Gln Ala Pro Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
            35                  40                  45

Gln Asp Ser Lys Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105

<210> SEQ ID NO 276
<211> LENGTH: 107
<212> TYPE: PRT
<213> ORGANISM: Homo sapiens

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Thr Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 277
<211> LENGTH: 107
<212> TYPE: PRT
<213> ORGANISM: Homo sapiens

<400> SEQUENCE: 277

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Arg Gln Gln Asn Thr Tyr Pro Leu
                85                  90                  95

Thr Phe Gly Gly Gly Thr Lys Val Glu Ile Lys
            100                 105
```

<210> SEQ ID NO 278
<211> LENGTH: 122
<212> TYPE: PRT
<213> ORGANISM: Homo sapiens

<400> SEQUENCE: 278

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser
        115                 120
```

<210> SEQ ID NO 279
<211> LENGTH: 124
<212> TYPE: PRT
<213> ORGANISM: Homo sapiens

<400> SEQUENCE: 279

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Val Arg Ser Arg Asn Trp Asn Tyr Asp Asn Tyr Tyr Tyr Gly Leu Asp
            100                 105                 110

Val Trp Gly Gln Gly Thr Thr Val Thr Val Ser Ser
        115                 120
```

<210> SEQ ID NO 280
<211> LENGTH: 123
<212> TYPE: PRT
<213> ORGANISM: Homo sapiens

<400> SEQUENCE: 280

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Cys Val
```

```
                35                  40                  45
Ala Asn Ile Lys Gln Asp Gly Ser Glu Glu Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Ser Ser Trp Tyr Tyr Tyr Asn Tyr Gly Met Asp Val
            100                 105                 110

Trp Gly Gln Gly Thr Thr Val Thr Val Ser Ser
        115                 120
```

<210> SEQ ID NO 281
<211> LENGTH: 11
<212> TYPE: PRT
<213> ORGANISM: Homo sapiens

<400> SEQUENCE: 281

```
Arg Ala Ser Gln Gly Ile Arg Asn Asn Leu Gly
1               5                   10
```

<210> SEQ ID NO 282
<211> LENGTH: 11
<212> TYPE: PRT
<213> ORGANISM: Homo sapiens

<400> SEQUENCE: 282

```
Arg Ala Ser Gln Gly Ile Arg Asn Asp Leu Gly
1               5                   10
```

<210> SEQ ID NO 283
<211> LENGTH: 7
<212> TYPE: PRT
<213> ORGANISM: Homo sapiens

<400> SEQUENCE: 283

```
Ala Ala Ser Ser Leu Gln Ser
1               5
```

<210> SEQ ID NO 284
<211> LENGTH: 9
<212> TYPE: PRT
<213> ORGANISM: Homo sapiens

<400> SEQUENCE: 284

```
Arg Gln Gln Asn Thr Tyr Pro Leu Thr
1               5
```

<210> SEQ ID NO 285
<211> LENGTH: 10
<212> TYPE: PRT
<213> ORGANISM: Homo sapiens

<400> SEQUENCE: 285

```
Gly Phe Thr Phe Ser Ser Tyr Gly Met His
1               5                   10
```

<210> SEQ ID NO 286
<211> LENGTH: 10
<212> TYPE: PRT
<213> ORGANISM: Homo sapiens

<400> SEQUENCE: 286

-continued

Gly Phe Thr Phe Ser Ser Tyr Trp Met Ser
1               5                   10

<210> SEQ ID NO 287
<211> LENGTH: 17
<212> TYPE: PRT
<213> ORGANISM: Homo sapiens

<400> SEQUENCE: 287

Asn Ile Lys Gln Asp Gly Ser Glu Glu Tyr Tyr Val Asp Ser Val Lys
1               5                   10                  15
Gly

<210> SEQ ID NO 288
<211> LENGTH: 14
<212> TYPE: PRT
<213> ORGANISM: Homo sapiens

<400> SEQUENCE: 288

Gly Ser Ser Ser Trp Tyr Tyr Tyr Asn Tyr Gly Met Asp Val
1               5                   10

<210> SEQ ID NO 289
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Gly Gly Gly Gly Gly
1               5

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Gly Gly Gly Gly Gly Gly Gly
1               5

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
gaaaaggagc agtcgcacag a                                            21

<210> SEQ ID NO 292
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292

-continued cttctggtgg gagtagcgg                                           19

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 293
atgctgcagg cccggcagtc                                          20

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
cccttgcttt ggctgagagg a                                        21

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
tcacaggtcg tcgtaggtcg                                          20

<210> SEQ ID NO 296
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
tgtgccgggg agaagag                                             17

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tacagtagtg ggttgaggtt c                                        21

<210> SEQ ID NO 298
<211> LENGTH: 33
<212> TYPE: DNA
<213> ORGANISM: Homo sapiens

<400> SEQUENCE: 298
tctggagata aattggggga taaatatgct tgt                            33

```
<210> SEQ ID NO 299
<211> LENGTH: 21
<212> TYPE: DNA
<213> ORGANISM: Homo sapiens

<400> SEQUENCE: 299
caagatagca agcggccctc a                                              21

<210> SEQ ID NO 300
<211> LENGTH: 27
<212> TYPE: DNA
<213> ORGANISM: Homo sapiens

<400> SEQUENCE: 300
caggcgtggg acagcagcac tgcggta                                        27

<210> SEQ ID NO 301
<211> LENGTH: 30
<212> TYPE: DNA
<213> ORGANISM: Homo sapiens

<400> SEQUENCE: 301
ggttacacct ttaccagtta tggtctcagc                                     30

<210> SEQ ID NO 302
<211> LENGTH: 51
<212> TYPE: DNA
<213> ORGANISM: Homo sapiens

<400> SEQUENCE: 302
tggatcatcc cttacaatgg taacacaaac tctgcacaga aactccaggg c             51

<210> SEQ ID NO 303
<211> LENGTH: 39
<212> TYPE: DNA
<213> ORGANISM: Homo sapiens

<400> SEQUENCE: 303
gacagggact acggtgtcaa ttatgatgct tttgatatc                           39

<210> SEQ ID NO 304
<211> LENGTH: 33
<212> TYPE: DNA
<213> ORGANISM: Homo sapiens

<400> SEQUENCE: 304
cgggcaagtc agggcattag aaataattta ggc                                 33

<210> SEQ ID NO 305
<211> LENGTH: 21
<212> TYPE: DNA
<213> ORGANISM: Homo sapiens

<400> SEQUENCE: 305
gctgcatcca gtttgcaaag t                                              21

<210> SEQ ID NO 306
<211> LENGTH: 30
<212> TYPE: DNA
<213> ORGANISM: Homo sapiens

<400> SEQUENCE: 306
ggattcacct tcagtagtta cggcatgcac                                     30
```

```
<210> SEQ ID NO 307
<211> LENGTH: 33
<212> TYPE: DNA
<213> ORGANISM: Homo sapiens

<400> SEQUENCE: 307
cgggcaagtc agggcattag aaatgattta ggc                                    33

<210> SEQ ID NO 308
<211> LENGTH: 21
<212> TYPE: DNA
<213> ORGANISM: Homo sapiens

<400> SEQUENCE: 308
gctgcatcca gtttgcaaag t                                                 21

<210> SEQ ID NO 309
<211> LENGTH: 27
<212> TYPE: DNA
<213> ORGANISM: Homo sapiens

<400> SEQUENCE: 309
cgacagcaaa atacttaccc gctcact                                           27

<210> SEQ ID NO 310
<211> LENGTH: 30
<212> TYPE: DNA
<213> ORGANISM: Homo sapiens

<400> SEQUENCE: 310
ggattcacct ttagtagtta ttggatgagc                                        30

<210> SEQ ID NO 311
<211> LENGTH: 51
<212> TYPE: DNA
<213> ORGANISM: Homo sapiens

<400> SEQUENCE: 311
aacataaagc aagatggaag tgaggaatac tatgtggact ctgtgaaggg c                51

<210> SEQ ID NO 312
<211> LENGTH: 42
<212> TYPE: DNA
<213> ORGANISM: Homo sapiens

<400> SEQUENCE: 312
ggtagcagca gctggtacta ctacaactac ggtatggacg tc                          42
```

ADMINISTRATION OF AN ANTI-ACTIVIN-A COMPOUND TO A SUBJECT

CROSS REFERENCE TO RELATED APPLICATIONS

This application is a divisional application of U.S. patent application Ser. No. 14/764,288, filed Jul. 29, 2015; which is a national stage application under 35 U.S.C. § 371 of International Application No. PCT/US2014/014490, having an international filing date of Feb. 3, 2014; which claims the benefit of U.S. Provisional Application No. 61/759,961, filed Feb. 1, 2013, and U.S. Provisional Application No. 61/815,220, filed Apr. 23, 2013, all of which are incorporated by reference herein in their entireties.

This application is further related to: U.S. application Ser. No. 12/626,375, filed Nov. 25, 2009; U.S. application Ser. No. 13/080,515, filed Apr. 5, 2011; U.S. application Ser. No. 13/329,897, filed Dec. 19, 2011; U.S. application Ser. No. 13/550,447, filed Jul. 16, 2012; U.S. Pat. No. 8,309,082, filed Sep. 7, 2007; U.S. Pat. No. 7,947,646, filed Mar. 5, 2008; PCT Application No. WO 2008/031061, filed Sep. 7, 2007; PCT Application No. WO 2008/109167, filed Mar. 6, 2008; and PCT Application No. WO 2010/062383, filed Nov. 25, 2009, all herein incorporated in their entirety by reference.

REFERENCE TO A SEQUENCE LISTING

This application includes a Sequence Listing submitted electronically as an ASCII text file. The sequence listing is incorporated by reference. The SEQ ID NO identifiers shown in the sequence listing should be disregarded. Said ASCII copy, created on Dec. 13, 2019, is named A-1798-US-PCD_Sequence_Listing.txt and is 218,613 bytes in size.

BACKGROUND

Activin-A is a member of the TGF-β family that was originally identified in gonadal fluids. It plays an important role in regulating the menstrual cycle by controlling Follicle Stimulating Hormone (FSH) release from the pituitary gland. Activin-A is also known to serve diverse other functions such as in cell growth and differentiation, immune responses, and wound healing.

Ovarian cancer is the deadliest of all gynecologic cancers. In the United States, approximately one in every 60 women develops ovarian cancer, and more than 25,000 new cases are diagnosed each year. Less than 25% of ovarian cancer cases are diagnosed before cancer has spread beyond the ovary, and the chance of five-year survival for late stage ovarian cancer is less than 30%.

SUMMARY

Disclosed herein are methods for treating ovarian cancer in a subject by administering anti-activin-A compounds to the subject, including anti-activin-A antibodies and/or activin receptors. Also disclosed are methods of identifying subjects for treatment of ovarian cancer by evaluating levels of specific proteins in a subject.

In one embodiment, the method comprises administering a therapeutically effective amount of an anti-activin-A compound to a subject. In another embodiment, the anti-activin-A compound is formulated with a pharmaceutically-acceptable carrier.

In a further embodiment, the anti-activin-A compound comprises:
(a) a light chain CDR3 comprising a sequence selected from the group consisting of:
 i. a light chain CDR3 sequence that differs by no more than a total of two amino acid additions, substitutions, and/or deletions from a CDR3 sequence selected from the group consisting of the light chain CDR3 sequences disclosed herein, and;

| | | |
|---|---|---|
| ii. | $X_{73}QX_{74}X_{75}X_{76}X_{77}X_{78}X_{79}X_{80}$; | (SEQ ID NO: 132) |
| iii. and | $LQHNX_{81}YX_{82}X_{83}T$; | (SEQ ID NO: 131) |
| iv. | $QAWDX_{84}STX_{85}X_{86}$; | (SEQ ID NO: 248) | wherein $X_{73}$ is a methionine residue, a glutamine residue, or an arginine residue, $X_{74}$ is an alanine residue, a tyrosine residue, a glutamine residue, or a serine residue, $X_{75}$ is a leucine residue, a tyrosine residue, or an asparagine residue, $X_{76}$ is a glutamine residue, a serine residue, or a threonine residue, $X_{77}$ is a threonine residue, a tyrosine residue, or an isoleucine residue, $X_{78}$ is a proline residue or a serine residue, $X_{79}$ is a cysteine residue, a tryptophan residue, a leucine residue, or a proline residue, $X_{80}$ is a serine residue or a threonine residue, $X_{81}$ is a threonine residue or a serine residue, $X_{82}$ is a proline residue or a threonine residue, $X_{83}$ is a phenylalanine residue or a tryptophan residue, $X_{84}$ is an arginine residue or a serine residue, $X_{85}$ is a valine residue or an alanine residue, and $X_{86}$ is a valine residue or no residue, and said anti-activin-A compound binds specifically to human activin-A; or (b) a heavy chain CDR3 comprising a sequence selected from the group consisting of:
 i. a heavy chain CDR3 sequence that differs by no more than a total of three amino acid additions, substitutions, and/or deletions from a CDR3 sequence selected from the group consisting of the heavy chain CDR3 sequences disclosed herein;

| | | |
|---|---|---|
| ii. | $X_{87}X_{88}X_{89}X_{90}X_{91}X_{92}X_{93}X_{94}FDY$; | (SEQ ID NO: 187) |
| iii. and | $X_{95}X_{96}X_{97}Y\ X_{98}\ D\ X_{99}\ X_{100}\ GWX_{101}X_{102}X_{103}$; | (SEQ ID NO: 188) |
| iv. | $X_{104}X_{105}X_{106}X_{107}X_{108}X_{109}YX_{110}X_{111}X_{112}X_{113}X_{114}X_{115}X_{116}X_{117}X_{118}$; | (SEQ ID NO: 249) | wherein $X_{87}$ is a valine residue or no residue, $X_{88}$ is a glutamine residue or no residue, $X_{89}$ is an aspartate residue, a tryptophan residue, or no residue, $X_{90}$ is a serine residue, a leucine residue, or no residue, $X_{91}$ is an isoleucine residue, a glutamate residue, or a glutamine residue, $X_{92}$ is an alanine residue, a leucine residue, or a glycine residue, $X_{93}$ is an alanine residue or a leucine residue, $X_{94}$ is a proline residue, a tyrosine residue, or a glycine residue, $X_{95}$ is an aspartate residue or no residue, $X_{96}$ is a glutamine residue or no residue, $X_{97}$ is an aspartate residue or an alanine residue, $X_{98}$ is a tyrosine residue or a glycine residue, $X_{99}$ is a serine residue or a tyrosine residue, $X_{100}$ is a serine residue or an arginine residue, $X_{101}$ is a phenylalanine residue or no residue, $X_{102}$ is a glycine residue or an aspartate residue, $X_{103}$ is a histidine residue or a proline residue, $X_{104}$ is a glycine residue or no residue $X_{105}$ is a serine residue, a glutamate residue, or no residue $X_{106}$ is an arginine residue, a serine residue, or no residue, $X_{107}$ is an aspartate residue, an asparagine residue, a serine residue, or a glutamine residue $X_{108}$ is a serine residue, an arginine residue, or a tryptophan residue, $X_{109}$ is a glycine residue, an aspartate residue, an asparagine residue, a tyrosine residue, or a leucine residue, $X_{110}$ is a serine residue, a glycine residue, an aspartate residue, or no residue, $X_{111}$ is a serine residue, a valine residue, an asparagine residue, or a tyrosine residue, $X_{112}$ is a serine residue, an asparagine residue, a tyrosine residue, or a histidine residue $X_{113}$ is a tryptophan residue, a tyrosine residue, or a glutamine residue, $X_{114}$ is a histidine residue, an aspartate residue, a tyrosine residue, or no residue, $X_{115}$ is a phenylalanine residue, an alanine residue, or a glycine residue, $X_{116}$ is an aspartate residue, a phenylalanine residue, a leucine residue, or a methionine residue, $X_{117}$ is a tyrosine residue, or an aspartate residue, $X_{118}$ is an isoleucine residue, a valine residue, or no residue, and said anti-activin-A compound binds specifically to human activin-A; or (c) the light chain CDR3 sequence of (a) and the heavy chain CDR3 sequence of (b), and said anti-activin-A compound binds specifically to human activin-A.

In another embodiment, the anti-activin-A compound comprises:
(a) a light chain variable domain comprising: i. a light chain CDR1 sequence disclosed herein; ii. a light chain CDR2 sequence disclosed herein; and iii. a light chain CDR3 sequence disclosed herein; or
(b) a heavy chain variable domain comprising: i. a heavy chain CDR1 sequence disclosed herein; ii. a heavy chain CDR2 sequence disclosed herein; and iii. a heavy chain CDR3 sequence disclosed herein; or
(c) the light chain variable domain of (a) and the heavy chain variable domain of (b).

In another embodiment, the anti-activin-A compound comprises:
(a) a light chain variable domain sequence selected from the group consisting of: i. a sequence of amino acids at least 80% identical to a light chain variable domain sequence of L1-L14 of a light chain variable domain sequence disclosed herein; ii. a sequence of amino acids encoded by a polynucleotide sequence that is at least 80% identical to a polynucleotide sequence encoding a light chain variable domain sequence of L1-L14 of a light chain variable domain sequence disclosed herein; and iii. a sequence of amino acids encoded by a polynucleotide sequence that hybridizes under moderately stringent conditions to the complement of a polynucleotide consisting of a light chain variable domain sequence of L1-L14 of a light chain variable domain sequence disclosed herein; or
(b) a heavy chain variable domain sequence selected from the group consisting of: i. a sequence of amino acids at least 80% identical to a heavy chain variable domain sequence of H1-H14 of a heavy chain variable domain sequence disclosed herein; ii. a sequence of amino acids encoded by a polynucleotide sequence that is at least 80% identical to a polynucleotide sequence encoding a heavy chain variable domain sequence of H1-H14 of a heavy chain variable domain sequence disclosed herein; and iii. a sequence of amino acids encoded by a polynucleotide sequence that hybridizes under moderately stringent conditions to the complement of a polynucleotide consisting of a heavy chain variable domain sequence of H1-H14 of a heavy chain variable domain sequence disclosed herein; or
(c) the light chain variable domain of (a) and the heavy chain variable domain of (b); wherein said antigen binding protein binds to human activin-A.

In another embodiment, the anti-activin-A compound comprises:
(a) a light chain variable domain sequence selected from the group consisting of L1-L14 of a light chain variable domain sequence disclosed herein; or
(b) a heavy chain variable domain sequence selected from the group consisting of H1-H14 of a heavy chain variable domain sequence disclosed herein; or
(c) the light chain variable domain of (a) and the heavy chain variable domain of (b).

In another embodiment, the anti-activin-A compound comprises a stabilized activin IIB receptor polypeptide (svActRIIB), wherein said polypeptide is selected from the group consisting of:
(a) a polypeptide comprising a variant of the sequence set forth in SEQ ID NO: 2, wherein said variant sequence comprises an amino acid substitution at position 28, and an amino acid substitution at position 44, wherein the substitution at position 28 is selected from the group consisting of W and Y, and the substitution at position 44 is T;
(b) a polypeptide comprising a variant of the sequence set forth in amino acids 19 through 134 of SEQ ID NO: 2, wherein said variant sequence comprises an amino acid substitution at position 28, and an amino acid substitution at position 44, wherein the substitution at position 28 is selected from the group consisting of W and Y, and the substitution at position 44 is T;
(c) a polypeptide comprising a variant of the sequence set forth in amino acids 23 through 134 of SEQ ID NO: 2, wherein said variant sequence comprises an amino acid substitution at position 28, and an amino acid substitution at position 44, wherein the substitution at position 28 is selected from the group consisting of W and Y, and the substitution at position 44 is T;
(d) a polypeptide comprising a variant of the sequence set forth in amino acids 25 through 134 of SEQ ID NO: 2, wherein said variant sequence comprises an amino acid substitution at position 28, and an amino acid substitution at position 44, wherein the substitution at position 28 is selected from the group consisting of W and Y, and the substitution at position 44 is T; and
(e) a polypeptide having at least 80% sequence identity to any one of (a) through (d), wherein the sequence comprises an amino acid substitution at position 28, and an amino acid substitution at position 44, wherein the substitution at position 28 is selected from the group consisting of W and Y, and the substitution at position 44 is T, wherein the polypeptide is capable of binding myostatin, activin-A, or GDF-11.

In another embodiment, the anti-activin-A compound comprises a stabilized activin IIB receptor polypeptide (svActRIIB), wherein said polypeptide is selected from the group consisting of:

(a) a polypeptide consisting of the sequence set forth in the group consisting of SEQ ID NO: 4, 6, 12 and 14;
(b) a polypeptide having at least 90% sequence identity to (a), wherein the polypeptide has a W or a Y at position 28 and a T at position 44, wherein the polypeptide is capable of binding myostatin, activin-A, or GDF-11, and
(c) a polypeptide having at least 95% sequence identity to (a), wherein the polypeptide has a W or a Y at position 28 and a T at position 44, wherein the polypeptide is capable of binding myostatin, activin-A, or GDF-11.

In a further embodiment, the polypeptide is operably linked to at least one heterologous polypeptide. In another embodiment, the polypeptide comprises an alanine residue at position 64. In another embodiment, the heterologous polypeptide comprises an IgG Fc domain. In another embodiment, the heterologous polypeptide is operably linked to the anti-activin-A compound by a linker sequence. In a further embodiment, the linker is selected from the group consisting of: SEQ ID NO: 25, SEQ ID NO: 27, SEQ ID NO: 38, SEQ ID NO: 40, SEQ ID NO: 42, SEQ ID NO: 44, SEQ ID NO: 45, SEQ ID NO: 46, SEQ ID NO: 48, SEQ ID NO: 49 and SEQ ID NO: 50.

In another embodiment, the anti-activin-A compound comprises a polypeptide selected from the group consisting of:
(a) a polypeptide consisting of the sequence set forth in the group consisting of SEQ ID NO: 8, 10, 16 and 18;
(b) a polypeptide having at least 90% sequence identity to (a), wherein the polypeptide has a W or a Y at position 28 and a T at position 44, wherein the polypeptide is capable of binding myostatin, activin-A, or GDF-11, and
(c) a polypeptide having at least 95% sequence identity to (a), wherein the polypeptide has a W or a Y at position 28 and a T at position 44, wherein the polypeptide is capable of binding myostatin, activin-A, or GDF-11.

In some embodiments, a method of treating ovarian cancer (including serous ovarian cancer and clear cell ovarian cancer) in a subject comprises administering a therapeutically effective amount of at least two compounds: a first compound and a second compound, wherein the first compound is an anti-activin-A compound, and wherein the second compound is a chemotherapeutic compound. For example, the chemotherapeutic compound can be capecitabine, or a doxorubicin lipid complex. In a further embodiment, one or more of the at least two compounds is formulated with a pharmaceutically-acceptable carrier. In another embodiment, the second compound is administered after the first compound is administered. In another embodiment, the first compound is administered after the second compound is administered. In another embodiment, the first compound and the second compound are administered simultaneously.

In a further embodiment, the subject is identified by detecting elevated levels of biomarker CA-125 and/or activin-A in the subject compared to a control. In another embodiment, the subject is identified by a method comprising: evaluating the subject's expression levels of biomarker CA-125 and/or activin-A; comparing the subject's expression levels of biomarker CA-125 and/or activin-A to expression levels of biomarker CA-125 and/or activin-A in a negative control sample; and determining that the expression levels of biomarker CA-125 and/or activin-A factors in the subject exceed the expression levels of biomarker CA-125 and/or activin-A in the negative control sample. In another embodiment, the subject is identified by a method comprising: evaluating the subject's expression levels of biomarker CA-125 and/or activin-A; comparing the subject's expression levels of biomarker CA-125 and/or activin-A to expression levels of biomarker CA-125 and/or activin-A in a positive control sample; and determining that the expression levels of biomarker CA-125 and/or activin-A factors in the subject meet or exceed the expression levels of biomarker CA-125 and/or activin-A in the positive control sample.

In another embodiment, the subject is identified by detecting elevated levels of activin-A, VEGF, and/or Ang-1 factors in the subject compared to a control. In another embodiment, the subject is identified by a method comprising: evaluating the subject's expression levels of activin-A, VEGF, and/or Ang-1 factors; comparing the subject's expression levels of activin-A, VEGF, and/or Ang-1 factors to expression levels of activin-A, VEGF, and/or Ang-1 factors in a negative control sample; and determining that the expression levels of activin-A, VEGF, and/or Ang-1 factors in the subject exceed the expression levels of activin-A, VEGF, and/or Ang-1 factors in the negative control sample. In another embodiment, the subject is identified by a method comprising: evaluating the subject's expression levels of activin-A, VEGF, and/or Ang-1 factors; comparing the subject's expression levels of activin-A, VEGF, and/or Ang-1 factors to expression levels of activin-A, VEGF, and/or Ang-1 factors in a positive control sample; and determining that the expression levels of activin-A, VEGF, and/or Ang-1 factors in the subject meet or exceed the expression levels of activin-A, VEGF, and/or Ang-1 factors in the positive control sample.

In another embodiment, the anti-activin-A compound is administered to a subject subcutaneously, intravenously, or intraperitoneally. In a further embodiment, the anti-activin-A compound is administered to a subject once a week at a dosage of at least 0.5 mg/kg. In another embodiment, the capecitabine is administered to a subject subcutaneously, intravenously, intraperitoneally. In a further embodiment, the capecitabine is administered to a subject orally. In a further embodiment, the capecitabine is administered to a subject twice daily for two weeks at a dosage of 1250 mg/m$^2$. In some embodiments, there is a one week rest period after the capecitabine is administered for two weeks. In another embodiment, the doxorubicin lipid complex is administered to a subject subcutaneously, intravenously, or intraperitoneally. In another embodiment, the doxorubicin lipid complex is administered to a subject once every four weeks at a dosage of 40 mg/m$^2$IV.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 4A is a graph showing the effects of sActRIIB treatment on the testicular tumor mass in inh-KO mice over time. In each group of 3 bars, the left bar is wild-type, the middle bar is KO plus PBS, and the right bar is KO plus sActRIIB.

FIG. 4B is a representative gross morphology depicting advanced testicular tumors in inh-KO mice after sActRIIB treatment. Scale bar=10 mm.

FIG. 5A shows two Northern blot analyses of activin-A mRNA in the ovarian tumors of inh-KO mice after sActRIIB treatment. n=10

FIG. 5B shows two Western blot analyses of p-Smad2 signaling in the ovarian tumors of inh-KO mice after sActRIIB treatment. n=10

FIG. 15B shows representative images of immunostaining depicting the effects of sActRIIB treatment on CD31 in TOV-21G xenograft tumors in mice. The bar graph shows the quantitative analysis of CD31 immunoreactivity. *$p<0.05$; $p<0.01$; *$p<0.001$.

FIG. 15C shows representative images of immunostaining depicting the effects of sActRIIB treatment on caspase-3 activation and cell apoptosis in TOV-21G xenograft tumors in mice. The bar graphs show the quantitative analysis of caspase-3 immunoreactivity and immunoreactivity changes due to apoptosis. *$p<0.05$; $p<0.01$; *$p<0.001$.

FIG. 38 shows the effect of activin-A antibody in combination with doxorubicin on muscle mass in TOV-21G tumor-bearing mice. Lean carcass and calf muscle weights were determined at terminal necropsy procedures. Data were plotted as mean±SEM; n=8-14 per group. Standard 2-tailed Student's t-test (MS Excel 5.0) was used to analyze the differences between groups. Statistical significance is represented by *: p<0.05; : p<0.01; *: p<0.001.

DETAILED DESCRIPTION

Figure 1:
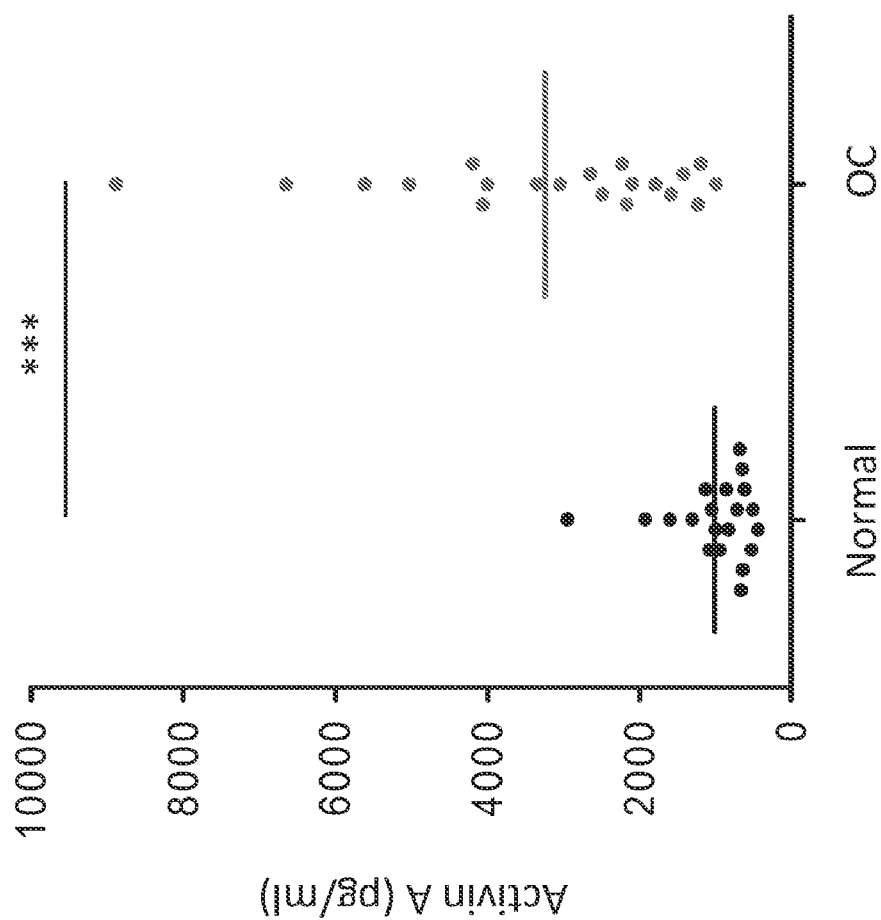
FIG. 1 shows activin-A levels in ovarian cancer subjects (OC) and normal control subjects. ***$p<0.001$; student's t-test; n=20.

The present invention relates to the effects of blocking activin-A. Blocking activin-A in vivo reduces several tumor angiogenesis factors and prevents tumor neovascularization, thereby inducing tumor apoptosis. In some aspects, the invention provides methods for identifying ovarian cancer in a subject by evaluating the subject's expression levels of various factors. In some aspects, the invention also provides methods of treating ovarian cancer, including serous ovarian cancer, by administering anti-activin-A compounds, including anti-activin-A antibodies and activin receptors, to a subject. In some aspects, the invention further provides methods of treating ovarian cancer, including serous ovarian cancer, clear cell ovarian cancer, Granulosa cell ovarian cancer, Leydig cell tumors, and sex cord stromal testicular tumors, by administering at least an anti-activin-A compound and a chemotherapeutic compound to a subject.

The details of one or more embodiments are set forth in the description below. Other features, objects, and advantages will be apparent from the description and the drawings, and from the claims.

Activin-A is the homodimer of the polypeptide chains βA (see GenBank Accession No: NM_002192). Activins A, B, and AB are the homodimers and heterodimer respectively of two polypeptide chains, βA and βB. The term "activin" refers to activin-A, -B, and -AB, as well as variants and species homologs of that protein.

The present invention provides compositions, kits, and methods relating to molecules that bind to activin-A, including molecules and antigen-binding proteins that agonize or antagonize activin-A, such as activin IIB receptor polypeptides (svActRIIB), svActRIIB fragments, svActRIIB derivatives, anti-activin-A antibodies, antibody fragments, and antibody derivatives, e.g., antagonistic anti-activin-A antibodies, antibody fragments, or antibody derivatives. Also provided are compositions, kits, and methods relating to molecules that specifically bind to a portion of activin-A, such as amino acids R13-Y39, or amino acids V82-N107 of activin-A. Such molecules can include antibodies, antibody fragments, and antibody derivatives. Also provided are nucleic acids, and derivatives and fragments thereof, comprising a sequence of nucleotides that encodes all or a portion of a polypeptide that binds to activin-A, e.g., a nucleic acid encoding all or part of an activin IIB receptor, svActRIIB fragment, svActRIIB derivative, anti-activin-A antibody, antibody fragment, antibody variant, or antibody derivative, plasmids and vectors comprising such nucleic acids, and cells or cell lines comprising such nucleic acids and/or vectors and plasmids. The provided methods include, for example, methods of making, identifying, or isolating molecules that bind to activin-A, such as activin IIB receptors, anti-activin-A antibodies, methods of determining whether a molecule binds to activin-A, methods of making compositions, such as pharmaceutical compositions, comprising a molecule that binds to activin-A, and methods for administering a molecule that binds activin-A to a subject, for example, methods for treating a condition mediated by activin-A, and for modulating a biological activity of activin-A in vivo or in vitro.

The present invention relates to regions of the human activin-A that contain cysteine knot domains recognized by antibodies that also bind to full-length activin-A, and/or a region of activin-A that overlaps or encompasses a cysteine knot region of activin-A, and methods of making and using these cysteine knot domains. The invention also provides antigen binding agents, including antibodies, that specifically bind to activin-A or portions of activin-A, and methods for using such binding agents. The binding agents are useful to block or impair binding of human activin-A to one or more ligand.

Activins can interact with two structurally related classes of serine/threonine kinase receptors (type I and type II). Inhibin antagonizes activin by binding to the proteoglycan, betaglycan, and forming a stable complex with and thereby sequestering type II activin receptors while excluding type I receptors. Two major forms of activin exist: activin-A is a homodimer of $β_A$-subunits and activin B is a homodimer of $β_B$-subunits. (Vale, et al., *Recent Prog Horm Res* V. 44: 1-34, 1988). Heterodimers of an α-subunit that is dissimilar to either β-subunit results in the functional antagonist inhibin.

The literature has shown that activin-A is overexpressed and/or localized in cancer tissues. For example, high levels of serum activin-A were found in women with endometrial and cervical carcinoma (Petraglia, F. et al., *Jour. Clin. Endocrin. Metab.* 83:1194-1200, 1998). Activin-A was overexpressed in stage IV colorectal cancer (Wildi, S. et al., Gut 49:409-417, 2001). A role of activin-A in ovarian cancer was reported (Steller, M. D. et al., *Mol. Cancer Res.* 3:50-61, 2005).

The literature has also implicated activin-A in renal disease. (Yamashita, S. et al. *J. Am. Soc. Nephrol.* 15:91-101, 2004.) Serum immunoreactive activin-A levels in normal subjects and patients with disease were reported by Harada, K. et al. in *J. Clin. Endocrin. and Metab.* 81:2125-2130, 1996. Activin-A is a potent activator of renal interstitial fibroblasts (Harada, K. et al., *J. Am. Soc. Nephrol.* 15:91-101, 2004). Glomerular activin-A overexpression is linked to fibrosis in anti-Thy 1 glomerulonephritis (Gaedeke, J. et al., *Neph. Dial. Transpl.* 20:319-328, 2005).

Serum activin-A levels in heart failure patients increased according to disease severity (Yndestal et al., *Circulation* 109:1379-1385, 2004). In a rat model of heart failure, serum activin-A elevated immediately after myocardial infarct and persisted for six months, and activin-A immunostaining was localized solely to cardiomyocytes (Yndestad et al., 2004). Elevated levels of activin-A were reported in heart failure (Yndestad, A. et al., *Circulation* 109:1379-1385, 2004).

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art.

Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with at least one naturally associated component that accompany it in its native state, (2) is substantially free of other molecules from the same species (3) is expressed by a cell from a different species, or (4) does not occur in nature. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "anti-activin-A compound", "activin-A inhibitor" and "activin-A antagonist" are used interchangeably. Each is a molecule that detectably inhibits at least one function of activin-A. Conversely, an "activin-A agonist" is a molecule that detectably increases at least one function of activin-A. The inhibition caused by an activin-A inhibitor need not be complete so long as it is detectable using an assay. Any assay of a function of activin-A can be used, examples of which are provided herein. Examples of functions of activin-A that can be inhibited by an activin-A inhibitor, or increased by an activin-A agonist, include binding to activin-A. Examples of types of activin-A inhibitors and activin-A agonists include, but are not limited to, activin-A binding polypeptides such as antigen binding proteins (e.g., activin-A inhibiting antigen binding proteins), activin IIB receptors (svActRIIB), svActRIIB fragments, svActRIIB derivatives, antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric. Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence. Unless otherwise indicated, it is understood that polynucleotide and polypeptide sequences include each nucleic acid or amino acid listed, respectively, as well as the intervening nucleic acids or amino acids. For example, the polypeptide sequence R13-Y39 sets forth a polypeptide sequence that includes the amino acids R13, and Y39, as well as the amino acids found between R13 and Y39 in the polypeptide sequence. Correspondingly, the polynucleotide sequence C1-T5 sets forth a polynucleotide sequence that includes nucleic acids C1, and T5, as well as nucleic acids at positions 2, 3, and 4 of the sequence. Accordingly, designations of SEQ ID NO: 1-5 likewise designates the inclusive group of SEQ ID NO: 1, SEQ ID NO: 2, SEQ ID NO: 3, SEQ ID NO: 4, and SEQ ID NO: 5. Finally, amino acid groupings are also intended to be inclusive, unless otherwise designated. For example, the phrase "amino acids 1-5 of SEQ ID NO: 28" includes amino acids at positions 1, 2, 3, 4, and 5 of SEQ ID NO: 28.

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

A "variant" of a polypeptide (e.g., an antibody) comprises an amino acid sequence wherein one or more amino acid residues are inserted into, deleted from and/or substituted into the amino acid sequence relative to the native polypeptide sequence, and retains essentially the same biological activity as the native polypeptide. The biological activity of the polypeptide can be measured using standard techniques in the art (for example, if the variant is an antibody, its activity may be tested by binding assays, as described herein). Variants of the invention include fragments, analogs, recombinant polypeptides, synthetic polypeptides, and/or fusion proteins. A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation.

Unless otherwise indicated, the term "antibody" includes, in addition to antibodies comprising two full-length heavy chains and two full-length light chains, derivatives, variants, fragments, and muteins thereof, examples of which are described below.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

The term percent "identity," in the context of two or more nucleic acid or polypeptide sequences, refer to two or more sequences or subsequences that have a specified percentage of nucleotides or amino acid residues that are the same, when compared and aligned for maximum correspondence, determined by comparing the sequences using the GAP computer program (a part of the GCG Wisconsin Package, version 10.3 (Accelrys, San Diego, Calif.)) using its default parameters. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include CS-9 cells, the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) can be isolated from B-cells of mice that have been immunized with activin-A. The nucleic acid can be isolated by conventional procedures such as polymerase chain reaction (PCR).

Nucleic acid sequences encoding the variable regions of the heavy and light chain variable regions are shown herein. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of any of A1-A14) under particular hybridization conditions. Methods for hybridizing nucleic acids are well-known in the art. See, e.g., Curr. Prot. in Mol. Biol., John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98, or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Curr. Prot. in Mol. Biol. 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues are changed using, for example, a random mutagenesis protocol. However it is made, a mutant polypeptide can be expressed and screened for a desired property (e.g., binding to activin-A).

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for A1-A14, or a desired fragment, variant, or derivative thereof, is mutated such that it encodes an amino acid sequence comprising one or more deletions or substitutions of amino acid residues that are shown herein for A1-A14 to be residues where two or more sequences differ. As described herein inter alia, A1-A14 refers to 14 sequences, A1, and A14, as well as the 12 intervening amino acid residues. In another embodiment, the mutagenesis inserts an amino acid adjacent to one or more amino acid residues shown herein for A1-A14 to be residues where two or more sequences differ. Alternatively, one or more mutations can be introduced into a nucleic acid that selectively change the biological activity (e.g., binding of activin-A) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., an activin-A binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

Expression Vectors

The present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

In another aspect of the present invention, expression vectors containing the nucleic acid molecules and polynucleotides of the present invention are also provided, and host cells transformed with such vectors, and methods of producing the polypeptides are also provided. The term "expression vector" refers to a plasmid, phage, virus or vector for expressing a polypeptide from a polynucleotide sequence. Vectors for the expression of the polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes polypeptides and proteins to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of polypeptides in targeted human or animal cells. For example, an expression vector suitable for expression of svActRIIB is the pDSRa, (described in WO 90/14363, herein incorporated by reference) and its derivatives, containing svActRIIB polynucleotides, as well as any additional suitable vectors known in the art.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, *Trends Biochem. Sci.* 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The invention further provides methods of making polypeptides. A variety of other expression/host systems may be utilized. Vector DNA can be introduced into prokaryotic or eukaryotic systems via conventional transformation or transfection techniques. These systems include but are not limited to microorganisms such as bacteria (for example, *E. coli*) transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein production include but are not limited to VERO cells, HeLa cells, Chinese hamster ovary (CHO) cell lines, or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20) COS cells such as the COS-7 line of monkey kidney cells (ATCC CRL 1651) (see Gluzman et al., 1981, Cell 23:175), W138, BHK, HepG2, 3T3 (ATCC CCL 163), RIN, MDCK, A549, PC12, K562, L cells, C127 cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Mammalian expression allows for the production of secreted or soluble polypeptides which may be recovered from the growth medium.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Once such cells are transformed with vectors that contain selectable markers as well as the desired expression cassette, the cells can be allowed to grow in an enriched media before they are switched to selective media, for example. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990). Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

In some cases, such as in expression using procaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization; however a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithiobME. In many instances, a co-solvent may be used to increase the efficiency of the refolding. Commonly used cosolvents include glycerol, polyethylene glycol of various molecular weights, and arginine.

In addition, the polypeptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. Ed., Pierce Chemical Co. (1984); Tam et al., J Am Chem Soc, 105:6442, (1983); Merrifield, Science 232:341-347 (1986); Barany and Merrifield, *The Peptides*, Gross and Meienhofer, eds, Academic Press, New York, 1-284; Barany et al., Int J Pep Protein Res, 30:705-739 (1987).

The polypeptides and proteins of the present invention can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography, isoelectric focusing, gel electrophoresis, and combinations of these techniques. As is generally known in the art, it is believed that the order of conducting the various purification steps may be changed, or that certain steps may be omitted, and still result in a suitable method for the preparation of a substantially purified polypeptide. Exemplary purification steps are provided in the Examples below.

Various methods for quantifying the degree of purification of polypeptide will be known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the polypeptide or peptide exhibits a detectable binding activity.

Anti-Activin-A Antibody

Activin-A can be purified from host cells that have been transfected by a gene encoding activin-A by elution of filtered supernatant of host cell culture fluid using a Heparin HP column, using a salt gradient.

The term "antibody" refers to an intact immunoglobulin, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include F(ab')$_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, *Nature Biotech.*, 23, 9, 1126-1136).

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

Polynucleotide and polypeptide sequences of particular light and heavy chain variable domains are described below. Antibodies comprising a light chain and heavy chain are designated by combining the name of the light chain and the name of the heavy chain variable domains. For example, "L4H7," indicates an antibody comprising the light chain variable domain of L4 and the heavy chain variable domain of H7.

Kappa light chain constant sequences are shown in SEQ ID NO: 84, 100 and 108, and heavy chain constant sequence are shown in SEQ ID NOs: 214, 215 and 221. Polynucleotides encoding these sequences are shown in, for the light chains, respectively, SEQ ID NOs: 222, 223 and 239, and for the heavy chains, respectively, SEQ ID NOs: 240, 241, and 242. Thus, in addition to the variable sequences as disclosed herein, an antibody can comprise one or both of SEQ ID NOs: 84 and 214; or SEQ ID NOs: 215 and 223; or SEQ ID NOs: 108 and 221. These sequences are illustrated in the table below:

| SEQ ID NO | Sequence |
|---|---|
| SEQ ID NO: 84 | Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser |
| SEQ ID NO: 100 | Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |
| SEQ ID NO: 108 | Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu Lys His Lys Val Tyr Ala Cys Glu Val Thr His Gln Gly Leu Ser Ser Pro Val Thr Lys Ser Phe Asn Arg Gly Glu Cys |

| SEQ ID NO | Sequence |
|---|---|
| SEQ ID NO: 214 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Asn Phe Gly Thr Gln Thr Tyr Thr Cys Asn Val Asp His Lys Pro Ser Asn Thr Lys Val Asp Lys Thr Val Glu Arg Lys Cys Cys Val Glu Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Gln Phe Asn Trp Tyr Val Asp Gly Val Glu Val His Asn Ala Lys Thr Lys Pro Arg Glu Glu Gln Phe Asn Ser Thr Phe Arg Val Val Ser Val Leu Thr Val Val His Gln Asp Trp Leu Asn Gly Lys Glu Tyr Lys Cys Lys Val Ser Asn Lys Gly Leu Pro Ala Pro Ile Glu Lys Thr Ile Ser Lys Thr Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Met Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| SEQ ID NO: 215 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Asn Phe Gly Thr Gln Thr Tyr Thr Cys Asn Val Asp His Lys Pro Ser Asn Thr Lys Val Asp Lys Thr Val Glu Arg Lys Cys Cys Val Glu Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Gln Phe Asn Trp Tyr Val Asp Gly Val Glu Val His Asn Ala Lys Thr Lys Pro Arg Glu Glu Gln Phe Asn Ser Thr Phe Arg Val Val Ser Val Leu Thr Val Val His Gln Asp Trp Leu Asn Gly Lys Glu Tyr Lys Cys Lys Val Ser Asn Lys Gly Leu Pro Ala Pro Ile Glu Lys Thr Ile Ser Lys Thr Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Met Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| SEQ ID NO: 221 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Asn Phe Gly Thr Gln Thr Tyr Thr Cys Asn Val Asp His Lys Pro Ser Asn Thr Lys Val Asp Lys Thr Val Glu Arg Lys Cys Cys Val Glu Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Gln Phe Asn Trp Tyr Val Asp Gly Val Glu Val His Asn Ala Lys Thr Lys Pro Arg Glu Glu Gln Phe Asn Ser Thr Phe Arg Val Val Ser Val Leu Thr Val Val His Gln Asp Trp Leu Asn Gly Lys Glu Tyr Lys Cys Lys Val Ser Asn Lys Gly Leu Pro Ala Pro Ile Glu Lys Thr Ile Ser Lys Thr Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Met Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys |
| SEQ ID NO: 222 | ggtcagccca aggctgcccc ctcggtcact ctgttcccgc cctcctctga ggagcttcaa gccaacaagg ccacactggt gtgtctcata agtgacttct acccgggagc cgtgacagtg gcctggaagg cagatagcaa ccccgtcaag gcgggagtgg agaccaccac ccctccaaca caaagtacgc ggccagcagc tatctgagcc tgacgcctga gcagtggaag tcccacagaa gctacagctg ccaggtcacg catgaaggga gcaccgtgga gaagacagtg gcccctacag aatgttca |
| SEQ ID NO: 223 | cgaactgtgg ctgcaccatc tgtcttcatc ttcccgccat ctgatgagca gttgaaatct ggaactgcct ctgttgtgtg cctgctgaat aacttctatc ccagagaggc caaagtacag tggaaggtgg ataacgccct ccaatcgggt aactcccagg agagtgtcac agagcaggac agcaaggaca gcacctacag cctcagcagc accctgacgc tgagcaaagc agactacgag aaacacaaag tctacgcctg cgaagtcacc catcagggcc tgagctcgcc cgtcacaaag agcttcaaca ggggagagtg t |
| SEQ ID NO: 239 | cgaactgtgg ctgcaccatc tgtcttcatc ttcccgccat ctgatgagca gttgaaatct ggaactgcct ctgttgtgtg cctgctgaat aacttctatc ccagagaggc caaagtacag tggaaggtgg ataacgccct ccaatcgggt aactcccagg agagtgtcac agagcaggac agcaaggaca gcacctacag cctcagcagc accctgacgc tgagcaaagc agactacgag aaacacaaag tctacgcctg cgaagtcacc catcagggcc tgagctcgcc cgtcacaaag agcttcaaca ggggagagtg t |
| SEQ ID NO: 240 | gcctccacca agggcccatc ggtcttcccc ctggcgccct gctccaggag cacctccgag agcacagcgg ccctgggctg cctggtcaag gactacttcc ccgaaccggt gacggtgtcg tggaactcag gcgctctgac cagcggcgtg cacaccttcc cagctgtcct acagtccagg ggactctact ccctcagcag cgtggtgacc gtgccctcca gcaacttcgg cacccagacc tacacctgca acgtagatca caagcccagc aacaccaagg tggacaagac agttgagcgc aaatgttgtg tcgagtgccc accgtgccca gcaccacctg tggcaggacc gtcagtcttc ctcttccccc caaaacccaa ggacaccctc atgatctctc ggaccctga ggtcacgtgc gtggtggtgg acgtgagcca cgaagacccc gaggtccagt tcaactggta cgtggacggc gtggaggtgc ataatgccaa gacaaagcca cgggaggagc agttcaacag cacgttccgt gtggtcagcg tcctcaccgt tgtgcaccag gactggctga acggcaagga gtacaagtgc aaggtctcca acaaaggcct cccagccccc atcgagaaaa ccatctccaa aaccaaaggg cagccccgag aaccacaggt gtacaccctg cccccatccc gggaggagat gaccaagaac caggtcagcc tgacctgcct ggtcaaaggc ttctacccca gcgacatcgc cgtggagtgg gagagcaatg ggcagccgga |

-continued

| SEQ ID NO | Sequence |
|---|---|
| | gaacaactac aagaccacac ctcccatgct ggactccgac ggctccttct tcctctacag caagctcacc gtggacaaga gcaggtggca gcaggggaac gtcttctcat gctccgtgat gcatgaggct ctgcacaacc actacacgca gaagagcctc tccctgtctc cgggtaaa |
| SEQ ID NO: 241 | gcctccacca agggcccatc ggtcttcccc ctggcgccct gctccaggag cacctccgag agcacagcgg ccctgggctg cctggtcaag gactacttcc ccgaaccggt gacggtgtcg tggaactcag gcgctctgac cagcggcgtg cacaccttcc cagctgtcct acagtcctca ggactctact ccctcagcag cgtggtgacc gtgccctcca gcaacttcgg cacccagacc tacacctgca acgtagatca caagcccagc aacaccaagg tggacaagac agttgagcgc aaatgttgtg tcgagtgccc accgtgccca gcaccacctg tggcaggacc gtcagtcttc ctcttccccc caaaaccccaa ggacaccctc atgatctccc ggacccctga ggtcacgtgc gtggtggtgg acgtgagcca cgaagacccc gaggtccagt tcaactggta cgtggacggc gtggaggtgc ataatgccaa gacaaagcca cgggaggagc agttcaacag cacgttccgt gtggtcagcg tcctcaccgt tgtgcaccag gactggctga acggcaagga gtacaagtgc aaggtctcca acaaaggcct cccagccccc atcgagaaaa ccatctccaa aaccaaaggg cagccccgag aaccacaggt gtacaccctg cccccatccc gggaggagat gaccaagaac caggtcagcc tgacctgcct ggtcaaaggc ttctacccca gcgacatcgc cgtggagtgg gagagcaatg ggcagccgga gaacaactac aagaccacac ctcccatgct ggactccgac ggctccttct tcctctacag caagctcacc gtggacaaga gcaggtggca gcaggggaac gtcttctcat gctccgtgat gcatgaggct ctgcacaacc actacacgca gaagagcctc tccctgtctc cgggtaaa |
| SEQ ID NO: 242 | gcctccacca agggcccatc ggtcttcccc ctggcgccct gctccaggag cacctccgag agcacagcgg ccctgggctg cctggtcaag gactacttcc ccgaaccggt gacggtgtcg tggaactcag gcgctctgac cagcggcgtg cacaccttcc cagctgtcct acagtcctca ggactctact ccctcagcag cgtggtgacc gtgccctcca gcaacttcgg cacccagacc tacacctgca acgtagatca caagcccagc aacaccaagg tggacaagac agttgagcgc aaatgttgtg tcgagtgccc accgtgccca gcaccacctg tggcaggacc gtcagtcttc ctcttccccc caaaaccccaa ggacaccctc atgatctccc ggacccctga ggtcacgtgc gtggtggtgg acgtgagcca cgaagacccc gaggtccagt tcaactggta cgtggacggc gtggaggtgc ataatgccaa gacaaagcca cgggaggagc agttcaacag cacgttccgt gtggtcagcg tcctcaccgt tgtgcaccag gactggctga acggcaagga gtacaagtgc aaggtctcca acaaaggcct cccagccccc atcgagaaaa ccatctccaa aaccaaaggg cagccccgag aaccacaggt gtacaccctg cccccatccc gggaggagat gaccaagaac caggtcagcc tgacctgcct ggtcaaaggc ttctacccca gcgacatcgc cgtggagtgg gagagcaatg ggcagccgga gaacaactac aagaccacac ctcc |

In other embodiments, an antibody may comprise a specific heavy or light chain, while the complementary light or heavy chain variable domain remains unspecified. In particular, certain embodiments herein include antibodies that bind a specific antigen (such as activin-A) by way of a specific light or heavy chain, such that the complementary heavy or light chain may be promiscuous, or even irrelevant, but may be determined by, for example, screening combinatorial libraries. Portolano et al., *J. Immunol.* V. 150 (3), pp. 880-887 (1993); Clackson et al., *Nature* v. 352 pp. 624-628 (1991).

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5th Ed., US Dept. of Health and Human Services, PHS, NIH, NIH Publication no. 91-3242, 1991.

The term "human antibody," also referred to as "fully human antibody," includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-activin-A antibody. In another embodiment, all of the CDRs are derived from a human anti-activin-A antibody. In another embodiment, the CDRs from more than one human anti-activin-A antibodies are mixed and matched in a chimeric antibody. For instance, a chimeric antibody may comprise a CDR1 from the light chain of a first human anti-activin-A antibody, a CDR2 and a CDR3 from the light chain of a second human anti-activin-A antibody, and the CDRs from the heavy chain from a third anti-activin-A antibody. Further, the framework regions may be derived from one of the same anti-activin-A antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind activin-A).

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, *Science* 253:164.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., *Arch. Biochem. Biophys.* 89:230, 1960; Porter, *Biochem. J.* 73:119, 1959; Edelman et al., in *Methods in Enzymology* 1:422 (Academic Press 1967); and by Andrews, S. M. and Titus, J. A. in *Current Protocols in Immunology* (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be incorporated into a molecule either covalently or noncovalently to make it an antigen binding protein. CDRs can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995)).

Thus, in one embodiment, the binding agent comprises at least one CDR as described herein. The binding agent may comprise at least two, three, four, five or six CDR's as described herein. The binding agent further may comprise at least one variable region domain of an antibody described herein. The variable region domain may be of any size or amino acid composition and will generally comprise at least one CDR sequence responsible for binding to human activin-A, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding human activin-A with an affinity at least equal to $1 \times 10^{-7}$M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as Fv). If desired, the chains may be covalently coupled either directly, for example via a disulfide bond between the two variable domains, or through a linker, for example a peptide linker, to form a single chain Fv (scFv).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, antibodies comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent.

Antigen specific (i.e. activin-A specific) antibodies can be produced by methods known in the art by using a specific VL or VH domain to screen a library of the complementary variable domain. Such methods of producing antibodies are known in the art. For example, antibody fragments fused to another protein, such as a minor coat protein, can be used to enrich phage with antigen. Then, using a random combinatorial library of rearranged heavy (VH) and light (VL) chains from mice immune to the antigen (e.g. activin-A), diverse libraries of antibody fragments are displayed on the surface of the phage. These libraries can be screened for complementary variable domains, and the domains purified by, for example, affinity column. See Clackson et al., *Nature*, V. 352 pp. 624-628 (1991).

In another example, individual VL or VH chains from an antibody (i.e. activin-A antibody) can be used to search for other VH or VL chains that could form antigen-binding fragments (or Fab), with the same specificity. Thus, random combinations of VH and VL chain Ig genes can be expresses as antigen-binding fragments in a bacteriophage library (such as fd or lambda phage). For instance, a combinatorial library may be generated by utilizing the parent VL or VH chain library combined with antigen-binding specific VL or VH chain libraries, respectively. The combinatorial libraries may then be screened by conventional techniques, for example by using radioactively labeled probe (such as radioactively labeled activin-A). See, for example, Portolano et al., *J. Immunol.* V. 150 (3) pp. 880-887 (1993).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein), and includes the end sequence amino acids listed. For example the polypeptide sequence R13-Y39 includes amino acids R13, and Y39, as well as the amino acids found between R13 and Y39 in the sequence. In embodiments in which the epitope comprises non-contiguous portions of a molecule, the sequences will be noted accordingly Antigen Binding Proteins In one aspect, the present invention provides antigen binding proteins (e.g., antibodies, antibody fragments, antibody derivatives, antibody muteins, and antibody variants), that bind to activin-A, e.g., human activin-A.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Antigen binding proteins in accordance with the present invention include antigen binding proteins that inhibit a biological activity of activin-A. For example, antigen binding proteins may attenuate cachexia, and this activity can be present when the antigen binding protein is fully human, such as a fully human antibody.

Different antigen binding proteins may bind to different domains or cysteine knot domains of activin-A or act by different mechanisms of action. Examples include but are not limited to antigen binding proteins that specifically bind one or more particular cysteine knot domains, or regions interspersed between disulfide bonds, including regions spanning from about amino acids 4-12, amino acids 11-81, amino acids 11-33, amino acids 13-39, amino acids 40-113, amino acids 44-115, amino acids 81-111, and/or amino acids 82-107 of the following sequence: tcctatgagg tgactcaggc accctcagtg tccgtgtccc caggacagac agccagcatc acctgctctg gagataaatt gggggataaa tatgcttgtt ggtatcagca gaagccaggc cagtcccctg tgctggtcat ctatcaagat agcaagcggc cctcagggat ccctgagcga ttctctggct ccaactctgg aaacacagcc actctgacca tcagcgggac ccaggctatg gatgaggctg actattactg tcaggcgtgg gacagcagca ctgcggtatt cggcggaggg accaagctga ccgtccta (SEQ ID NO: 267)). As indicated herein inter alia, the domain region are designated such as to be inclusive of the group, unless otherwise indicated. For example, amino acids 4-12 refers to nine amino acids: amino acids at positions 4, and 12, as well as the seven intervening amino acids in the sequence. Other examples include antigen binding proteins that inhibit binding of activin-A to its receptor. An antigen binding protein need not completely inhibit an activin-A-induced activity to find use in the present invention; rather, antigen binding proteins that reduce a particular activity of activin-A are contemplated for use as well. (Discussions herein of particular mechanisms of action for activin-A-binding antigen binding proteins in treating particular diseases are illustrative only, and the methods presented herein are not bound thereby.)

In another aspect, the present invention provides antigen binding proteins that comprise a light chain variable region selected from the group consisting of A1-A14 or a heavy chain variable region selected from the group consisting of A1-A14, and fragments, derivatives, muteins, and variants thereof. Such an antigen binding protein can be denoted using the nomenclature "LxHy", wherein "x" corresponds to the number of the light chain variable region and "y" corresponds to the number of the heavy chain variable region as they are labeled in the sequences below. That is to say, for example, that "A1HC" denotes the heavy chain variable region of antibody A1; "A1LC" denotes the light chain variable region of antibody A1, and so forth. More generally speaking, "L2H1" refers to an antigen binding protein with a light chain variable region comprising the amino acid sequence of L2 and a heavy chain variable region comprising the amino acid sequence of H1. For clarity, all ranges denoted by at least two members of a group include all members of the group between and including the end range members. Thus, the group range A1-A14, includes all members between A1 and A14, as well as members A1 and A14 themselves. The group range A4-A6 includes members A4, A5, and A6, etc.

Also shown below are the locations of the CDRs (underlined) that create part of the antigen-binding site, while the Framework Regions (FRs) are the intervening segments of these variable domain sequences. In both light chain variable regions and heavy chain variable regions there are three CDRs (CDR 1-3) and four FRs (FR 1-4). The CDR regions of each light and heavy chain also are grouped by antibody type (A1, A2, A3, etc.). Antigen binding proteins of the invention include, for example, antigen binding proteins having a combination of light chain and heavy chain variable domains selected from the group of combinations consisting of L1H1 (antibody A1), L2H2 (antibody A2), L3H3 (antibody A3), L4H4 (antibody A4), L5H5 (antibody A5), L6H6 (antibody A6), L7H7 (antibody A7), L8H8 (antibody A8), L9H9 (antibody A9), L10H10 (antibody A10), L11H11 (antibody A11), L12H12 (antibody A12), L13H13 (antibody A13), and L14H14 (antibody A14).

Antibodies A1-A14 heavy and light chain variable region polynucleotides (also referred to herein as H1-H14 and L1-L14).

A1 HC
(SEQ ID NO: 268)
CAGGTTCAGCTGGTGCAGTCTGGAGCTGAGGTGAAGAAGCCTGGGGCCTC

AGTGAAGGTCTCCTGCAAGGCTTCTGGTTACACCTTTACCAGTTATGGTC

TCAGCTGGGTGCGACAGGCCCCTGGACAAGGGCTTGAGTGGATGGGATGG

ATCATCCCTTACAATGGTAACACAAACTCTGCACAGAAACTCCAGGGCAG

AGTCACCATGACCACAGACACATCCACGAGCACAGCCTACATGGAGCTGA

GGAGCCTGAGATCTGACGACACGGCCGTGTATTTCTGTGCGAGAGACAGG

GACTACGGTGTCAATTATGATGCTTTTGATATCTGGGGCCAAGGGACAAT

GGTCACCGTCTCTTCA

A1 LC
(SEQ ID NO: 267)
TCCTATGAGGTGACTCAGGCACCCTCAGTGTCCGTGTCCCAGGACAGAC

AGCCAGCATCACCTGCTCTGGAGATAAATTGGGGGATAAATATGCTTGTT

GGTATCAGCAGAAGCCAGGCCAGTCCCCTGTGCTGGTCATCTATCAAGAT

AGCAAGCGGCCCTCAGGGATCCCTGAGCGATTCTCTGGCTCCAACTCTGG

AAACACAGCCACTCTGACCATCAGCGGGACCCAGGCTATGGATGAGGCTG

ACTATTACTGTCAGGCGTGGGACAGCAGCACTGCGGTATTCGGCGGAGGG

ACCAAGCTGACCGTCCTA

A2 HC
(SEQ ID NO: 269)
CAGGTGCAGCTGGTGGAGTCTGGGGGAGGCGTGGTCCAGCCTGGGAGGTC

CCTGAGACTCTCCTGTGCAGCGTCTGGATTCACCTTCAGTAGTTACGGCA

TGCACTGGGTCCGCCAGGCTCCAGGCAAGGGGCTGGAGTGGGTGGCAGTT

ATATGGTATGATGGAAGTAATAAATACCATGCAGACTCCGTGAAGGGCCG

ATTCACCATCTCCAGAGACAATTCCAAGAACACGCTGTATCTGCAAGTGA

ACAGCCTGAGAGCCGAGGACACGGCTGTGTATTACTGTGTGAGAAGTCGG

AACTGGAACTACGACAACTACTACTACGGTCTGGACGTCTGGGGCCAAGG

GACCACGGTCACCGTCTCCTCAG

A2 LC
(SEQ ID NO: 270)
GACATCCAGATGACCCAGTCTCCATCCTCCCTGTCTGCATCTGTAGGAGA

CAGAGTCACCATCACTTGCCGGGCAAGTCAGGGCATTAGAAATAATTTAG

GCTGGTATCAGCAGAAACCAGGGAAAGCCCCTAAGCGCCTGATTTATGCT

GCATCCAGTTTGCAAAGTGGGGTCCCATCAAGGTTCAGCGGCAGTGGATC

TGGGACAGAATTCACTCTCACAATCAGCAGTCTGCAGCCTGAAGATTTTA

CAACTTATTACTGTCTACAGCATAATAGTTACCCGTGGACGTTCGGCCAA

GGGACCAAGGTGGAAATCAAA

A3 HC
(SEQ ID NO: 271)
GAGGTGCAGTTGGTGGAGTCTGGGGGAGGCTTGGTCCAGCCTGGGGGGTC

CCTGAGACTCTCCTGTGCAGCCTCTGGATTCACCTTTAGTAGTTATTGGA

TGAGCTGGGTCCGCCAGGCTCCAGGGAAGGGGCTGGAGTGCGTGGCCAAC

ATAAAGCAAGATGGAAGTGAGGAATACTATGTGGACTCTGTGAAGGGCCG

ATTCACCATCTCCAGAGACAACGCCAAGAATTCACTGTATCTGCAAATGA

ACAGCCTGAGAGCCGAGGACACGGCTGTGTATTACTGTGCGAGAGGTAGC

AGCAGCTGGTACTACTACAACTACGGTATGGACGTCTGGGGCCAAGGGAC

CACGGTCACCGTCTCCTCA

A3 LC
(SEQ ID NO: 272)
GACATCCAGATGACCCAGTCTCCATCCTCCCTGTCTGCATCTGTAGGAGA

CAGAGTCACCATCACTTGCCGGGCAAGTCAGGGCATTAGAAATGATTTAG

GCTGGTATCAGCAGAAACCAGGGAAAGCCCCTAAGCGCCTGATCTATGCT

GCATCCAGTTTGCAAAGTGGGGTCCCATCAAGGTTCAGCGGCAGTGGATC

TGGGACAGAATTCACTCTCACAATCAGCAGCCTGCAGCCTGAAGATTTTG

CAACTTATTACTGTCGACAGCAAAATACTTACCCGCTCACTTTCGGCGGA
GGGACCAAGGTGGAGATCAAA

A4 HC
(SEQ ID NO: 273)
CAGGTGCAGCTGGTGCAGTCTGGGGCTGAGGTGAAGAAGCCTGGGGCCTC
AGTGAAGGTCTCCTGCAAGGCTTCTGGATACACCTTCACCGGCTACTATA
TCCACTGGGTGCGACAGGCCCCTGGACAAGGGCTTGAGTGGATGGGATGG
ATCAACCCTAACAGTGGTGGCACAAACTATGCACAGAAGTTTCAGGGCAG
GGTCACCATGACCAGGGACACGTCCATCAGCACAGCCTACATGGAGCTGA
GCAGGCTGAGATCTGACGACACGGCCGTGTATTTCTGTGCGAGAGATTCG
GGGTATAGCAGCAGCTGGCACTTTGACTACTGGGGCCAGGGAACCCTGGT
CACCGTCTCCTCA

A4 LC
(SEQ ID NO: 274)
GATATTGTGATGACTCAGTCTCCACTCTCCCTGCCCGTCACCCCTGGAGA
GCCGGCCTCCATCTCCTGCAGGTCTAGTCAGAGCCTCCTGCATAGTACTG
GATACAACTATTTGGATTGGTACCTGCAGAAGCCAGGGCAGTCTCCACAG
CTCCTGATCTATTTGGGTTCTTTTCGGGCCTCCGGGGTCCCTGACAGGTT
CAGTGGCAGTGGGTCAGGCACAGATTTTACACTGAAAATCAGCAGAGTGG
AGGCTGAGGATGTTGGGGTTTATTACTGCATGCAAGCTCTCCAAACTCCG
TGCAGTTTTGGCCAGGGGACCAAGCTGGAGATCAAG

A5 HC
(SEQ ID NO: 66)
CAGGTGCAGCTGCAGGAGTCGGGCCCAGGACTGGTGAAGCCTTCGGAGAC
CCTGTCCCTCACCTGCACTGTCTCTGGTGGCTCCATCAATAGTTTCTACT
GGAGCTGGATCCGGCAGCCCCCAGGGAAGGGACTGGAGTGGATTGGGTAT
ATCTATTACAGTGGGAGCACCAACTACAATCCCTCCCTCAAGAGTCGAGT
CACCATATCAGTAGACACGTCCAAGACCCAGTTCTCCCTGAAGCTGAGCT
CTGTGACCGCTGCGGACACGGCCGTGTATTACTGTGCGAGAGACAGTATA
GCAGCCCCCTTTGACTACTGGGGCCAGGGAACCCTGGTCACCGTCTCCTC
AGCTTCCACCAAGGGCCCATCCGTCTTCCCCCTGGCGCCCTGCTCCAGGA
GCACCTCCGAGAGCACAGCCGCCCTGGGCTGCCTGGTCAAGGACTACTTC
CCCGAACCGGTGACGGTGTCGTGGAACTCATGCGCCCT

A5 LC
(SEQ ID NO: 65)
GACATCGTGATGACCCAGTCTCCAGACTCCCTGGCTGTGTCTCTGGGCGA
GAGGGCCACCATCACCTGCAAGTCCAGCCAGAGTATTTTATACAGTTCCA
ACAATAAGAAGTATCTAGTTTGGTACCAGCAGAAACCAGGACAGCCTCCT
AAGCTGATCATTTACTGGACATCTATGCGGGAATCCGGGGTCCCTGACCG
ATTCAGTGGCAGCGGGTCTGGGACAGATTTCACTCTCACCATCAACAGCC
TGCAGGCTGAAGATGTGGCAGTTTATTACTGTCAGCAATATTATAGTACT
CCGTGGACGTTCGGCCAAGGGACCAAGGTGGAAATCAAA

A6 HC
(SEQ ID NO: 82)
CAGGTGCAGCTACAGCAGTGGGGCGCAGGACTGTTGAAGCCTTCGGAGAC
CCTGTCCCTCACCTGCGCTGTCTATGGTGGGTCCTTCAGTGCTTACTACT
GGAGCTGGATCCGCCAGCCCCCAGGGAAGGGACTGGAGTGGATTGGGGAA
ATCAATCATAGTGGAGGCACCAACTACAACCCGTCCCTCAAGAGTCGAGT
CACCATATCAGTAGACACGTCCAAGAACCAGTTCTCCCTGAAGCTGAGCT
CTGTGACCGCCGCGGACACGGCTGTGTATTACTGTGCGAGAGTACAGTGG
CTCGAACTGGCCTACTTTGACTACTGGGGCCAGGGAACCCTGGTCACCGT
CTCCTCA

A6 LC
(SEQ ID NO: 81)
GACATCCAGATGACCCAGTCTCCATCCTCCCTGTCTGCATCTGTAGGAGA
CAGAGTCACCATCACTTGCCGGGCAAGTCAGAGCATTAGCAACTATTTAA
ATTGGTATCAGCAGAGACCAGGGAAAGCCCCTAAGCTCCTGATCTATGCT
ACATCCAGTTTGCAAAGTGTGGTCCCATCAAGGTTCAGTGGCAGTGGATC
TGGGACAGATTTCACTCTCACCATCAGCAGTCTGCAACCTGAAGATTTTG
TAAGTTACTACTGTCAACAGAGTTACAGTATTTCGCCCACTTTCGGCGGC
GGGACCAAGGTGGAGAACAAA

A7 HC
(SEQ ID NO: 98)
CAGGTGCAGCTGGTGGACTCTGGGGGAGGCGTGGTCCAGCCTGGGAGGTC
CCTGAGACTCTCCTGTGCAGCGTCTGGATTCACCTTCATTAGCTATGGCA
TGCACTGGGTCCGCCAGGCTCCAGGCAAGGGGCTGGAGTGGGTGGCAGTT
ATCTGGTATGATGGAAGTACTGAATACTATGCAGACTCCGTGAAGGGCCG
ATTCACCATCTCCAGAGACAATTCCAAGAACACGCTGTATCTGCAAATGA
ACAGCCTGAGAGCCGAGGACACGGCTGTGTATTACTGTGCGAGAGAGAGG
CAGTGGCTCTACCACTACGGTATGGACGTCTGGGGCCAAGGGACCACGGT
CACCGTCTCCTCA

A7 LC
(SEQ ID NO: 97)
GACATCCAGATGACCCAGTCTCCATCCTCCCTGTCTGCATCTGTAGGAGA
CAGAGTCACCATCACTTGCCGGGCAGGTCAGGGCATTAGAAATGATTTAG
TCTGGTATCAGCAGAAACCAGGGAAAGCCCCTAAGCGCCTGATCTATGCT
GCATCCAGTTTGCAAAGTGGGGTCCCATCAAGGTTCAGCGGCAGTGGATC
TGGGACAGAATTCACTCTCACAATCAGCAGCCTGCAGCCTGAAGATTTTG
CAACTTATTACTGTCTACAACATAATACTTACCCATTCACTTTCGGCCCT
GGGACCAAAGTGGATATCAAA

A8 HC
(SEQ ID NO: 114)
CAGGTGCAGCTGCAGGAGTCGGGCCCAGGACTGGTGAAGCCTCGGAGAC
CCTGTCCCTCACCTGCACTGTCTCTGGTGGCTCCATCAATAGTTTCTACT
GGAGCTGGATCCGGCAGCCCCCAGGGAAGGGACTGGAGTGGATTGGGTAT
ATCTATTACAGTGGGAGCACCAACTACAATCCCTCCCTCAAGAGGCGAGT
CACCATATCAGTAGACACGTCCAAGACCCAGTTCTCCCTGAAGCTGAGCT

-continued

CTGTGACCGCTGCGGACACGGCCGTGTATTACTGTGCGAGA<u>GACAGTATA</u>
<u>GCAGCCCCCTTTGACTAC</u>TGGGGCCAGGGAACCCTGGTCACCGTCTCCTC
A

A8 LC (SEQ ID NO: 113)
GACATCGTGATGACCCAGTCTCCAGACTCCCTGGCTGTGTCTCTGGGCGA
GAGGGCCACCATCACCTGC<u>AAGTCCAGCCAGAGTATTTTATACAGCTCCA</u>
<u>ACAATAAGAAGTATCTAGTTT</u>GGTACCAGCAGAAACCAGGACAGCCTCCT
AAGTTGATCATTTAC<u>TGGACATCTATGCGGGAATCC</u>GGGGTCCCTGACCG
ATTCAGTGGCAGCGGGTCTGGGACAGATTTCACTCTCACCATCAGCAGCC
TGCAGGCTGAAGATGTGGCAGTTTATTACTGT<u>CAGCAATATTATAGTACT</u>
<u>CCGTGGACG</u>TTCGGCCAAGGGACCAAGGTGGAAATCAAA

A9 HC (SEQ ID NO: 130)
CAGGTGCAGCTGGTGGAGTCTGGGGGAGGCGTGGTCCAGCCTGGGAGGTC
CCTGAGACTCTCCTGTGCAGCGTCT<u>GGATTCACCTTCAGTAGTTACGGCA</u>
<u>TGCACT</u>GGGTCCGCCAGGCTCCAGGCAAGGGGCTGGAGTGGGTGGCA<u>GTT</u>
<u>ATATGGTATGATGGAAGTAATAAATACCATGCAGACTCCGTGAAGGGCCG</u>
ATTCACCATCTCCAGAGACAATTCCAAGAACACGCTGTATCTGCAAGTGA
ACAGCCTGAGAGCCGAGGACACGGCTGTGTATTACTGTGTGAGA<u>AGTCGG</u>
<u>AACTGGAACTACGACAACTACTACTACGGTCTGGACGTCTGGGGCCAAGG</u>
GACCACGGTCACCGTCTCCTCA

A9 LC (SEQ ID NO: 129)
GACATCCAGATGACCCAGTCTCCATCCTCCCTGTCTGCATCTGTAGGAGA
CAGAGTCACCATCACTTGC<u>CGGGCAAGTCAGGGCATTAGAAATAATTTAG</u>
<u>GC</u>TGGTATCAGCAGAAACCAGGGAAAGCCCCTAAGCGCCTGATTTAT<u>GCT</u>
GCATCCAGTTTGCAAAGTGGGGTCCCATCAAGGTTCAGCGGCAGTGGATC
TGGGACAGAATTCACTCTCACAATCAGCAGCCTGCAGCCTGAAGATTTTA
CAACTTATTACTGT<u>CTACAGCATAATAGTTACCCGTGGACG</u>TTCGGCCAA
GGGACCAAGGTGGAAATCAAA

A10 HC (SEQ ID NO: 146)
GAGGTGCAGCTGGTGCAGTCTGGAGCAGAGGTGAAAAAGCCCGGGGAGTC
TCTGAAGATCTCCTGTCAGGGTTCT<u>GGATACAGCTTTACCAGCTACTGGA</u>
<u>TCGGC</u>TGGGTGCGCCAGATGCCCGGGAAAGGCCTGGAGTGGATGGGG<u>ATC</u>
<u>ATCTATCCTGGTGACTCTGATACCAGATACAGCCCGTCCTTCCAAGGCCA</u>
GGTCACCATCTCAGCCGACAAGTCCATCAGCACCGCCTACCTGCAGTGGA
GCAGCCTGAAGGCCTCGGACACCGCCATGTATT
ACTGTGCGAGA<u>CAAGGACTGGGGTTTGACTAC</u>TGGGGCCAGGGAACCCTG
GTCACCGTCTCCTCA

A10 LC (SEQ ID NO: 145)
TCCTATGAGCTGACTCAGCCACCCTCAGTGTCCGTGTCCCAGGACAGAC
AGCCAGCATCACCTGC<u>TCTGGAGAAAAATGGGGAGAGAAATATGCTTGTT</u>
GGTATCAGCAGAAGCCAGGCCAGTCCCCTGTGCTGGTCATCTAT<u>CAAGAT</u>

-continued

<u>ACCAAGCGGCCCTCC</u>GGGATCCCTGAGCGATTCTCTGGCTCCATTTCTGG
GAACACAGCCACTCTGACCATCAGCGGGACCCAGGCTATGGATGAGGCTG
ACTATTATTGT<u>CAGGCGTGGGACAGGAGCACTGTA</u>TTCGGCGGAGGGACC
AAGCTGACCGTCCTA

A11 HC (SEQ ID NO: 162)
CAGGTGCAGCTGCAGGAGTCGGGCCCAGGACTGGTGAAGCCTTCACAGAC
CCTGTCCCTCACCTGCACTGTCTCT<u>GGTGGCTCCATCAGCAGTGGTGGTT</u>
<u>ACTACTGGAGC</u>TGGATCCGCCAGCACCCAGGGAAGGGCCTGGAGTGGATT
GGG<u>TACATCTCTTACAGTGGGAGCACCTACTACAACCCGTCCCTCAAGAG</u>
TCGAGTTACCATATCAGTTGACACGTCTAAGAACCAGTTCTCCCTGAAGC
TGAACTCTGTGACTGCCGCGGACACGGCCGTGTATTACTGTGCGCGC<u>GCT</u>
<u>TACGGTGACTATCGCGGCTGGTTCGACCCC</u>TGGGGCCAGGGAACCCTGGT
CACCGTCTCCTCA

A11 LC (SEQ ID NO: 161)
TCCTATGAGCTGACTCAGCCACCCTCAGTGTCCGTGTCCCAGGACAGAC
AGCCAGCATCACCTGC<u>TCTGGAGATAAATTGGGGGATAAATTTGCTTTCT</u>
GGTATCAGCTGAAGCCAGGCCAGTCCCCTGTGCTGGTCATCTAT<u>CAAGAT</u>
<u>AACAAGCGGCCCTCA</u>GGGATCCCTGAGCGATTCTCTGGCTCCAACTCTGG
GAACACAGCCACTCTGACCATCAGCGGGACCCAGGCTATGGATGCGGCTG
ACTTTTACTGT<u>CAGGCGTGGGACAGCAGCACTGTGGTA</u>TTCGGCGGAGGG
ACCAAGCTGACCGTCCTA

A12 HL (SEQ ID NO: 178)
CAGGTGCAGCTGGTGGAGTCTGGGGGAGGCGTGGTCCAGCCTGGGAGGTC
CCTGAGACTCTCCTGTGTAGCGTCT<u>GGATTCACCTTCAGTGCCTATGGCA</u>
<u>TGCACT</u>GGGTCCGCCAGGCTCCAGGCAAGGGGCTGGAGTGGGTGGCA<u>GTT</u>
<u>ATATGGTATGATGGAAGTAATAAATACTATGCAGACTCCGTGAAGGGCCG</u>
ATTCATCATCTCCAGAGACAATTCCAAGAACACGCTGTATCTGCAAATGA
ACAGCCTGAGAGCCGAGGACACGGCTGTGTATTACTGTGCGAGA<u>AGTCGG</u>
<u>AACTGGAACTACGACTCCTACCAATACGGTTTGGACGTCTGGGGCCAAGG</u>
GACCACGGTCACCGTCTCCTCA

A12 LC (SEQ ID NO: 177)
GACATCCAGATGACCCAGTCTCCATCCTCCCTGTCTGCATCTGTAGGAGA
CAGAGTCACCATCACTTGC<u>CGGGCAAGTCAGGGCATTAGAAATGATTTAG</u>
<u>GC</u>TGGTATCAGCAGAAACCAGGGAAAGCCCCTAAGCGCCTGATCTAT<u>GCT</u>
<u>GCATCCAGTTTGCAAAGT</u>GGGGTCCCATCAAGGTTCAGCGGCAGTGGATC
TGGGACAGAATTCACTCTCACAATCAGCAGCCTGCAGCCTGAAGATTGTG
CAACTTATTATTGT<u>CTACAGCATAATAGTTATACGTGGACG</u>TTCGGCCAA
GGGACCAAGGTGGAAATCAAA

-continued

A13 HC
(SEQ ID NO: 194)
CAGGTTCAGCTGGTGCAGTCTGGAGCTGAGGTGAAGAAGCCTGGGGCCTC

AGTGAAGGTCTCCTGCAAGGCTTCTGGTTACACCTTTACCAGCTATGGTA

TCAGCTGGGTGCGACAGGCCCCTGGACAAGGGCTTGAGAGGATGGGATGG

ATCAGCGCTTACAATGGTAACACAAACTATGCACAGAAGTTCCAGGGCAG

AGTCACCATGACCACAGACACATCAACGACCACAGCCTACATGGAGCTGA

GGAGCCTGAGATCTGACGACACGGCCGTGTATTACTGTGCGAGAGATCAA

GATTACTATGATAGTAGTGGTTGGGGCCACTGGGGCCAGGGAACCCTGGT

CACCGTCTCCTCA

A13 LC
(SEQ ID NO: 193)
TCCTATGAGCTGACTCAGCCACCCTCAGTGTCCGTGTCCCCAGGACAGAC

AGCCAGCATCACCTGCTCTGGAGATAAATTGGGGGATAAATATGTTTGTT

GGTATCAGCAGAAGCCAGGCCAGTCCCCTGAACTGGTCATCTATCTAGAT

AACAAGCGGCCCTCAGGGATCCCTGAGCGATTCTCTGGCTCCAACTCTGG

GAACACAGCCACTCTGACCATCAGCGGGACCCAGGCTATGGATGAGGCTG

ACTATTACTGTCAGGCGTGGGACAGCAGCACGGTATTCGGCGGAGGGACC

AAACTGACCGTCCTG

A14 HC
(SEQ ID NO: 210)
CAGGTTCAGCTGGTGCAATCTGGAGCTGAGGTGAAGAAGCCTGGGGCCTC

AGTGAAGGTCTCCTGCAAGACTTCTGGTTACACCTTTACCAGCTATGGTA

TCAGCTGGGTGCGACAGGCCCCTGGACAAGGGCTTGAGTGGATGGGATGG

ATCAGCCCTTACAATGGTAACACAAACTATGCACAGAAGTTCCAGGGCAG

AGTCACCATGACCACAGACAAATCCACGAGCACAGCCTACATGGAGCTGA

GGAGCCTGCGATCTGACGACACGGCCGTGTATTACTGTGCGAGAGATCAA

GATTACTATGATAGTAGTGGTTGGGACCCCTGGGGCCAGGGAACCCTGGT

CACCGTCTCCTCG

A14 LC
(SEQ ID NO: 209)
TCCTATGAGCTGACTCAGCCACCCTCAGTGTCCGTGTCCCCAGGACAGAC

AGCCTCCATCACCTGCTCTGGAGATAAATTGGGGGATAAATATGCTTTCT

GGTATCAGCAGAAGCCAGGCCAGTCCCCTGTGCTGGTCTTCTATCATGAT

ACCAAGCGGCCCTCAGGGATCCCTGAGCGATTCTCTGGCTCCAACTCTGG

GAACACAGCCACTCTGACCATCAGCGGGACCCAGGCTATGGATGAGGCTG

ACTATCACTGTCAGGCGTGGGACAGCAGCACGGTCTTCGGCGGAGGGACC

AAGCTGACCGTCCTAC

Antibodies A1-A14 amino acid sequences, light chain variable regions. CDR regions are underlined; the intervening segments or regions are referred to as framework (FR) herein.

A1
(SEQ ID NO: 275)
SYEVTQAPSVSVSPGQTASITCSGDKLGDKYACWYQQKPGQSPVLVIYQ

DSKRPSGIPERFSGSNSGNTATLTISGTQAMDEADYYCQAWDSSTAVFG

GGTKLTVL

A2
(SEQ ID NO: 276)
DIQMTQSPSSLSASVGDRVTITCRASQGIRNNLGWYQQKPGKAPKRLIY

AASSLQSGVPSRFSGSGSGTEFTLTISSLQPEDFTTYYCLQHNSYPWTF

GQGTKVEIK

A3
(SEQ ID NO: 277)
DIQMTQSPSSLSASVGDRVTITCRASQGIRNDLGWYQQKPGKAPKRLIY

AASSLQSGVPSRFSGSGSGTEFTLTISSLQPEDFATYYCRQQNTYPLTF

GGGTKVEIK

A4
(SEQ ID NO: 57)
DIVMTQSPLSLPVTPGEPASISCRSSQSLLHSTGYNYLDWYLQKPGQSP

QLLIYLGSFRASGVPDRFSGSGSGTDFTLKISRVEAEDVGVYYCMQALQ

TPCSFGQGTKLEIK

A5
(SEQ ID NO: 73)
DIVMTQSPDSLAVSLGERATITCKSSQSILYSSNNKKYLVWYQQKPGQP

PKLIIYWTSMRESGVPDRFSGSGSGTDFTLTINSLQAEDVAVYYCQQYY

STPWTFGQGTKVEIK

A6
(SEQ ID NO: 89)
DIQMTQSPSSLSASVGDRVTITCRASQSISNYLNWYQQRPGKAPKLLIY

ATSSLQSGVPSRFSGSGSGTDFTLTISSLQPEDFVSYYCQQSYSISPTF

GGGTKVENK

A7
(SEQ ID NO: 105)
DIQMTQSPSSLSASVGDRVTITCRAGQGIRNDLVWYQQKPGKAPKRLIY

AASSLQSGVPSRFSGSGSGTEFTLTISSLQPEDFATYYCLQHNTYPFTF

GPGTKVDIK

A8
(SEQ ID NO: 121)
DIVMTQSPDSLAVSLGERATITCKSSQSILYSSNNKKYLVWYQQKPGQP

PKLIIYWTSMRESGVPDRFSGSGSGTDFTLTISSLQAEDVAVYYCQQYY

STPWTFGQGTKVEIK

A9
(SEQ ID NO: 137)
DIQMTQSPSSLSASVGDRVTITCRASQGIRNNLGWYQQKPGKAPKRLIY

AASSLQSGVPSRFSGSGSGTEFTLTISSLQPEDFTTYYCLQHNSYPWTF

GQGTKVEIK

A10
(SEQ ID NO: 153)
SYELTQPPSVSVSPGQTASITCSGEKWGEKYACWYQQKPGQSPVLVIYQ

DTKRPSGIPERFSGSISGNTATLTISGTQAMDEADYYCQAWDRSTVFGG

GTKLTVL

A11
(SEQ ID NO: 169)
SYELTQPPSVSVSPGQTASITC<u>SGDKLGDKFAF</u>WYQLKPGQSPVLVIYQ

<u>DNKRPS</u>GIPERFSGSNSGNTATLTISGTQAMDAADFYC<u>QAWDSSTVV</u>FG

GGTKLTVL

A12
(SEQ ID NO: 185)
DIQMTQSPSSLSASVGDRVTITC<u>RASQGIRNDLG</u>WYQQKPGKAPKRLIY

<u>AASSLQS</u>GVPSRFSGSGSGTEFTLTISSLQPEDCATYYC<u>LQHNSYTWT</u>F

GQGTKVEIK

A13
(SEQ ID NO: 201)
SYELTQPPSVSVSPGQTASITC<u>SGDKLGDKYVC</u>WYQQKPGQSPELVIYL

<u>DNKRPS</u>GIPERFSGSNSGNTATLTISGTQAMDEADYYC<u>QAWDSSTV</u>FGG

GTKLTVL

A14
(SEQ ID NO: 217)
SYELTQPPSVSVSPGQTASITC<u>SGDKLGDKYAF</u>WYQQKPGQSPVLVFYH

<u>DTKRPS</u>GIPERFSGSNSGNTATLTISGTQAMDEADYHC<u>QAWDSSTV</u>FGG

GTKLTVL

Antibodies A1-A14, amino acid sequences of heavy chain variable regions. CDR regions are shaded and underlined; the other regions are referred to as framework (FR) herein.

A1
(SEQ ID NO: 278)
QVQLVQSGAEVKKPGASVKVSCKAS<u>GYTFTSYGLS</u>WVRQAPGQGLEWMG

<u>WIIPYNGNTNSAQKLQ</u>GRVTMTTDTSTSTAYMELRSLRSDDTAVYFCAR

<u>DRDYGVNYDAFDI</u>WGQGTMVTVSS

A2
(SEQ ID NO: 279)
QVQLVESGGGVVQPGRSLRLSCAAS<u>GFTFSSYGMH</u>WVRQAPGKGLEWVA

<u>VIWYDGSNKYHADSVKG</u>RFTISRDNSKNTLYLQVNSLRAEDTAVYYCVR

<u>SRNWNYDNYYYGLDV</u>WGQGTTVTVSS

A3
(SEQ ID NO: 280)
EVQLVESGGGLVQPGGSLRLSCAAS<u>GFTFSSYWMS</u>WVRQAPGKGLECVA

<u>NIKQDGSEEYYVDSVKG</u>RFTISRDNAKNSLYLQMNSLRAEDTAVYYCAR

<u>GSSSWYYNYGMDV</u>WGQGTTVTVSS

A4
(SEQ ID NO: 58)
QVQLVQSGAEVKKPGASVKVSCKAS<u>GYTFTGYYIH</u>WVRQAPGQGLEWMG

<u>WINPNSGGTNYAQKFQ</u>GRVTMTRDTSISTAYMELSRLSDDTAVYFCAR

<u>DSGYSSSWHFDY</u>WGQGTLVTVSS

A5
(SEQ ID NO: 74)
QVQLQESGPGLVKPSETLSLTCTVS<u>GGSINSFYWS</u>WIRQPPGKGLEWIG

<u>YIYYSGSTYNPSLKS</u>RVTISVDTSKTQFSLKLSSVTAADTAVYYCAR<u>D

SIAAPFDY</u>WGQGTLVTVSS

A6
(SEQ ID NO: 90)
QVQLQQWGAGLLKPSETLSLTCAVY<u>GGSFSAYYWS</u>WIRQPPGKGLEWIG

<u>EINHSGGTNYNPSLKS</u>RVTISVDTSKNQFSLKLSSVTAADTAVYYCAR<u>V

QWLELAYFDY</u>WGQGTLVTVSS

A7
(SEQ ID NO: 106)
QVQLVDSGGGVVQPGRSLRLSCAAS<u>GFTFISYGMH</u>WVRQAPGKGLEWVA

<u>VIWYDGSTEYYADSVKG</u>RFTISRDNSKNTLYLQMNSLRAEDTAVYYCAR

<u>ERQWLYHYGMDV</u>WGQGTTVTVSS

A8
(SEQ ID NO: 122)
QVQLQESGPGLVKPSETLSLTCTVS<u>GGSINSFYWS</u>WIRQPPGKGLEWIG

<u>YIYYSGSTNYNPSLKR</u>RVTISVDTSKTQFSLKLSSVTAADTAVYYCAR<u>D

SIAAPFDY</u>WGQGTLVTVSS

A9
(SEQ ID NO: 138)
QVQLVESGGGVVQPGRSLRLSCAAS<u>GFTFSSYGMH</u>WVRQAPGKGLEWVA

<u>VIWYDGSNKYHADSVKG</u>RFTISRDNSKNTLYLQVNSLRAEDTAVYYCVR

<u>SRNWNYDNYYYGLDV</u>WGQGTTVTVSS

A10
(SEQ ID NO: 154)
EVQLVQSGAEVKKPGESLKISCQGS<u>GYSFTSYWIG</u>WVRQMPGKGLEWMG

<u>IIYPGDSDTRYSPSFQ</u>GQVTISADKSISTAYLQWSSLKASDTAMYYCAR

<u>QGLGFDY</u>WGQGTLVTVSS

A11
(SEQ ID NO: 170)
QVQLQESGPGLVKPSQTLSLTCTVS<u>GGSISSGGYYWS</u>WIRQHPGKGLEW

IG<u>YISYSGSTYYNPSLKS</u>RVTISVDTSKNQFSLKLNSVTAADTAVYYCA

R<u>AYGDYRGWFDP</u>WGQGTLVTVSS

A12
(SEQ ID NO: 186)
QVQLVESGGGVVQPGRSLRLSCVAS<u>GFTFSAYGMH</u>WVRQAPGKGLEWVA

<u>VIWYDGSNKYYADSVKG</u>RFIISRDNSKNTLYLQMNSLRAEDTAVYYCAR

<u>SRNWNYDSYQYGLDV</u>WGQGTTVTVSS

A13
(SEQ ID NO: 202)
QVQLVQSGAEVKKPGASVKVSCKAS<u>GYTFTSYGIS</u>WVRQAPGQGLERMG

<u>WISAYNGNTNYAQKFQ</u>GRVTMTTDTSTTTAYMELRSLRSDDTAVYYCAR

<u>DQDYYDSSGWGH</u>WGQGTLVTVSS

A14
(SEQ ID NO: 218)
QVQLVQSGAEVKKPGASVKVSCKTS<u>GYTFTSYGIS</u>WVRQAPGQGLEWMG

<u>WISPYNGNTNYAQKFQ</u>GRVTMTTDKSTSTAYMELRSLRSDDTAVYYCAR

<u>DQDYYDSSGWDP</u>WGQGTLVTVSS

TABLE 1

Light chain CDR1 consensus sequences for Antibodies A1-A14.

| Light Chain | CDR1 Sequence |
|---|---|
| L4 | R S S Q S L L H S T G Y N - Y L D |
| L5, L8 | K S S Q S I L Y S S N N K K Y L V |
| CONSENSUS: | $X_1$ S S Q S $X_2$ L $X_3$ S $X_4$ $X_5$ $X_6$ $X_7$ $X_8$ Y L $X_9$ (SEQ ID NOS 253, 75 and 115, respectively, in order of appearance) |
| L2, L9 | R A S Q G I R N N L G |
| L3, L12 | R A S Q G I R N D L G |
| L6 | R A S Q S I S N Y L N |
| L7 | R A G Q G I R N D L V |
| CONSENSUS: | R A $X_{10}$ Q $X_{11}$ $X_{12}$ N $X_{13}$ L $X_{14}$ (SEQ ID NOS 281-282, 91, 107 and 116, respectively, in order of appearance) |
| L1 | S G D K L G D K Y A C |
| L10 | S G E K W G E K Y A C |
| L11 | S G D K L G D K F A F |
| L13 | S G D K L G D K Y V C |
| L14 | S G D K L G D K Y A F |
| CONSENSUS: | S G $X_{15}$ K $X_{16}$ G $X_{17}$ K$X_{18}$$X_{19}$$X_{20}$ (SEQ ID NOS 59, 155, 171, 203, 219 and 123, respectively, in order of appearance) |

$X_1$ is an arginine residue or a lysine residue,
$X_2$ is a leucine residue or a isoleucine residue,
$X_3$ is a histidine residue or a tyrosine residue,
$X_4$ is a threonine residue or a serine residue,
$X_5$ is a glycine residue or an asparagine residue,
$X_6$ is a tyrosine residue or an asparagine residue,
$X_7$ is an asparagine residue or a lysine residue,
$X_8$ is a lysine residue or no residue,
$X_9$ is an aspartate residue or a valine residue
$X_{10}$ is a serine residue or a glycine residue,
$X_{11}$ is a serine residue or a glycine residue,
$X_{12}$ is a serine residue or an arginine residue,
$X_{13}$ is a tyrosine residue, an aspartate residue, or an asparagine residue
$X_{14}$ is an aspartate residue, a valine residue, or a glycine residue,
$X_{15}$ is a glutamate residue or an aspartate residue,
$X_{16}$ is a tryptophan residue or a leucine residue,
$X_{17}$ is a glutamate residue or an aspartate residue,
$X_{18}$ is a tyrosine residue or a phenylalanine residue,
$X_{19}$ is an alanine residue or a valine residue,
$X_{20}$ is a cysteine residue or a phenylalanine residue

TABLE 2

Light chain CDR2 consensus sequences for Antibodies A1-A14.

| Light Chain | CDR2 Sequence |
|---|---|
| L2 | A T S S L Q S |
| L3, L6, L7, L9, L12 | A A S S L Q S |
| L5, L8 | W T S M R E S |
| L4 | L G S F R A S |
| CONSENSUS: | $X_{40}$$X_{41}$S$X_{42}$$X_{43}$$X_{44}$S (SEQ ID NOS 92, 283, 76, 254 and 124, respectively, in order of appearance) |
| L10 | Q D T K R P S |
| L11 | Q D N K R P S |
| L1 | Q D S K R P S |
| L13 | L D N K R P S |
| L14 | H D T K R P S |
| CONSENSUS: | $X_{45}$ D$X_{46}$ K R P S (SEQ ID NOS 156, 172, 60, 204, 220 and 128, respectively, in order of appearance) |

$X_{40}$ is an alanine residue, a tryptophan residue, or a leucine residue,
$X_{41}$ is a threonine residue, an alanine residue, or a glycine residue,
$X_{42}$ is a serine residue, a methionine residue, or a phenylalanine residue,
$X_{43}$ is a leucine residue or an arginine residue,
$X_{44}$ is a glutamine residue, a glutamate residue, or an alanine residue
$X_{45}$ is a glutamine residue, a leucine residue, or a histidine residue,
$X_{46}$ is a threonine residue, an asparagine residue, or a serine residue

TABLE 3

Light chain CDR3 consensus sequences for Antibodies A1-A14.

| Light Chain | CDR3 Sequence |
|---|---|
| L1 | Q A W D S S T A V |
| L10 | Q A W D R S T - V |
| L11 | Q A W D S S T V V |
| L13, L14 | Q A W D S S T V - |
| L2 | L Q H N S Y P W T |
| L7 | L Q H N T Y P F T |
| L9 | L Q H N S Y P W T |
| L12 | L Q H N S Y T W T |

TABLE 3-continued

Light chain CDR3 consensus sequences for Antibodies A1-A14.

| Light Chain | CDR3 Sequence |
|---|---|
| CONSENSUS: | L Q H N $X_{81}$ Y $X_{82}$ $X_{83}$ T<br>(SEQ ID NOS 61, 157, 173, 205, 141, 109, 141, 189 and 131, respectively, in order of appearance) |
| L3 | R Q Q N T Y P L T |
| L4 | M Q A L Q T P C S |
| L5 | Q Q Y Y S T P W T |
| L6 | Q Q S Y S I S P T |
| L8 | Q Q Y Y S T P W T |
| CONSENSUS: | $X_{73}$ Q$X_{74}X_{75}X_{76}X_{77}X_{78}X_{79}X_{80}$<br>(SEQ ID NOS 284, 255, 77, 93, 125 and 132, respectively, in order of appearance) |

$X_{73}$ is a methionine residue, a glutamine residue, or an arginine residue,
$X_{74}$ is an alanine residue, a tyrosine residue, a glutamine residue, or a serine residue,
$X_{75}$ is a leucine residue, a tyrosine residue, or an asparagine residue,
$X_{76}$ is a glutamine residue, a serine residue, or a threonine residue,
$X_{77}$ is a threonine residue, a tyrosine residue, or an isoleucine residue,
$X_{78}$ is a proline residue or a serine residue,
$X_{79}$ is a cysteine residue, a tryptophan residue, a leucine residue, or a proline residue,
$X_{80}$ is a serine residue or a threonine residue
$X_{81}$ is a threonine residue or a serine residue,
$X_{82}$ is a proline residue or a threonine residue,
$X_{83}$ is a phenylalanine residue or a tryptophan residue

TABLE 4

Heavy chain CDR1 consensus sequences for Antibodies A1-A14.

| Heavy Chain | CDR1 Sequence |
|---|---|
| H5 | G G S I N S - - F Y W S |
| H6 | G G S F S A - - Y Y W S |
| H8 | G G S I N S - - F Y W S |
| H11 | G G S I S S G G Y Y W S |
| CONSENSUS: | G G S$X_{21}X_{22}X_{23}X_{24}X_{25}X_{26}$YW S<br>(SEQ ID NOS 126, 94, 126, 174 and 252, respectively, in order of appearance) |

$X_{21}$ is an isoleucine residue or a phenylalanine residue
$X_{22}$ is an asparagine residue or a serine residue
$X_{23}$ is a serine residue or an alanine residue
$X_{24}$ is a glycine residue or no residue
$X_{25}$ is a glycine residue or no residue
$X_{26}$ is a phenylalanine residue or a tyrosine residue

| H7 | G F T F I S Y G M H |
|---|---|
| H4 | G Y T F T G Y Y I H |
| H2, H9 | G F T F S S Y G M H |
| H10 | G Y S F T S Y W I G |
| CONSENSUS: | G $X_{27}X_{28}$F$X_{29}X_{30}$Y$X_{31}X_{32}X_{33}$<br>(SEQ ID NOS 110, 256, 285, 158 and 257, respectively, in order of appearance) |

$X_{27}$ is a tyrosine residue or a phenylalanine residue,
$X_{28}$ is a threonine residue or a serine residue,
$X_{29}$ is a threonine residue, a serine residue, or an isoleucine residue,
$X_{30}$ is a glycine residue or a serine residue,
$X_{31}$ is a tyrosine residue, a glycine residue, or a tryptophan residue,
$X_{32}$ is an isoleucine residue or a methionine residue,
$X_{33}$ is a histidine residue or a glycine residue

| H13 | G Y T F T S Y G L S |
|---|---|
| H12 | G F T F S A Y G M H |
| H3 | G F T F S S Y W M S |
| H1, H14 | G Y T F T S Y G I S |
| CONSENSUS: | G$X_{34}$TF$X_{35}X_{36}$Y$X_{37}X_{38}X_{39}$<br>(SEQ ID NOS 62, 190, 286, 206 and 140, respectively, in order of appearance) |

$X_{34}$ is a tyrosine residue or a phenylalanine residue,
$X_{35}$ is a threonine residue or a serine residue,
$X_{36}$ is a serine residue or an alanine residue,
$X_{37}$ is a glycine residue or a tryptophan residue,
$X_{38}$ is a leucine residue, a methionine residue, or an isoleucine residue,
$X_{39}$ is a serine residue or a histidine residue

TABLE 5

Heavy chain CDR2 consensus sequences for Antibodies A1-A14.

| Heavy Chain | CDR2 Sequence |
|---|---|
| H11 | Y I S Y S G S T Y Y N P S L K S |
| H5 | Y I Y Y S G S T N Y N P S L K S |
| H6 | E I N H S G G T N Y N P S L K S |
| H8 | Y I Y Y S G S T N Y N P S L K R |
| CONSENSUS: | $X_{47}$ I $X_{48}$ $X_{49}$ S G $X_{50}$ T $X_{51}$ Y N P S L K $X_{52}$ (SEQ ID NOS 175, 79, 95, 127 and 142, respectively, in order of appearance) |

$X_{47}$ is a tyrosine residue or a glutamate residue,
$X_{48}$ is a serine residue, a tyrosine residue, or an asparagine residue,
$X_{49}$ is a tyrosine residue or a histidine residue
$X_{50}$ is a serine residue or a glycine residue,
$X_{51}$ is a tyrosine residue or an asparagine residue,
$X_{52}$ is a serine residue or an arginine residue

| | |
|---|---|
| H2, H9 | V I W Y D G S N K Y H A D S V K G |
| H12 | V I W Y D G S N K Y Y A D S V K G |
| H3 | N I K Q D G S E E Y Y V D S V K G |
| H7 | V I W Y D G S T E Y Y A D S V K G |
| CONSENSUS: | $X_{53}$ I $X_{54}$ $X_{55}$ D G S $X_{56}$ $X_{57}$ Y $X_{58}$ $X_{59}$ D S V K G (SEQ ID NOS 143, 191, 287, 111 and 179, respectively, in order of appearance) |

$X_{53}$ is an asparagine residue or a valine residue,
$X_{54}$ is a tryptophan residue or a lysine residue,
$X_{55}$ is a tyrosine residue or a glutamine residue,
$X_{56}$ is an asparagine residue, a glutamate residue, or a serine residue,
$X_{57}$ is a lysine residue or a glutamate residue,
$X_{58}$ is a histidine residue or a tyrosine residue,
$X_{59}$ is an alanine residue or a valine residue

| | |
|---|---|
| H4 | W I N P N S G G T N Y A Q K F Q G |
| H1 | W I I P Y N G N T N S A Q K L Q G |
| H13 | W I S A Y N G N T N Y A Q K F Q G |
| H14 | W I S P Y N G N T N Y A Q K F Q G |
| H10 | I I Y P G D S D T R Y S P S F Q G |
| CONSENSUS: | $X_{60}$ I $X_{61}$ $X_{62}$ $X_{63}$ $X_{64}$ $X_{65}$ $X_{66}$ T $X_{67}$ $X_{68}$ $X_{69}$ $X_{70}$ $X_{71}$ $X_{72}$ Q G (SEQ ID NOS 258, 63, 207, 259, 159 and 180, respectively, in order of appearance) |

$X_{60}$ is a tryptophan residue or an isoleucine residue,
$X_{61}$ is an asparagine residue, an isoleucine residue, a serine residue, or a tyrosine residue,
$X_{62}$ is a proline residue or an alanine residue,
$X_{63}$ is an asparagine residue, a tyrosine residue, or a glycine residue,
$X_{64}$ is a serine residue, an asparagine residue, or an aspartate residue,
$X_{65}$ is a glycine residue or a serine residue,
$X_{66}$ is a glycine residue, an asparagine residue, or an aspartate residue,
$X_{67}$ is an asparagine residue or an arginine residue,
$X_{68}$ is a tyrosine residue or a serine residue,
$X_{69}$ is an alanine residue or a serine residue
$X_{70}$ is a glutamine residue or a proline residue,
$X_{71}$ is a lysine residue or a serine residue,
$X_{72}$ is a phenylalanine residue or a leucine residue

TABLE 6

Heavy chain CDR3 consensus sequences for Antibodies A1-A14.

| Heavy Chain | CDR3 Sequence |
|---|---|
| H5, H8 | - - D S I A A P F D Y |
| H6 | V Q W L E L A Y F D Y |
| H10 | - - - - Q G L G F D Y |
| CONSENSUS: | $X_{87}X_{88}X_{89}X_{90}X_{91}X_{92}X_{93}X_{94}$FDY (SEQ ID NOS 80, 96, 160 and 187, respectively, in order of appearance) |

$X_{87}$ is a valine residue or no residue,
$X_{88}$ is a glutamine residue or no residue,
$X_{89}$ is an aspartate residue, a tryptophan residue, or no residue,
$X_{90}$ is a serine residue, a leucine residue, or no residue, TABLE 6-continued Heavy chain CDR3 consensus sequences for Antibodies A1-A14.

| Heavy Chain | CDR3 Sequence |
|---|---|

$X_{91}$ is an isoleucine residue, a glutamate residue, or a glutamine residue,
$X_{92}$ is an alanine residue, a leucine residue, or a glycine residue,
$X_{93}$ is an alanine residue or a leucine residue,
$X_{94}$ is a proline residue, a tyrosine residue, or a glycine residue

```
H13         D Q D Y Y D S S G W - G H
H14         D Q D Y Y D S S G W - D P
H11         - - A Y G D Y R G W F D P
CONSENSUS:  X95 X96 X97 Y X98 D X99 X100 G W X101 X102 X103
            (SEQ ID NOS 208, 224, 176 and 188, respectively,
            in order of appearance)
```

$X_{95}$ is an aspartate residue or no residue,
$X_{96}$ is a glutamine residue or no residue,
$X_{97}$ is an aspartate residue or an alanine residue,
$X_{98}$ is a tyrosine residue or a glycine residue,
$X_{99}$ is a serine residue or a tyrosine residue,
$X_{100}$ is a serine residue or an arginine residue,
$X_{101}$ is a phenylalanine residue or no residue,
$X_{102}$ is a glycine residue or an aspartate residue,
$X_{103}$ is a histidine residue or a proline residue

```
H4          - - - D S G Y S S S W H F D Y -
H1          - - - D R D Y G V N Y D A F D I
H2          - S R N W N Y D N Y Y Y G L D V
H12         - S R N W N Y D S Y Q Y G L D V
H9          - S R N W N Y D N Y Y Y G L D V
H3          G S S S W Y Y - Y N G M D V -
H7          - E R Q W L Y - - H Y G M D V
CONSENSUS:  X104X105X106X107X108X109YX110X111X112X113X114X115
            X116X117X118
            (SEQ ID NOS 260, 64, 144, 192, 144, 261, 112 and
            249, respectively, in order of appearance)
```

$X_{104}$ is a glycine residue or no residue
$X_{105}$ is a serine residue, a glutamate residue, or no residue
$X_{106}$ is an arginine residue, a serine residue, or no residue,
$X_{107}$ is an aspartate residue, an asparagine residue, a serine residue, or a glutamine resiude
$X_{108}$ is a serine residue, an arginine residue, or a tryptophan residue,
$X_{109}$ is a glycine residue, an aspartate residue, an asparagine residue, a tyrosine residue, or a leucine residue,
$X_{110}$ is a serine residue, a glycine residue, an aspartate residue, or no residue,
$X_{111}$ is a serine residue, a valine residue, an asparagine residue, or a tyrosine residue,
$X_{112}$ is a serine residue, an asparagine residue, a tyrosine residue, or a histidine residue
$X_{113}$ is a tryptophan residue, a tyrosine residue, or a glutamine residue,
$X_{114}$ is a histidine residue, an aspartate residue, a tyrosine residue, or no residue,
$X_{115}$ is a phenylalanine residue, an alanine residue, or a glycine residue,
$X_{116}$ an aspartate residue, a phenylalanine residue, a leucine residue, or a methionine residue
$X_{117}$ a tyrosine residue, or an aspartate residue,
$X_{118}$ is an isoleucine residue, a valine residue, or no residue In one embodiment, the present invention provides an antigen binding protein comprising a light chain variable domain comprising a sequence of amino acids that differs from the sequence of a light chain variable domain selected from the group consisting of L1 through L14 only at 15, 14, 13, 12, 11, 10, 9, 8, 7, 6, 5, 4, 3, 2, or 1 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the group consisting of L1-L14. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence that encodes a light chain variable domain selected from the group consisting of L1-L14 (which includes L1, L2, L3, L4, L5, L6, L7, L8, L9, L10, L11, L12, L13, and L14). In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L14. In another embodiment, the light chain variable domain comprises a sequence of amino acids that is encoded by a polynucleotide that hybridizes under moderately stringent conditions to the complement of a polynucleotide that encodes a light chain variable domain selected from the group consisting of L1-L14. In another embodiment, the light chain variable domain comprises a sequence of amino acids that is encoded by a polynucleotide that hybridizes under moderately stringent conditions to a complement of a light chain polynucleotide of L1-L14.

In another embodiment, the present invention provides an antigen binding protein comprising a heavy chain variable domain comprising a sequence of amino acids that differs from the sequence of a heavy chain variable domain selected from the group consisting of H1-H14 only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the group consisting of H1-H14. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the group consisting of H1-H14. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H14. In another embodiment, the heavy chain variable domain comprises a sequence of amino acids that is encoded by a polynucleotide that hybridizes under moderately stringent conditions to the complement of a polynucleotide that encodes a heavy chain variable domain selected from the group consisting of H1-H14. In another embodiment, the heavy chain variable domain comprises a sequence of amino acids that is encoded by a polynucleotide that hybridizes under moderately stringent conditions to a complement of a heavy chain polynucleotide disclosed herein.

Particular embodiments of antigen binding proteins of the present invention comprise one or more amino acid sequences that are identical to the amino acid sequences of one or more of the CDRs and/or FRs referenced herein. In one embodiment, the antigen binding protein comprises a light chain CDR1 sequence illustrated above. In another embodiment, the antigen binding protein comprises a light chain CDR2 sequence illustrated above. In another embodiment, the antigen binding protein comprises a light chain CDR3 sequence illustrated above. In another embodiment, the antigen binding protein comprises a heavy chain CDR1 sequence illustrated above. In another embodiment, the antigen binding protein comprises a heavy chain CDR2 sequence illustrated above. In another embodiment, the antigen binding protein comprises a heavy chain CDR3 sequence illustrated above. In another embodiment, the antigen binding protein comprises a light chain FR1 sequence illustrated above. In another embodiment, the antigen binding protein comprises a light chain FR2 sequence illustrated above. In another embodiment, the antigen binding protein comprises a light chain FR3 sequence illustrated above. In another embodiment, the antigen binding protein comprises a light chain FR4 sequence illustrated above. In another embodiment, the antigen binding protein comprises a heavy chain FR1 sequence illustrated above. In another embodiment, the antigen binding protein comprises a heavy chain FR2 sequence illustrated above. In another embodiment, the antigen binding protein comprises a heavy chain FR3 sequence illustrated above. In another embodiment, the antigen binding protein comprises a heavy chain FR4 sequence illustrated above.

In one embodiment, the present invention provides an antigen binding protein that comprises one or more CDR sequences that differ from a CDR sequence shown above by no more than 5, 4, 3, 2, or 1 amino acid residues.

In another embodiment, at least one of the antigen binding protein's CDR3 sequences is a CDR3 sequence from A1-A14, as shown in Table 7 or Table 8. In another embodiment, the antigen binding protein's light chain CDR3 sequence is a light chain CDR3 sequence from A1-A14 as shown in Table 7 and the antigen binding protein's heavy chain CDR3 sequence is a heavy chain sequence from A1-A14 as shown in Table 8. In another embodiment, the antigen binding protein comprises 1, 2, 3, 4, or 5 CDR sequence(s) that each independently differs by 6, 5, 4, 3, 2, 1, or 0 single amino acid additions, substitutions, and/or deletions from a CDR sequence of A1-A14, and the antigen binding protein further comprises 1, 2, 3, 4, or 5 CDR sequence(s) that each independently differs by 6, 5, 4, 3, 2, 1, or 0 single amino acid additions, substitutions, and/or deletions from a CDR sequence.

The light chain CDRs of antibodies A1-A14 are shown below in Table 7, and the heavy chain CDRs of antibodies A1-A14 are shown below in Table 8.

TABLE 7

| Light chain CDRs | | | |
|---|---|---|---|
| Antibody | CDR1 | CDR2 | CDR3 |
| A1 | SGDKLGDKYAC (SEQ ID NO: 59) | QDSKRPS (SEQ ID NO: 60) | QAWDSSTAV (SEQ ID NO: 61) |
| A2 | RASQGIRNNLG (SEQ ID NO: 281) | AASSLQS (SEQ ID NO: 283) | LQHNSYPWT (SEQ ID NO: 141) |
| A3 | RASQGIRNDLG (SEQ ID NO: 282) | AASSLQS (SEQ ID NO: 283) | RQQNTYPLT (SEQ ID NO: 284) |
| A4 | RSSQSLLHSTGYNYLD (SEQ ID NO: 253) | LGSFRAS (SEQ ID NO: 254) | MQALQTPCS (SEQ ID NO: 255) |
| A5 | KSSQSILYSSNNKKYLV (SEQ ID NO: 75) | WTSMRES (SEQ ID NO: 76) | QQYYSTPWT (SEQ ID NO: 77) |

TABLE 7-continued

Light chain CDRs

| Antibody | CDR1 | CDR2 | CDR3 |
| --- | --- | --- | --- |
| A6 | RASQSISNYLN (SEQ ID NO: 91) | ATSSLQS (SEQ ID NO: 92) | QQSYSISPT (SEQ ID NO: 93) |
| A7 | RAGQGIRNDLV (SEQ ID NO: 107) | AASSLQS (SEQ ID NO: 283) | LQHNTYPFT (SEQ ID NO: 109) |
| A8 | KSSQSILYSSNNKKYLV (SEQ ID NO: 75) | WTSMRES (SEQ ID NO: 76) | QQYYSTPWT (SEQ ID NO: 77) |
| A9 | RASQGIRNNLG (SEQ ID NO: 281) | AASSLQS (SEQ ID NO: 283) | LQHNSYPWT (SEQ ID NO: 141) |
| A10 | SGEKWGEKYAC (SEQ ID NO: 155) | QDTKRPS (SEQ ID NO: 156) | QAWDRSTV (SEQ ID NO: 157) |
| A11 | SGDKLGDKFAF (SEQ ID NO: 171) | QDNKRPS (SEQ ID NO: 172) | QAWDSSTVV (SEQ ID NO: 173) |
| A12 | RASQGIRNDLG (SEQ ID NO: 282) | AASSLQS (SEQ ID NO: 283) | LQHNSYTWT (SEQ ID NO: 189) |
| A13 | SGDKLGDKYVC (SEQ ID NO: 203) | LDNKRPS (SEQ ID NO: 204) | QAWDSSTV (SEQ ID NO: 205) |
| A14 | SGDKLGDKYAF (SEQ ID NO: 219) | HDTKRPS (SEQ ID NO: 220) | QAWDSSTV (SEQ ID NO: 205) |

TABLE 8

Heavy chain CDRs

| Antibody | CDR1 | CDR2 | CDR3 |
| --- | --- | --- | --- |
| A1 | GYTFTSYGLS (SEQ ID NO: 62) | WIIPYNGNTNSAQKLQG (SEQ ID NO: 63) | DRDYGVNYDAFDI (SEQ ID NO: 64) |
| A2 | GFTFSSYGMH (SEQ ID NO: 285) | VIWYDGSNKYHADSVKG (SEQ ID NO: 143) | SRNWNYDNYYYGLDV (SEQ ID NO: 144) |
| A3 | GFTFSSYWMS (SEQ ID NO: 286) | NIKQDGSEEYYVDSVKG (SEQ ID NO: 287) | GSSSWYYYNYGMDV (SEQ ID NO: 288) |
| A4 | GYTFTGYYIH (SEQ ID NO: 256) | WINPNSGGTNYAQKFQG (SEQ ID NO: 258) | DSGYSSSWHFDY (SEQ ID NO: 260) |
| A5 | GGSINSFYWS (SEQ ID NO: 78) | YIYYSGSTNYNPSLKS (SEQ ID NO: 79) | DSIAAPFDY (SEQ ID NO: 80) |
| A6 | GGSFSAYYWS (SEQ ID NO: 94) | EINHSGGTNYNPSLKS (SEQ ID NO: 95) | VQWLELAYFDY (SEQ ID NO: 96) |
| A7 | GFTFISYGMH (SEQ ID NO: 110) | VIWYDGSTEYYADSVKG (SEQ ID NO: 111) | ERQWLYHYGMDV (SEQ ID NO: 112) |
| A8 | GGSINSFYWS (SEQ ID NO: 126) | YIYYSGSTNYNPSLKR (SEQ ID NO: 127) | DSIAAPFDY (SEQ ID NO: 80) |
| A9 | GFTFSSYGMH (SEQ ID NO: 285) | VIWYDGSNKYHADSVKG (SEQ ID NO: 143) | SRNWNYDNYYYGLDV (SEQ ID NO: 144) |
| A10 | GYSFTSYWIG (SEQ ID NO: 158) | IIYPGDSDTRYSPSFQG (SEQ ID NO: 159) | QGLGFDY (SEQ ID NO: 160) |
| A11 | GGSISSGGYYWS (SEQ ID NO: 174) | YISYSGSTYYNPSLKS (SEQ ID NO: 175) | AYGDYRGWFDP (SEQ ID NO: 176) |
| A12 | GFTFSAYGMH (SEQ ID NO: 190) | VIWYDGSNKYYADSVKG (SEQ ID NO: 191) | SRNWNYDSYQYGLDV (SEQ ID NO: 192) |
| A13 | GYTFTSYGIS (SEQ ID NO: 206) | WISAYNGNTNYAQKFQG (SEQ ID NO: 207) | DQDYYDSSGWGH (SEQ ID NO: 208) |

TABLE 8-continued

Heavy chain CDRs

| Antibody | CDR1 | CDR2 | CDR3 |
|---|---|---|---|
| A14 | GYTFTSYGIS (SEQ ID NO: 206) | WISPYNGNTNYAQKFQG (SEQ ID NO: 259) | DQDYYDSSGWDP (SEQ ID NO: 224) |

The nucleotide sequences of A1-A14, or the amino acid sequences of A1-A14, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of anti-activin-A antibodies that have a desired property, for example, increased affinity, avidity, or specificity for activin-A, increased activity or stability in vivo or in vitro, or reduced in vivo side-effects as compared to the underivatized antibody.

Other derivatives of anti-activin-A antibodies within the scope of this invention include covalent or aggregative conjugates of anti-activin-A antibodies, or fragments thereof, with other proteins or polypeptides, such as by expression of recombinant fusion proteins comprising heterologous polypeptides fused to the N-terminus or C-terminus of an anti-activin-A antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide Asp-Tyr-Lys-Asp-Asp-Asp-Asp-Lys (DYKDDDDK) (SEQ ID NO: 226) as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-activin-A antibody may be substituted for the variable portion of an antibody heavy and/or light chain.

Oligomers that contain one or more antigen binding proteins may be employed as activin-A antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have activin-A binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 Curr. Prot.s in Immunol., Suppl. 4, pages 10.19.1-10.19.11.

One embodiment of the present invention is directed to a dimer comprising two fusion proteins created by fusing an activin-A binding fragment of an anti-activin-A antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-activin-A antibody fragment or derivative fused to a leucine zipper peptide are expressed in suitable host cells, and the soluble oligomeric anti-activin-A antibody fragments or derivatives that form are recovered from the culture supernatant.

In one aspect, the present invention provides antigen binding proteins that interfere with the binding of activin-A to an activin-A receptor. Such antigen binding proteins can be made against activin-A, or a fragment, variant or derivative thereof, and screened in conventional assays for the ability to interfere with binding of activin-A to activin-A receptor. Examples of suitable assays are assays that test the antigen binding proteins for the ability to inhibit binding of activin-A to cells expressing activin-A receptor, or that test antigen binding proteins for the ability to reduce a biological or cellular response that results from the binding of activin-A to cell surface activin-A receptors. For example, antibodies can be screened according to their ability to bind to immobilized antibody surfaces (activin-A and/or activin B). Antigen binding proteins that block the binding of activin-A to an activin-A receptor can be employed in treating any activin-A-related condition, including but not limited to cachexia. In an embodiment, a human anti-activin-A monoclonal antibody generated by procedures involving immunization of transgenic mice is employed in treating such conditions.

Antigen-binding fragments of antigen binding proteins of the invention can be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619, 5,225,539, 5,821,337, 5,859,205, 6,881,557, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with an activin-A polypeptide, such that antibodies directed against the activin-A polypeptide are generated in the animal.

One example of a suitable immunogen is a soluble human activin-A, such as a polypeptide comprising the extracellular domain of the protein having the following sequence: Gly Leu Glu Cys Asp Gly Lys Val Asn Ile Cys Cys Lys Lys Gln Phe Phe Val Ser Phe Lys Asp Ile Gly Trp Asn Asp Trp Ile Ile Ala Pro Ser Gly Tyr His Ala Asn Tyr Cys Glu Gly Glu Cys Pro Ser His Ile Ala Gly Thr Ser Gly Ser Ser Leu Ser Phe His Ser Thr Val Ile Asn His Tyr Arg Met Arg Gly His Ser Pro Phe Ala Asn Leu Lys Ser Cys Cys Val Pro Thr Lys Leu Arg Pro Met Ser Met Leu Tyr Tyr Asp Asp Gly Gln Asn Ile Ile Lys Lys Asp Ile Gln Asn Met Ile Val Glu Glu Cys Gly Cys Ser (SEQ ID NO: 225)), or other immunogenic fragment of the protein. Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, N.J.: 191-200, Kellermann et al., 2002, *Curr Opin Biotechnol.* 13:593-97, Russel et al., 2000, *Infect Immun.* 68:1820-26, Gallo et al., 2000, *Eur J Immun.* 30:534-40, Davis et al., 1999, *Cancer Metastasis Rev.* 18:421-25, Green, 1999, *J Immunol Methods.* 231:11-23, Jakobovits, 1998, *Advanced Drug Delivery Reviews* 31:33-42, Green et al., 1998, *J Exp Med.* 188:483-95, Jakobovits A, 1998, *Exp. Opin. Invest. Drugs.* 7:607-14, Tsuda et al., 1997, *Genomics.* 42:413-21, Mendez et al., 1997, *Nat Genet.* 15:146-56, Jakobovits, 1994, *Curr Biol.* 4:761-63, Arbones et al., 1994, *Immunity.* 1:247-60, Green et al., 1994, *Nat Genet.* 7:13-21, Jakobovits et al., 1993, *Nature.* 362:255-58, Jakobovits et al., 1993, *Proc Natl Acad Sci USA.* 90:2551-55. Chen, J., M. Trounstine, F. W. Alt, F. Young, C. Kurahara, J. Loring, D. Huszar. *Inter'l Immunol.* 5 (1993): 647-656, Choi et al., 1993, *Nature Genetics* 4: 117-23, Fishwild et al., 1996, *Nature Biotech.* 14: 845-51, Harding et al., 1995, Annals of the New York Academy of Sciences, Lonberg et al., 1994, *Nature* 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, *Nature Biotechnology* 14: 826, Taylor et al., 1992, *Nucleic Acids Res.* 20: 6287-95, Taylor et al., 1994, *Inter'l Immunol.* 6: 579-91, Tomizuka et al., 1997, *Nature Genetics* 16: 133-43, Tomizuka et al., 2000, *Pro. Nat'l Acad. Sci. USA* 97: 722-27, Tuaillon et al., 1993, *Pro. Nat'l Acad. Sci. USA* 90: 3720-24, and Tuaillon et al., 1994, *J. Immunol.* 152: 2912-20.

In another aspect, the present invention provides monoclonal antibodies that bind to activin-A. Monoclonal antibodies of the invention may be generated using a variety of known techniques. In general, monoclonal antibodies that bind to specific antigens may be obtained by methods known to those skilled in the art (see, for example, Kohler et al., *Nature* 256:495, 1975; Coligan et al. (eds.), *Current Protocols in Immunology*, 1:2.5.12.6.7 (John Wiley & Sons 1991); U.S. Pat. Nos. RE 32,011, 4,902,614, 4,543,439, and U.S. Pat. No. 4,411,993; *Monoclonal Antibodies, Hybridomas: A New Dimension in Biological Analyses*, Plenum Press, Kennett, McKearn, and Bechtol (eds.) (1980); and *Antibodies: A Laboratory Manual*, Harlow and Lane (eds.), Cold Spring Harbor Laboratory Press (1988); Picksley et al., "Production of monoclonal antibodies against proteins expressed in *E. coli*," in DNA Cloning 2: Expression Systems, 2nd Edition, Glover et al. (eds.), page 93 (Oxford University Press 1995)). Antibody fragments may be derived therefrom using any suitable standard technique such as proteolytic digestion, or optionally, by proteolytic digestion (for example, using papain or pepsin) followed by mild reduction of disulfide bonds and alkylation. Alternatively, such fragments may also be generated by recombinant genetic engineering techniques as described herein.

Monoclonal antibodies can be obtained by injecting an animal, for example, a rat, hamster, a rabbit, or preferably a mouse, including for example a transgenic or a knock-out, as known in the art, with an immunogen comprising human activin-A (caggtgcagc tgcaggagtc gggcccagga ctggtgaagc cttcggagac cctgtccctc acctgcactg tctctggtgg ctccatcaat agtttctact ggagctggat ccggcagccc ccagggaagg gactggagtg gattgggtat atctattaca gtgggagcac caactacaat ccctccctca agagtcgagt caccatatca gtagacacgt ccaagaccca gttctccctg aagctgagct ctgtgaccgc tgcggacacg gccgtgtatt actgtgcgag agacagtata gcagccccct ttgactactg gggccaggga accctggtca ccgtctcctc agcttccacc aagggcccat ccgtcttccc cctggcgccc tgctccagga gcacctccga gagcacagccgccctgggct gcctggtcaa ggactacttc cccgaaccgg tgacggtgtc gtggaactca tgcgccct (SEQ ID NO: 66)), or a fragment thereof, according to methods known in the art and described herein. The presence of specific antibody production may be monitored after the initial injection and/or after a booster injection by obtaining a serum sample and detecting the presence of an antibody that binds to human activin-A or peptide using any one of several immunodetection methods known in the art and described herein. From animals producing the desired antibodies, lymphoid cells, most commonly cells from the spleen or lymph node, are removed to obtain B-lymphocytes. The B lymphocytes are then fused with a drug-sensitized myeloma cell fusion partner, preferably one that is syngeneic with the immunized animal and that optionally has other desirable properties (e.g., inability to express endogenous Ig gene products, e.g., P3X63-Ag 8.653 (ATCC No. CRL 1580); NSO, SP20) to produce hybridomas, which are immortal eukaryotic cell lines.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. A preferred selection media is HAT (hypoxanthine, aminopterin, thymidine). After a sufficient time, usually about one to two weeks, colonies of cells are observed. Single colonies are isolated, and antibodies produced by the cells may be tested for binding activity to human activin-A, using any one of a variety of immunoassays known in the art and described herein. The hybridomas are cloned (e.g., by limited dilution cloning or by soft agar plaque isolation) and positive clones that produce an antibody specific to activin-A are selected and cultured. The monoclonal antibodies from the hybridoma cultures may be isolated from the supernatants of hybridoma cultures.

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Hybridoma cell lines are identified that produce an antibody that binds an activin-A polypeptide. Such hybridoma cell lines, and anti-activin-A monoclonal antibodies produced by them, are encompassed by the present invention. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6. Hybridomas or mAbs may be further screened to identify mAbs with particular properties, such as the ability to block an activin-A-induced activity.

An antibody of the present invention may also be a fully human monoclonal antibody. An isolated fully human antibody is provided that specifically binds to the cysteine knot region (amino acids C11-S33 and/or amino acids C81-E111) of activin-A, wherein the antigen binding protein possesses at least one in vivo biological activity of a human anti-activin-A antibody. The biological activity may be attenuation of cachexia, for example cachexia in colon cancer, such as in a mouse model of colon cancer described herein. The cachexia amenable to such treatment is associated with loss of body weight, loss of muscle mass, and/or loss of fat mass. The cachexia may be associated with rheumatoid arthritis, such as in a collagen-induced animal model of rheumatoid arthritis. Treatment with a fully human antibody described herein ameliorates the loss of body weight, the loss of muscle mass, and/or the loss of fat mass in vivo in a collagen-induced animal model of rheumatoid arthritis. A fully human antibody described herein ameliorates the loss of body weight in a AAV-activin-A transfected animal model. A fully human antibody described herein, that specifically binds to the cysteine knot region (amino acids C11-S33 and/or amino acids C81-E111) of activin-A, inhibits the binding of activin-A to activin-A receptor in vitro. A fully human isolated antibody that specifically binds to the cysteine knot region (amino acids C11-S33 and/or amino acids C81-E111) of activin-A, inhibits the binding of activin-A to activin-A receptor in vivo.

Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein. For example, fully human monoclonal antibodies may be obtained from transgenic mice that have been engineered to produce specific human antibodies in response to antigenic challenge. Methods for obtaining fully human antibodies from transgenic mice are described, for example, by Green et al., *Nature Genet.* 7:13, 1994; Lonberg et al., *Nature* 368:856, 1994; Taylor et al., *Int. Immun.* 6:579, 1994; U.S. Pat. No. 5,877,397; Bruggemann et al., 1997 *Curr. Opin. Biotechnol.* 8:455-58; Jakobovits et al., 1995 *Ann. N.Y. Acad. Sci.* 764:525-35. In this technique, elements of the human heavy and light chain locus are introduced into strains of mice derived from embryonic stem cell lines that contain targeted disruptions of the endogenous heavy chain and light chain loci (see also Bruggemann et al., *Curr. Opin. Biotechnol.* 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue. Fully human monoclonal antibodies may be obtained by immunizing the transgenic mice, which may then produce human antibodies specific for activin-A. Lymphoid cells of the immunized transgenic mice can be used to produce human antibody-secreting hybridomas according to the methods described herein. Polyclonal sera containing fully human antibodies may also be obtained from the blood of the immunized animals.

Another method for generating human antibodies of the invention includes immortalizing human peripheral blood cells by EBV transformation. See, e.g., U.S. Pat. No. 4,464, 456. Such an immortalized B-cell line (or lymphoblastoid cell line) producing a monoclonal antibody that specifically binds to activin-A can be identified by immunodetection methods as provided herein, for example, an ELISA, and then isolated by standard cloning techniques. The stability of the lymphoblastoid cell line producing an anti-activin-A antibody may be improved by fusing the transformed cell line with a murine myeloma to produce a mouse-human hybrid cell line according to methods known in the art (see, e.g., Glasky et al., *Hybridoma* 8:377-89 (1989)). Still another method to generate human monoclonal antibodies is in vitro immunization, which includes priming human splenic B-cells with human activin-A, followed by fusion of primed B-cells with a heterohybrid fusion partner. See, e.g., Boerner et al., 1991 *J. Immunol.* 147:86-95.

In certain embodiments, a B-cell that is producing an anti-human activin-A antibody is selected and the light chain and heavy chain variable regions are cloned from the B-cell according to molecular biology techniques known in the art (WO 92/02551; U.S. Pat. No. 5,627,052; Babcook et al., *Proc. Natl. Acad. Sci. USA* 93:7843-48 (1996)) and described herein. B-cells from an immunized animal may be isolated from the spleen, lymph node, or peripheral blood sample by selecting a cell that is producing an antibody that specifically binds to activin-A. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human activin-A. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 *Annu. Rev. Immunol.* 12:433-55; Burton et al., 1994 *Adv. Immunol.* 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 *Science* 246:1275-81; Sastry et al., *Proc. Natl. Acad. Sci. USA* 86:5728-32 (1989); Alting-Mees et al., *Strategies in Molecular Biology* 3:1-9 (1990); Kang et al., 1991 *Proc. Natl. Acad. Sci. USA* 88:4363-66; Hoogenboom et al., 1992 *J. Molec. Biol.* 227:381-388; Schlebusch et al., 1997 *Hybridoma* 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™(H) and λImmunoZap™(L) vectors (Stratagene, La Jolla, Calif.). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, Calif.), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™H or ImmunoZAP™L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., *Science* 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

Activin-A binding agents of the present invention preferably modulate activin-A function in the cell-based assay described herein and/or the in vivo assay described herein and/or bind to one or more of the cysteine knot domains described herein and/or cross-block the binding of one of the antibodies described in this application and/or are cross-blocked from binding activin-A by one of the antibodies described in this application. Accordingly such binding agents can be identified using the assays described herein.

In certain embodiments, antibodies are generated by first identifying antibodies that bind to one more of the cysteine knot domains provided herein and/or neutralize in the cell-based and/or in vivo assays described herein and/or cross-block the antibodies described in this application and/or are cross-blocked from binding activin-A by one of the antibodies described in this application. The CDR regions from these antibodies are then used to insert into appropriate biocompatible frameworks to generate activin-A binding agents. The non-CDR portion of the binding agent may be composed of amino acids, or may be a non-protein molecule. The assays described herein allow the characterization of binding agents. Preferably the binding agents of the present invention are antibodies as defined herein.

Other antibodies according to the invention may be obtained by conventional immunization and cell fusion procedures as described herein and known in the art.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, *J. Mol. Biol.* 263:551. Accordingly, such techniques are useful in preparing antibodies to activin-A. Antigen binding proteins directed against an activin-A can be used, for example, in assays to detect the presence of activin-A polypeptides, either in vitro or in vivo. The antigen binding proteins also may be employed in purifying activin-A proteins by immunoaffinity chromatography.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, *Methods Mol. Biol.* 178:303-16.

In one embodiment, an antigen binding protein of the invention comprises the IgG1 heavy chain domain of any of A1-A14 (H1-H14) or a fragment of the IgG1 heavy chain domain of any of A1-A14 (H1-H14). In another embodiment, an antigen binding protein of the invention comprises the kappa light chain constant chain region of A1-A14 (L1-L14), or a fragment of the kappa light chain constant region of A1-A14 (L1-L14). In another embodiment, an antigen binding protein of the invention comprises both the IgG1 heavy chain domain, or a fragment thereof, of A1-A14 (L1-L14) and the kappa light chain domain, or a fragment thereof, of A1-A14 (L1-L14).

Accordingly, the antigen binding proteins of the present invention include those comprising, for example, the variable domain combinations L1H1, L2H2, L3H3, L4H4, L5H5, L6H6, L7H7, L8H8, L9H9, L10H10, L11H11, L12H12, L13H13, and L14H14, having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation (CPSCP→CPPCP) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

In one embodiment, the antigen binding protein has a $K_{off}$ of $1 \times 10^{-4}$ s$^{-1}$ or lower. In another embodiment, the $K_{off}$ is $5 \times 10^{-5}$ s$^{-1}$ or lower. In another embodiment, the $K_{off}$ is substantially the same as an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, and L14H14. In another embodiment, the antigen binding protein binds to activin-A with substantially the same $K_{off}$ as an antibody that comprises one or more CDRs from an antibody having a combination of light chain and heavy chain variable domain sequences selected from the group of combinations consisting of L1H1, L2H2, L3H3, L4H4, L5H5, L6H6, L7H7, L8H8, L9H9, L10H10, L11H11, L12H12, L13H13, and L14H14. In another embodiment, the antigen binding protein binds to activin-A with substantially the same $K_{off}$ as an antibody that comprises one of the amino acid sequences illustrated above. In another embodiment, the antigen binding protein binds to activin-A with substantially the same $K_{off}$ as an antibody that comprises one or more CDRs from an antibody that comprises one of the amino acid sequences illustrated above.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble activin-A polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared, and screened for desired properties, by any of a number of conventional techniques. Certain of the techniques involve isolating a nucleic acid encoding a polypeptide chain (or portion thereof) of an antigen binding protein of interest (e.g., an anti-activin-A antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example. Furthermore, the antigen binding proteins may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. Expression systems are detailed comprehensively above. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or Bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

The transformed cells can be cultured under conditions that promote expression of the polypeptide, and the polypeptide recovered by conventional protein purification procedures (as defined above). One such purification procedure includes the use of affinity chromatography, e.g., over a matrix having all or a portion (e.g., the extracellular domain) of activin-A bound thereto. Polypeptides contemplated for use herein include substantially homogeneous recombinant mammalian anti-activin-A antibody polypeptides substantially free of contaminating endogenous materials.

In one aspect, the present invention provides antigen-binding fragments of an anti-activin-A antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies (scFv) may be formed by linking heavy and light chain variable domain (Fv region) fragments via an amino acid bridge (short peptide linker, e.g., a synthetic sequence of amino acid residues), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108, Bird et al., 1988, *Science* 242:423-26 and Huston et al., 1988, *Proc. Natl. Acad. Sci. USA* 85:5879-83). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol Biol.* 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, L10H10, L11H11, L12H12, L13H13, and L14H14 are encompassed by the present invention.

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, *Proc. Natl. Acad. Sci. USA* 90:6444-48, and Poljak et al., 1994, *Structure* 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

In certain preferred embodiments, an antibody comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative binding agent comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antibody of the present invention may have at least one amino acid substitution, providing that the antibody retains binding specificity. Therefore, modifications to the antibody structures are encompassed within the scope of the invention. These may include amino acid substitutions, which may be conservative or non-conservative, that do not destroy the activin-A binding capability of an antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

Non-conservative substitutions may involve the exchange of a member of one class of amino acids or amino acid mimetics for a member from another class with different physical properties (e.g. size, polarity, hydrophobicity, charge). Such substituted residues may be introduced into regions of the human antibody that are homologous with non-human antibodies, or into the non-homologous regions of the molecule.

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules.

A number of scientific publications have been devoted to the prediction of secondary structure. See Moult J., Curr. Op. in Biotech., 7(4):422-427 (1996), Chou et al., Biochem., 13(2):222-245 (1974); Chou et al., Biochem., 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. An N-linked glycosylation site is characterized by the sequence:

Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to activin-A, or to increase or decrease the affinity of the antibodies to activin-A described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (5) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. *Nature* 354:105 (1991), which are each incorporated herein by reference.

In certain embodiments, antibodies of the invention may be chemically bonded with polymers, lipids, or other moieties.

The binding agents may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, *Curr. Opin. in Struct. Biol.*, 7, 463-469).

It will be appreciated that the antibodies of the invention include the humanized antibodies described herein. Humanized antibodies such as those described herein can be produced using techniques known to those skilled in the art (Zhang, W., et al., *Molecular Immunology.* 42(12):1445-1451, 2005; Hwang W. et al., *Methods.* 36(1):35-42, 2005; Dall'Acqua W F, et al., *Methods* 36(1):43-60, 2005; and Clark, M., *Immunology Today.* 21(8):397-402, 2000).

Additionally, one skilled in the art will recognize that suitable binding agents include portions of these antibodies, such as one or more of CDR-H1, CDR-H2, CDR-H3, CDR-L1, CDR-L2 and CDR-L3 as specifically disclosed herein. At least one of the regions of CDR-H1, CDR-H2, CDR-H3, CDR-L1, CDR-L2 and CDR-L3 may have at least one amino acid substitution, provided that the antibody retains the binding specificity of the non-substituted CDR. The non-CDR portion of the antibody may be a non-protein molecule, wherein the binding agent cross-blocks the binding of an antibody disclosed herein to activin-A and/or neutralizes activin-A. The non-CDR portion of the antibody may be a non-protein molecule in which the antibody exhibits a similar binding pattern to human activin-A peptides in a competition binding assay as that exhibited by at least one of antibodies A1-A14, and/or neutralizes activin-A. The non-CDR portion of the antibody may be composed of amino acids, wherein the antibody is a recombinant binding protein or a synthetic peptide, and the recombinant binding protein cross-blocks the binding of an antibody disclosed herein to activin-A and/or neutralizes activin-A. The non-CDR portion of the antibody may be composed of amino acids, wherein the antibody is a recombinant antibody, and the recombinant antibody exhibits a similar binding pattern to human activin-A peptides in the human activin-A peptide epitope competition binding assay (described hereinbelow) as that exhibited by at least one of the antibodies A1-A14, and/or neutralizes activin-A.

Where an antibody comprises one or more of CDR-H1, CDR-H2, CDR-H3, CDR-L1, CDR-L2 and CDR-L3 as described above, it may be obtained by expression from a host cell containing DNA coding for these sequences. A DNA coding for each CDR sequence may be determined on the basis of the amino acid sequence of the CDR and synthesized together with any desired antibody variable region framework and constant region DNA sequences using oligonucleotide synthesis techniques, site-directed mutagenesis and polymerase chain reaction (PCR) techniques as appropriate. DNA coding for variable region frameworks and constant regions is widely available to those skilled in the art from genetic sequences databases such as GenBank®.

Once synthesized, the DNA encoding an antibody of the invention or fragment thereof may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be preferred in a eukaryotic host cell, including yeast (e.g., *Saccharomyces cerevisiae, Schizosaccharomyces pombe*, and *Pichia pastoris*), animal cells (including mammalian cells) or plant cells. Examples of suitable animal cells include, but are not limited to, myeloma (such as a mouse NSO line), COS, CHO, or hybridoma cells. Examples of plant cells include tobacco, corn, soybean, and rice cells.

One or more replicable expression vectors containing DNA encoding an antibody variable and/or constant region may be prepared and used to transform an appropriate cell line, for example, a non-producing myeloma cell line, such as a mouse NSO line or a bacteria, such as *E. coli*, in which production of the antibody will occur. In order to obtain efficient transcription and translation, the DNA sequence in each vector should include appropriate regulatory sequences, particularly a promoter and leader sequence operatively linked to the variable domain sequence. Particular methods for producing antibodies in this way are generally well-known and routinely used. For example, basic molecular biology procedures are described by Maniatis et al. (*Molecular Cloning, A Laboratory Manual*, 2nd ed., Cold Spring Harbor Laboratory, New York, 1989; see also Maniatis et al, 3rd ed., Cold Spring Harbor Laboratory, New York, (2001)). DNA sequencing can be performed as described in Sanger et al. (PNAS 74:5463, (1977)) and the Amersham International plc sequencing handbook, and site directed mutagenesis can be carried out according to methods known in the art (Kramer et al., *Nucleic Acids Res.* 12:9441, (1984); Kunkel *Proc. Natl. Acad. Sci. USA* 82:488-92 (1985); Kunkel et al., *Methods in Enzymol.* 154:367-82 (1987); the Anglian Biotechnology Ltd. handbook). Additionally, numerous publications describe techniques suitable for the preparation of antibodies by manipulation of DNA, creation of expression vectors, and transformation and culture of appropriate cells (Mountain A and Adair, J R in *Biotechnology and Genetic Engineering Reviews* (ed. Tombs, M P, 10, Chapter 1, 1992, Intercept, Andover, UK); "Current Protocols in Molecular Biology", 1999, F. M. Ausubel (ed.), Wiley Interscience, New York).

Where it is desired to improve the affinity of antibodies according to the invention containing one or more of the above-mentioned CDRs can be obtained by a number of affinity maturation protocols including maintaining the CDRs (Yang et al., *J Mol. Biol.*, 254, 392-403, 1995), chain shuffling (Marks et al., *Bio/Technology*, 10, 779-783, 1992), use of mutation strains of *E. coli*. (Low et al., *J. Mol. Biol.*, 250, 350-368, 1996), DNA shuffling (Patten et al., *Curr. Opin. Biotechnol.*, 8, 724-733, 1997), phage display (Thompson et al., *J. Mol. Biol.*, 256, 7-88, 1996) and sexual PCR (Crameri, et al., *Nature*, 391, 288-291, 1998). All of these methods of affinity maturation are discussed by Vaughan et al. (*Nature Biotech.*, 16, 535-539, 1998).

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. *Journal of Chromatography* 705:129-134, 1995).

svActRIIB: Activin IIB Receptor

The present invention discloses an isolated protein comprising a stabilized human activin IIB receptor (svActRIIB) polypeptide. The protein and polypeptide of the invention are characterized by their ability to bind to at least one of three TGF-β proteins, myostatin (GDF-8), activin-A, or GDF-11, to inhibit the activities of at least one of these proteins, and to have improved manufacturability properties compared with other ActRIIB soluble receptors. The stabilized human activin IIB receptor polypeptide is characterized by amino acid substitutions at both positions E28 and S44 with reference to the extracellular domain of ActRIIB, as set forth in the following sequence: Met Thr Ala Pro Trp Val Ala Leu Ala Leu Leu Trp Gly Ser Leu Cys Ala Gly Ser Gly Arg Gly Glu Ala Glu Thr Arg Glu Cys Ile Tyr Tyr Asn Ala Asn Trp Glu Leu Glu Arg Thr Asn Gln Ser Gly Leu Glu Arg Cys Glu Gly Glu Gln Asp Lys Arg Leu His Cys Tyr Ala Ser Trp Arg Asn Ser Ser Gly Thr Ile Glu Leu Val Lys Lys Gly Cys Trp Leu Asp Asp Phe Asn Cys Tyr Asp Arg Gln Glu Cys Val Ala Thr Thr Glu Glu Asn Pro Gln Val Tyr Phe Cys Cys Cys Glu Gly Asn Phe Cys Asn Glu Arg Phe Thr His Leu Pro Glu Ala Gly Gly Pro Glu Val Thr Tyr Glu Pro Pro Pro Thr Ala Pro Thr (SEQ ID NO:2). In one embodiment, a stabilized human activin IIB receptor polypeptide can have a further substitution of alanine at position 64 with respect to the above sequence.

"TGF-β family members" or "TGF-β proteins" refers to the structurally related growth factors of the transforming growth factor family including activins, and growth and differentiation factor (GDF) proteins (Kingsley et al. Genes Dev. 8: 133-146 (1994), McPherron et al., Growth factors and cytokines in health and disease, Vol. 1B, D. LeRoith and C. Bondy. ed., JAI Press Inc., Greenwich, Conn, USA: pp 357-393).

GDF-8, also referred to as myostatin, is a negative regulator of skeletal muscle tissue (McPherron et al. PNAS USA 94:12457-12461 (1997)). Myostatin is synthesized as an inactive protein approximately 375 amino acids in length, having GenBank Accession No: AAB86694 for human. The precursor protein is activated by proteolytic cleavage at a tetrabasic processing site to produce an N-terminal inactive prodomain and an approximately 109 amino acid C-terminal protein which dimerizes to form a homodimer of about 25 kDa. This homodimer is the mature, biologically active protein (Zimmers et al., Science 296, 1486 (2002)).

A "prodomain" or "propeptide" is the inactive N-terminal protein which is cleaved off to release the active C-terminal protein. As used herein the term "myostatin" or "mature myostatin" refers to the mature, biologically active C-terminal polypeptide, in monomer, dimer or other form, as well as biologically active fragments or related polypeptides including allelic variants, splice variants, and fusion peptides and polypeptides. The mature myostatin has been reported to have 100% sequence identity among many species including human, mouse, chicken, porcine, turkey, and rat (Lee et al., PNAS 98, 9306 (2001)).

GDF-11 refers to the BMP (bone morphogenic protein) having Swissprot accession number 095390, as well as variants and species homologs of that protein. GDF-11 is involved in the regulation of anterior/posterior patterning of the axial skeleton (McPherron et al, Nature Genet. 22 (93): 260-264 (1999); Gamer et al, Dev. Biol. 208 (1), 222-232 (1999)) but postnatal functions are unknown.

Receptor Polypeptides

An activin type II B receptor (ActRIIB) can be a human activin receptor having accession number NP_001097 or a variant thereof, such as that having the arginine at position 64 substituted with alanine. The term soluble ActRIIB (wild type) refers to the extracellular domain of ActRIIB, amino acids 1 to 134 (with signal sequence), or amino acids 19 through 134 of SEQ ID NO: 2 (without signal sequence).

The present invention provides an isolated protein comprising a stabilized ActIIB receptor polypeptide (referred herein as "svActRIIB polypeptide"). A "svActRIIB protein" is a protein comprising a stabilized ActRIIB polypeptide. The term "isolated" refers to a protein or polypeptide molecule purified to some degree from endogenous material. These polypeptides and proteins are characterized as having the ability to bind and inhibit the activity of any one of activin-A, myostatin, or GDF-11, in addition to having improved manufacturability characteristics.

The stabilized ActRIIB polypeptide is characterized by having an amino acid substitution at both position 28 and 44 with respect to SEQ ID NO: 2. For consistency, the amino acid positions on the stabilized ActRIIB polypeptides and proteins are always referred to with respect to the positions in SEQ ID NO: 2, regardless of whether the polypeptide is mature or truncated. As used herein, the term "mature" refers to a polypeptide or peptide without its signal sequence. As used herein, the term "truncated" refers to polypeptides having N terminal amino acids or C terminal amino acids removed.

In one embodiment, the isolated stabilized activin IIB receptor polypeptide (svActRIIB) has the polypeptide sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polypeptide has an amino acid sequence with at least 80%, 85%, 90%, 95%, 96%, 97%, 98% or 99% identity to any one of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin-A, or GDF-11. In one embodiment, the substitution of the above polypeptides at position 28 is W, and the substitution at position 44 is T, wherein the polypeptide is capable of binding myostatin, activin-A, or GDF-11.

In one embodiment, the svActRIIB polypeptide includes a signal sequence, for example, SEQ ID NO: 4, 8, 12, and 16 (see below for sequences). However, various signal peptides can be used in the preparation of the polypeptides of the instant application. The signal peptides can have the sequence set forth in amino acids 1 to 19 of SEQ ID NO: 4, for example, or the signal sequences set forth in SEQ ID NO: 31 and 32. Any other signal peptides useful for expressing svActRIIB polypeptides may be used. In other embodiments, the signal sequence is removed, leaving the mature peptide. Examples of svActRIIB polypeptides lacking a signal sequence includes, for example, SEQ ID NO: 6, 10, 14 and 18.

In one embodiment, the protein comprises a stabilized activin IIB receptor polypeptide, wherein the polypeptide is selected from the group consisting of polypeptides having the sequence set forth in the group consisting of SEQ ID NO: 4, 6, 12 and 14. These polypeptides represent amino acids 25 to 134 of SEQ ID NO: 2, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin-A, or GDF-11, with and without a signal sequence different from that shown in SEQ ID NO: 2. In another embodiment the protein comprises a polypeptide having at least 80%, 85%, 90%, 95%, 96%, 97%, 98%, or 99% sequence identity to SEQ ID NO: 4, 6, 12 or 14, wherein the polypeptide has a W or Y at position 28 and a T at position 44, and wherein the polypeptide is capable of binding myostatin, activin-A, or GDF-11. In one embodiment, the substitution at position 28 is W and the substitution at position 44 is T, wherein the polypeptide is capable of binding myostatin, activin-A or GDF-11.

In a further embodiment the svActRIIB protein further comprises a heterologous protein. In one embodiment, the heterologous protein is an Fc domain. In a further embodiment, the Fc domain is a human IgG Fc domain. In one embodiment, the protein comprises a polypeptide having the sequence set forth in the group consisting of SEQ ID NO: 8, 10, 16 and 18. In another embodiment, the protein comprises a polypeptide having at least 80%, 85%, 90%, 95%, 96%, 97%, 98%, or 99% sequence identity to SEQ ID NO: 8, 10, 16 or 18, wherein the polypeptide has a W or Y at position 28 and a T at position 44, and wherein the polypeptide is capable of binding myostatin, activin-A, or GDF-11. In one embodiment, the substitution at position 28 is W and the substitution at position 44 is T, wherein the polypeptide is capable of binding myostatin, activin-A or GDF-11.

In a further embodiment, the protein comprises the any one of the polypeptides described above, wherein the amino acid residue at position 64 is alanine.

In another embodiment, the term svActRIIB polypeptide and protein encompasses proteins comprising fragments of SEQ ID NO: 2, 4, 6, 12 and 14, including N and C terminal truncations, wherein position 28 is W or Y, and position 44 is T, and wherein the polypeptide is capable of binding myostatin, activin-A or GDF-11.

The term "derivative" of the svActRIIB polypeptide refers to the attachment of at least one additional chemical moiety, or at least one additional polypeptide to form covalent or aggregate conjugates such as glycosyl groups, lipids, acetyl groups, or C-terminal or N-terminal fusion polypeptides, conjugation to PEG molecules, and other modifications which are described more fully below. Stabilized ActRIIB receptor polypeptides can also include additional modifications and derivatives, including modifications to the C and N termini which arise from processing due to expression in various cell types such as mammalian cells, *E. coli*, yeasts and other recombinant host cells.

The svActRIIB proteins of the present invention may further comprise heterologous polypeptides attached to the svActRIIB polypeptide either directly or through a linker sequence to form a fusion protein. As used herein the term "fusion protein" refers to a protein having a heterologous polypeptide attached via recombinant DNA techniques. Heterologous polypeptides include but are not limited to Fc polypeptides, his tags, and leucine zipper domains to promote oligomerization and further stabilization of the stabilized ActRIIB polypeptides as described in, for example, WO 00/29581, which is herein incorporated by reference. In one embodiment, the heterologous polypeptide is an Fc polypeptide or domain. In one embodiment, the Fc domain is selected from a human IgG1 Fc (SEQ ID NO: 23), modified IgG1 Fc (SEQ ID NO: 47), IgG2 Fc (SEQ ID NO: 22), and IgG4 Fc (SEQ ID NO: 24) domain. The svActRIIB protein can further comprise all or a portion of the hinge sequence of the IgG1 (SEQ ID NO: 29), IgG2 (SEQ ID NO: 28), or IgG4 (SEQ ID NO: 30). Exemplary svActRIIB polypeptides are selected from polypeptides consisting of the sequences as set forth in SEQ ID NO: 8, 10, 16 and 18, as well as those polypeptides having substantial similarity to these sequences, wherein the substitutions at positions 28 and 44 are retained. As used herein, "substantial similarity" refers to sequences that are at least 80% identical, 85% identical, 90% identical, 95% identical, 96% identical, 97% identical, 98% identical, 99% identical to any of SEQ ID NO: 8, 10, 16, and 18, wherein the polypeptides retain W or Y at position 28 and T at position 44, and wherein the polypeptide is capable of binding myostatin, activin-A or GDF-11. In one embodiment, the substitution at position 28 is W and the substitution at position 44 is T, wherein the polypeptide is capable of binding myostatin, activin-A or GDF-11.

The svActRIIB polypeptide can optionally further comprise a "linker" sequence. Linkers serve primarily as a spacer between a polypeptide and a second heterologous polypeptide or other type of fusion or between two or more stabilized ActRIIB polypeptides. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those of skill in the art. In one embodiment, the 1 to 20 amino acids may be selected from glycine, alanine, proline, asparagine, glutamine, and lysine. In one embodiment, a linker is made up of a majority of amino acids that are sterically unhindered, such as glycine and alanine. Exemplary linkers are polyglycines (particularly $(Gly)_5$ (SEQ ID NO: 289), $(Gly)_8$ (SEQ ID NO: 290), poly(Gly-Ala), and polyalanines. One exemplary suitable linker as shown in the Examples below is $(Gly)_4$Ser (SEQ ID NO: 25). In a further embodiment, svActRIIB can comprise a "hinge linker", that is a linker sequence provided adjacent to a hinge region or a partial hinge region of an IgG, as exemplified in SEQ ID NO: 27. Hinge sequences include IgG2Fc (SEQ ID NO: 28), IgG1Fc (SEQ ID NO: 29), and IgG4Fc (SEQ ID NO: 30).

Hinge linker sequences may also be designed to improve manufacturability and stability of the svActRIIB-Fc proteins. In one embodiment, the hinge linkers of SEQ ID NO: 27, 38, 40, 42, 44, 45, and 46 are designed to improve manufacturability with the IgG2 Fc (SEQ ID NO: 22) when attached to svActRIIB polypeptides. In one embodiment, the hinge linker sequences is designed to improve manufacturability when attaching svActRIIB polypeptides to a human IgG1 Fc (SEQ ID NO: 23) or a modified human IgG1 Fc (SEQ ID NO: 47), for example, the hinge linkers having SEQ ID NO: 48, SEQ ID NO: 49 and SEQ ID NO: 50.

Linkers may also be non-peptide linkers. For example, alkyl linkers such as —NH—$(CH_2)$s-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

The svActRIIB polypeptides disclosed herein can also be attached to a non-polypeptide molecule for the purpose of conferring desired properties such as reducing degradation and/or increasing half-life, reducing toxicity, reducing immunogenicity, and/or increasing the biological activity of the svActRIIB polypeptides. Exemplary molecules include but are not limited to linear polymers such as polyethylene glycol (PEG), polylysine, a dextran; a lipid; a cholesterol group (such as a steroid); a carbohydrate, or an oligosaccharide molecule.

The svActRIIB proteins and polypeptides have improved manufacturability properties when compared to other ActRIIB soluble polypeptides. As used herein, the term "manufacturability" refers to the stability of a particular protein during recombinant expression and purification of that protein. Manufacturability is believed to be due to the intrinsic properties of the molecule under conditions of expression and purification.

Activities of the svActRIIB polypeptides include, but are not limited to, the ability to bind to myostatin or activin-A or GDF-11, and the ability to inhibit or neutralize an activity of myostatin or activin-A or GDF-11. As used herein, the term "capable of binding" to myostatin, activin-A, or GDF-11 refers to binding measured by methods known in the art. In vitro inhibition of myostatin, activin-A, or GDF-11 can be measured using, for example, the pMARE C2C12 cell-based assay. In vivo activity, is demonstrated by increased lean muscle mass in mouse models. In vivo activities of the svActRIIB polypeptides and proteins include but are not limited to increasing body weight, increasing lean muscle mass, and increasing the ratio of lean muscle to fat mass. Therapeutic activities further include reducing or preventing cachexia caused by certain types of tumors, preventing the growth of certain types of tumors, and increasing survival of certain animal models. Further discussion of the svActRIIB protein and polypeptide activities is provided below.

In another aspect, the present invention provides an isolated nucleic acid molecule comprising a polynucleotide encoding an svActRIIB polypeptide of the present invention. As used herein the term "isolated" refers to nucleic acid molecules purified to some degree from endogenous material.

In one embodiment, the polynucleotide encodes a polypeptide having the sequence set forth in SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 19 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 23 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes a polypeptide having the sequence set forth in amino acids 25 through 134 of SEQ ID NO: 2, except for a single amino acid substitution at position 28, and a single amino acid substitution at position 44, wherein the substitution at position 28 is selected from W or Y, and the substitution at position 44 is T. In another embodiment, the polynucleotide encodes the a polypeptide having an amino acid sequence at least 80%, 85%, 90%, 95%, 98% or 99% identity to any one of the polypeptides above, wherein the polypeptide has single amino acid substitution at position 28, and a single amino acid substitution at position 44, wherein the substitution at position 28 is selected from W or Y, and the substitution at position 44 is T, and wherein the polypeptide is capable of binding myostatin, activin-A, or GDF-11. In one embodiment, the polynucleotide of the above embodiments encodes a polypeptide wherein the substitution at position 28 is W and the substitution at position 44 is T.

In one embodiment, the isolated nucleic acid molecule of the present invention comprises a polynucleotide encoding a polypeptide having the sequence set forth in the group consisting of SEQ ID NO: 4, 6, 12, and 14. In another embodiment, the nucleic acid comprises a polynucleotide encoding a polypeptide having at least 80%, 90%, 95%, 96%, 97%, 98%, 99% sequence identity to SEQ ID NO: 4, 6, 12 or 14, wherein the polypeptide has a W or Y at position 28 and a T at position 44, and wherein the polypeptide is capable of binding activin-A, GDF-11, or myostatin. In one embodiment, the polynucleotide of the above embodiments encodes a polypeptide wherein the substitution at position 28 is W and the substitution at position 44 is T, and wherein the polypeptide is capable of binding activin-A, GDF-11 or myostatin.

In another embodiment, the isolated nucleic acid molecule further comprises a polynucleotide encoding at least one heterologous protein. In one embodiment, the heterologous protein is an Fc domain, in a further embodiment, the Fc domain is a human IgG Fc domain. In another embodiment, the nucleic acid molecule further comprises polynucleotides encoding the linkers and hinge linkers set forth in SEQ ID NO: 25, 27, 38, 40, 42, 44, 45, 46, 48, 49 or 50. In a further embodiment, such polynucleotides have sequences selected from the group consisting of SEQ ID NO: 26, 37, 39, 41, and 43.

In one embodiment, the nucleic acid molecule comprises a polynucleotide encoding a polypeptide consisting of the sequence set forth in the group consisting of SEQ ID NO: 8, 10, 16 and 18. In another embodiment, the nucleic acid comprises a polynucleotide encoding a polypeptide having at least 80%, 90%, 95%, 96%, 97%, 98%, 99% sequence identity to the group consisting of SEQ ID NO: 8, 10, 16 and 18, wherein the polypeptide has a W or Y at position 28 and a T at position 44, and wherein the polypeptide is capable of binding activin-A, GDF-11, or myostatin. In one embodiment, the polynucleotide of the above embodiments encodes a polypeptide wherein the substitution at position 28 is W and the substitution at position 44 is T, and wherein the polypeptide is capable of binding myostatin, activin-A or GDF-11.

In one embodiment, the isolated nucleic acid molecule comprises a polynucleotide having the sequence selected from the group consisting of SEQ ID NO: 3, 5, 11 or 13, or its complement. In another embodiment, the isolated nucleic acid molecule comprises a polynucleotide having the sequence selected from the group consisting of the sequence SEQ ID NO: 7, 9, 15 and 17, or its complement. In a further embodiment the isolated nucleic acid molecule hybridizes under stringent or moderate conditions with SEQ ID NO: 3, 5, 7, 9, 11, 13, 15 or 17 wherein the encoded polypeptide is substantially similar to SEQ ID NO: 4, 6, 8, 10, 12, 14, 16, or 18, wherein the polypeptide comprises an amino acid sequence having W or Y at position 28, and T at position 44, and wherein the encoded polypeptide is capable of binding or inhibiting activin-A, myostatin or GDF-11.

Nucleic acid molecules of the invention include DNA in both single-stranded and double-stranded form, as well as the RNA complement thereof. DNA includes, for example, cDNA, genomic DNA, synthetic DNA, DNA amplified by PCR, and combinations thereof. Genomic DNA may be isolated by conventional techniques, such as by using the DNA of SEQ ID NO: 3, 5, 11 or 13, or a suitable fragment thereof, as a probe. Genomic DNA encoding ActRIIB polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from procaryotic expression vectors which direct high-level synthesis of mRNA, such as vectors using T7 promoters and RNA polymerase. cDNA is obtained from libraries prepared from mRNA isolated from various tissues that express ActRIIB. The DNA molecules of the invention include full length genes as well as polynucleotides and fragments thereof. The full length gene may also include sequences encoding the N-terminal signal sequence.

The invention further provides the nucleic acid molecule described above, wherein the polynucleotide is operably linked to a transcriptional or translational regulatory sequence.

Exemplary Polynucleotide and Polypeptide Sequences.

```
svActRIIB without signal sequence
                                                              (SEQ ID NO: 2)
Met Thr Ala Pro Trp Val Ala Leu Ala Leu Leu Trp Gly Ser Leu Cys Ala Gly Ser Gly Arg Gly Glu Ala Glu Thr Arg Glu Cys Ile Tyr Tyr Asn Ala Asn Trp Glu Leu Glu Arg Thr Asn Gln Ser Gly Leu Glu Arg Cys Glu Gly Glu Gln Asp Lys Arg Leu His Cys Tyr Ala Ser Trp Arg Asn Ser Ser Gly Thr Ile Glu Leu Val Lys Lys Gly Cys Trp Leu Asp Asp Phe Asn Cys Tyr Asp Arg Gln Glu Cys Val Ala Thr Glu Glu Asn Pro Gln Val Tyr Phe Cys Cys Cys Glu Gly Asn Phe Cys Asn Glu Arg Phe Thr His Leu Pro Glu Ala Gly Gly Pro Glu Val Thr Tyr Glu Pro Pro Pro Thr Ala Pro Thr
```

-continued svActRIIB (E28W, S44T) with signal sequence (SEQ ID NO: 3)

atggagtttgggctgagctgggttttcctcgttgctcttttaagaggtgtccagtgtgagacacggtggtgcatctactacaac gccaactgggagctggagcgcaccaaccagaccggcctggagcgctgcgaaggcgagcaggacaagcggctgcactgctacgcc tcctggcgcaacagctctggcaccatcgagctcgtgaagaagggctgctggctagatgacttcaactgctacgataggcaggag tgtgtggccactgaggagaaccccaggtgtacttctgctgctgtgagggcaacttctgcaacgagcgcttcactcatttgcca gaggctgggggcccggaagtcacgtacgagccaccccgacagcccccacc svActRIIB (E28W, S44T) with signal sequence (SEQ ID NO: 4)

mefglswvflvallrgvqcetrwciyynanwelertnqtglercegeqdkrlhcyaswrnssgtielvkkgcwlddfn cydrqecvateenpqvyfcccegnfcnerfthlpeaggpevtyeppptapt svActRIIB (E28W, S44T) without signal sequence (SEQ ID NO: 5)

gagacacggtggtgcatctactacaacgccaactgggagctggagcgcaccaaccagaccggcctggagcgctgcgaa ggcgagcaggacaagcggctgcactgctacgcctcctggcgcaacagctctggcaccatcgagctcgtgaagaagggc tgctggctagatgacttcaactgctacgataggcaggagtgtgtggccactgaggagaaccccaggtgtacttctgc tgctgtgagggcaacttctgcaacgagcgcttcactcatttgccagaggctgggggcccggaagtcacgtacgagcca ccccgacagcccccacc svActRIIB (E28W, S44T) without signal sequence (SEQ ID NO: 6)

etrwciyynanwelertnqtglercegeqdkrlhcyaswrnssgtielvkkgcwlddfncydrqecvateen pqvyfcccegnfcnerfthlpeaggpevtyeppptapt svActRIIB-Fc (E28W, S44T) polynucleotide sequence with signal sequence (SEQ ID NO: 7)

atggagtttgggctgagctgggttttcctcgttgctcttttaagaggtgtccagtgtgagacacggtggtgcatc tactacaacgccaactgggagctggagcgcaccaaccagaccggcctggagcgctgcgaaggcgagcaggacaag cggctgcactgctacgcctcctggcgcaacagctctggcaccatcgagctcgtgaagaagggctgctggctagat gacttcaactgctacgataggcaggagtgtgtggccactgaggagaaccccaggtgtacttctgctgctgtgag ggcaacttctgcaacgagcgcttcactcatttgccagaggctgggggcccggaagtcacgtacgagccaccccg acagcccccaccggaggggaggatctgtcgagtgccaccgtgcccagcacctgtggcaggaccgtcagtc ttcctcttccccccaaaacccaaggacaccctcatgatctcccggacccctgaggtcacgtgcgtggtggtggac gtgagccacgaagaccccgaggtccagttcaactggtacgtggacggcgtggaggtgcataatgccaagacaaag ccacgggaggagcagttcaacagcacgttccgtgtggtcagcgtcctcaccgttgtgcaccaggactggctgaac ggcaaggagtacaagtgcaaggtctccaacaaggcctcccagccccatcgagaaaaccatctccaaaaccaaa gggcagccccgagaaccacaggtgtacaccctgcccccatcccgggaggagatgaccaagaaccaggtcagcctg acctgcctggtcaaaggcttctatcccagcgacatcgccgtggagtgggagagcaatgggcagccggagaacaac tacaagaccacacctcccatgctggactccgacggctccttcttcctctacagcaagctcaccgtggacaagagc aggtggcagcaggggaacgtcttctcatgctccgtgatgcatgaggctctgcacaaccactacacgcagaagagc ctctccctgtctccgggtaaa svActRIIB-Fc (E28W, S44T) polypeptide sequence with signal sequence (SEQ ID NO: 8)

mefglswvflvallrgvqcetrwciyynanwelertnqtglercegeqdkrlhcyaswrnssgtielvkkgcwld dfncydrqecvateenpqvyfcccegnfcnerfthlpeaggpevtyeppptaptgggsvecppcpappvagpsv flfppkpkdtlmisrtpevtcvvvdvshedpevqfnwyvdgvevhnaktkpreeqfnstfrvvsvltvvhqdwln gkeykckvsnkglpapiektisktkgqprepqvytlppsreemtknqvsltclvkgfypsdiavewesngqpenn ykttppmldsdgsfflysklvdksrwqqgnvfscsvmhealhnhytqkslslspgk svActRIIB-Fc (E28W, S44T) polynucleotide sequence without signal sequence
(SEQ ID NO: 9)

gagacacggtggtgcatctactacaacgccaactgggagctggagcgcaccaaccagaccggcctggagcgct gcgaaggcgagcaggacaagcggctgcactgctacgcctcctggcgcaacagctctggcaccatcgagctcgt gaagaagggctgctggctagatgacttcaactgctacgataggcaggagtgtgtggccactgaggagaacccc caggtgtacttctgctgctgtgagggcaacttctgcaacgagcgcttcactcatttgccagaggctgggggcc cggaagtcacgtacgagccaccccgacagccccaccggaggggaggatctgtcgagtgcccaccgtgccc agcaccacctgtggcaggaccgtcagtcttcctcttcccccaaaacccaaggacaccctcatgatctcccgg acccctgaggtcacgtgcgtggtggtggacgtgagccacgaagaccccgaggtccagttcaactggtacgtgg acggcgtggaggtgcataatgccaagacaaagccacgggaggagcagttcaacagcacgttccgtgtggtcag cgtcctcaccgttgtgcaccaggactggctgaacggcaaggagtacaagtgcaaggtctccaacaaaggcctc ccagcccccatcgagaaaaccatctccaaaaccaaagggcagccccgagaaccacaggtgtacaccctgcccc catcccgggaggagatgaccaagaaccaggtcagcctgacctgcctggtcaaaggcttctatcccagcgacat cgccgtggagtgggagagcaatgggcagccggagaacaactacaagaccacacctcccatgctggactccgac ggctccttcttcctctacagcaagctcaccgtggacaagagcaggtggcagcaggggaacgtcttctcatgct ccgtgatgcatgaggctctgcacaaccactacacgcagaagagcctctccctgtctccgggtaaa svActRIIB-Fc (E28W, S44T), polypeptide sequence without signal sequence
(SEQ ID NO: 10)

etrwciyynanwelertnqtglercegeqdkrlhcyaswrnssgtielvkkgcwlddfncydrqecvateenp qvyfcccegnfcnerfthlpeaggpevtyeppptaptggggsvecppcpappvagpsvflfppkpkdtlmisr tpevtcvvvdvshedpevqfnwyvdgvevhnaktkpreeqfnstfrvvsvltvvhqdwlngkeykckvsnkgl papiektisktkgqprepqvytlppsreemtknqvsltclvkgfypsdiavewesngqpennyktttppmldsd gsfflysklvtdksrwqqgnvfscsvmhealhnhytqkslslspgk svActRIIB (E28Y, S44T) with signal sequence
(SEQ ID NO: 11)

atggagtttgggctgagctgggttttcctcgttgctcttttaagaggtgtccagtgtgagacacggtactgcatc tactacaacgccaactgggagctggagcgcaccaaccagaccggcctggagcgctgcgaaggcgagcaggacaag cggctgcactgctacgcctcctggcgcaacagctctggcaccatcgagctcgtgaagaagggctgctggctagat gacttcaactgctacgataggcaggagtgtgtggccactgaggagaaccccaggtgtacttctgctgctgtgag ggcaacttctgcaacgagcgcttcactcatttgccagaggctgggggcccggaagtcacgtacgagccaccccg acagccccacc svActRIIB (E28Y, S44T) with signal sequence
(SEQ ID NO: 12)

mefglswvflvallrgvqcetryciyynanwelertnqtglercegeqdkrlhcyaswrnssgtielvkkgcwl ddfncydrqecvateenpqvyfcccegnfcnerfthlpeaggpevtyeppptapt svActRIIB (E28Y, S44T) without signal sequence
(SEQ ID NO: 13)

gagacacggtactgcatctactacaacgccaactgggagctggagcgcaccaaccagaccggcctggagcgct gcgaaggcgagcaggacaagcggctgcactgctacgcctcctggcgcaacagctctggcaccatcgagctcgt gaagaagggctgctggctagatgacttcaactgctacgataggcaggagtgtgtggccactgaggagaacccc caggtgtacttctgctgctgtgagggcaacttctgcaacgagcgcttcactcatttgccagaggctgggggcc cggaagtcacgtacgagccaccccgacagccccacc svActRIIB (E28Y, S44T) without signal sequence
(SEQ ID NO: 14)

etryciyynanwelertnqtglercegeqdkrlhcyaswrnssgtielvkkgcwlddfncydrqecvateenpqvyfc ccegnfcnerfthlpeaggpevtyeppptapt svActRIIB-Fc (E28Y, S44T) polynucleotide sequence with signal sequence
(SEQ ID NO: 15)

atggagtttgggctgagctgggttttcctcgttgctcttttaagaggtgtccagtgtgagacacggtactgcatctac tacaacgccaactgggagctggagcgcaccaaccagaccggcctggagcgctgcgaaggcgagcaggacaagcggctg cactgctacgcctcctggcgcaacagctctggcaccatcgagctcgtgaagaagggctgctggctagatgacttcaac tgctacgataggcaggagtgtgtggccactgaggagaaccccaggtgtacttctgctgctgtgagggcaacttctgc aacgagcgcttcactcatttgccagaggctgggggcccggaagtcacgtacgagccaccccgacagcccccaccgga gggggaggatctgtcgagtgcccaccgtgcccagcaccacctgtggcaggaccgtcagtcttcctcttccccccaaaa cccaaggacacccctcatgatctcccggacccctgaggtcacgtgcgtggtggtggacgtgagccacgaagacccgag gtccagttcaactggtacgtggacggcgtggaggtgcataatgccaagacaaagccacgggaggagcagttcaacagc acgttccgtgtggtcagcgtcctcaccgttgtgcaccaggactggctgaacggcaaggagtacaagtgcaaggtctcc aacaaaggcctcccagcccccatcgagaaaaccatctccaaaaccaaagggcagccccgagaaccacaggtgtacacc ctgcccccatcccgggaggagatgaccaagaaccaggtcagcctgacctgcctggtcaaaggcttctatcccagcgac atcgccgtggagtgggagagcaatgggcagccggagaacaactacaagaccacacctcccatgctggactccgacggc tccttcttcctctacagcaagctcaccgtggacaagagcaggtggcagcaggggaacgtcttctcatgctccgtgatg catgaggctctgcacaaccactacacgcagaagagcctctccctgtctccgggtaaa svActRIIB-Fc (E28Y, S44T) polypeptide sequence with signal sequence
(SEQ ID NO: 16)

mefglswvflvallrgvqcetryciyynanwelertnqtglercegeqdkrlhcyaswrnssgtielvkkgcwlddfn cydrqecvateenpqvyfcccegnfcnerfthlpeaggpevtyeppptaptggggsvecppcpappvagpsvflfppk pkdtlmisrtpevtcvvvdvshedpevqfnwyvdgvevhnaktkpreeqfnstfrvvsyltvvhqdwlngkeykckvs nkglpapiektisktkgqprepqvytlppsreemtknqvsltclvkgfypsdiavewesngqpennykttppmldsdg sfflyskltvdksrwqqgnvfscsvmhealhnhytqkslslspgk svActRIIB-Fc (E28Y, S44T) polynucleotide sequence without signal sequence
(SEQ ID NO: 17)

gagacacggtactgcatctactacaacgccaactgggagctggagcgcaccaaccagaccggcctggagcgctgc gaaggcgagcaggacaagcggctgcactgctacgcctcctggcgcaacagctctggcaccatcgagctcgtgaag aagggctgctggctagatgacttcaactgctacgataggcaggagtgtgtggccactgaggagaaccccaggtg tacttctgctgctgtgagggcaacttctgcaacgagcgcttcactcatttgccagaggctgggggcccggaagtc acgtacgagccaccccgacagcccccaccggagggggaggatctgtcgagtgcccaccgtgcccagcaccacct gtggcaggaccgtcagtcttcctcttccccccaaaacccaaggacacccctcatgatctcccggacccctgaggtc acgtgcgtggtggtggacgtgagccacgaagacccgaggtccagttcaactggtacgtggacggcgtggaggtg cataatgccaagacaaagccacgggaggagcagttcaacagcacgttccgtgtggtcagcgtcctcaccgttgtg caccaggactggctgaacggcaaggagtacaagtgcaaggtctccaacaaaggcctcccagcccccatcgagaaa accatctccaaaaccaaagggcagccccgagaaccacaggtgtacaccctgcccccatcccgggaggagatgacc aagaaccaggtcagcctgacctgcctggtcaaaggcttctatcccagcgacatcgccgtggagtgggagagcaat gggcagccggagaacaactacaagaccacacctcccatgctggactccgacggctccttcttcctctacagcaag ctcaccgtggacaagagcaggtggcagcaggggaacgtcttctcatgctccgtgatgcatgaggctctgcacaac cactacacgcagaagagcctctccctgtctccgggtaaa svActRIIB-Fc (E28Y, S44T) polypeptide sequence without signal sequence
(SEQ ID NO: 18)

etryciyynanwelertnqtglercegeqdkrlhcyaswrnssgtielvkkgcwlddfncydrqecvateenp qvyfcccegnfcnerfthlpeaggpevtyeppptaptggggsvecppcpappvagpsvflfppkpkdtlmisr tpevtcvvvdvshedpevqfnwyvdgvevhnaktkpreeqfnstfrvvsvltvvhqdwlngkeykckvsnkgl -continued papiektisktkgqprepqvytlppsreemtknqvsltclvkgfypsdiavewesngqpennykttppmldsd gsfflyskltvdksrwqqgnvfscsvmhealhnhytqkslslspgk (SEQ ID NO: 19)
Glu Thr Arg Trp Cys Ile Tyr Tyr Asn Ala Asn Trp Glu Leu Glu Arg Thr Asn Gln
Ser Gly Leu Glu Arg Cys Glu Gly Glu Gln Asp Lys Arg Leu His Cys Tyr Ala Ser Trp Arg
Asn Ser Ser Gly Thr Ile Glu Leu Val Lys Lys Gly Cys Trp Leu Asp Asp Phe Asn Cys Tyr
Asp Arg Gln Glu Cys Val Ala Thr Glu Glu Asn Pro Gln Val Tyr Phe Cys Cys Cys Glu Gly
Asn Phe Cys Asn Glu Arg Phe Thr His Leu Pro Glu Ala Gly Gly Pro Glu Val Thr Tyr Glu
Pro Pro Pro Thr Ala Pro Thr (SEQ ID NO: 22)
Ala Pro Pro Val Ala Gly Pro Ser Val Phe Leu Phe Pro Pro Lys Pro Lys Asp Thr
Leu Met Ile Ser Arg Thr Pro Glu Val Thr Cys Val Val Val Asp Val Ser His Glu Asp Pro
Glu Val Gln Phe Asn Trp Tyr Val Asp Gly Val Glu Val His Asn Ala Lys Thr Lys Pro Arg
Glu Glu Gln Phe Asn Ser Thr Phe Arg Val Val Ser Val Leu Thr Val Val His Gln Asp Trp
Leu Asn Gly Lys Glu Tyr Lys Cys Lys Val Ser Asn Lys Gly Leu Pro Ala Pro Ile Glu Lys
Thr Ile Ser Lys Thr Lys Gly Gln Pro Arg Glu Pro Gln Val Tyr Thr Leu Pro Pro Ser Arg
Glu Glu Met Thr Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr Lys Thr Thr Pro Pro
Met Leu Asp Ser Asp Gly Ser Phe Phe Leu Tyr Ser Lys Leu Thr Val Asp Lys Ser Arg
Trp Gln Gln Gly Asn Val Phe Ser Cys Ser Val Met His Glu Ala Leu His Asn His Tyr Thr
Gln Lys Ser Leu Ser Leu Ser Pro Gly Lys (SEQ ID NO: 23)
Ala Pro Glu Leu Leu Gly Gly Pro Ser Val Phe Leu Phe Pro Pro Lys Pro Lys Asp
Ile Leu Met Ile Ser Arg Thr Pro Glu Val Thr Cys Val Val Val Asp Val Ser His Glu Asp
Pro Glu Val Lys Phe Asn Trp Tyr Val Gly Gly Val Glu Val His Asn Ala Lys Thr Lys Pro
Arg Glu Glu Gln Tyr Asn Ser Thr Tyr Arg Val Val Ser Val Leu Thr Val Leu His Gln Asp
Trp Leu Asn Gly Lys Glu Tyr Lys Cys Lys Val Ser Asn Lys Ala Leu Pro Ala Pro Ile Glu
Lys Thr Ile Ser Lys Ala Lys Gly Gln Pro Arg Glu Pro Gln Val Tyr Thr Leu Pro Pro Ser
Arg Asp Glu Leu Thr Lys Asn Gln Val Ser Leu Thr Cys Leu Val Lys Gly Phe Tyr Pro
Ser Asp Ile Ala Val Glu Trp Glu Ser Asn Gly Gln Pro Glu Asn Asn Tyr Lys Thr Thr Pro
Pro Val Leu Asp Ser Asp Gly Ser Phe Phe Leu Tyr Ser Lys Leu Thr Val Asp Lys Ser
Arg Trp Gln Gln Gly Asn Val Phe Ser Cys Ser Val Met His Glu Ala Leu His Asn His Tyr
Thr Gln Lys Ser Leu Ser Leu Ser Pro Gly Lys (SEQ ID NO: 24)
Ala Pro Glu Phe Leu Gly Gly Pro Ser Val Phe Leu Phe Pro Pro Lys Pro Lys Asp
Thr Leu Met Ile Ser Arg Thr Pro Glu Val Thr Cys Val Val Val Asp Val Ser Gln Glu Asp
Pro Glu Val Gln Phe Asn Trp Tyr Val Asp Gly Val Glu Val His Asn Ala Lys Thr Lys Pro
Arg Glu Glu Gln Phe Asn Ser Thr Tyr Arg Val Val Ser Val Leu Thr Val Leu His Gln Asp
Trp Leu Asn Gly Lys Glu Tyr Lys Cys Lys Val Ser Asn Lys Gly Leu Pro Ser Ser Ile Glu
Lys Thr Ile Ser Lys Ala Lys Gly Gln Pro Arg Glu Pro Gln Val Tyr Thr Leu Pro Pro Ser
Gln Glu Glu Met Thr Lys Asn Gln Val Ser Leu Thr Cys Leu Val Lys Gly Phe Tyr Pro Ser
Asp Ile Ala Val Glu Trp Glu Ser Asn Gly Gln Pro Glu Asn Asn Tyr Lys Thr Thr Pro Pro
Val Leu Asp Ser Asp Gly Ser Phe Phe Leu Tyr Ser Arg Leu Thr Val Asp Lys Ser Arg -continued Trp Gln Glu Gly Asn Val Phe Ser Cys Ser Val Met His Glu Ala Leu His Asn His Tyr Thr
Gln Lys Ser Leu Ser Leu Ser Leu Gly Lys Linker
(SEQ ID NO: 25)
Gly Gly Gly Gly Ser Hinge Linker
(SEQ ID NO: 26)
gga ggg gga gga tct gtc gag tgc cca ccg tgc cca Hinge Linker
(SEQ ID NO: 27)
Gly Gly Gly Gly Ser Val Glu Cys Pro Pro Cys Pro (SEQ ID NO: 28)
Glu Arg Lys Cys Cys Val Glu Cys Pro Pro Cys Pro (SEQ ID NO: 29)
Glu Pro Lys Ser Cys Asp Lys Thr His Thr Cys Pro Pro Cys Pro (SEQ ID NO: 30)
Glu Ser Lys Thr Gly Pro Pro Cys Pro Ser Cys Pro (SEQ ID NO: 31)
Met Thr Ala Pro Trp Val Ala Leu Ala Leu Leu Trp Gly Ser Leu Trp Pro Gly (SEQ ID NO: 32)
Met Thr Ala Pro Trp Val Ala Leu Ala Leu Leu Trp Gly Ser Leu Cys Ala Gly Hinge Linker
(SEQ ID NO: 37)
gga ggg gga gga tct gag cgc aaa tgt tgt gtc gag tgc cca ccg tgc Hinge Linker
(SEQ ID NO: 38)
Gly Gly Gly Gly Ser Glu Arg Lys Cys Cys Val Glu Cys Pro Pro Cys Hinge Linker
(SEQ ID NO: 39)
gga ggg gga gga tct ggt gga ggt ggt tca ggt cca ccg tgc Hinge Linker
(SEQ ID NO: 40)
Gly Gly Gly Gly Ser Gly Gly Gly Gly Ser Gly Pro Pro Cys (SEQ ID NO: 41)
gga ggg gga gga tct ggt gga ggt ggt tca ggt cca ccg gga (SEQ ID NO: 42)
Gly Gly Gly Gly Ser Gly Gly Gly Gly Ser Gly Pro Pro Gly Hinge Linker
(SEQ ID NO: 43)
gga ggg gga gga tct gag cgc aaa tgt cca cct tgt gtc gag tgc cca ccg tgc Hinge Linker
(SEQ ID NO: 44)
Gly Gly Gly Gly Ser Glu Arg Lys Cys Pro Pro Cys Val Glu Cys Pro Pro Cys Hinge Linker
(SEQ ID NO: 45)
Gly Pro Ala Ser Gly Gly Pro Ala Ser Gly Pro Pro Cys Pro Hinge Linker
(SEQ ID NO: 46)
Gly Pro Ala Ser Gly Gly Pro Ala Ser Gly Cys Pro Pro Cys Val Glu Cys Pro Pro
Cys Pro (SEQ ID NO: 47)
Ala Pro Glu Leu Leu Gly Gly Pro Ser Val Phe Leu Phe Pro Pro Lys Pro Lys Asp
Thr Leu Met Ile Ser Arg Thr Pro Glu Val Thr Cys Val Val Val Asp Val Ser His Glu Asp
Pro Glu Val Lys Phe Asn Trp Tyr Val Asp Gly Val Glu Val His Asn Ala Lys Thr Lys Pro
Arg Glu Glu Gln Tyr Asn Ser Thr Tyr Arg Val Val Ser Val Leu Thr Val Leu His Gln Asp

```
                                                     -continued
Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys Hinge Linker
                                                                           (SEQ ID NO: 48)
Gly Gly Gly Gly Ser Val Asp Lys Thr His Thr Cys Pro Pro Cys Pro Hinge Linker
                                                                           (SEQ ID NO: 49)
Gly Gly Gly Gly Ser Val Asp Lys Thr His Thr Gly Pro Pro Cys Pro (SEQ ID NO: 50)
Gly Gly Gly Gly Ser Gly Gly Gly Gly Ser Val Asp Lys Thr His Thr Gly Pro Pro Cys Pro
```

Stabilized activin type IIB polypeptides bind to ligands that activate muscle-degradation cascades. svActRIIB polypeptides capable of binding and inhibiting the activity of the ligands activin-A, myostatin, and/or GDF-11, and have the ability to treat diseases that involve muscle atrophy, as well as the treatment of certain cancers, and other diseases.

Pharmaceutical Compositions and Methods for Treatment Methods of Treatment

In one aspect, the present invention provides methods of treating a subject. The method can, for example, have a generally beneficial effect on the subject's health, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of activin-A. In some such conditions, the expression or activity level is too high, and the treatment comprises administering an activin-A antagonist as described herein. As used herein the term "subject" refers to any animal, such as mammals including humans.

One example of a type of condition that can be treated using the methods and compositions of the present invention is a condition that involves cell growth, for example, a cancerous condition which is accompanied by cachexia. Thus, in one embodiment, the present invention provides compositions and methods for treating a cancerous condition. In particular, the cancerous condition is a gonadal cancer, including tumors of the ovary and testis. (Fujii, Y. et al., *Am. J Phys. Endocrin. Metab.*, 286:E927-E931, 2004; Reis, F. M. et al., *J Clin. Endocrin.* 87:2277-2282, 2005.) Activin-A is known for its action in stimulating FSH biosynthesis and secretion in the pituitary gland, and has a physiological role in the regulation of gonadal function. Activin-A has been associated with many types of human cancers and in particular with tumors of the reproductive system. Specifically, overexpression or deregulation of activin-A has been implicated in ovarian cancer, (Menon U, et al., *BJOG: An International Journal of Obstetrics & Gynaecology;* 107(9): 1069-74, 2000. Choi K C, et al., *Molecular & Cellular Endocrinology.* 174(1-2):99-110, 2001; Zheng W, et al., *American Journal of Reproductive Immunology.* 44(2): 104-13, 2000; Lambert-Messerlian G M, et al., *Gynecologic Oncology.* 74(1):93-7, 1999; Steller M D, et al., *Molecular Cancer Research: MCR.* 3(1):50-61, 2005; Corbellis L., et al., *Journal of the Society for Gynecologic Investigation.* 11(4):203-6, 2004; Welt C K, et al., *Journal of Clinical Endocrinology & Metabolism.* 82(11): 3720-7, 1997; and Harada K., et al., *Journal of Clinical Endocrinology & Metabolism.* 81(6): 2125-30, 1996, endometrial adenocarcinoma Otani, T, et a., *Gynecologic Oncology.* 83(1):31-8, 2001; Tanaka T, et al., *International Journal of Oncology.* 23(3):657-63, 2003 and prostate cancer (Thomas T Z, et al., *Journal of Clinical Endocrinology & Metabolism.* 82(11): 3851-8, 1997; Zhang, Z, et al., *Biochemical & Biophysical Research Communications.* 234(2): 362-5, 1997; and Risbridger G P, et al., *Molecular & Cellular Endocrinology.* 180(1-2):149-53, 2001

The cancerous condition can be any cancerous condition that can be treated using the compositions comprised herein, for example, anti-activin-A compounds such as activin IIB receptor polypeptides (svActRIIB), and activin-A antigen binding proteins such as anti-activin-A antibodies, antibody fragments, or antibody derivatives. Examples of cancerous conditions include, for example, acute lymphoblastic leukemia, adrenocortical carcinoma, AIDS-related cancers, AIDS-related lymphoma, anal cancer, childhood cerebellar astrocytoma, childhood cerebral astrocytoma, basal cell carcinoma, extrahepatic bile duct cancer, bladder cancer, osteosarcoma/malignant fibrous histiocytoma bone cancer, brain tumors (e.g., brain stem glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's Lymphoma, carcinoid tumor, gastrointestinal carcinoid tumor, carcinoma of unknown primary, primary central nervous system, cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, colorectal cancer, cutaneous t-cell lymphoma, endometrial cancer, ependymoma, esophageal cancer, ewing's family of tumors, extracranial germ cell tumor, extragonadal germ cell tumor, extrahepatic bile duct cancer, intraocular melanoma eye cancer, retinoblastoma eye cancer, gallbladder cancer, gastric (stomach) cancer, gastrointestinal carcinoid tumor, germ cell tumors (e.g., extracranial, extragonadal, and ovarian), gestational trophoblastic tumor, glioma (e.g., adult, childhood brain stem, childhood cerebral astrocytoma, childhood visual pathway and hypothalamic), hairy cell leukemia, head and neck cancer, hepatocellular (liver) cancer, Hodgkin's lymphoma, hypopharyngeal cancer, hypothalamic and visual pathway glioma, intraocular melanoma, islet cell carcinoma (endocrine pancreas), Kaposi's Sarcoma, kidney (renal cell) cancer, laryngeal cancer, leukemia (e.g., acute lymphoblastic, acute myeloid, chronic lymphocytic, chronic myelogenous, and hairy cell), lip and oral cavity cancer, liver cancer, non-small cell lung cancer, small cell lung cancer, lymphoma (e.g., AIDS-related, Burkitt's, cutaneous t-cell, Hodgkin's, non-Hodgkin's, and primary central nervous system), Waldenström's Macroglobulinemia, malignant fibrous histiocytoma of bone/osteosarcoma, medulloblastoma, melanoma, intraocular (eye) melanoma, Merkel cell carcinoma, mesothelioma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, myelogenous leukemia, chronic myeloid leukemia, multiple myeloma, chronic myeloproliferative disorders, nasal cavity and paranasal sinus cancer, nasopharyngeal cancer, neuroblastoma, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, islet cell pancreatic cancer, paranasal sinus and nasal cavity cancer, parathyroid cancer, penile cancer, pheochromocytoma, pineoblastoma, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter transitional cell cancer, retinoblastoma, rhabdomyosarcoma, salivary gland cancer, soft tissue sarcoma, uterine sarcoma, Sezary syndrome, non-melanoma skin cancer, merkel cell skin carcinoma, small intestine cancer, soft tissue sarcoma, squamous cell carcinoma, cutaneous t-cell lymphoma, testicular cancer, thymoma, thymic carcinoma, thyroid cancer, gestational trophoblastic tumor, carcinoma of unknown primary site, cancer of unknown primary site, urethral cancer, endometrial uterine cancer, uterine sarcoma, vaginal cancer, visual pathway and hypothalamic glioma, vulvar cancer, Waldenström's Macroglobulinemia, and Wilms' Tumor.

Certain methods provided herein comprise administering an activin-A binding protein to a subject, thereby reducing an activin-A-induced biological response that plays a role in a particular condition. In particular embodiments, methods of the invention involve contacting endogenous activin-A with an activin-A binding protein, e.g., via administration to a subject or in an ex vivo procedure.

The term "treatment" encompasses alleviation or prevention of at least one symptom or other aspect of a disorder, or reduction of disease severity, and the like. In addition, "treatment" further relates to administering a therapeutic agent described herein for preventing or alleviating at least one symptom or other aspect of a disorder in a subject in need thereof. An antigen binding protein need not affect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an activin-A antagonist in an amount and for a time sufficient to induce a sustained improvement over baseline of an indicator that reflects the severity of the particular disorder.

Use of antigen binding proteins in ex vivo procedures also is contemplated. For example, a patient's blood or other bodily fluid may be contacted with a protein that binds full-length activin-A, one or more activin-A isoform, or other partial length activin-A ex vivo. The antigen binding protein may be bound to a suitable insoluble matrix or solid support material.

Identifying a Subject for Treatment

A subject's levels of biomarker CA-125 and/or activin-A can be monitored to identify a subject in need of treatment for ovarian cancer, including serous ovarian cancer (ovarian neoplasms, including surface epithelial-stromal tumors). For example, levels of biomarker CA-125 and/or activin-A can be detected in the subject and compared to a control. First, the subject's expression levels of CA-125 and/or activin A are evaluated. Next, the subject's expression levels of CA-125 and/or activin-A are compared to expression levels in a negative control sample or a positive control sample. If the expression levels of CA-125 and/or activin-A in the subject exceed the expression levels in the negative control sample, or if the expression levels meet or exceed the expression levels in the positive control sample, the subject is identified as one needing ovarian cancer treatment. In some aspects, if the expression levels exceed the expression levels of the subject taken at a previous time, in particular when the tumor was in its early stages, the subject can be identified as one needing ovarian cancer treatment. Known techniques can be employed for measuring CA-125 and/or activin-A levels, e.g., in a subject's serum. CA-125 and/or activin-A levels in blood samples can be measured using any suitable technique, for example, ELISA or RT-PCR.

A subject's levels of activin-A, VEGF, and/or Ang-1 factors can be monitored to identify a subject in need of treatment for ovarian cancer, including clear cell ovarian cancer (epithelial ovarian neoplasm arising from embryonic mesonephros), Granulosa cell ovarian cancer (neoplasms from sex-cord stromal cells), Leydig cell tumors (testicular tumor derived from Leydig cells), and sex cord stromal testicular tumors (derived from testicular and ovarian stroma). Levels of activin-A, VEGF, and/or Ang-1 factors can be detected in the subject and compared to a control. First, the subject's expression levels of activin-A, VEGF, and/or Ang-1 are evaluated. Next, the subject's expression levels of activin-A, VEGF, and/or Ang-1 are compared to expression levels in a negative control sample or a positive control sample. If the expression levels of activin-A, VEGF, and/or Ang-1 in the subject exceed the expression levels in the negative control sample, or if the expression levels meet or exceed the expression levels of the respective factors in the positive control sample, the subject is identified as one needing ovarian cancer treatment. In one embodiment, if activin-A levels in a subject are three times the activin-A levels in the average person of the same age, or if activin-A levels in a subject exceed 3200 pg/mL, it can predict that the particular subject should begin receiving treatment. Known techniques can be employed for measuring activin-A, VEGF, and/or Ang-1 levels, e.g., in a subject's serum. Activin-A, VEGF, and/or Ang-1 levels in blood samples can be measured using any suitable technique, for example, ELISA.

In some embodiments, the subject has a mutated activin gene or a mutated activin counterregulator gene, such as inhibin. In further embodiments, the mutation is an Asn386Ser mutation in the Beta-A-subunit of inhibin or activin proteins (GenBank Accession Number: NM_002192.2; MIM #147290), an Arg60Leu mutation of the alpha prodomain of inhibin or activin proteins, (GenBank Accession Number: NM_002191), or a Gly280Glu mutation of the alpha prodomain of inhibin or activin proteins (GenBank Accession Number: NM_002192.2) (see Tournier et al., *Hum. Mutat.* 0: 1-4, 2013).

Compositions

Pharmaceutical compositions containing the proteins and polypeptides of the present invention are also provided. Such compositions comprise a therapeutically or prophylactically effective amount of the polypeptide or protein in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition.

Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16$^{th}$ Ed. (1980) and 20$^{th}$ Ed. (2000), Mack Publishing Company, Easton, Pa.

Optionally, the composition additionally comprises one or more physiologically active agents, for example, a second activin-A receptor-inhibiting substance, an anti-angiogenic substance, a chemotherapeutic substance (such as capecitabine, 5-fluorouracil, or doxorubicin), an analgesic substance, etc., non-exclusive examples of which are provided herein. In various particular embodiments, the composition comprises one, two, three, four, five, or six physiologically active agents in addition to an activin-A-binding protein.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

Administration of Treatment

The formulations can be delivered in a variety of methods, for example, subcutaneously, intravenously, intraperitoneally, orally, or by inhalation therapy. Such approaches are well known to the skilled artisan, some of which are further described, for example, in U.S. Pat. Nos. 5,543,158; 5,641,515 and 5,399,363. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, *Remington's Pharmaceutical Sciences*, 15th ed., pp. 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly (2-hydroxyethyl-methacrylate) (Langer et al., J. Biomed. Mater. Res., 15:167-277, (1981); Langer et al., Chem. Tech., 12:98-105(1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, *Trends Biotechnol.* 16(7):307-21, 1998; Takakura, *Nippon Rinsho* 56(3):691-95, 1998; Chandran et al., *Indian J. Exp. Biol.* 35(8):801-09, 1997; Margalit, *Crit. Rev. Ther. Drug Carrier Syst.* 12(2-3):233-61, 1995; U.S. Pat. Nos. 5,567,434; 5,552,157; 5,565,213; 5,738,868 and 5,795,587, each specifically incorporated herein by reference in its entirety). The use of liposomes does not appear to be associated with autoimmune responses or unacceptable toxicity after systemic delivery. In certain embodiments, liposomes are formed from phospholipids that are dispersed in an aqueous medium and spontaneously form multilamellar concentric bilayer vesicles (also termed multilamellar vesicles (MLVs)).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., *Drug Dev. Ind. Pharm.* 24(12):1113-28, 1998). To avoid side effects due to intracellular polymeric overloading, such ultrafine particles (sized around 0.1 μm) may be designed using polymers able to be degraded in vivo. Such particles can be made as described, for example, by Couvreur et al., *Crit. Rev. Ther. Drug Carrier Syst.* 5(1):1-20, 1988; zur Muhlen et al., *Eur. J. Pharm. Biopharm.* 45(2):149-55, 1998; Zambaux et al., *J. Controlled Release* 50(1-3):31-40, 1998; and U.S. Pat. No. 5,145,684.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

In addition, pharmaceutical compositions of the present invention may be placed within containers, along with packaging material that provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) that may be necessary to reconstitute the pharmaceutical composition.

The invention also provides a diagnostic kit comprising at least one anti-activin-A binding agent according to the present invention. The binding agent may be an antibody. In addition, such a kit may optionally comprise one or more of the following: (1) instructions for using the one or more binding agent(s) for screening, diagnosis, prognosis, therapeutic monitoring or any combination of these applications; (2) a labeled binding partner to the anti-activin-A binding agent(s); (3) a solid phase (such as a reagent strip) upon which the anti-activin-A binding agent(s) is immobilized; and (4) a label or insert indicating regulatory approval for screening, diagnostic, prognostic or therapeutic use or any combination thereof. If no labeled binding partner to the binding agent(s) is provided, the binding agent(s) itself can be labeled with one or more of a detectable marker(s), e.g. a chemiluminescent, enzymatic, fluorescent, or radioactive moiety.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

Dosages and the frequency of administration may vary according to such factors as the route of administration, the particular proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A polypeptide or protein of the invention may be administered, for example, once or more than once, e.g., at regular intervals over a period of time. In particular embodiments, a protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the protein is administered until the patient manifests a medically relevant degree of improvement over baseline for the chosen indicator or indicators.

Particular embodiments of the present invention involve administering a protein at a dosage of from about 1 ng of protein per kg of subject's weight per day ("1 ng/kg/day") to about 10 mg/kg/day, more preferably from about 500 ng/kg/day to about 5 mg/kg/day, and most preferably from about 5 μg/kg/day to about 2 mg/kg/day, to a subject. In additional embodiments, a protein is administered to adults one time per week, two times per week, or three or more times per week, to treat an activin-A mediated disease, condition or disorder, e.g., a medical disorder disclosed herein. If injected, the effective amount of protein per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of protein one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of protein administered two or three times per week.

Particular embodiments of the methods provided herein involve subcutaneous injection of from 0.5 mg to 10 mg, preferably from 3 to 5 mg, of a protein, once or twice per week. Another embodiment is directed to pulmonary administration (e.g., by nebulizer) of 3 or more mg of protein once a week.

Examples of therapeutic regimens provided herein comprise subcutaneous injection of a protein once a week, at a dose of 1.5 to 3 mg, to treat a condition in which activin-A signaling plays a role. Examples of such conditions are provided herein and include, for example, cachexia, cancer, rheumatoid arthritis, and all conditions in which loss of body weight, body mass, body fat, or inability to maintain body weight, body mass, body fat, play a role. Weekly administration of protein is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 0.5, 1, 3, 5, 6, 7, 8, 9, 10, 11, 12, 15, or 20 milligrams of an activin-A inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

Other routes of administration of the pharmaceutical composition are in accord with known methods, e.g. orally, through injection by intraperitoneal, intracerebral (intraparenchymal), intracerebroventricular, intramuscular, intraocular, intraarterial, intraportal, intralesional routes, intramedullary, intrathecal, intraventricular, transdermal, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In another embodiment, a protein is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

A subject's levels of activin-A may be monitored before, during and/or after treatment with a protein, to detect changes, if any, in their levels. For some disorders, the incidence of elevated activin-A levels may vary according to such factors as the stage of the disease or the particular form of the disease. Known techniques may be employed for measuring activin-A levels, e.g., in a subject's serum. Activin-A levels in blood samples may be measured using any suitable technique, for example, ELISA. In one embodiment, if activin-A levels in a subject are three times the activin-A levels in the average person of the same age, or if activin-A levels in a subject exceed 3200 pg/mL, it indicates that the particular subject should begin receiving treatment. In a further embodiment, activin-A levels can be monitored to determine whether treatment should continue. For example, if activin-A levels in a subject have declined from a baseline level after a certain period of treatment, it indicates that the particular subject is benefiting from the treatment and should continue to receive treatment In some cases, the polypeptides of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the polypeptide product(s) but prevent the destruction of the cells by the patient's immune system or by other detrimental factors from the surrounding tissues.

Gene therapy in vivo is also envisioned wherein a nucleic acid molecule encoding a polypeptide of the present invention, or a derivative of a polypeptide of the present invention is introduced directly into the subject. For example, a nucleic acid sequence encoding a polypeptide of the present invention is introduced into target cells via local injection of a nucleic acid construct with or without an appropriate delivery vector, such as an adeno-associated virus vector. Alternative viral vectors include, but are not limited to, retroviruses, adenovirus, herpes simplex, virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

Combination Therapy

The compositions of the present disclosure may be used alone or in combination with other therapeutic agents to enhance their therapeutic effects or decrease potential side effects. Particular embodiments of methods and compositions of the invention involve the use of an antigen binding protein and one or more additional activin-A antagonists, for example, two or more antigen binding proteins of the invention, or an antigen binding protein of the invention and one or more other activin-A antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which a protein is administered at least once during a course of treatment that involves administering at least one other therapeutic agent to the patient.

Examples of other agents that may be co-administered with a protein are other proteins or therapeutic polypeptides that are chosen according to the particular condition to be treated. Alternatively, non-proteinaceous drugs that are useful in treating one of the particular conditions discussed above may be co-administered with an activin-A antagonist.

In one embodiment, a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue (e.g., within a tumor). For example, an activin-A inhibitor of the present invention can be combined with a treatment that promotes apoptosis or inhibits angiogenesis. In another embodiment, a targeted agent, that, when used by itself, fails to elicit a therapeutically desired effect, could be used to, for example, sensitize cancer cells or augment treatment effect of other agents. In another embodiment, an activin-A inhibitor according to the invention is used in combination with a cytotoxic drug or other targeted agent that induces apoptosis. In another embodiment, an activin-A inhibitor is used in combination with one or more agents that inhibit different targets that are involved in cell survival (e.g., PKB, mTOR), different receptor tyrosine kinases (e.g., ErbB1, ErbB2, c-Met, c-kit), or different cell types (e.g., KDR inhibitors, c-fms). In another embodiment, an activin-A inhibitor of the invention is added to the existing standard of care for a particular condition. In another embodiment, the combination therapy comprises treating a subject with an activin-A inhibiting proteins and anti-cancer treatments (such as surgery, ultrasound, radiotherapy, chemotherapy, or treatment with another anti-cancer agent).

Where a method of combination therapy comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen. Examples of agents that can be administered in combination with the activin-A antagonists described herein include, but are not limited to, capecitabine, 5-fluorouracil, doxorubicin, taxol, taxotere, CPT-11, neutrophil-boosting agents, irinothecan, SN-38, gemcitabine, herstatin, or an activin-A-binding herstatin derivative (as described, for example, in U.S. patent application Ser. No. 05/027,2637), AVASTIN® (Genentech, South San Francisco, Calif.), HERCEPTIN® (Genentech), RITUXAN® (Genentech), ARIMIDEX® (AstraZeneca, Wilmington, Del.), IRESSA® (AstraZeneca), BEXXAR® (Corixa, Seattle, Wash.), ZEVALIN® (Biogen Idec, Cambridge, Mass.), ERBITUX® (Imclone Systems Inc., New York, N.Y.), GEMZAR® (Eli Lilly and Co., Indianapolis, Ind.), CAMPTOSAR® (Pfizer, New York, N.Y.), GLEEVEC® (Novartis), SU-11248 (Pfizer), BMS-354825 (Bristol-Myers Squibb), panitumumab (Abgenix, Fremont, Calif./Amgen Inc., Thousand Oaks, Calif.), and denosumab (Amgen Inc., Thousand Oaks, Calif.).

In one embodiment, both an anti-activin-A compound and capecitabine are administered to a subject. The capecitabine, or XELODAR® (Roche) (which is converted in the body to 5-fluorouracil), can be administered orally to a subject at 1250 mg/m$^2$ twice a day for two weeks, followed by a one week rest period. The capecitabine can also be administered at a different dosage and schedule. In another embodiment, both an anti-activin-A compound and a doxorubicin lipid complex are administered to a subject. The doxorubicin lipid complex, or DOXIL® (Janssen Biotech, Inc.), can be administered to a subject at 40 mg/m$^2$IV once every four weeks. The doxorubicin lipid complex can also be administered as a different dosage and schedule.

The development of suitable dosing and treatment regimens for using the particular compositions described herein in a variety of treatment regimens, including e.g., subcutaneous, oral, parenteral, intravenous, intranasal, and intramuscular administration and formulation, is well known in the art, and is described above.

Antibody Treatment

Therapeutic antibodies may be used that specifically bind to intact activin-A, in which sequences in the region of approximately C11-S33 (first loop) and approximately C81-E111 (second loop) retain the conformation of native activin-A.

An oligopeptide or polypeptide is within the scope of the invention if it has an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to least one of the CDR's of antibodies A1-A14; and/or to a CDR of a activin-A binding agent that cross-blocks the binding of at least one of antibodies A1-A14 to activin-A, and/or is cross-blocked from binding to activin-A by at least one of antibodies A1-A14; and/or to a CDR of a activin-A binding agent wherein the binding agent can block the binding of activin-A to activin-A receptor.

Activin-A binding agent polypeptides and antibodies are within the scope of the invention if they have amino acid sequences that are at least 85%, 86%, 87%, 88%, 89%, 90%, 91%, 92%, 93%, 94%, 95%, 96%, 97%, 98% or 99% identical to a variable region of at least one of antibodies A1-A14, and cross-block the binding of at least one of antibodies A1-A14 to activin-A, and/or are cross-blocked from binding to activin-A by at least one of antibodies A1-A14; and/or can block the inhibitory effect of activin-A on an activin-A receptor.

Antibodies according to the invention may have a binding affinity for human activin-A of less than or equal to $1\times10^{-7}$ M, less than or equal to $1\times10^{-8}$M, less than or equal to $1\times10^{-9}$M, less than or equal to $1\times10^{-10}$M, less than or equal to $1\times10^{-11}$M, or less than or equal to $1\times10^{-12}$ M.

The affinity of an antibody or binding partner, as well as the extent to which an antibody inhibits binding, can be determined by one of ordinary skill in the art using conventional techniques, for example those described by Scatchard et al. (*Ann. N.Y. Acad. Sci.* 51:660-672 (1949)) or by surface plasmon resonance (SPR; BIAcore, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

An antibody according to the present invention may belong to any immunoglobin class, for example IgG, IgE, IgM, IgD, or IgA. It may be obtained from or derived from an animal, for example, fowl (e.g., chicken) and mammals, which includes but is not limited to a mouse, rat, hamster, rabbit, or other rodent, cow, horse, sheep, goat, camel, human, or other primate. The antibody may be an internalizing antibody. Production of antibodies is disclosed generally in U.S. Patent Publication No. 2004/0146888 A1.

In the methods described above to generate antibodies according to the invention, including the manipulation of the specific A1-A14 CDRs into new frameworks and/or constant regions, appropriate assays are available to select the desired antibodies (i.e. assays for determining binding affinity to activin-A; cross-blocking assays; Biacore-based competition binding assay;" in vivo assays).

svActRIIB Treatment

The present invention provides methods and pharmaceutical compositions for reducing or neutralizing the amount or activity of myostatin, activin-A, or GDF-11 in vivo and in vitro. svActRIIB polypeptides have a high binding affinity for myostatin, activin-A, and GDF-11, and are capable of reducing and inhibiting the biological activities of at least one of myostatin, activin-A and GDF-11.

In one aspect, the present invention provides methods and reagents for treating myostatin-related and/or activin-A related disorders in a subject in need of such a treatment by administering an effective dosage of an svActRIIB composition to the subject.

The compositions of the present invention are useful for increasing lean muscle mass in a subject. The compositions may also be useful to increase lean muscle mass in proportion to fat mass, and thus decrease fat mass as percentage of body weight in a subject. Example 3 demonstrates that the svActRIIB polypeptides and proteins of the invention can increase lean muscle mass in animals.

The disorders that can be treated by an svActRIIB composition include but are not limited to various forms of muscle wasting, as well as metabolic disorders such as diabetes and related disorders, and bone degenerative diseases such as osteoporosis.

Muscle wasting disorders also include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. Additional muscle wasting disorders arise from chronic diseases or disorders such as amyotrophic lateral sclerosis, congestive obstructive pulmonary disease, cancer, AIDS, renal failure, organ atrophy, androgen deprivation, and rheumatoid arthritis.

Over-expression of myostatin and/or activin may contribute to cachexia, a severe muscle wasting syndrome. Cachexia results from cancers, and also arises due to rheumatoid arthritis, diabetic nephropathy, renal failure, chemotherapy, injury due to burns, as well as other causes. In another example, serum and intramuscular concentrations of myostatin-immunoreactive protein was found to be increased in men exhibiting AIDS-related muscle wasting and was inversely related to fat-free mass (Gonzalez-Cadavid et al., PNAS USA 95: 14938-14943 (1998)). Myostatin levels have also been shown to increase in response to burns injuries, resulting in a catabolic muscle effect (Lang et al, FASEB J 15, 1807-1809 (2001)). Additional conditions resulting in muscle wasting may arise from inactivity due to disability such as confinement in a wheelchair, prolonged bed rest due to stroke, illness, spinal chord injury, bone fracture or trauma, and muscular atrophy in a microgravity environment (space flight). For example, plasma myostatin immunoreactive protein was found to increase after prolonged bed rest (Zachwieja et al. J Gravit Physiol. 6(2):11 (1999). It was also found that the muscles of rats exposed to a microgravity environment during a space shuttle flight expressed an increased amount of myostatin compared with the muscles of rats which were not exposed (Lalani et al., J. Endocrin 167 (3):417-28 (2000)).

In addition, age-related increases in fat to muscle ratios, and age-related muscular atrophy appear to be related to myostatin. For example, the average serum myostatin-immunoreactive protein increased with age in groups of young (19-35 yr. old), middle-aged (36-75 yr. old), and elderly (76-92 yr old) men and women, while the average muscle mass and fat-free mass declined with age in these groups (Yarasheski et al. J Nutr Aging 6(5):343-8 (2002)). In addition, myostatin has now been found to be expressed at low levels in heart muscle and expression is upregulated in cardiomyocytes after infarct (Sharma et al., J Cell Physiol. 180 (1):1-9 (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. *FASEB J.* 8:479 (1994). The svActRIIB polypeptides of the present disclosure are suitable for treating such metabolic disorders. Therefore, administering the compositions of the present invention will improve diabetes, obesity, and hyperglycemic conditions in suitable subjects. In addition, compositions containing the svActRIIB polypeptides may decrease food intake in obese individuals.

Administering the stabilized ActRIIB polypeptides of the present invention may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. Calcif Tissue Int 71(1):63-8 (2002)). In addition, the svActRIIB compositions of the present invention can be used to treat the effects of androgen deprivation in cases such as androgen deprivation therapy used for the treatment of prostate cancer, for example.

The present invention also provides methods and compositions for increasing muscle mass in food animals by administering an effective dosage of the svActRIIB proteins to the animal. Since the mature C-terminal myostatin polypeptide is similar or identical in all species tested, svActRIIB polypeptides would be expected to be effective for increasing lean muscle mass and reducing fat in any agriculturally important species including cattle, chicken, turkeys, and pigs.

The svActRIIB polypeptides and compositions of the present invention also antagonize the activity of activin-A, as shown in the in vitro assays below. Activin-A is known to be expressed in certain types of cancers, particularly gonadal tumors such as ovarian carcinomas, and to cause severe cachexia. (Ciprano et al. Endocrinol 141 (7):2319-27 (2000), Shou et al., Endocrinol 138 (11):5000-5 (1997); Coerver et al, Mol Endocrinol 10(5):534-43 (1996); Ito et al. British J Cancer 82(8):1415-20 (2000), Lambert-Messerlian, et al, Gynecologic Oncology 74:93-7 (1999). Therefore, the compositions of the present disclosure may be used to treat conditions related to activin-A overexpression, as well as myostatin expression, such as cachexia from certain cancers and the treatment of certain gonadal type tumors.

In addition, the svActRIIB polypeptides of the present invention are useful for detecting and quantitating myostatin, activin-A, or GDF-11 in any number of assays. In general, the stabilized ActRIIB polypeptides of the present invention are useful as capture agents to bind and immobilize myostatin, activin-A, or GDF-11 in a variety of assays, similar to those described, for example, in Asai, ed., Methods in Cell Biology, 37, *Antibodies in Cell Biology*, Academic Press, Inc., New York (1993). The polypeptides may be labeled in some manner or may react with a third molecule such as an antibody which is labeled to enable myostatin to be detected and quantitated. For example, a polypeptide or a third molecule can be modified with a detectable moiety, such as biotin, which can then be bound by a fourth molecule, such as enzyme-labeled streptavidin, or other proteins. (Akerstrom, *J Immunol* 135:2589 (1985); Chaubert, *Mod Pathol* 10:585 (1997)).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B(1992).

Methods

Materials sActRIIB (soluble ActRIIB-Fc) expression construct was engineered by subcloning a cDNA fragment corresponding to the extracellular domain of human activin type-2B receptor (aa7-100) into an IgG2 Fc fusion split vector. The construct was transfected into CHO cells and the recombinant sActRIIB was purified from culture medium using a mAb Select SuRe affinity column (GE) followed by Fractogel chromatography (EMD Chemicals).

Activin-A antibody (fully human monoclonal antibody against activin-A) was generated using XenoMouse technology (Amgen Inc). Recombinant activin-A was produced using mammalian expression system (Amgen Inc).

The sequences of the sActRIIB peptide and the Activin-A antibody used below are shown in the tables below.

TABLE 9 sActRIIB sequences

| | ActRIIB Peptide | Linker | IgG2 Fc Domain | Full Length |
|---|---|---|---|---|
| sActRIIB | ETRWCIYYNANWE LERTNQSGLERCE GEQDKRLHCYASW RNSSGTIELVKKG CWLDDFNCYDRQE CVATEENPQVYFC CCEGNFCNERFTH LPEAGGPEVTYEP PPTAPT (SEQ ID NO: 19) | GGGGSV ECPPCP (SEQ ID NO: 27) | APPVAGPSVFLFPPK PKDTLMISRTPEVTC VVVDVSHEDPEVQFN WYVDGVEVHNAKTKP REEQFNSTFRVVSVL TVVHQDWLNGKEYKC KVSNKGLPAPIEKTI SKTKGQPREPQVYTL PPSREEMTKNQVSLT CLVKGFYPSDIAVEW ESNGQPENNYKTTPP MLDSDGSFFLYSKLT VDKSRWQQGNVFSCS VMHEALHNHYTQKSL SLSPGK (SEQ ID NO: 22) | ETRWCIYYNANWELERTNQSGLERCEG EQDKRLHCYASWRNSSGTITLVKKGCW LDDFNCYDRQECVATEENPQVYFCCCE GNFCNERFTHLPEAGGPEVTYEPPPTA PTGGGGSVECPPCPAPPVAGPSVFLFP PKPKDTLMISRTPEVTCVVVDVSHEDP EVQFNWYVDGVEVHNAKTKPREEQFNS TFRVVSVLTVVHQDWLNGKEYKCKVSN KGLPAPIEKTISKTKGQPREPQVYTLP PSREEMTKNQVSLTCLVKGFYPSDIAV EWESNGQPENNYKTTPPMLDSDGSFFL YSKLTVDKSRWQQGNVFSCSVMHEALH NHYTQKSLSLSPGK (SEQ ID NO: 21) |

TABLE 10

Activin-A light and heavy chain variable domain sequences

| | Light Chain Variable Domain | Heavy Chain Variable Domain |
|---|---|---|
| Activin A Antibody | SYEVTQAPSVSVSPGQTASITC<u>SGD</u> <u>KLGDKYA</u>CWYQQKPGQSPVLVIY<u>QD</u> <u>SKRPS</u>GIPERFSGSNSGNTATLTIS GTQAMDEADYYC<u>QAWDSSTAVF</u>GGG TKLTVL (SEQ ID NO: 275) | QVQLVQSGAEVKKPGASVKVSCKAS<u>GYTF</u> <u>TSYGLS</u>WVRQAPGQGLEWMG<u>WIIPYNGNT</u> <u>NSAQKLQ</u>GRVTMTTDTSTSTAYMELRSLR SDDTAVYFCAR<u>DRDYGVNYDAFD</u>IWGQGT MVTVSS (SEQ ID NO: 278) |

TABLE 11

Activin-A light and heavy chain constant domain sequences

| | Light Chain Constant Domain | Heavy Chain Constant Domain |
|---|---|---|
| Activin A Antibody | Gly Gln Pro Lys Ala Ala Pro Ser Val Thr Leu Phe Pro Pro Ser Ser Glu Glu Leu Gln Ala Asn Lys Ala Thr Leu Val Cys Leu Ile Ser Asp Phe Tyr Pro Gly Ala Val Thr Val Ala Trp Lys Ala Asp Ser Ser Pro Val Lys Ala Gly Val Glu Thr Thr Thr Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser (SEQ ID NO: 84) | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Asn Phe Gly Thr Gln Thr Tyr Thr Cys Asn Val Asp His Lys Pro Ser Asn Thr Lys Val Asp Lys Thr Val Glu Arg Lys Cys Cys Val Glu Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Gln Phe Asn Trp Tyr Val Asp Gly Val Glu Val His Asn Ala Lys Thr Lys Pro Arg Glu Glu Gln Phe Asn Ser Thr Phe Arg Val Val Ser Val Leu Thr Val Val His Gln Asp Trp Leu Asn Gly Lys Glu Tyr Lys Cys Lys Val Ser Asn Lys Gly Leu Pro Ala Pro Ile Glu Lys Thr Ile Ser Lys Thr Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Met Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys (SEQ ID NO: 214) |

Mouse Models

Ethics Committee Approval.

All mouse experiments were performed with the approval of Institutional Animal Care and Use Committee and are in accordance with the NIH Guide for the Care and Use of Laboratory Animals.

Inh-KO Mice.

12-week-old female and 8-week-old male inh-KO mice with fully established ovarian or testicular tumors received a single injection of PBS or sActRIIB (30 mg/kg, SC). As a control, age-matched wild-type littermates received a single injection of PBS. Ovarian and testicular organ weights were determined by necropsy 14 days after the injection.

TOV-21G Xenograft.

$5 \times 10^6$ TOV-21G ovarian cancer cells were implanted subcutaneously into individual female athymic nu/nu mice (Harlan). Treatment was initiated at day 12 after tumor implantation, when the average tumor volume reached approximately 150 mm$^3$. The mice received PBS, sActRIIB (30 mg/kg, SC, 1×/week) or activin-A antibody (30 mg/kg, SC, 2×/week). In a separate chemotherapy combination experiment, the mice were treated with PBS, sActRIIB (10 mg/kg, SC, IX/week), 5-FU (50 mg/kg, IP, 3 cycles, 4 daily injections per cycle) or sActRIIB and 5-FU combination at the same doses above.

Cho Xenograft.

$3 \times 10^6$ naïve or activin-A-transfected CHO cells were implanted intramuscularly into the right quadriceps in individual female CD1 nude mice (Harlan). The mice received PBS or activin-A antibody (20 mg/kg, 1×/week, SC) at the time of implantation.

OV-90 Xenograft.

$3 \times 10^6$ OV-90 ovarian cancer cells transfected with activin-A were implanted SC in individual female CD1 nude mice (CRL). The mice were treated with PBS or sActRIIB (20 mg/kg, SC, 1×/week) beginning at day 11 post tumor implantation, when the average tumor volume had reached approximately 150 mm$^3$.

G361 and 5637 Xenografts.

$5 \times 10^6$ G361 melanoma cells and 5637 bladder carcinoma cells, respectively, were inoculated SC into individual athymic nu/nu mice (Harlan Inc). Treatment was initiated 4 days after 5637 implantation and 14 days after G361 implantation, when the tumor volumes reached 130 mm$^3$-150 mm$^3$. 5637-implanted mice received PBS or activin-A antibody (10 mg/kg, SC, 2×/week). G361-implanted mice received PBS or sActRIIB (20 mg/kg, SC, 1X/week).

Tumor Size and Weight

For all xenograft experiments, the tumor sizes were measured longitudinally by using an electronic caliper. Immediately prior to the 1$^{st}$ dose, the tumor-bearing mice were randomized to ensure even distribution in tumor sizes across different groups. Tumor volumes (mm$^3$) were calculated as tumor length (mm)×tumor width (mm)×tumor height (mm). Tumor weights were determined by necropsy.

Cell Cultures

Primary BAEC cultures (Lanza) were grown at 37° C. in 5% CO2 in DMEM with 10% fetal bovine serum (Invitrogen). TOV-21G cells (ATCC) were cultured in a 1:1 mixture of MCDB 105 medium (Sigma, M6395) and Medium 199 (Invitrogen) containing 15% fetal bovine serum. MRC-5 and CCD-Lu cells (ATCC) were cultured in MEM (Invitrogen), supplemented with 10% FBS. U937 and THP-1 cells (ATCC) were grown in RPMI 1640 medium (Invitrogen) containing 10% FBS and L-glutamine.

In Vitro Proliferation Assay

In vitro growth rates of TOV-21G cancer cells were analyzed by using a real-time live cell imaging system (IncuCyte) following the manufacturer's recommended protocol.

Real-Time RT-PCR

Total RNA was isolated from cell cultures using the RNeasy mini RNA kit (QIAGEN). 25 ng of total RNA was subjected to one-step quantitative RT-PCR analysis using the TaqMan one-Step RT-PCR Master Mix Reagents and the Prism 7900HT Detection System (Applied Biosystems). GAPDH was used to normalize gene expression levels. All primers used for real-time PCR analyses except the human βA primer set were obtained from Applied Biosystems. The catalog numbers for the specific primers used in the current studies are as follows:

Bovine primers: VEGF (Bt03213282), Ang-1 (Bt03249559); Activin (βA) (Bt03259358), GAPDH (Bt03210913); Human Primers: VEGF (Hs00900054), Ang-1 (Hs00375822), GAPDH (Hs02758991). The human βA primer sequences used are as follows: 5'-GAA AAG GAG CAG TCG CAC AGA-3' (SEQ ID NO: 291), 5'-C TTC TGG TGG GAG TAG CGG-3' (SEQ ID NO: 292), and TaqMan probe ATG CTG CAG GCC CGG CAG TC (SEQ ID NO: 293).

Northern Blot

Total RNA was isolated from individual tissue samples after homogenization in Trizol (Invitrogen). A pool of 10 µg RNA for each group containing equal amounts of total RNA isolated from individual animals was subjected to Northern blot analysis. The northern probes used for βA and Ang-2 were generated by using RT-PCR (Phusion, Biolabs). βA primer set: 5'-CCC TTG CTT TGG CTG AGA GGA-3' (SEQ ID NO: 294) and 5'-TC ACA GGT CGT CGT AGG TCG-3' (SEQ ID NO: 295); Ang-2 primer set: 5'-TGT GCC GGG GAG AAG AG (SEQ ID NO: 296) and 5'-TAC AGT AGT GGG TTG AGG TTC-3' (SEQ ID NO: 297). To normalize the expression, northern blot membranes were re-probed with β-actin.

Western Blot

Protein extracts were prepared from cell cultures or tissues in T-PER tissue protein extraction reagent (Pierce) containing a mixture of protease inhibitors (Roche). A pool of 50 µg total protein for each group containing equal amounts of protein extract isolated from individual animals was separated by NuPAGE 4-12% Bis-Tris gel (Invitrogen) and transferred to PVDF. The membranes were probed with primary antibodies against total Smad2, p-Smad2 or E-cadherin (1:1000; Cell Signaling), endoglin, osteopontin (1:500; R&D Systems), IGFBP-1, IGFBP-2 (1:500; Abcam) followed by HRP-conjugated secondary antibody (1:2000; Cell Signaling). The membranes were stripped and re-probed with antibody against α-tubulin (1:1000; Cell Signaling).

Activin-A ELISA

All serum samples from ovarian cancer patients and healthy subjects were collected under informed consent and were purchased from Bioreclamation, Inc. The serum samples were diluted in buffer (DY995, R&D Systems) and pretreated overnight at 4° C. with 4 M urea (Sigma) to dissociate any protein bound to activin-A. The samples were then transferred to 96 well plates pre-coated with an activin-A monoclonal antibody. After 2 hr incubation at room temperature and a washing step (0.05% Tween 20 in DPBS), a biotin-labeled activin-A monoclonal antibody was added for 1 hr at room temperature. The plates were then washed and incubated with Streptavidin-Horseradish Peroxidase (Amersham) for 1 h at room temperature. Following a washing step, tetramethylbenzidine (KPL) substrate was added to the wells for 10 minutes at room temperature. An acidic stopping solution (KPL) was added and the degree of enzymatic turnover of the substrate was determined by wavelength absorbance measurement at 450 nm. The absorbance measured is directly proportional to the concentration of activin-A present. A standard curve of absorbance versus activin-A concentration was used to determine the amount of Activin-A in the test sample. Serum activin-A levels in inh-KO mice were measured by using ELISA.

VEGF and Ang-1 ELISA

The serum VEGF levels in inh-KO mice were measured by using immunoassay kit (R&D Systems), and the levels of human VEGF and Ang-1 in cell line culture medium were quantified using ELISA kits purchased from Invitrogen (VEGF) and R&D Systems (Ang-1), by following the manufacturers' recommended protocols.

Histology and Light Microscopy

Testes and ovaries from inh-KO mice were fixed with Zinc-formalin. Tissue sections were subjected to H&E staining and then examined with a Nikon Eclipse 90i microscope.

Immunohistochemistry

Zinc-formalin fixed paraffin tumor tissue sections of 4 µm in thickness were prepared. The sections were subjected to antigen retrieval by microwave 3 min in Unmask solution (Vector H-3300) followed by incubation in 10 µg/ml Proteinase-K for 20 min and in 1% H$_2$O$_2$ in dH$_2$O for 10 min at room temperature. The sections were further incubated in 0.1% Tween-20 in PBS for 3 min to permeabilize the cell membrane and in goat serum for 30 min to block non-specific binding. The sections were then incubated at room temperature with specific primary antibody for 3 hours followed by incubation in biotinylated or fluorescently labeled secondary antibody. Substrate developed in Vector SG kit (SK-4700) or DAB and nuclear-counterstained in Vector Fast Red (H-3403) or in hematoxylin. The immunostained tissue sections were analyzed and photographed using a Nikon Eclipse 90i microscope equipped with DS-Ri1 camera. The primary antibodies used and their dilutions are as follows: VEGF (BD Pharmingen 550549) 1:20 or VEGF (Abcam ab46154) 1:100, active caspase-3 (Abcam ab32042) 1:50, Ang-1 (Abcam ab8451) 1:500, osteopontin (Abcam ab8448) 1:200, CD-31 (Abcam ab56299) 1:100, E-cadherin (Abcam ab76319) 1:80. For immunofluorescence staining, FITC-conjugated secondary antibody (Invitrogen) was added at 1:50 dilution in PBS and incubated for 30 min. Cell nuclei were counterstained with Vectashield PE (Vector).

TUNEL Assay

Cell apoptosis in TOV-21G tumors was analyzed by measuring the amounts of fragmented DNA in the tumor sections using the DeadEnd Fluorometric TUNEL System following the manufacturer's recommended protocols (Promega, G3250). The fluorescein-12-dUTP-labeled DNA was visualized by Nikon fluorescence microscopy.

Statistics

Groups of tissue samples were compared using Student's t-test. Longitudinal measurements were analyzed by repeat measures ANOVA. P values <0.05 were considered significant.

Example 1: Activin Blockade Causes Regression of Advanced Ovarian and Testicular Tumors in Inhibin-Deficient Mice Activin-A Measurements in Inh-KO Mice Serum activin-A levels were measured in patients with ovarian cancer and in healthy controls. As shown in FIG. 1, circulating activin-A levels were significantly higher in ovarian cancer patients.

Next, to understand the mechanism by which activin-A influences tumor growth, effects were analyzed of activin blockade on further growth of gonadal tumors that had been fully established in the inhibin-α KO mice (a model of activin deregulation, spontaneous tumor formation and cancer cachexia) (referred to below as inh-KO mice). Activin signaling was interrupted after the gonadal tumors had developed to an advanced stage to better evaluate the therapeutic potential of activin-Antagonism.

Figure 2A:
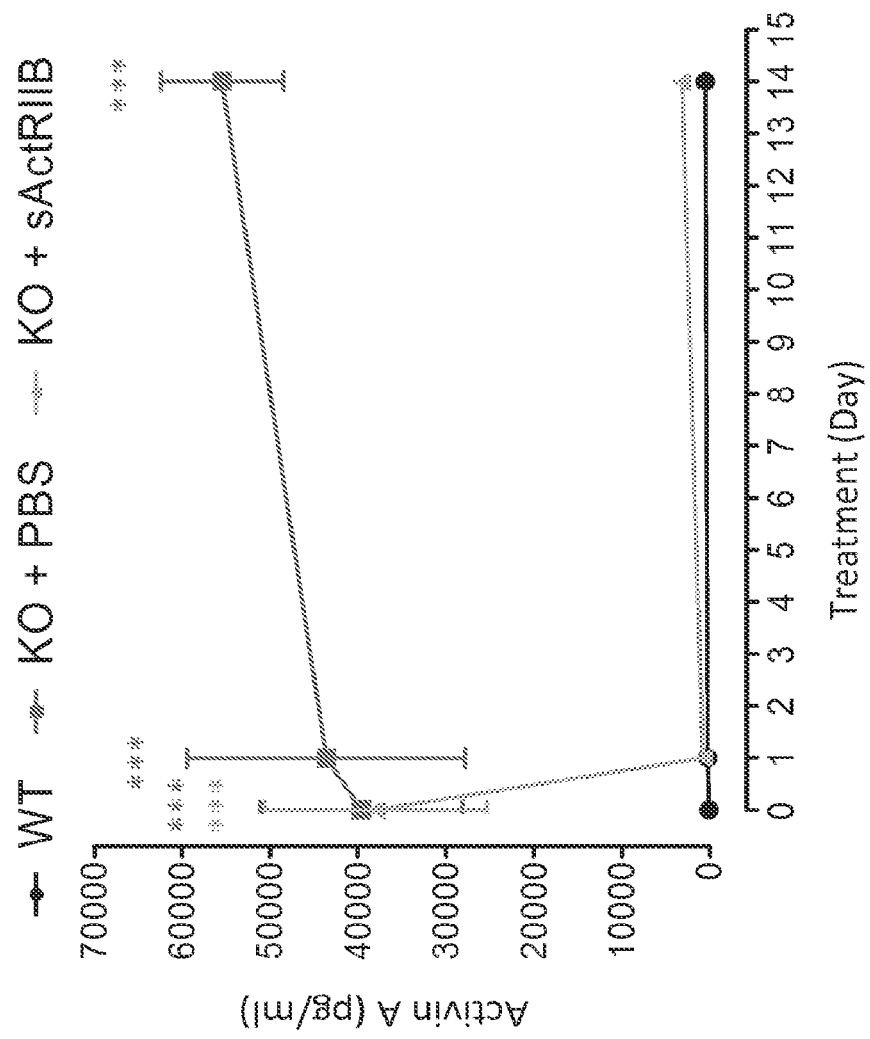
FIG. 2A is a graph showing the effects of sActRIIB treatment on serum activin-A levels in inh-KO mice over time. ***$p<0.001$ vs. WT; student's t-test; n=6-12.
Figure 2B:
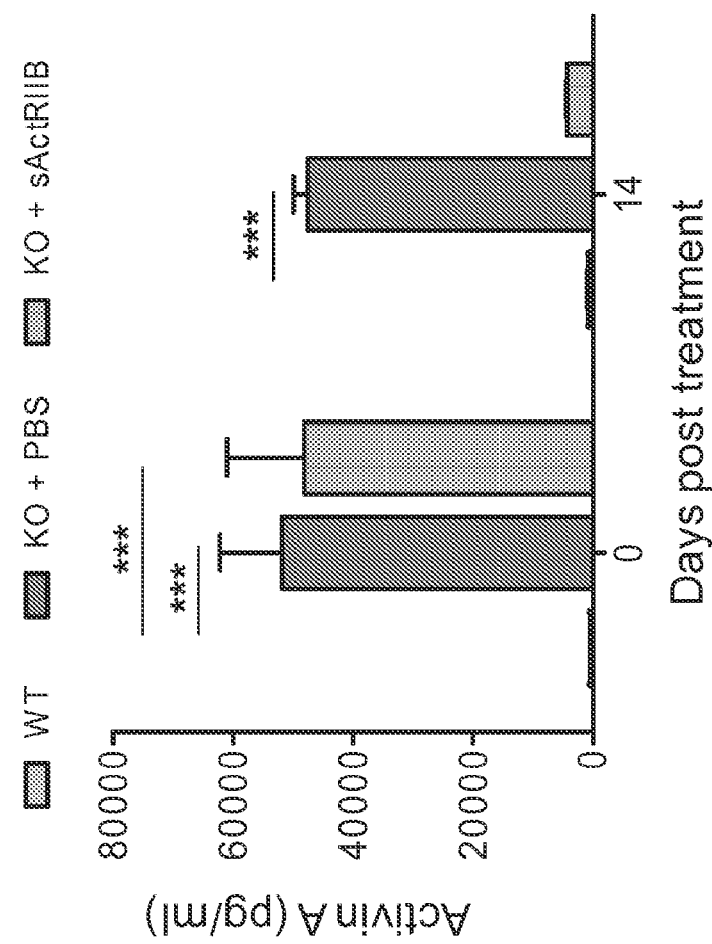
FIG. 2B is a bar graph showing the effects of sActRIIB treatment on serum activin-A levels in inh-KO mice over time. In each group of 3 bars, the left bar is wild-type, the middle bar is KO plus PBS, and the right bar is KO plus sActRIIB.
Figure 3A:
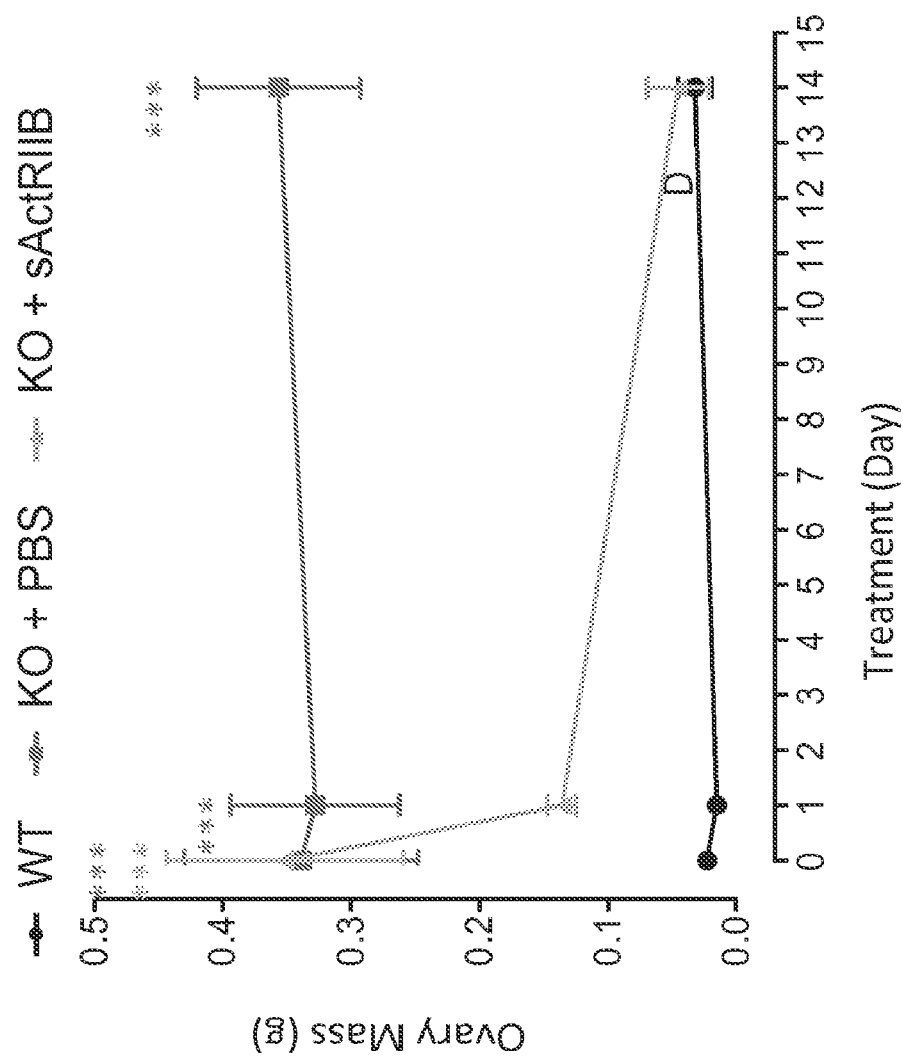
FIG. 3A is a graph showing the effects of sActRIIB treatment on the ovarian tumor mass in inh-KO mice over time. ***$p<0.001$ vs. WT. Student's t-test; n=6-12.
Figure 3B:
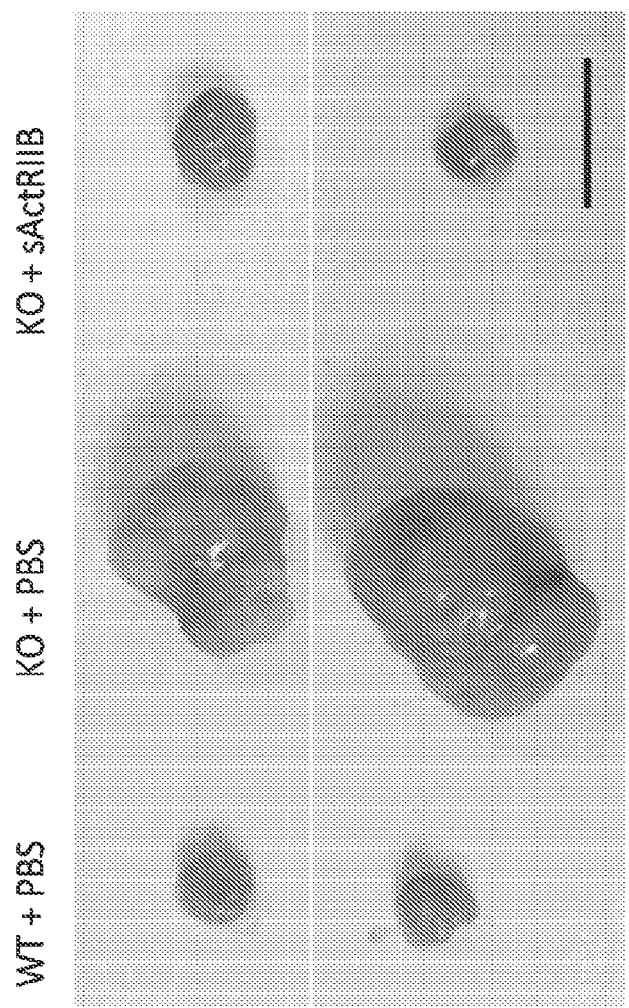
FIG. 3B is a representative gross morphology depicting advanced ovarian tumors in inh-KO mice after sActRIIB treatment. Scale bar=5 mm.

Measurements of tumor weights as a function of age in inh-KO mice indicated that by 12 weeks in females and 8 weeks in males, the ovarian and testicular tumors had been fully established. A single dose of the activin-Antagonist sActRIIB was administered to 12-week-old-female and 8-week-old male inh-KO mice and the resulting alterations in activin-A levels and ovarian and testicular tumor sizes were examined. As expected, there was a marked increase in serum activin-A levels in these inh-KO mice with established gonadal tumors (FIG. 2A and FIG. 2B). However, within one day after administration, sActRIIB reduced the elevated activin-A in the inh-KO mice to normal control levels seen in the wild-type (WT) mice, and this activin-A-neutralizing effect persisted throughout the 14-day study period. Unexpectedly, necropsy analysis revealed that upon activin neutralization by the sActRIIB treatment, the very large ovarian tumor masses in the inh-KO mice regressed rapidly to the sizes seen in the WT control mice (FIG. 3A and FIG. 3B). Similarly, in the male inh-KO mice treated with sActRIIB, there was a dramatic regression of testicular tumor masses to the WT control levels (FIG. 4A and FIG. 4B). Thus, sActRIIB rapidly and completely eradicated the ovarian and testicular tumor masses that had been fully established in the inh-KO mice.

Northern Blot Analysis

Next, activin-A (βA) mRNA expression in the tumors was examined by Northern blot analysis. The levels of βA transcripts in the tumors were much greater than in WT controls, but this increase was completely blocked by the sActRIIB treatment (FIG. 5A). This finding suggests the existence of a novel feed-forward loop within the tumors by which activin-A upregulates its own expression (see below). Activin-A-induced Smad2 signaling was also markedly increased in the tumors above levels in the WT controls, as shown by Western blot assay of the amounts of phospho-Smad2. Furthermore, sActRIIB treatment eliminated this increase in phospho-Smad2 in the tumor tissues (FIG. 5B). Thus, sActRIIB prevented both the upregulation of activin-A mRNA and the activation of Smad2 signaling in the ovarian and testicular tumors.

Western Blot Analysis

Figure 6A:
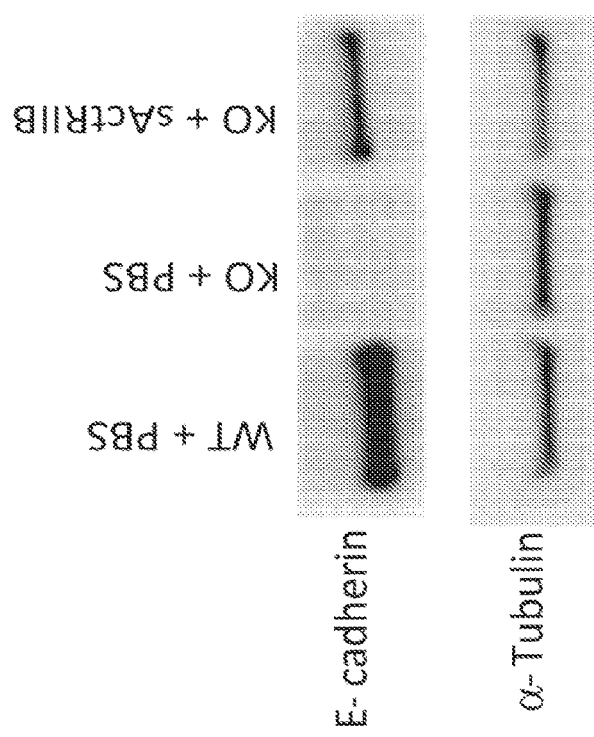
FIG. 6A shows a Western blot analysis of E-cadherin protein in the ovarian tumors of inh-KO mice after sActRIIB treatment. n=10
Figure 6B:
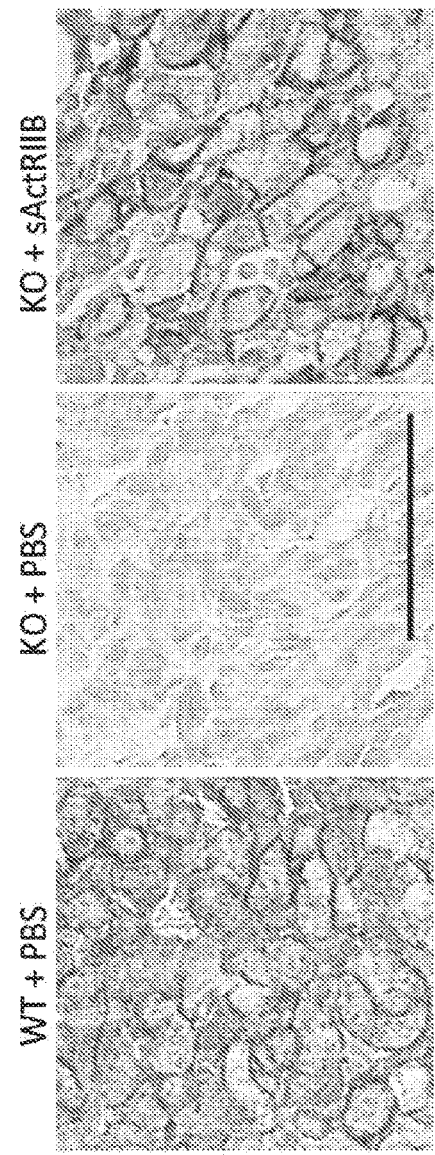
FIG. 6B shows an immunohistochemical staining of E-cadherin in ovarian sections in inh-KO mice after sActRIIB treatment, where E-cadherin is stained in gray and cell nuclei are counterstained in red. Scale bar=50 μm.

To verify that the marked decreases in ovarian tumor size in response to sActRIIB treatment indeed reflected tumor regression, Western blot analysis was used to examine the expression in the tumors of E-cadherin, a cell adhesion protein that is critical in maintaining normal differentiation of the ovary. Remarkably, no E-cadherin protein could be detected in the ovarian tumors from the untreated inh-KO mice, but the single injection of sActRIIB dramatically restored the lost E-cadherin (FIG. 6A). These observations were corroborated by immunostaining. Although no immunoreactivity for E-cadherin was detected in the sections of the ovarian tumors in untreated inh-KO mice, the treatment with sActRIIB led to the reappearance of distinctive E-cadherin immunoreactivity in the ovarian sections (FIG. 6B). Thus, the increased activin signaling down-regulates E-cadherin in the ovary. The reversal of this down-regulation is noteworthy because the loss of E-cadherin has been implicated in ovarian cancer progression.

Light Microscopy Analysis

Figures 7A, 7B:
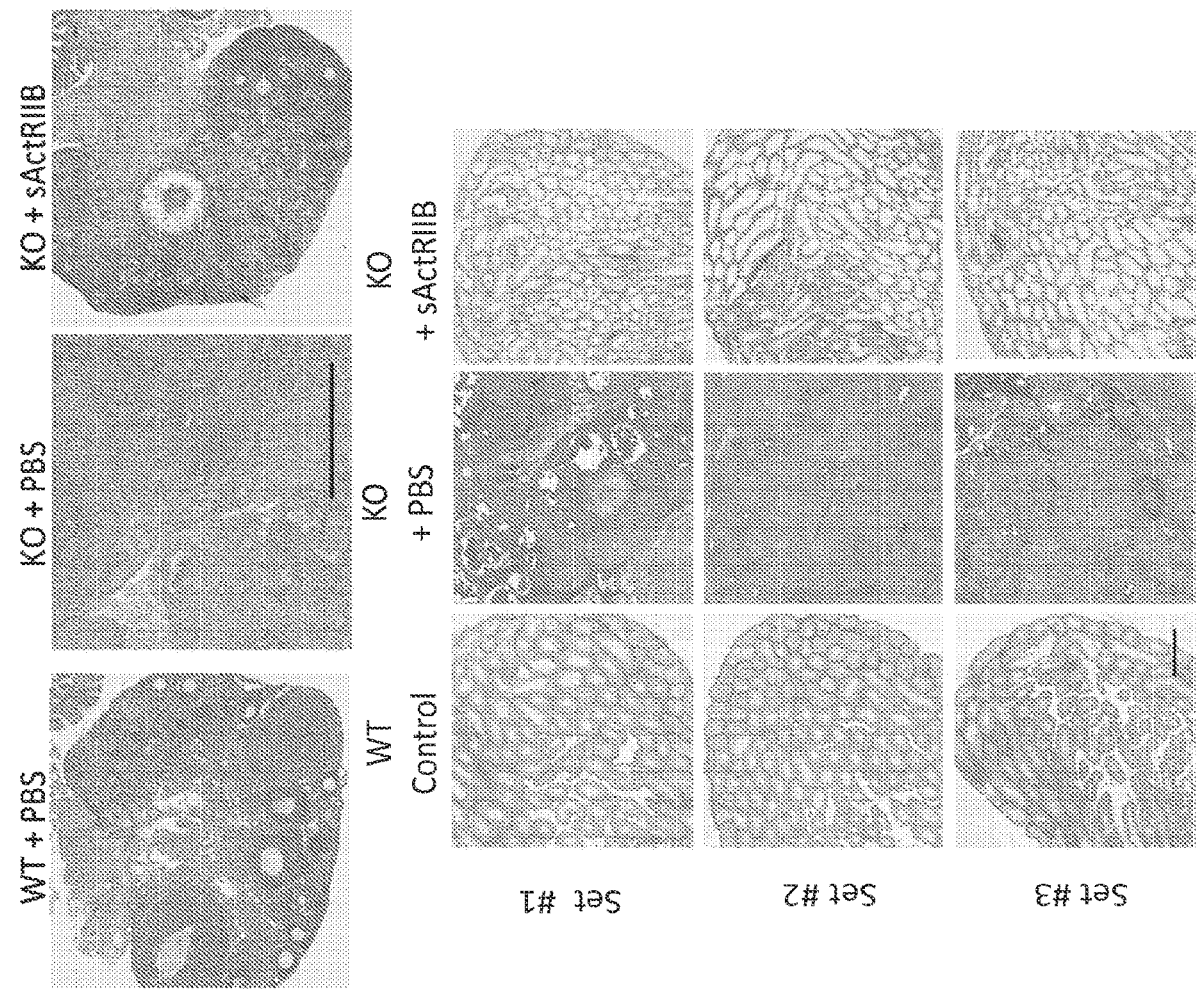
FIG. 7A shows representative H&E microscopic images of ovarian sections in inh-KO mice after sActRIIB treatment. Scale bar=500 μm.
FIG. 7B shows representative H&E microscopic images of testicular tissue sections in inh-KO mice after sActRIIB treatment. Scale bar=500 μm.

The morphological changes in the ovarian and testicular tumors were examined by light microscopy. In the untreated female inh-KO mice, the greatly enlarged ovaries were predominantly filled with solid tumor mass and many hemorrhagic lesions with virtually no recognizable follicles remaining. By contrast, in the sActRIIB-treated female inh-KO mice, the ovaries were normal in size and contained many recognizable follicles, minimal tumor cell invasion and few hemorrhagic lesions (FIG. 7A). In the untreated male inh-KO mice, the normal structures in the testes were displaced by massive, undifferentiated solid tumor mass, and no seminiferous tubules were evident. By contrast, in the sActRIIB-treated male inh-KO mice, the testes were normal in size and filled with seminiferous tubules, although the number of spermatogonia was less than normal and a few small areas still contained tumor cells (FIG. 7B). These histological findings imply that sActRIIB treatment not only caused regression of the gonadal tumors, but also promoted normal tissue differentiation. Thus, the shrinkage of tumors upon sActRIIB treatment (FIG. 3A, FIG. 3B, FIG. 4A, and FIG. 4B) is not simply an involution of mass, but represents a reversal to a differentiated phenotype.

Figure 8A:
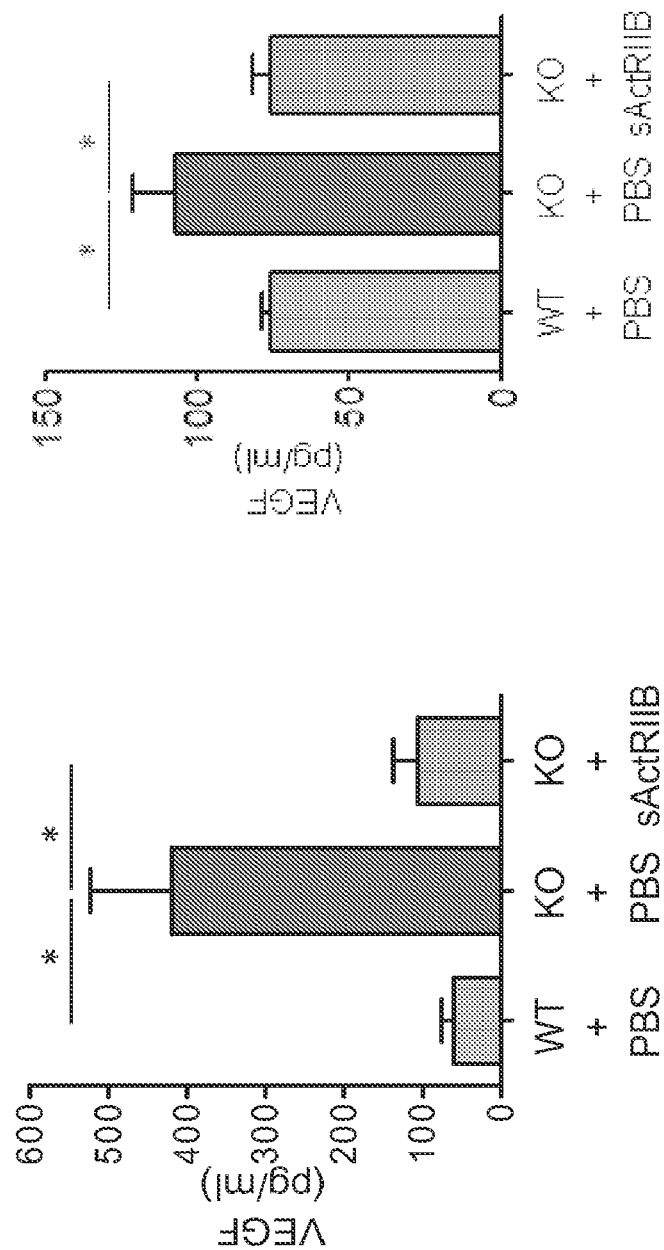
FIG. 8A shows two graphs depicting the effects of sActRIIB treatment on serum VEGF in inh-KO mice. *$p<0.05$; student's t-test; n=10.
Figure 8B:
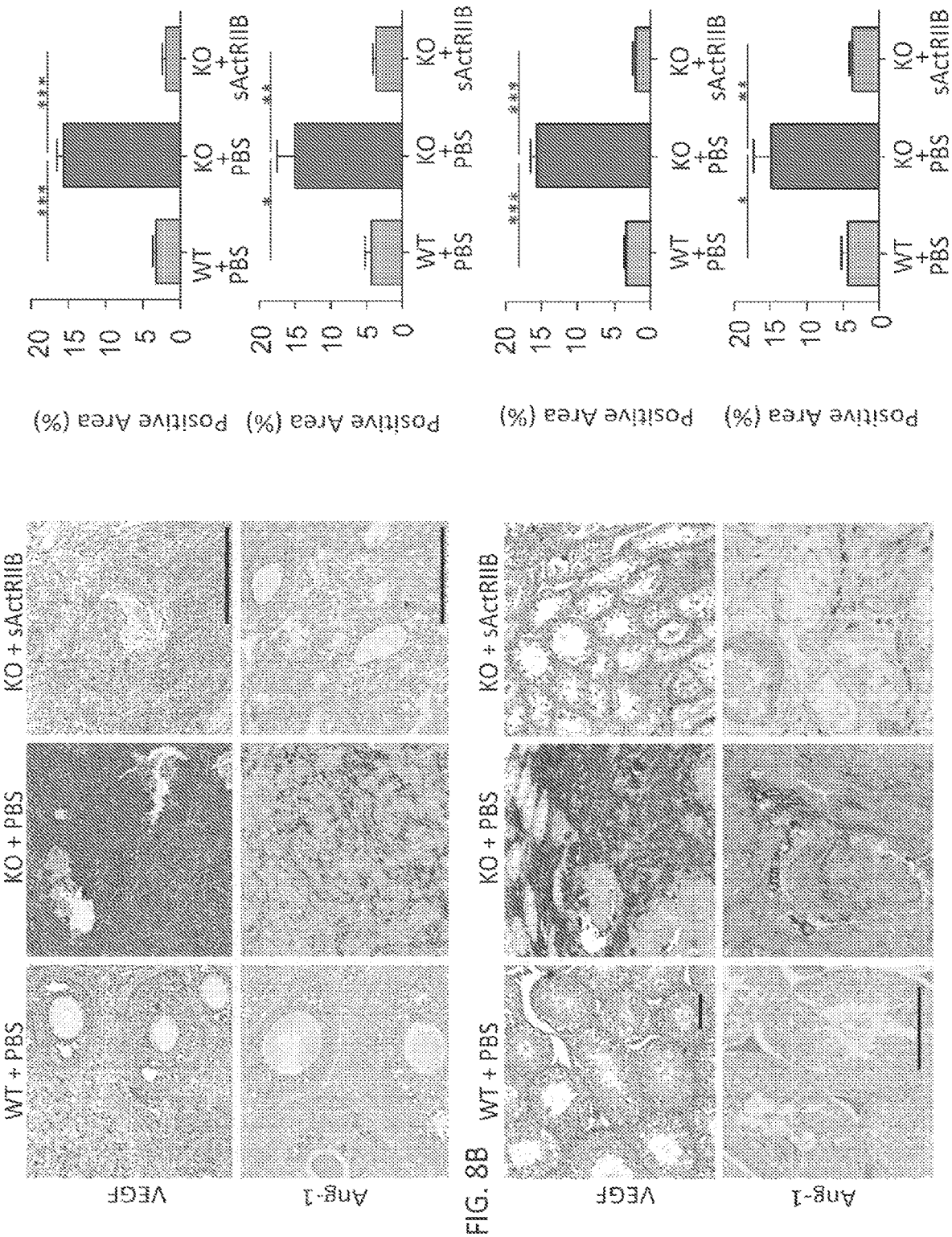
FIG. 8B shows representative images of immunostaining depicting the effects of sActRIIB treatment on VEGF and Ang-1 immunoreactivities in ovarian (top) and testicular (bottom) tumor sections in inh-KO mice. Scale bar=100 μm. **$p<0.01$; student's t-test. The bar graphs show the quantitative analyses of the VEGF and Ang-1 immunoreactivities.
Figure 8D:
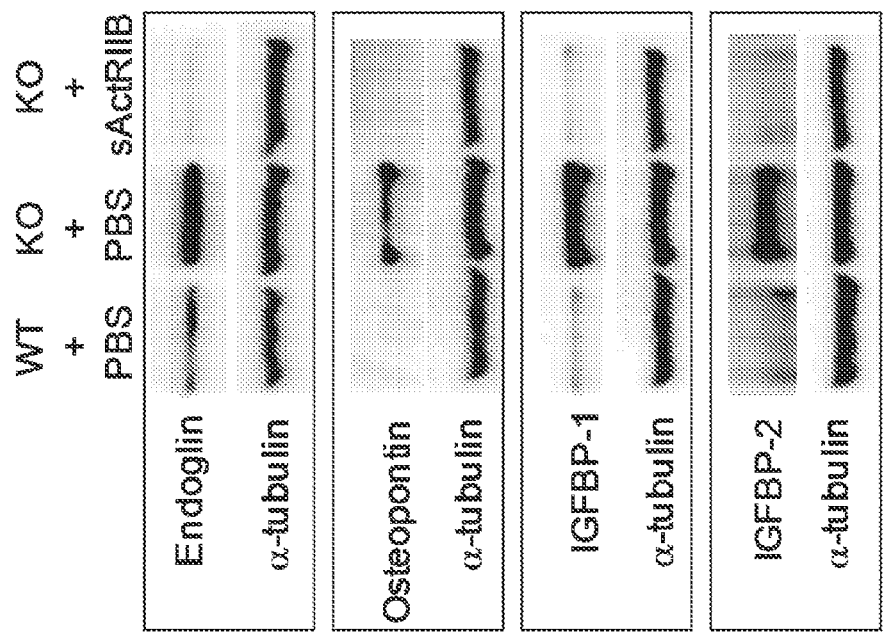
FIG. 8D shows Western blot analyses of endoglin, osteopontin, IGFBP-1 and IGFBP-2 proteins in the ovarian tumors of inh-KO mice after sActRIIB treatment.
Figure 8C:
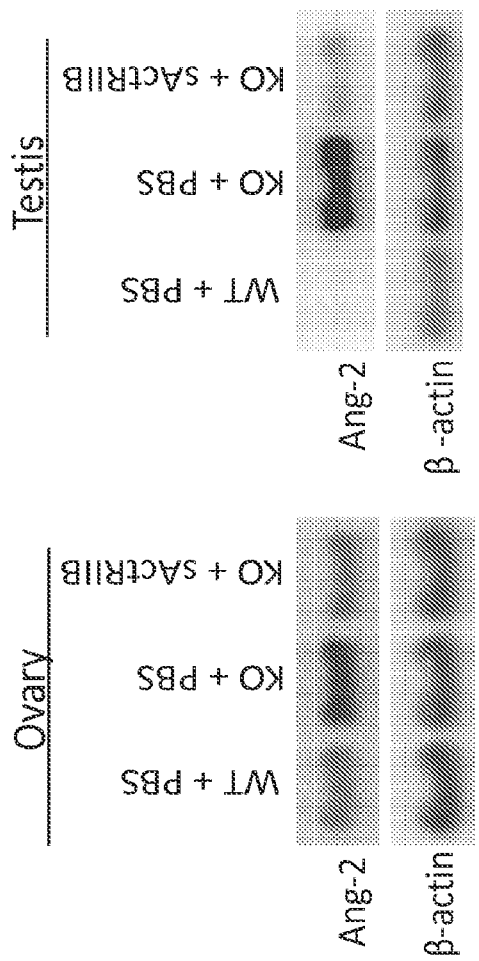
FIG. 8C shows Northern blot analyses of Ang-2 mRNA expression levels in the ovarian or testicular tumors of inh-KO mice after sActRIIB treatment.

Example 2: Activin Blockade Abolishes Angiogenesis Factor Induction and Causes Caspase-3 Activation in Gonadal Tumors The profound tumor suppression seen upon activin neutralization makes it likely that tumor-derived activin-A stimulates tumor progression by inducing known tumorigenesis-related factors. To test this possibility, angiogenic factors VEGF and angiopoietins that play well-established roles in tumor angiogenesis and tumorigenesis were analyzed. ELISA revealed that the inh-KO mice with advanced ovarian and testicular tumors had greatly increased levels of VEGF in their circulation. A single dose of sActRIIB rapidly lowered the elevated VEGF to WT control levels (FIG. 8A). Furthermore, both VEGF and Ang-1 immunoreactivities were dramatically increased in sections of the ovarian and testicular tumors; however, sActRIIB treatment completely abolished the VEGF and Ang-1 inductions in the tumors (FIG. 8B, top and bottom respectively). In addition, Northern blot analysis revealed that Ang-2 mRNA was expressed at high levels in the ovarian and testicular tumors, while sActRIIB treatment inhibited its overexpression (FIG. 8C). Furthermore, Western blot analyses revealed that several other factors known to be involved in ovarian tumor angiogenesis and growth, including endoglin, osteopontin, IGFBP-1, and IGFPB-2, were markedly upregulated in the ovarian tumors, but the inductions of these tumorigenesis-related proteins were abolished completely by sActRIIB administration (FIG. 8D).

Figure 9:
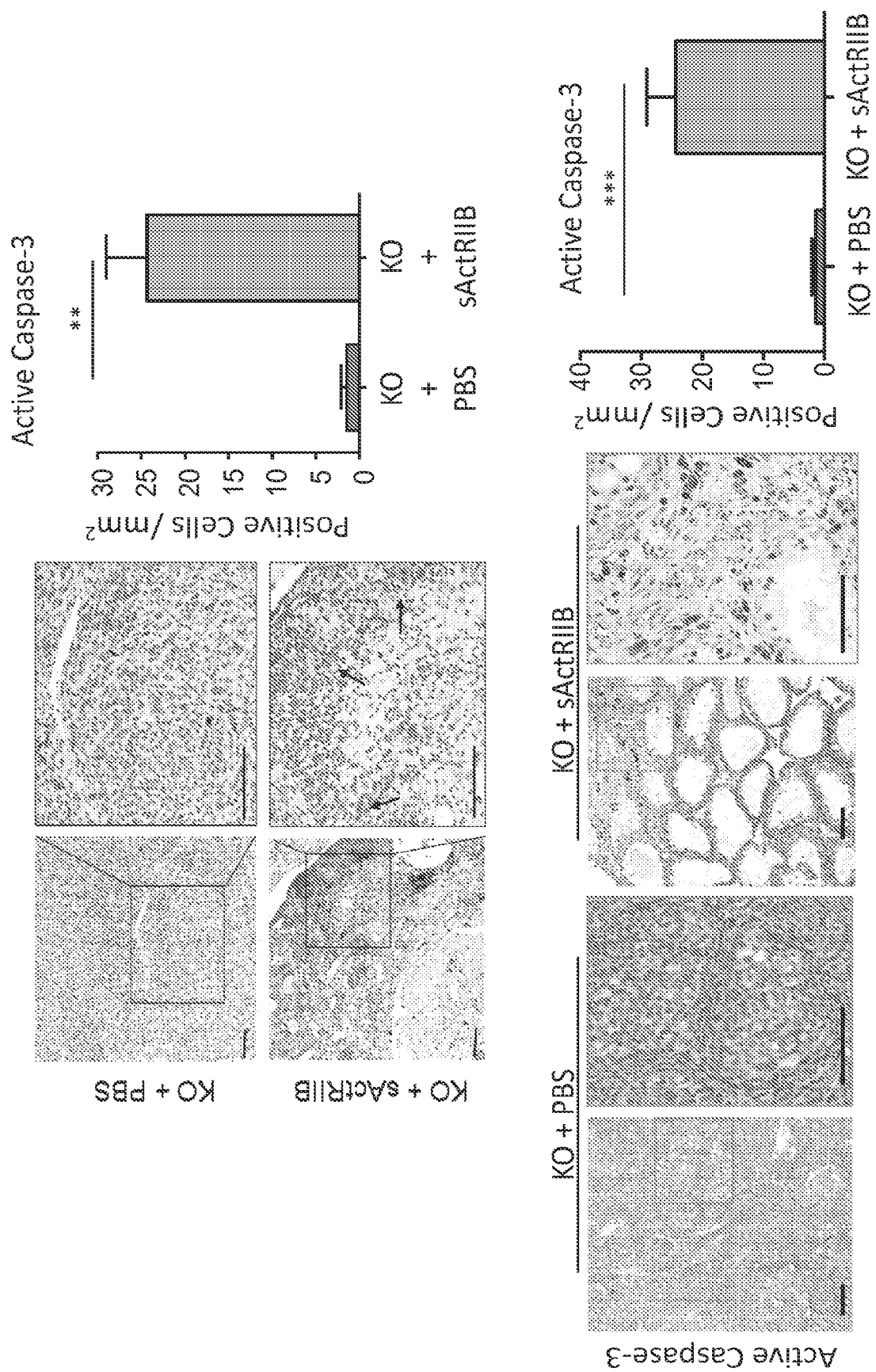
FIG. 9 shows representative images of immunostaining depicting the effects of sActRIIB treatment on caspase-3 activation in the ovarian (top) and testicular (bottom) tumors of inh-KO mice. Arrows point to active caspase-3. The bar graphs show the quantitative analyses of the active caspase-3. n=10. *$p<0.05$, **$p<0.01$; student's t-test.

Next, immunostaining was used to analyze the activity of apoptotic enzyme caspase-3 in tumor tissue sections. No active caspase-3 was detected in the ovarian or testicular tumor sections from the untreated inh-KO mice; however, in sActRIIB-treated inh-KO mice, strong immunostaining of active caspase-3 was found in the ovarian and testicular tissue sections at the regions where residual tumor cells were clustered (FIG. 9), indicating activation of tumor apoptosis. These results show that elevated activin-A in the tumors drives the overproduction of multiple tumor angiogenesis- and tumorigenesis-related factors and accordingly, blocking tumor-derived activin-A causes the deprivation of these factors, which in turn induces caspase-3 activation and apoptosis in the tumor cells, leading to tumor suppression.

Figures 10A, 10B:
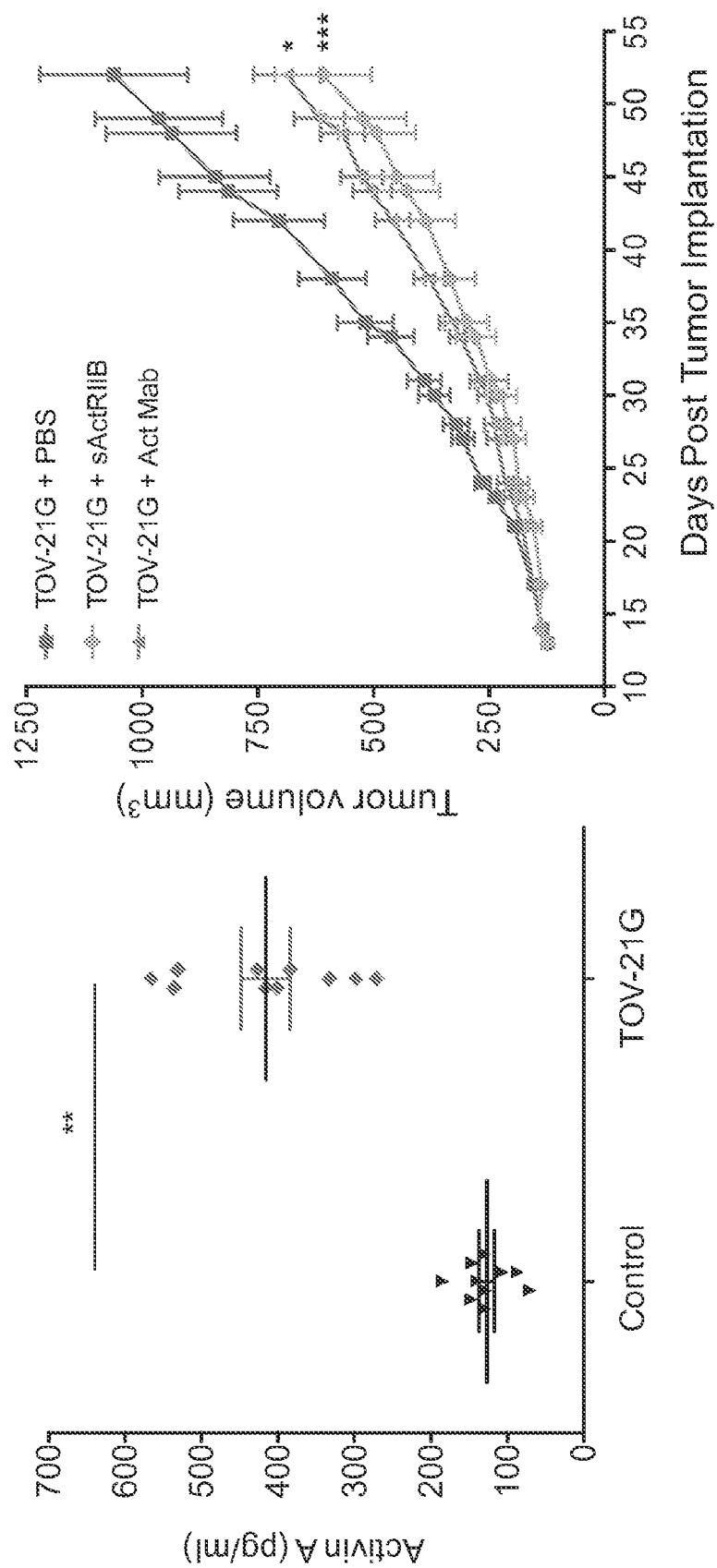
FIG. 10A is a graph showing serum activin-A levels in nude mice after subcutaneous TOV-21G implantation. **$p<0.01$; student's t-test; n=10.
FIG. 10B is a graph showing the changes in TOV-21G tumor volumes after treatment with sActRIIB or activin-A antibody; *$p<0.05$, ***$p<0.001$ vs. PBS; n=12.

Example 3: Activin-Antagonist Inhibits In Vivo Growth of Human Ovarian Cancer Xenografts with Additive Effects with Chemotherapy To further determine whether activin-antagonism can suppress growth of tumors that secrete activin-A, the in vivo growth of multiple xenograft tumors in nude mice was analyzed. The analysis heavily focused on the growth in vivo of TOV-21G xenograft, a human epithelial ovarian cancer model, because in cultures, these cancer cells secrete a high amount of activin-A. Subcutaneous implantation of TOV-21G in nude mice resulted in a sharp rise in serum activin-A (FIG. 10A). We administered sActRIIB or activin-A antibody to TOV-21G-implanted mice after the tumors had established. Both activin-A antagonists significantly inhibited the growth of the TOV-21G ovarian cancer xenografts (FIG. 10B).

Figure 11:
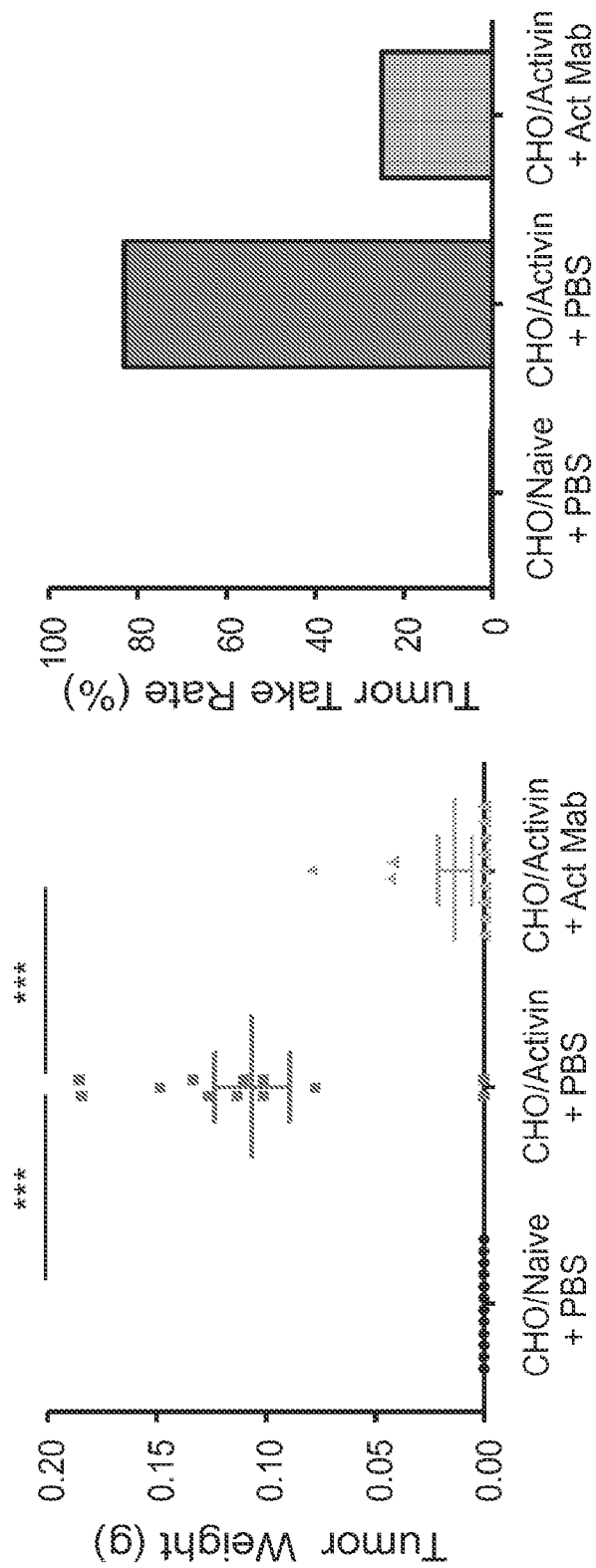
FIG. 11 shows two graphs depicting either the tumor weight or tumor take rate (defined by the percentage of mice with visually identifiable tumors in the quadriceps on day 21 post-implantation) after activin-A antibody treatment of CD1 nude mice implanted with naïve or activin-A-transfected CHO cells. ***$p<0.001$; one-way ANOVA; n=12.
Figure 12:
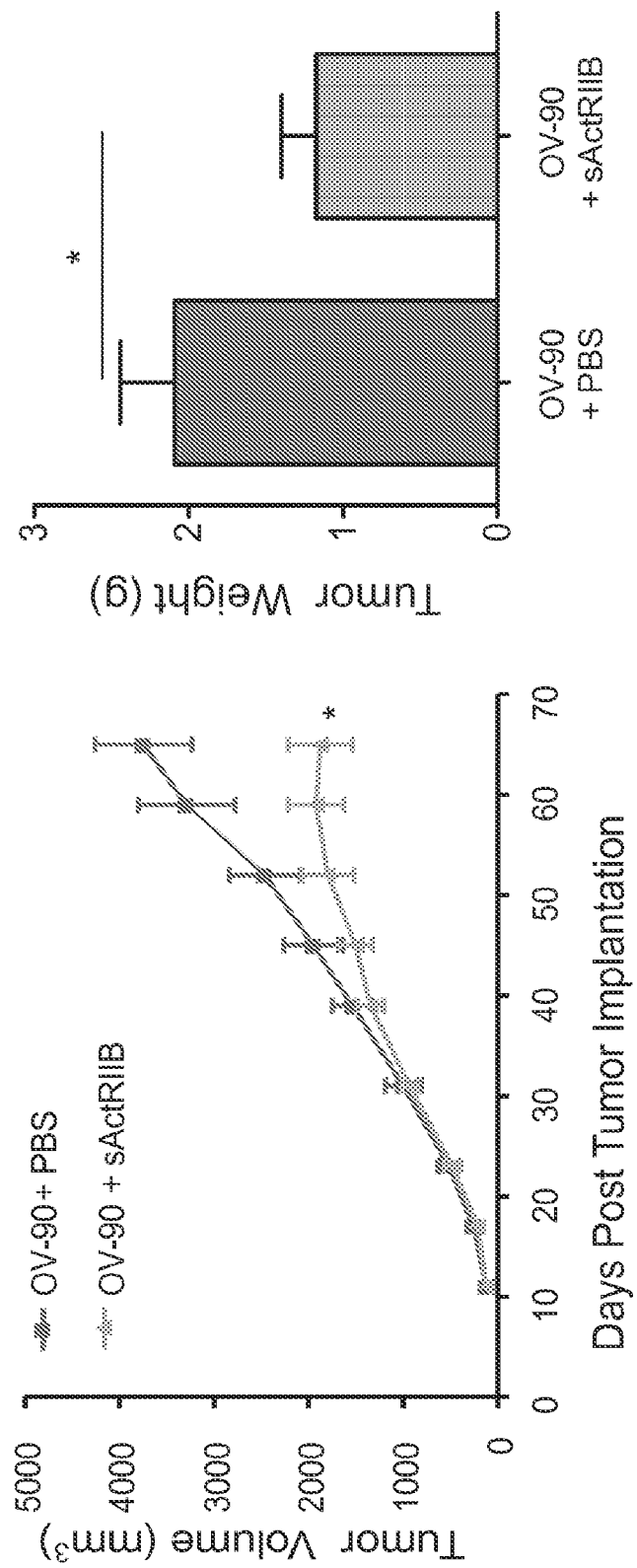
FIG. 12 shows two graphs depicting either tumor volume or tumor weight after sActRIIB treatment of CD1 nude mice implanted with activin-A-transfected OV-90 cells. *$p<0.05$; n=12-13.

To further evaluate the functional relevance of elevated activin-A to ovarian tumor growth, two additional ovarian tumor xenografts were analyzed, including the Chinese hamster ovary (CHO) and the human ovarian cancer OV-90 xenografts. After implantation into the quadriceps, naïve CHO cells failed to form detectable tumors. However, when the CHO cells were transfected with activin-A, they became highly capable of forming tumors in the nude mice. Moreover, activin-Antagonist treatment greatly reduced the rate of tumor formation by the activin-A transfected CHO cells (FIG. 11). Furthermore, activin blockade markedly inhibited the growth of activin-A overexpressing OV-90 xenografts in nude mice (FIG. 12). These observations provide additional evidence that the elevated activin-A is an important stimulus of tumor growth.

Figure 13:
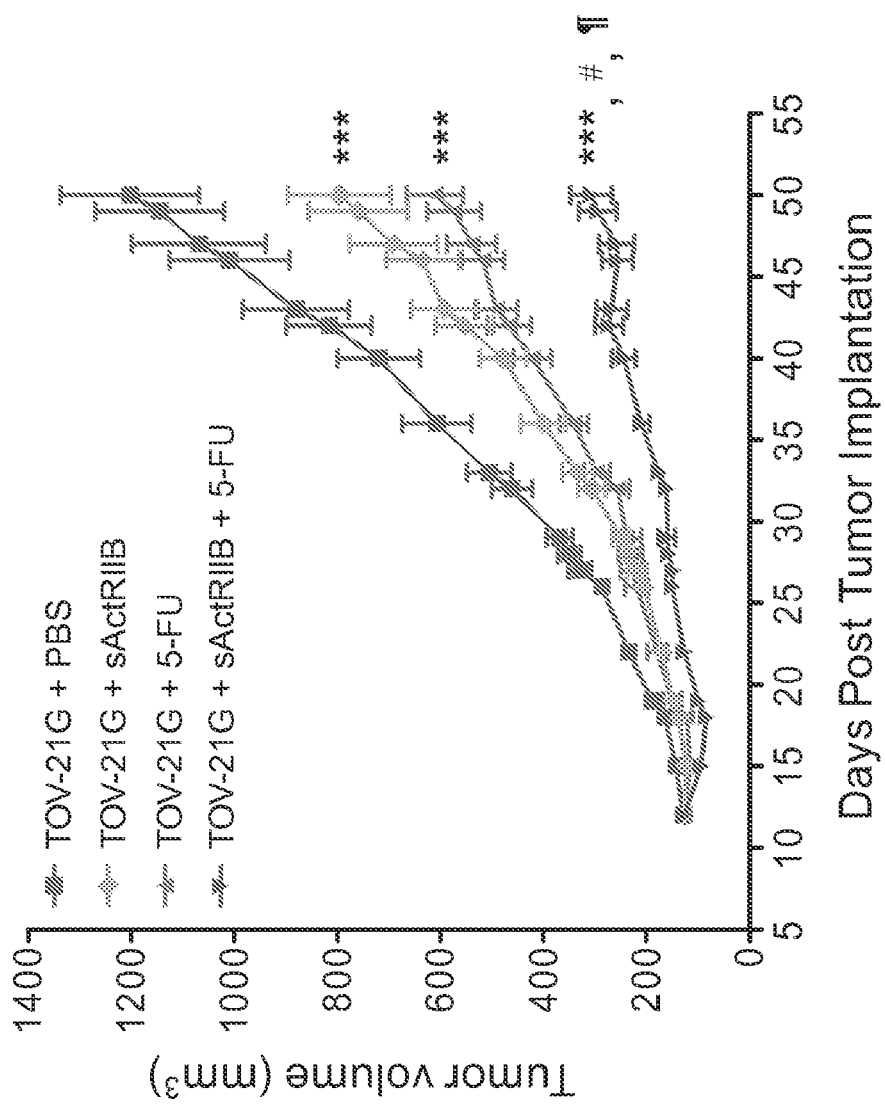
FIG. 13 is a graph showing tumor volumes after treatment with sActRIIB and 5-fluorouracil in nude mice implanted with TOV-21G cells. ***$p<0.001$ vs. PBS; #$p<0.05$ vs. 5-FU; $p<0.01$ vs. sActRIIB; n=12.

These findings suggested that activin-Antagonism might be a valuable therapy in ovarian cancer treatment. The effects of sActRIIB on the growth of TOV-21G xenografts receiving 5-Fluorouracil (5-FU) chemotherapy was examined. When sActRIIB treatment or 5-FU was administered alone to TOV-21G xenograft-bearing mice, each decreased the rate of tumor growth significantly (FIG. 13), but when sActRIIB and 5-FU were injected together, an even greater effect on tumor growth inhibition was observed (FIG. 13). Thus, sActRIIB and 5-FU clearly show additive effects in tumor suppression.

In another experiment, athymic nude mice received TOV-21G xenografts in the abdominal flank. After 14 days, subcutaneous hu-sActRIIB-Fc was administered weekly alone or in combination with 5-FU.

52 days after tumor cell injection, hu-sActRIIB-Fc treatment resulted in 43% ($p<0.0001$) tumor growth reduction, versus the vehicle-treated tumor-bearing group tested using ANOVA. 5-FU monotherapy resulted in 47% ($p<0.0001$) tumor growth reduction, and the combination of hu-sActRIIB-Fc and 5-FU together resulted in 73% ($p<0.0001$) tumor growth reduction. During the course of this experiment, the body weight of the mice receiving hu-sActRIIB-Fc increased by 26%, while the body weight of the mice receiving hu-sActRIIB-Fc and 5-FU increased by 22%, while control tumor-bearing mice receiving vehicle exhibited a 10% body weight loss.

Figure 14:
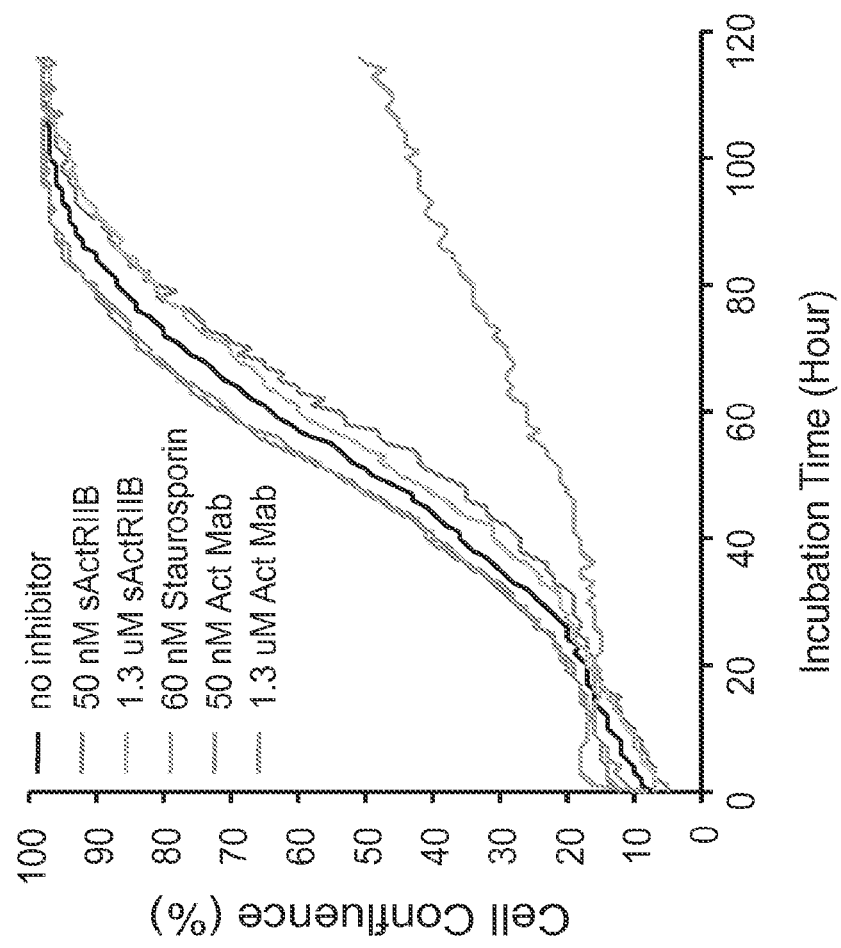
FIG. 14 is a graph showing the effects of sActRIIB and activin-A antibody on TOV-21G cell growth.

Next, the effects of activin-A antagonists on the growth of TOV-21G in cell cultures was examined. Surprisingly, increasing concentrations of sActRIIB or activin-A antibody were found to have no direct effect on TOV-21G cell proliferation in vitro (FIG. 14). Thus, the tumor-suppressive effect of the activin-Antagonists in TOV-21G xenograft mice must have been achieved through an indirect mechanism in vivo.

Figure 15A:
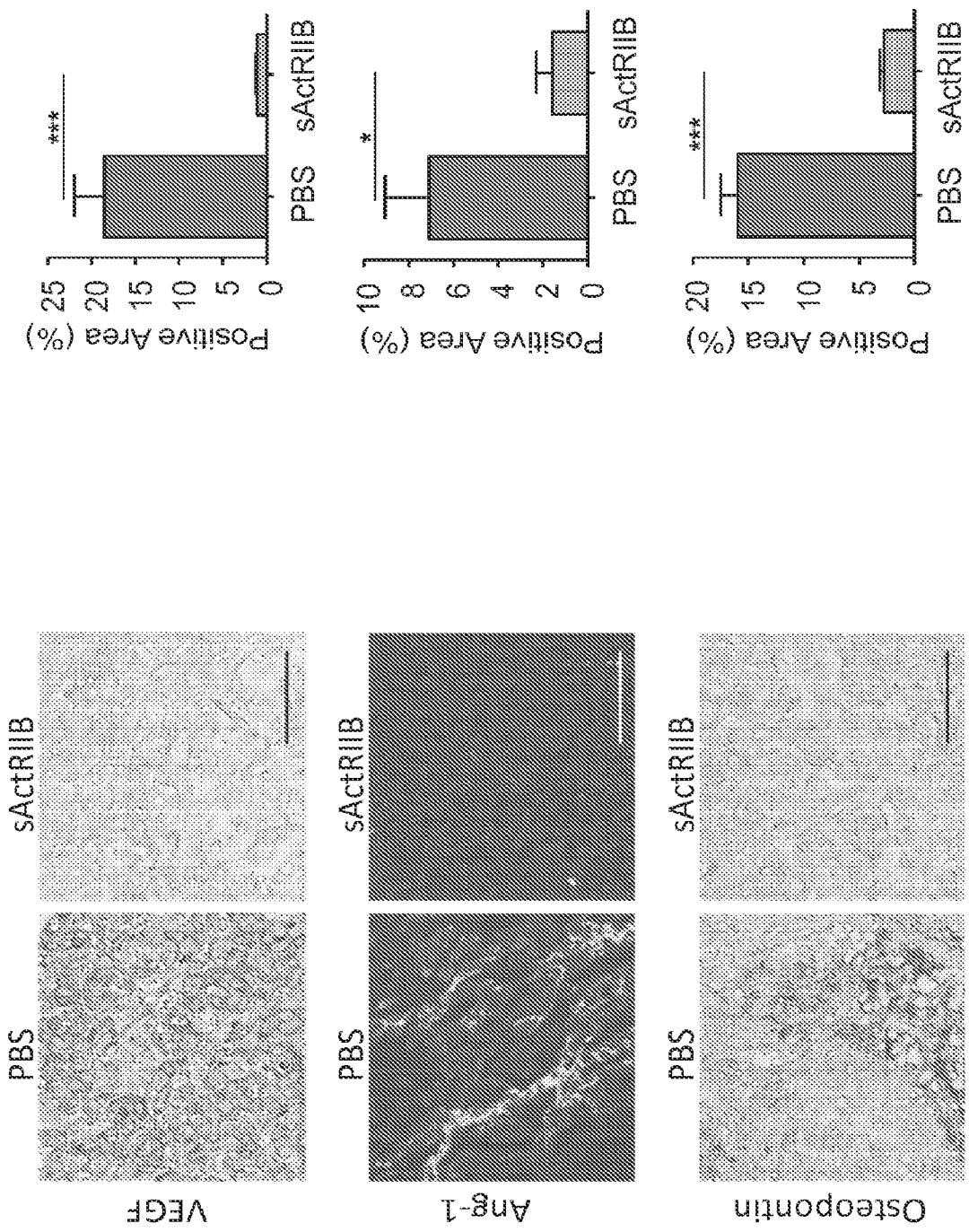
FIG. 15A shows representative images of immunostaining depicting the effects of sActRIIB treatment on VEGF, Ang-1, and osteopontin in TOV-21G xenograft tumors in mice. The bar graphs show the quantitative analyses of the VEGF, Ang-1, and osteopontin immunoreactivities. *$p<0.05$; $p<0.01$; *$p<0.001$.

Example 4: Blocking Activin-A Prevents Angiogenesis and Induces Apoptosis in Human Ovarian Cancer Xenografts Because activin-A induced overexpression of several angiogenic factors in the tumors in inh-KO mice, the influence of blockade of activin-A on angiogenesis in TOV-21G tumor xenografts in vivo was analyzed. Examination of the TOV-21G tumor sections revealed strong immunostaining for VEGF and Ang-1 in the untreated sections, but virtually none in the sActRIIB-treated sections (FIG. 15A). Similar results were found for immunostaining of osteopontin, a secreted protein involved in tumor angiogenesis and cancer progression, in the tumor sections (FIG. 15A). Immunostaining of CD31, a marker for newly formed microvessels, further demonstrated the existence of neo-microvasculature in the untreated tumor sections and the lack of such new microvessels in sections of the sActRIIB-treated tumors (FIG. 15B). These results indicate that sActRIIB treatment suppressed multiple angiogenesis factors and prevented neovascularization in the TOV-21G tumors. To assess the possible impact of this angiogenesis deprivation on tumor apoptosis, active caspase-3 immunostaining and TUNEL assays were performed on the tumor sections. As shown in FIG. 15C, sActRIIB treatment led to profound increases in active caspase-3 and DNA fragmentation in the treated tumors. Therefore, consistent with those on gonadal tumors in the inh-KO mice, these findings from the TOV-21G ovarian cancer xenografts further demonstrate a major role of activin-A in tumor angiogenesis and growth.

Figure 16A:
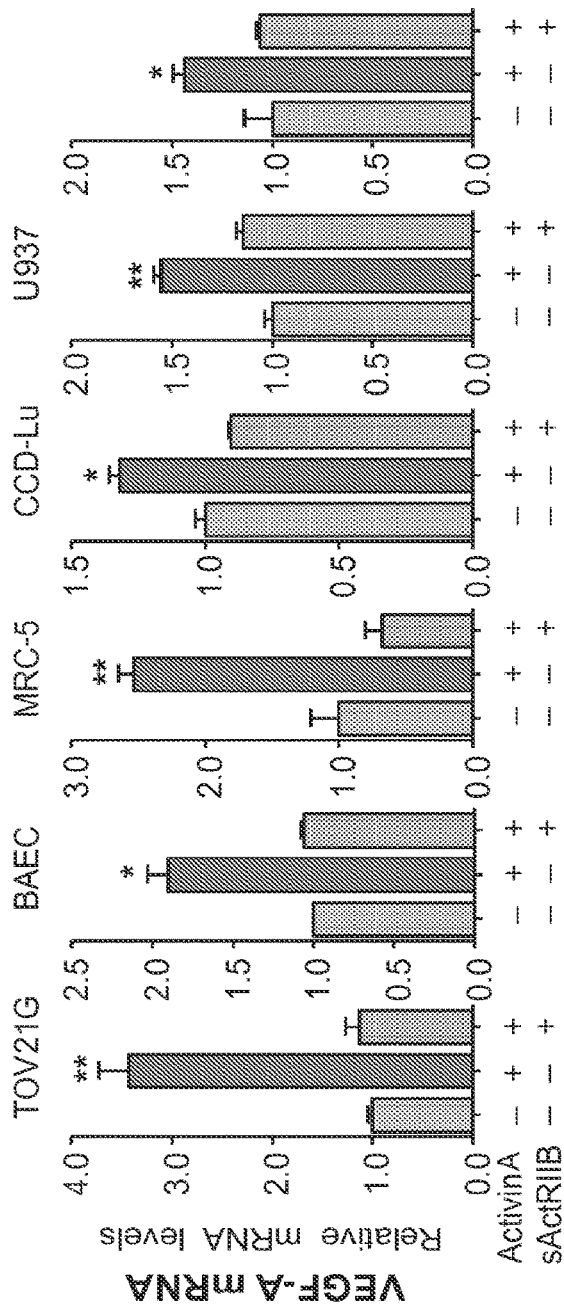
FIG. 16A shows graphs of VEGF-A mRNA expression levels in TOV-21G, BAEC, MRC-5, CCD-Lu, and U937 cell cultures after treatment with recombinant activin-A and sActRIIB. *$p<0.05$; $p<0.01$; *$p<0.001$; student's t-test; n=3.
Figure 16B:
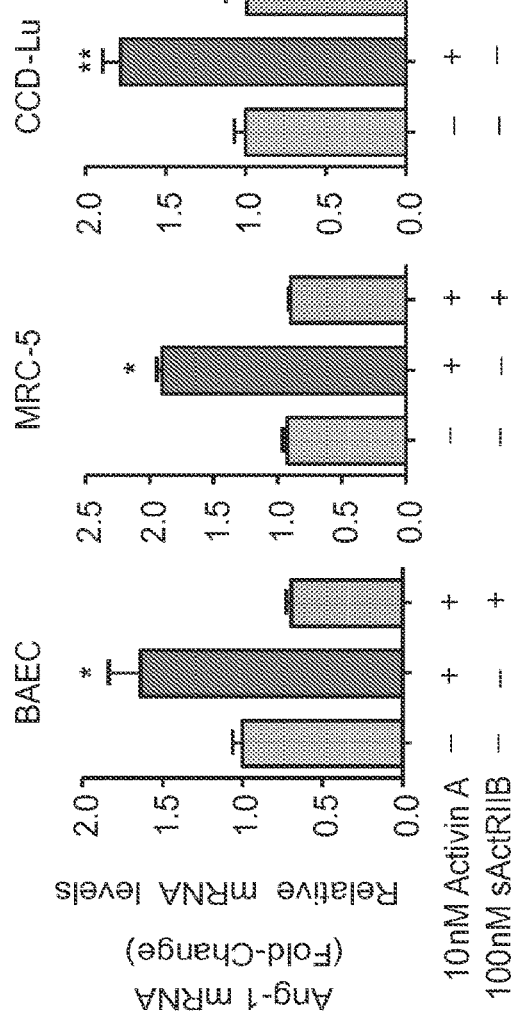
FIG. 16B shows graphs of Ang-1 mRNA expression levels in BAEC, MRC-5, and CCD-Lu cell cultures after treatment with recombinant activin-A and sActRIIB. *$p<0.05$; $p<0.01$; *$p<0.001$; student's t-test; n=3.
Figure 17A:
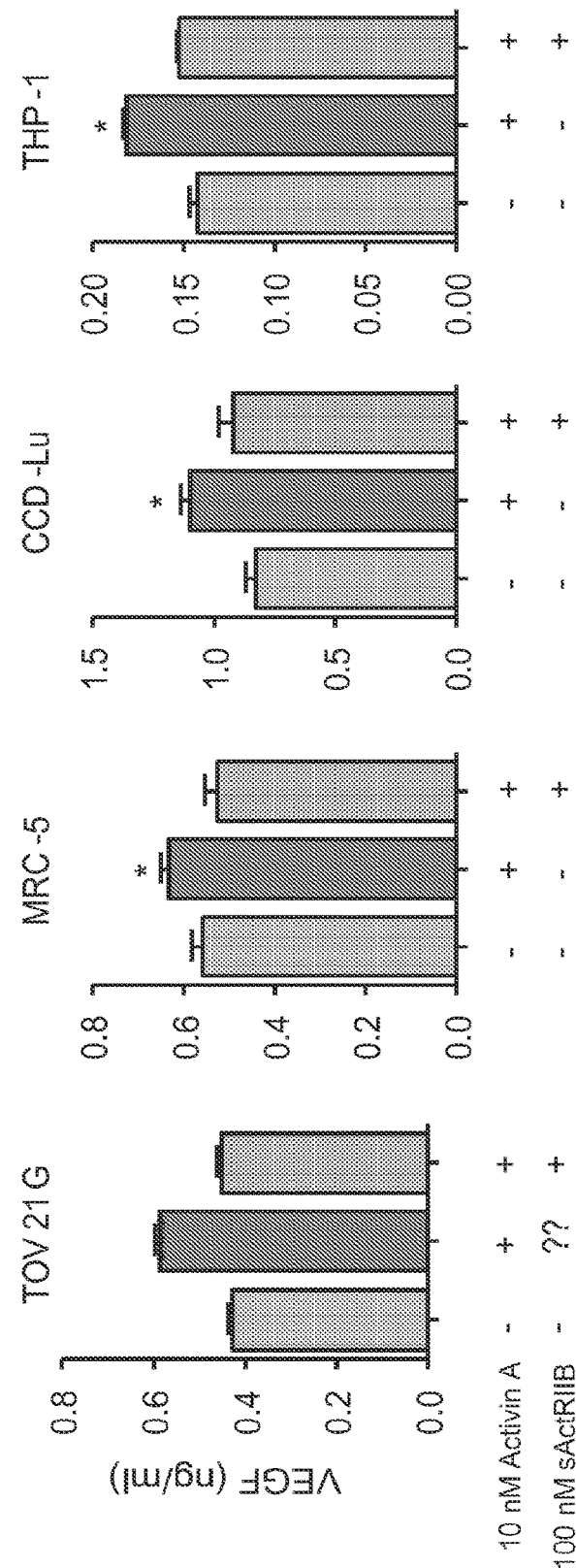
FIG. 17A shows graphs of VEGF levels in TOV-21G, MRC-5, CCD-Lu, and THP-1 cell cultures after treatment with recombinant activin-A and sActRIIB. *$p<0.05$; $p<0.01$; *$p<0.001$; student's t-test; n=3.
Figure 17B:
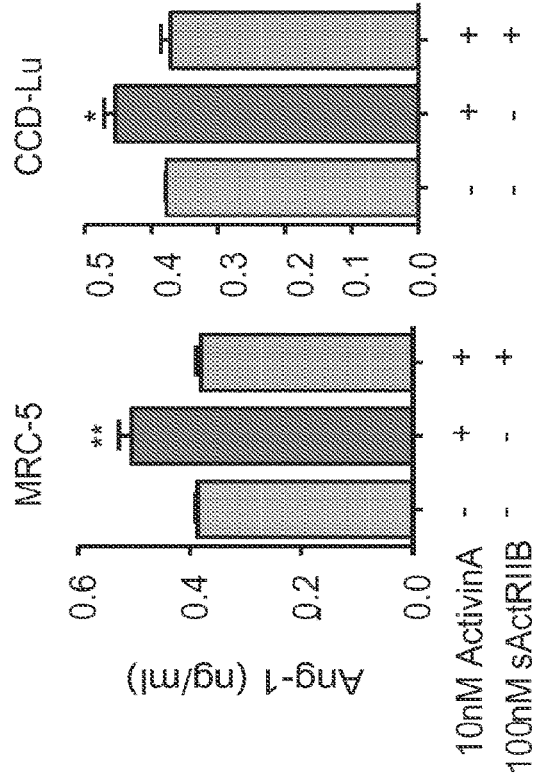
FIG. 17B shows graphs of Ang-1 levels in MRC-5 and CCD-Lu cell cultures after treatment with recombinant activin-A and sActRIIB. *$p<0.05$; $p<0.01$; *$p<0.001$; student's t-test; n=3.
Figure 18:
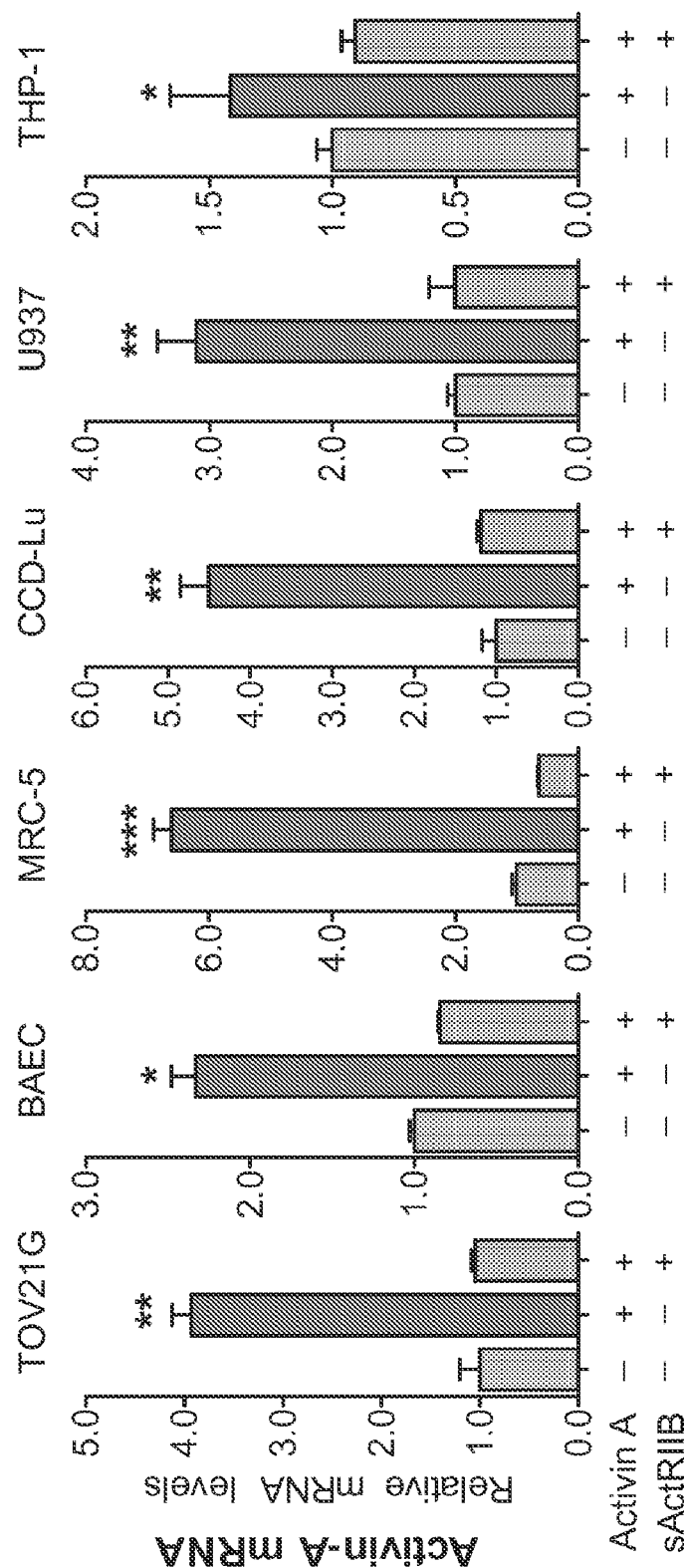
FIG. 18 shows graphs of activin-A mRNA expression levels in TOV-21G, BAEC, MRC-5, CCD-Lu, U937, and THP-1 cell cultures after treatment with recombinant activin-A and sActRIIB.

Example 5: Activin-A Stimulates Angiogenic Factor Overproduction in Cancer and Stromal Cells In addition to cancer cells, the tumor microenvironment contains the neighboring stromal, endothelial and infiltrating immune cells. There is growing evidence that the complex interplay between the cancer and non-cancer cells in the tumor is critical in determining the tumor's malignant state and progression. To understand the cellular mechanisms by which activin-A regulates tumor growth, the effect of activin-A on the expression of angiogenesis factors was examined in four different cell types found in tumors—cancer cells, fibroblasts, endothelial cells, and monocytes. Specially, cultures of TOV-21G cancer cells, BAEC endothelial cells, MRC-5 or CCD-Lu fibroblasts, and U937 monocytic cells were each treated with recombinant activin-A and the expression of VEGF and Ang-1 were analyzed by real-time PCR. Activin-A treatment caused marked increases in the levels of VEGF transcripts in all these cultures (FIG. 16A) and also of Ang-1 mRNA in BAEC, MRC-5 and CCD-Lu cultures (FIG. 16B). Accordingly, the activin-Antagonist sActRIIB prevented this induction of VEGF and Ang-1 by recombinant activin-A (FIG. 16A and FIG. 16B). Moreover, ELISA revealed that activin-A treatment increased the release of VEGF by the TOV21G, MRC-5, CCD-Lu and TPH-1 cells (FIG. 17A) and of Ang-1 by MRC-5 and CCD-Lu cells (FIG. 17B) into the culture medium, while sActRIIB blocked completely this activin-A-induced release of angiogenic factors (FIG. 17A and FIG. 17B). Thus, activin-A is able to upregulate the transcription and secretion of angiogenesis factors in various cell types that reside in the tumor microenvironment. In addition, the effects of exposure to activin-A were examined, particularly to determine whether the exposure could induce endogenous expression of activin-A (βA) mRNA in these cell lines. Remarkably, addition of recombinant activin-A to the TOV21G, BAEC, MRC-5, CCD-Lu, U937 and THP-1 cultures markedly upregulated βA expression in all these cells (FIG. 18), and this induction could be blocked completely by sActRIIB. Thus, activin-A production can amplify its own expression in cancer cells and also in endothelial cells, fibroblasts and monocytes. These findings demonstrate a novel feed-forward angiogenic mechanism, in which cancer cell-derived activin-A via autocrine and paracrine actions triggers increasingly higher activin-A overexpression in multiple cell types, leading to enhanced production of VEGF and Ang-1 in the tumor microenvironment.

Figure 19:
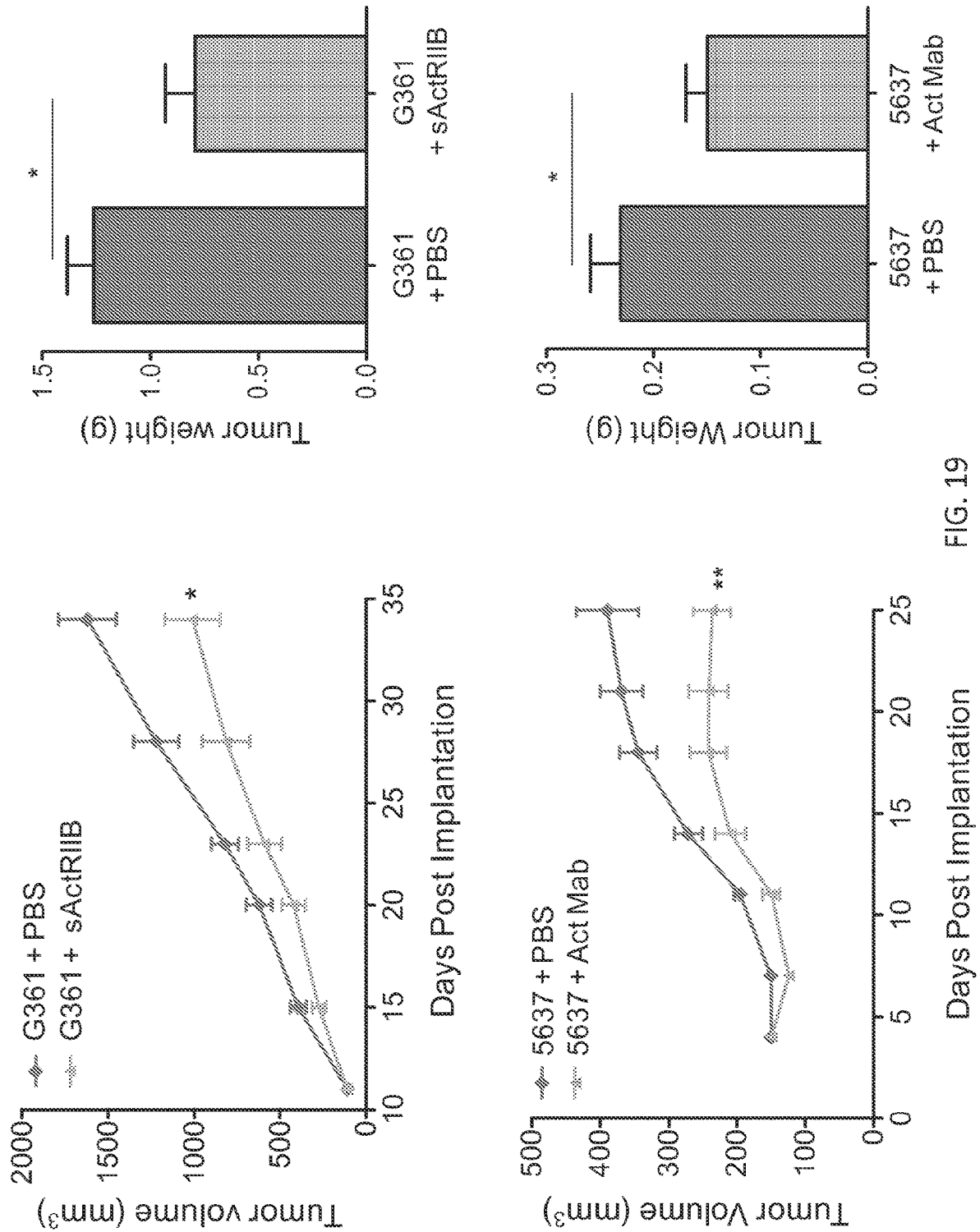
FIG. 19 shows the effects of sActRIIB treatment on the growth of human G361 melanoma xenografts in nude mice, and the effects of activin-A antibody on the growth of 5637 bladder carcinoma xenografts in nude mice. *$p<0.05$; **$p<0.01$.

Example 6: Activin Blockade Inhibits Growth of Human Melanoma and Bladder Carcinoma Xenografts To learn whether activin-A may also contribute to pathogenesis of non-ovarian cancers, the in vivo growth of two other cancer types, the G361 human melanoma and 5637 human bladder carcinoma were examined, because they were shown to release activin-A when cultured in vitro. Nude mice were implanted with G361 and 5637 xenografts and after the tumors were established, the implanted mice were treated with sActRIIB or activin-A antibody. As shown in FIG. 19, activin-A blockade significantly decreased the growth rates and sizes of both these non-ovarian xenografts. This inhibition raises the possibility that activin-A may influence the progression of various malignancies.

Example 7: Activin-A Transcripts are Highly Elevated in Many Human Cancers

Figure 20:
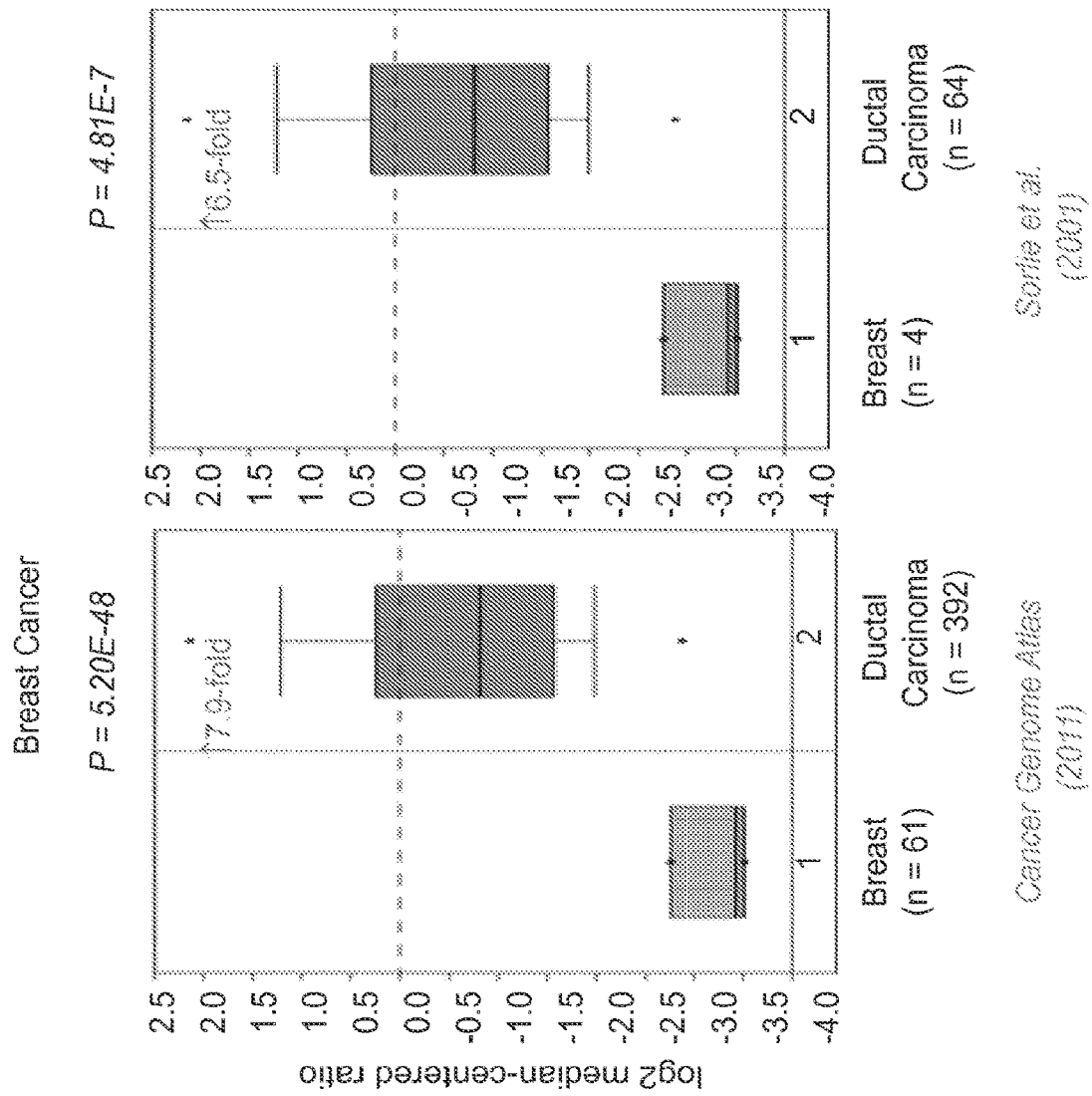
FIG. 20 shows levels of activin-A transcripts in various cell types, based on analysis of the Oncomine microarray databases.
Figure 20:
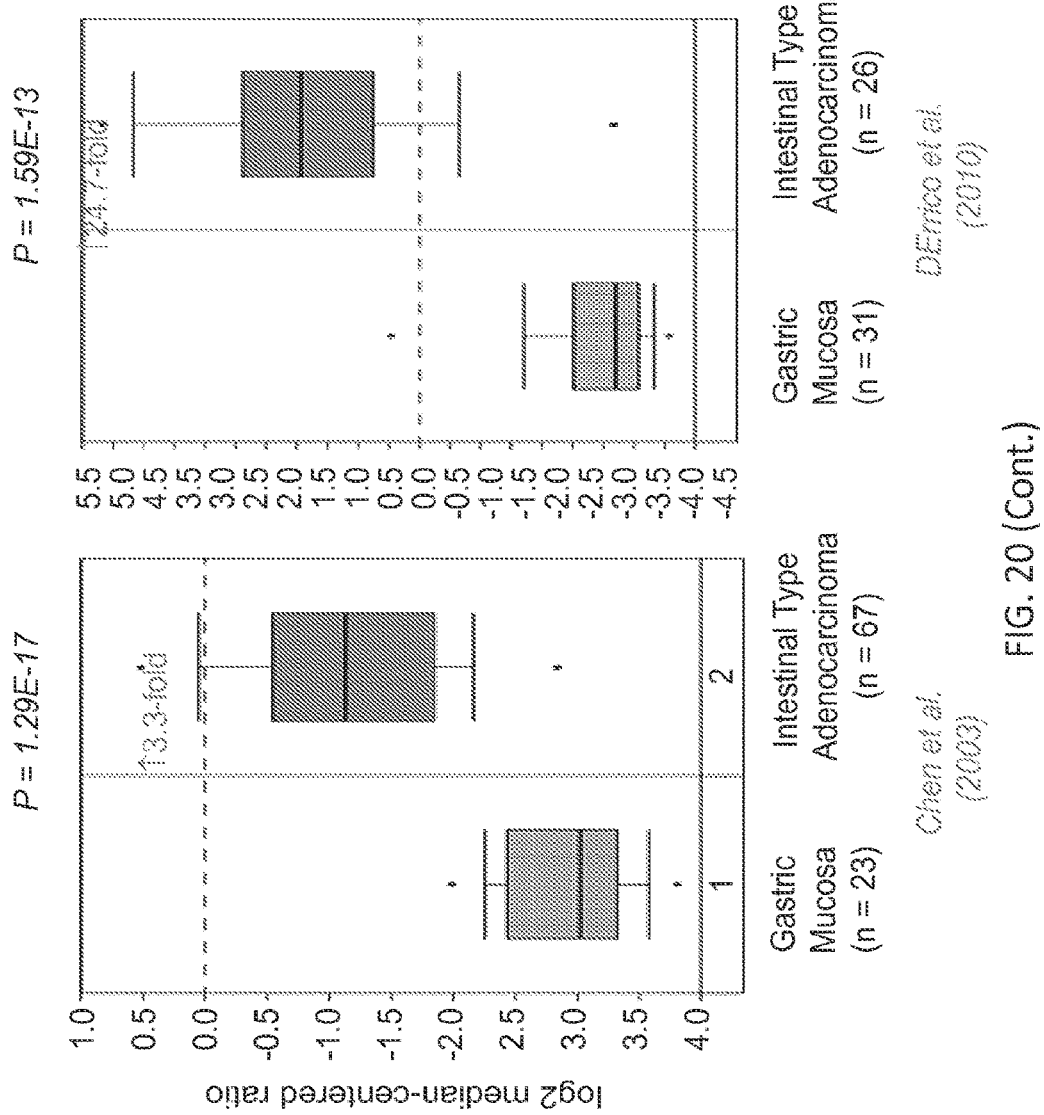
Figure 20:
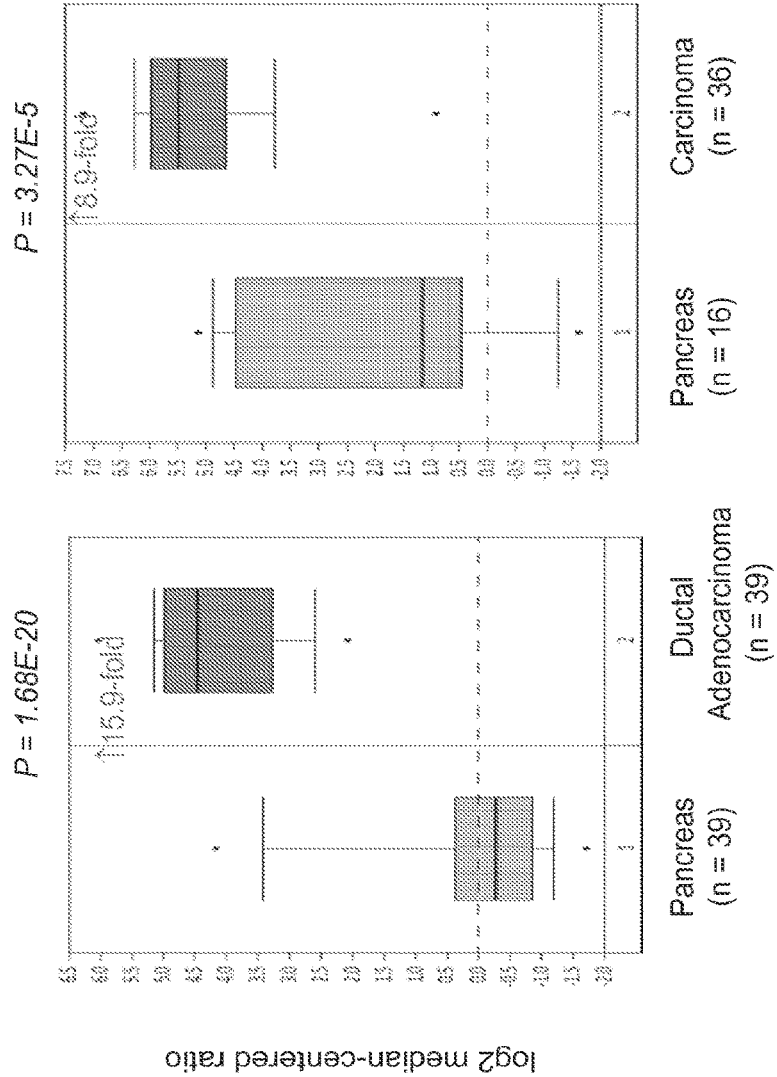
Figure 20:
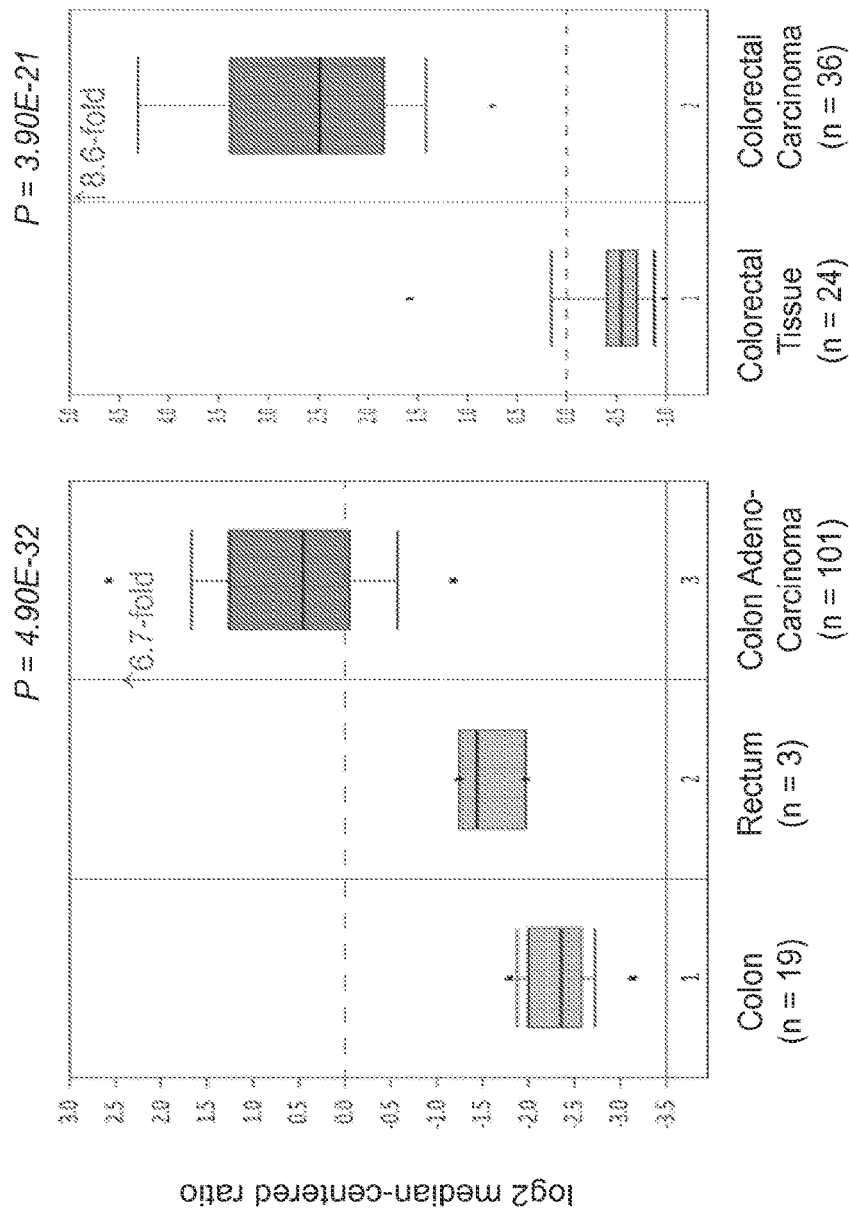
Figure 20:
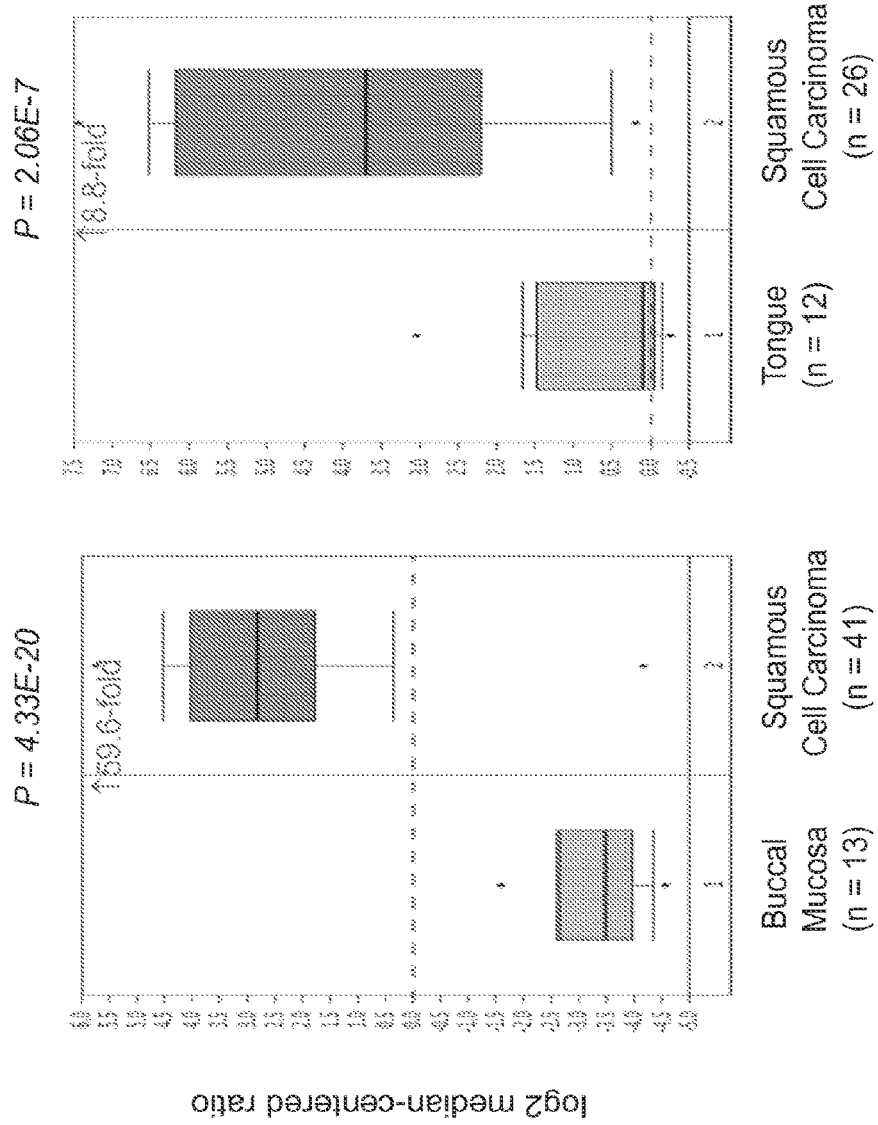

There is increasing evidence for elevated activin-A in multiple kinds of cancer. To further validate activin-A overexpression in human cancers, the Oncomine microarray databases were used to search for activin-A (βA) expression levels. As shown in FIG. 20, in a wide variety of human cancer types examined, including breast, gastric, pancreatic, colorectal, and head and neck cancers, the levels of βA transcript were elevated in the cancerous tissues compared to the respective control tissues.

Example 8: Effects of Withdrawal and Re-Administration of sActRIIB on Ovarian Tumor Growth and Cachexia in Female Inhibin-α Knockout Mice The objectives of this study were to examine the long term pharmacological effects of sActRIIB withdrawal and re-administration on body weight, tumor mass and survival in Inhα KO (inhibin-α-deficient knock-out) mice with established ovarian tumors. Inhα KO mice (Matzuk et al, 1992) were licensed from Dr. Martin M. Matzuk (Baylor College of Medicine, Houston, Tex.). Mice were maintained on a mixed C57BL6/129S6/SvEv genetic background and the colonies were bred at Charles River Laboratories, Inc. (Wilmington, Mass.). Genotyping of Inhα KO mice was conducted by PCR using genomic tail DNA and performed by Genetically Engineered Models and Services (Charles River Laboratories, Inc. Wilmington, Mass.).

Eleven-to-fourteen-week-old female Inhα KO mice with body weight from 19.41 to 26.82 grams were subcutaneously (SC) injected with either 30 mg/kg sActRIIB or PBS. Age-matched WT littermate control mice were injected with PBS and served as baseline controls. The study ended by necropsy 2 weeks after injections. Two cohorts of mice were used in the study. Eleven-to-thirteen-week-old female Inhα KO mice with body weight from 17.7 to 27.4 grams were SC injected with either 30 mg/kg sActRIIB or PBS. Age-matched WT littermate control mice were injected with PBS and served as baseline controls. The withdrawal lasted for 8 weeks. At the end of the withdrawal, the sActRIIB treated mice were divided by balanced body weight into 2 groups (Group 3 and Group 4).

Group 2 and Group 3 were euthanized to examine the ovarian tumors. Group 4 received another dose of 30 mg/kg sActRIIB and the mice were euthanized together with the WT mice 4 weeks later (total 12 weeks). Mouse body weights were recorded once per week up to 12 weeks. For necropsy, mice were euthanized in a $CO_2$ chamber. Normal ovaries in WT mice and ovarian tumors in Inhα KO mice were collected and weighed. All results were expressed as the mean±standard error of the mean (SEM). Statistical significance of difference between groups was analyzed using Student's 2-tailed t-test on MS Excel 5.0 software. The Chi-Square test (GraphPad Software Inc, San Diego, Calif.) was used to examine the differences in animal survival time. Statistical significance between groups is represented by $p<0.05$ values.

TABLE 12 sActRIIB Single Dosing for Two Weeks, Study Schedule

| Group No. | Treatment | n | Route | Dose (mg/kg) | Conc. (mg/mL) | Volume (mL) | Dosing Schedule |
|---|---|---|---|---|---|---|---|
| 1 (WT) | PBS | 8 | SC | — | 0 | 0.1 | Single Dose Week 0 |
| 2 (Inhα KO) | PBS | 8 | SC | — | 0 | 0.1 | Single Dose Week 0 |
| 3 (Inhα KO-wk2) | sActRIIB | 8 | SC | 30 | 9 | 0.1 | Single Dose Week 0 |

TABLE 13 sActRIIB Withdrawal and Re-administration Schedule

| Group No. | Treatment | n | Route | Dose (mg/kg) | Conc. (mg/mL) | Volume (mL) | Dosing Schedule |
|---|---|---|---|---|---|---|---|
| 1 (WT) | PBS | 11 | SC | — | 0 | 0.1 | Single Dose Week 0 and Week 8 |
| 2 (Inhα KO) | PBS | 8 | SC | — | 0 | 0.1 | Single Dose Week 0 |
| 3 (Inhα KO-wk8) | sActRIIB | 7 | SC | 30 | 9 | 0.1 | Single Dose Week 0 |
| 4 (Inhα KO-wk12) | sActRIIB | 11 | SC | 30 | 9 | 0.1 | Single Dose Week 0 and Week 8 |

Figure 21:
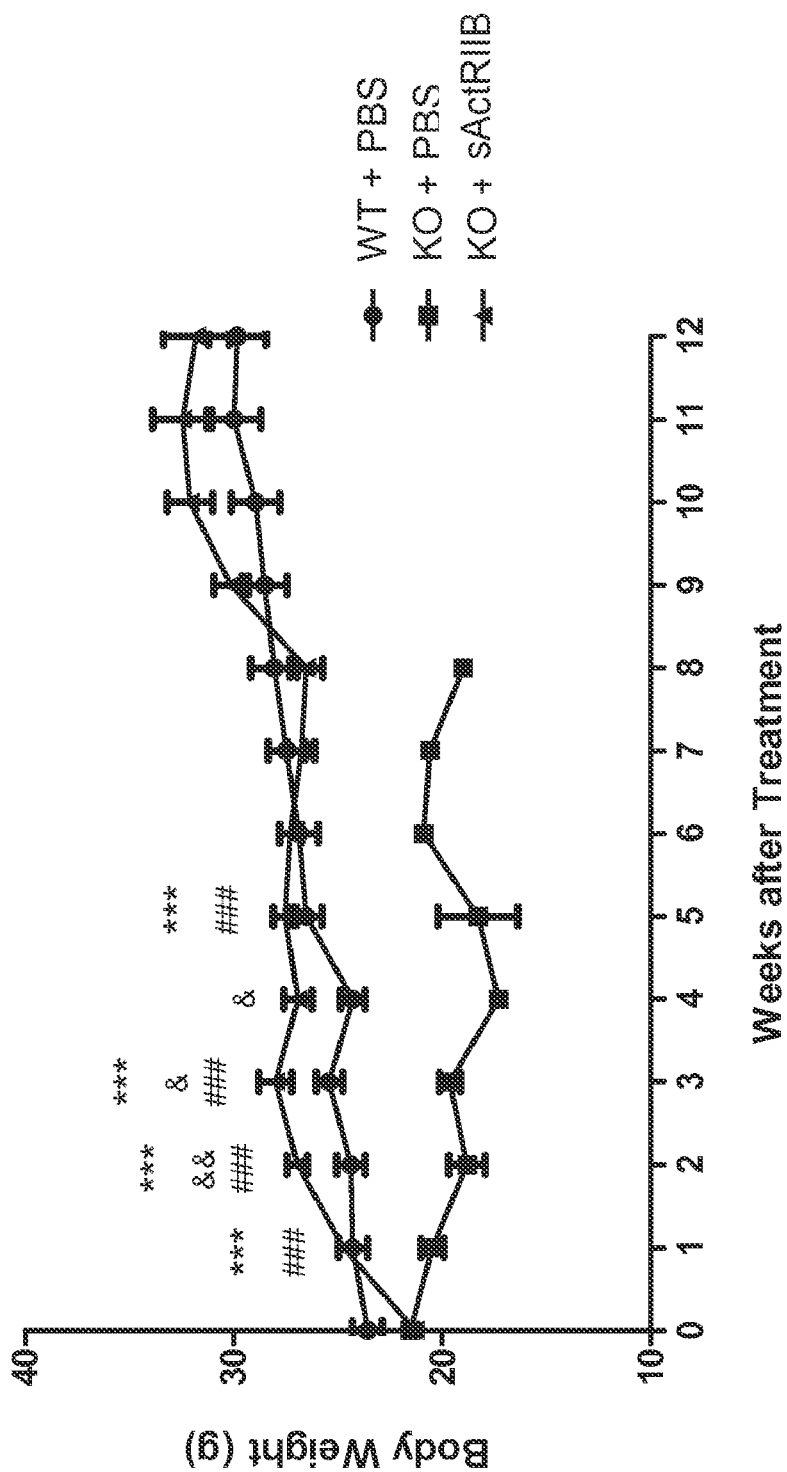
FIG. 21 shows the effect of sActRIIB single dose, withdrawal, and re-dose on body weight in female Inhα KO mice and wild-type littermate control mice. Body weights for female Inhα KO mice were plotted as the mean±SEM; *** $p<0.001$ for Inhα KO groups treated with sActRIIB vs. PBS. & $p<0.05$ and && $p<0.01$ for sActRIIB treated Inhα KO group vs. WT group. ###$p<0.001$ for PBS-treated Inhα KO group vs. WT group.

A single dose of sActRIIB (30 mg/kg, SC) resulted in sustained weight gain in Inhα KO mice that exceeded the level of WT littermate control during the first 4 weeks. Thereafter and up to 8 weeks after the initial dose, the body weight of the sActRIIB-treated Inhα KO mice was similar to the WT control, while the average body weight of PBS-treated KO mice was significantly below WT control throughout the study period. At week 8, eleven of the sActRIIB-treated Inhα KO mice were given another single dose of sActRIIB. The re-administration of sActRIIB stimulated further weight gain in Inhα KO mice during the proceeding 4-week period (up to week 12) (FIG. 21).

Figure 22:
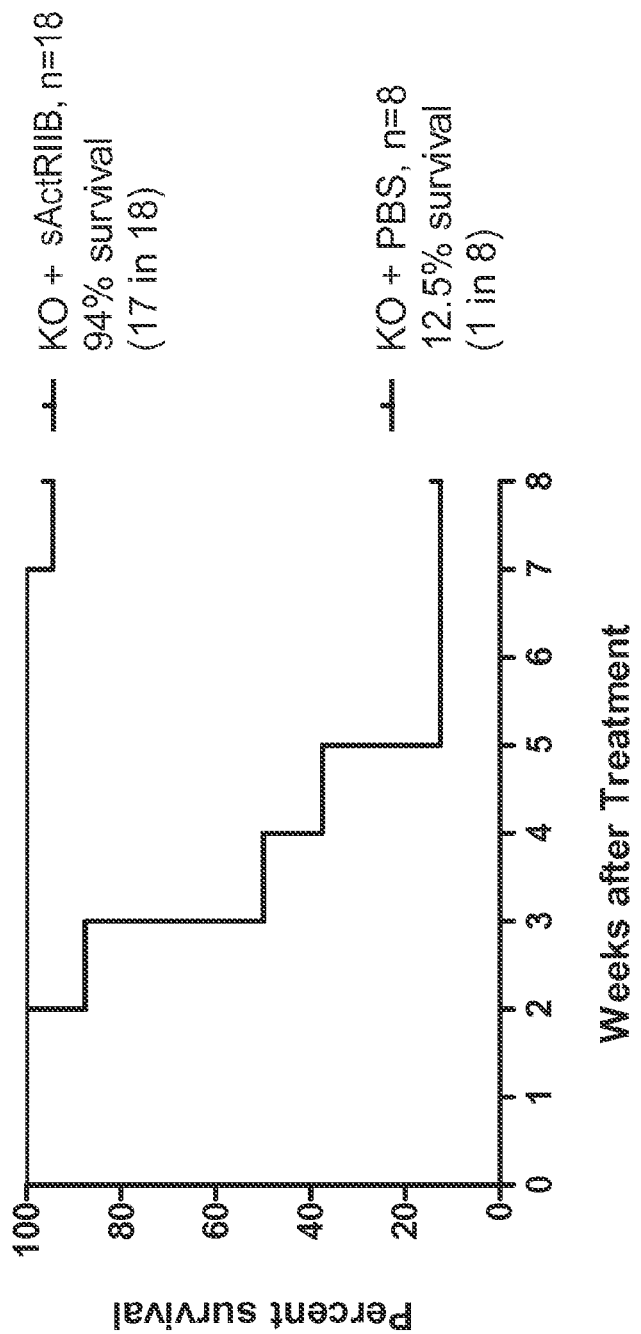
FIG. 22 shows a graph of percent survival in female Inhα KO mice and wild-type littermate control mice resulting from a single dose of sActRIIB, where chi square=23.72, P value <0.0001, and the survival curves are significantly different. Survival data were analyzed by chi-square t-test using GraphPad Prism 5.0 Software. p<0.0001: sActRIIB vs. PBS, n=8 to 18.

The Inhα KO mice treated with PBS developed ovarian tumors and displayed dramatic muscle and organ wasting around 15 weeks of age. When the lethal conditions occurred in the mice, they were euthanized by CO2 inhalation. There was one WT mouse found dead in cage (DIC) with no clear explanation as to the cause of death. There was also one Inhα KO mouse treated with sActRIIB found DIC at week 7 post the initial dose. The Inhα KO mice were analyzed for survival rates during the 8-week period after a single dose of sActRIIB. At week 8, survival rate of sActRIIB-treated Inhα KO mice was 94% (17 in 18 survival) compared to 12.5% (1 in 8 survival) in the PBS-treated Inhα KO group (FIG. 22).

Figure 23:
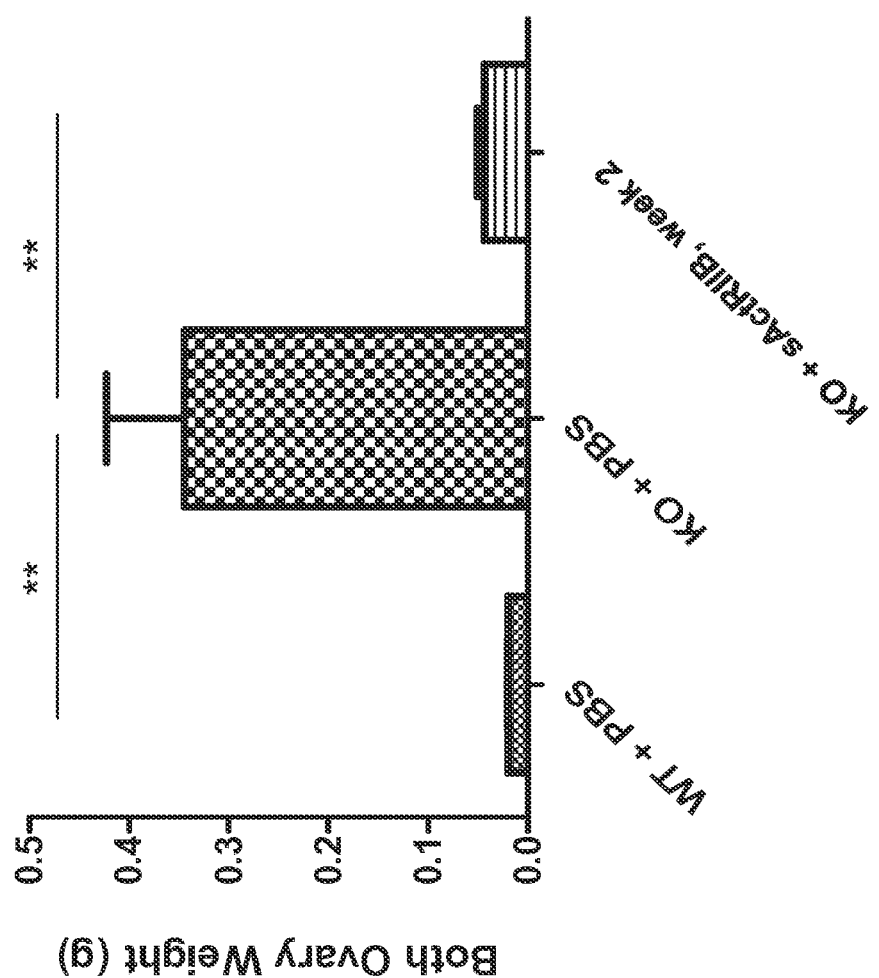
FIG. 23 shows a bar graph depicting ovarian tumor weights in female Inhα KO mice and wild-type littermate control mice at week 2 after a single dose of sActRIIB. Data were plotted as mean±SEM; **p<0.01. Standard 2-tailed Student's t-test (MS Excel 5.0), n=8.
Figure 24:
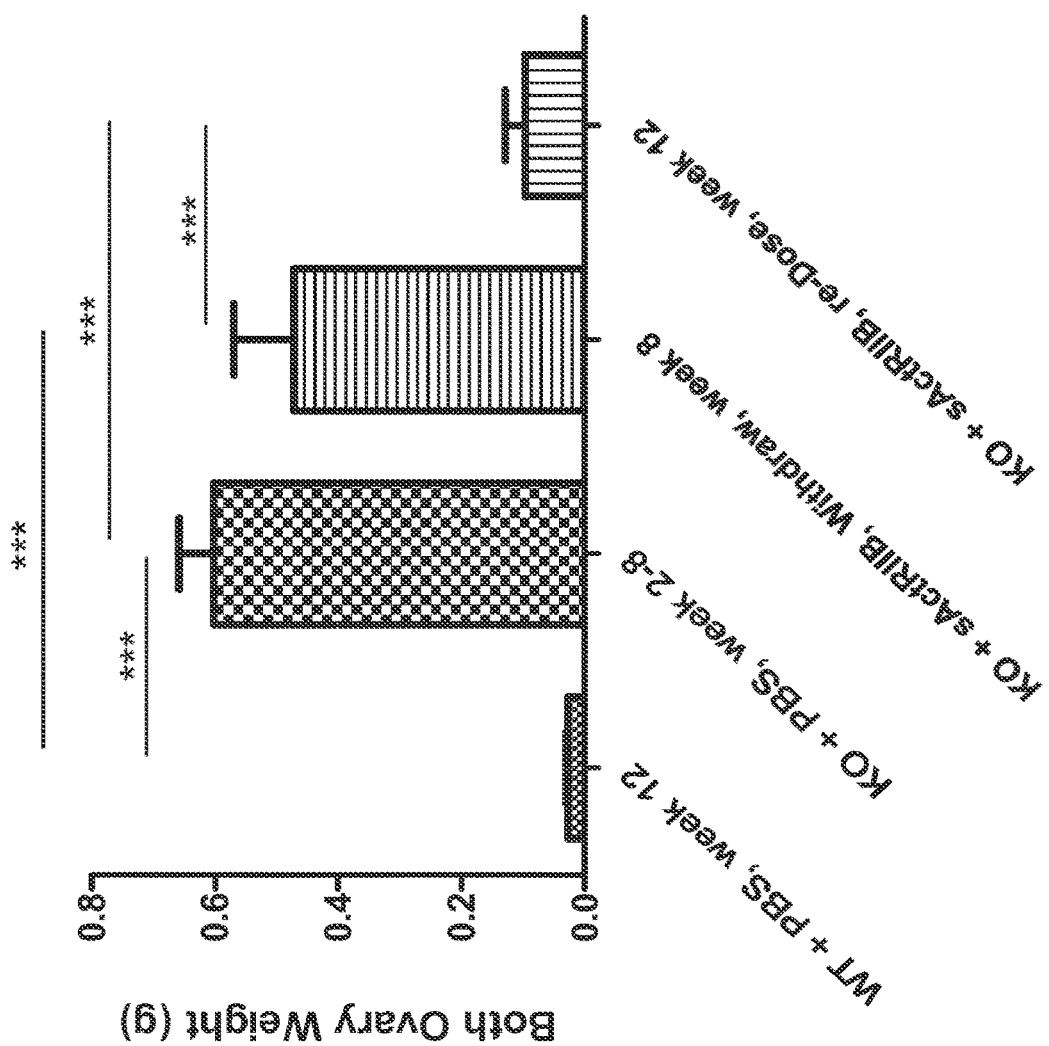
FIG. 24 shows a bar graph depicting ovary tumor weights in female Inhα KO mice and wild-type littermate control mice at week 8 after a single dose of sActRIIB and at week 12 after re-administration (at week 8) of a single dose of sActRIIB. Data were plotted as mean±SEM; ***p<0.001.

Two weeks after a single dose of sActRIIB, the average tumor weight of KO mice was reduced to the WT control level. During the same period the PBS-treated Inhα KO mice developed large ovarian tumors (FIG. 23). At 8 weeks after withdrawal from the initial single dose, the ovarian tumor weight in sActRIIB-treated Inhα KO mice had grown in size similar to that of the PBS-treated Inhα KO mice, suggesting a regrowth of the ovarian tumors during the compound withdrawal period. Re-administration of sActRIIB was given to 11 of the withdrawal Inhα KO mice at week 8. Data on ovarian tumor mass analyzed at week 12 (4 weeks after re-administration) indicate that the re-administration of sActRIIB after 8 weeks withdrawal effectively reduced the tumor mass (FIG. 24).

The present study demonstrates that sActRIIB is effective in reversing cancer cachexia and suppressing ovarian tumor growth in female Inhα KO mice. A single dose of sActRIIB has a long-lasting effect on body weight gain in the Inhα KO mice. The data indicates that sActRIIB treatment significantly suppressed ovarian tumor growth in the Inhα KO mice. The ovarian tumor mass in the Inhα KO mice regressed to WT control level after 2 weeks of a single dose treatment with sActRIIB. After 8 weeks of withdrawal from the initial dose of sActRIIB, the weight of the ovarian tumors in Inhα KO mice was nearly the same as that seen in the PBS-treated group. However, re-administration of sActRIIB effectively regressed the ovarian tumor mass to the size of the WT control group. These data indicate that intermittent administration of sActRIIB given at a prolonged interval of 8 weeks is highly effective in preventing weight loss, suppressing ovarian tumor growth, and prolonging survival in female Inhα KO mice.

Example 9: Effects of sActRIIB in Combination with Doxorubicin on Tumor Growth, Body Weight and Muscle Mass in TOV-21G Ovarian Carcinoma-Implanted Nude Female Mice The objective of the present study was to examine the effect of pharmacological administration of sActRIIB, doxorubicin (dox), and sActRIIB plus doxorubicin, respectively, on body weight, tumor growth and muscle mass in nude mice implanted with TOV-21G ovarian xenograft tumors. Eight-week-old female Athymic nude mice were SC injected with 0.2 mL of $5 \times 10^6$ TOV-21G cells into the left site of the lower flank of the mice. After 10 days of tumor implantation, the mice were divided into 4 groups by body weight and tumor size and then treated with vehicle, sActRIIB, doxorubicin or the combination of sActRIIB and doxorubicin. In addition, a group of non-tumor bearing mice was used as normal control and received PBS. The dosing and treatment schedule are indicated in the table below:

TABLE 14

Dosing and treatment schedule

| Group | n | Test Article | Dose mg/kg | Conc. mg/mL | Volume mL/20 g | Route | Regimen |
|---|---|---|---|---|---|---|---|
| Normal | 10 | PBS | NA | NA | NA | SC | 1 x/week |
| TOV-21G + PBS | 18 | PBS | NA | NA | NA | SC | 1 x/week |
| TOV-21G + sActRIIB | 14 | sActRIIB | 10 mg/kg | 1 | 0.2 | SC | 1 x/week |
| TOV-21G + DOX | 14 | DOX | 2 mg/kg | 0.2 | 0.2 | IP | 1 x/week 4 consecutive IP injections |
| TOV-21G + sActRIIB + DOX | | sActRIIB | 10 mg/kg | 1 | 0.2 | SC | 1 x/week |
| TOV-21G + sActRIIB + DOX | 14 | DOX | 2 mg/kg | 0.2 | 0.2 | IP | 1 x/week 4 consecutive IP injections |

Mice were weighed weekly. Body weight data were recorded longitudinally. Tumor size was measured longitudinally by using an electronic caliper. The following formula was used to calculate actual tumor volume (Tomayko M and Reynolds C, 1989): (Volume of a rectangular solid tumor: Tumor volume (mm$^3$)=length (mm)×width (mm)×height (mm) of tumor). At the end of the study, mice in all groups were subjected to terminal necropsy and lean carcass weight (excluding skin, adipose tissue, internal organs, and head) was determined by using standard anatomical dissection procedures. The calf muscles from left and right sides of each mouse were excised and weighed. All results were expressed as the mean±SEM (standard error of the mean). For statistical analysis, a standard 2-tailed t-test was used in conjunction with the MS Excel 5.0 software to determine the statistical differences. Any p value less than 0.05 was considered to be statistically significant.

Figure 25:
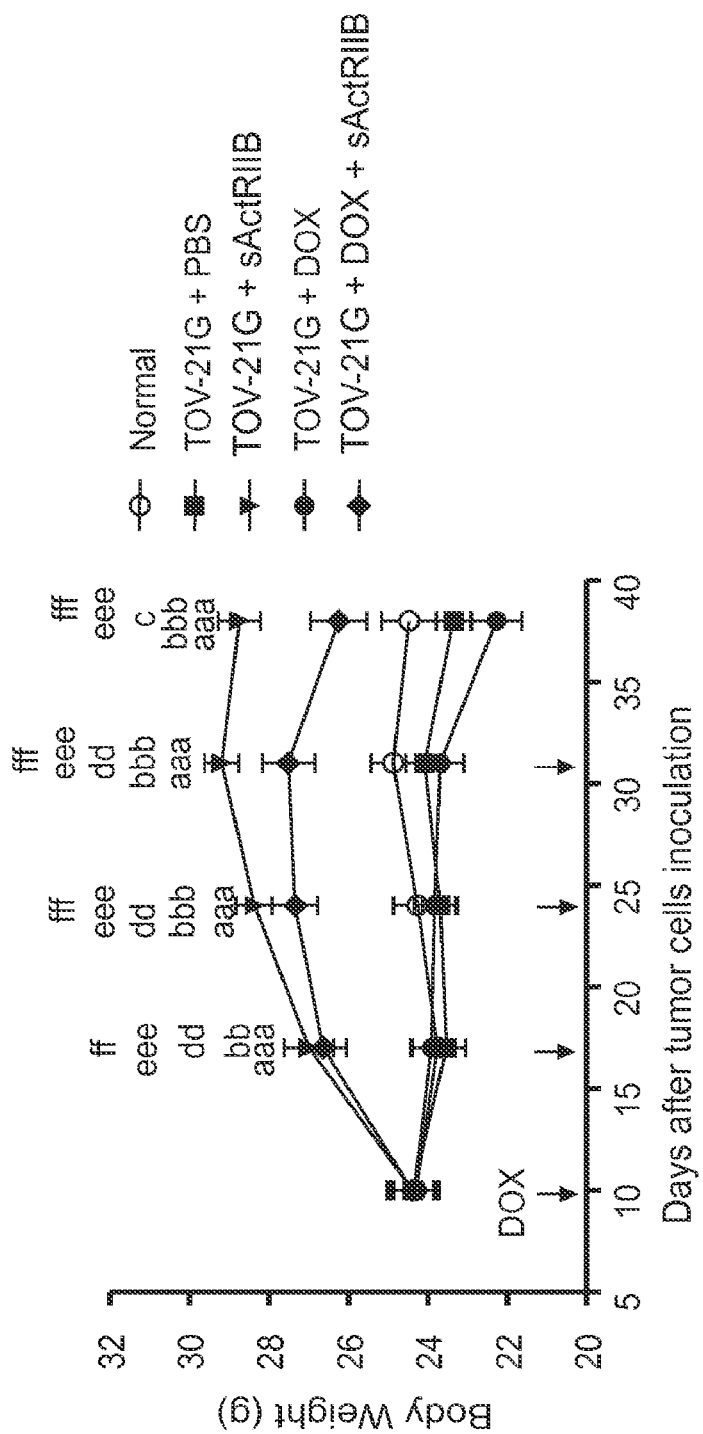
FIG. 25 shows a graph of the effect of sActRIIB in combination with doxorubicin on body weight in TOV-21G tumor-bearing mice. Body weight was recorded longitudinally. Data were plotted as mean±SEM, n=10 to 18/group. Statistical significance is represented by $^{aaa}$p<0.001: TOV-21G+sActRIIB vs. TOV-21G+PBS; $^{bb}$p<0.01, $^{bbb}$p<0.001: TOV-21G+sActRIIB vs. Normal+PBS; $^{c}$p<0.05 TOV-21G+DOX vs. Normal+PBS; $^{dd}$p<0.01: TOV-21G+DOX+sActRIIB vs. Normal+PBS; $^{eee}$p<0.001: TOV-21G+DOX+sActRIIB vs. TOV-21G+PBS; $^{ff}$p<0.01, $^{fff}$p<0.001 TOV-21G+DOX+sActRIIB vs. TOV-21G+DOX+PBS.

As shown in FIG. 25, TOV-21G tumor-bearing mice showed a loss in body weight compared with non-tumor-bearing normal control mice. sActRIIB administration in TOV-21G tumor-bearing mice effectively prevented the weight loss. Doxorubicin treatment resulted in a further decline (non-statistically significant) in body weight in the TOV-21G implanted mice; however, the decrease was significant when compared to normal control mice at day 38. sActRIIB administered in combination with doxorubicin effectively mitigated the weight loss as seen in doxorubicin treated TOV-21G implanted mice.

Figure 26:
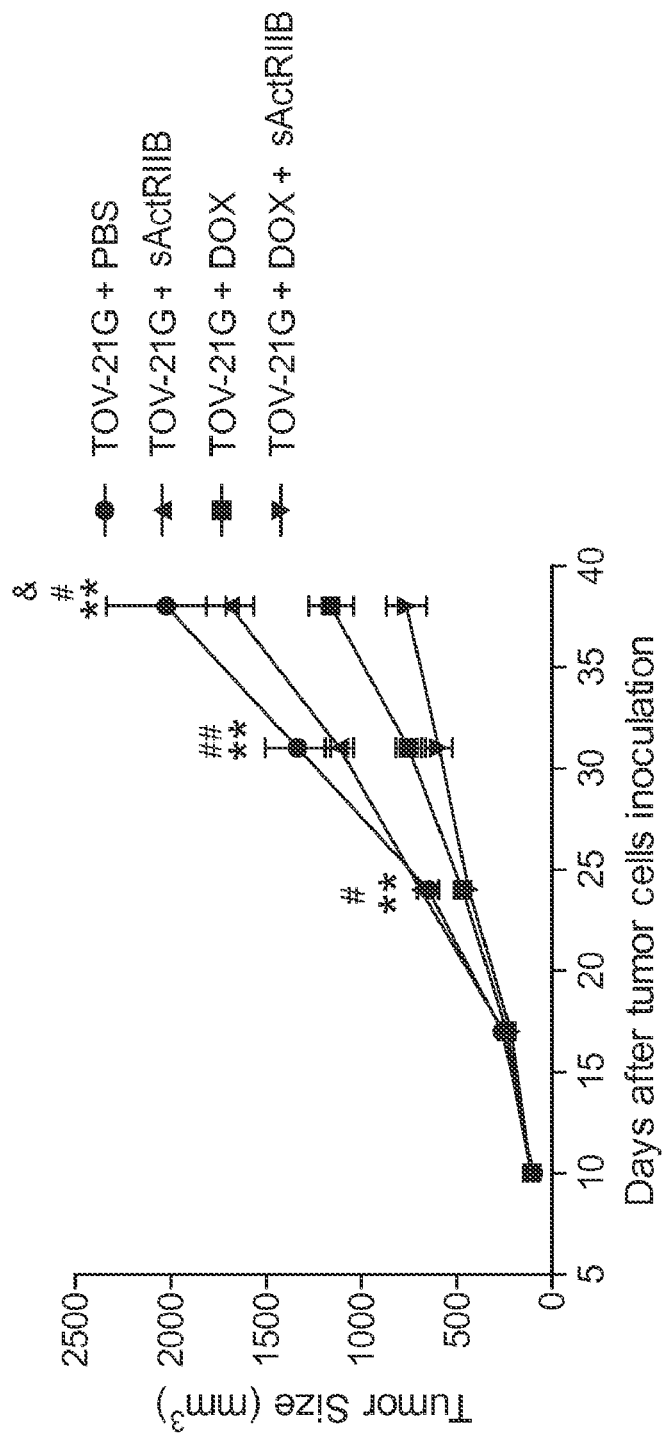
FIG. 26 shows the effects of sActRIIB in combination with doxorubicin on tumor size (top) and weight (bottom) in TOV-21G tumor-bearing mice. Tumor size (upper panel) and tumor weight (lower panel) were plotted as the mean±standard error of the mean (SEM); n=10 to 18/group. Statistical significance is represented by * p<0.05, ** p<0.01: TOV-21G+DOX+sActRIIB vs. TOV-21G+PBS; $^{#}$p<0.05; $^{##}$p<0.01: TOV-21G+DOX vs. TOV-21G+PBS; $^{&}$p<0.05: TOV-21G+DOX+sActRIIB vs. TOV-21G+DOX.
Figure 26:
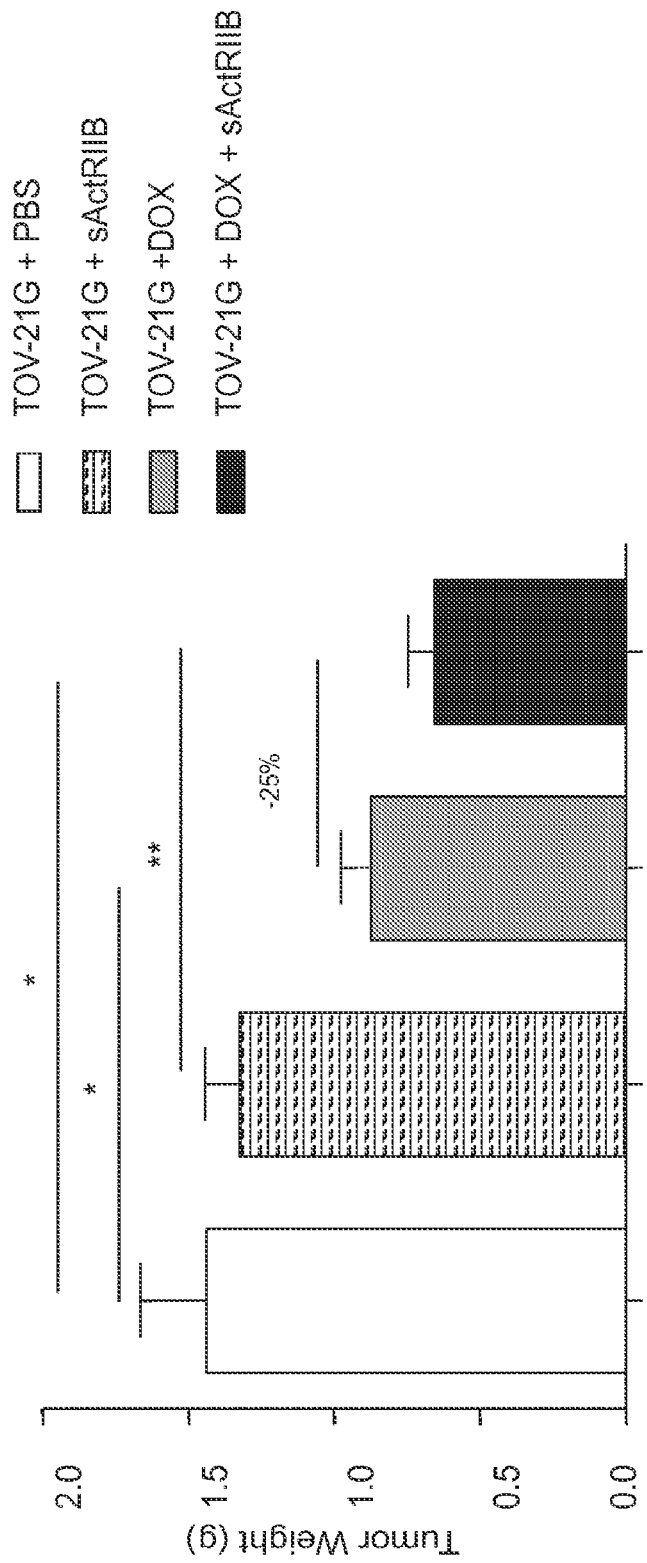

Tumor size of each individual mouse was measured every week throughout the 4-week study period. Tumor weights were recorded via terminal necropsy procedures at week 4. As shown in FIG. 26, DOX significantly reduced tumor size and tumor weight in TOV-21G tumor bearing mice compared with vehicle-treated TOV-21G group. sActRIIB in combination with DOX treatment further inhibited the tumor growth and reduced the tumor size compared with vehicle-treated TOV-21G tumor bearing mice. At day 38, sActRIIB in combination with DOX treatment significantly reduced the tumor size compared to DOX-treated TOV-21G tumor bearing mice, the tumor weight was reduced 25%. In addition, sActRIIB and doxorubicin had additive effects on tumor suppression. Thus, sActRIIB and doxorubicin were each capable of inhibiting TOV-21G tumor growth in nude mice and when combined, they led to greater inhibition of TOV-21G tumor growth.

Figure 27:
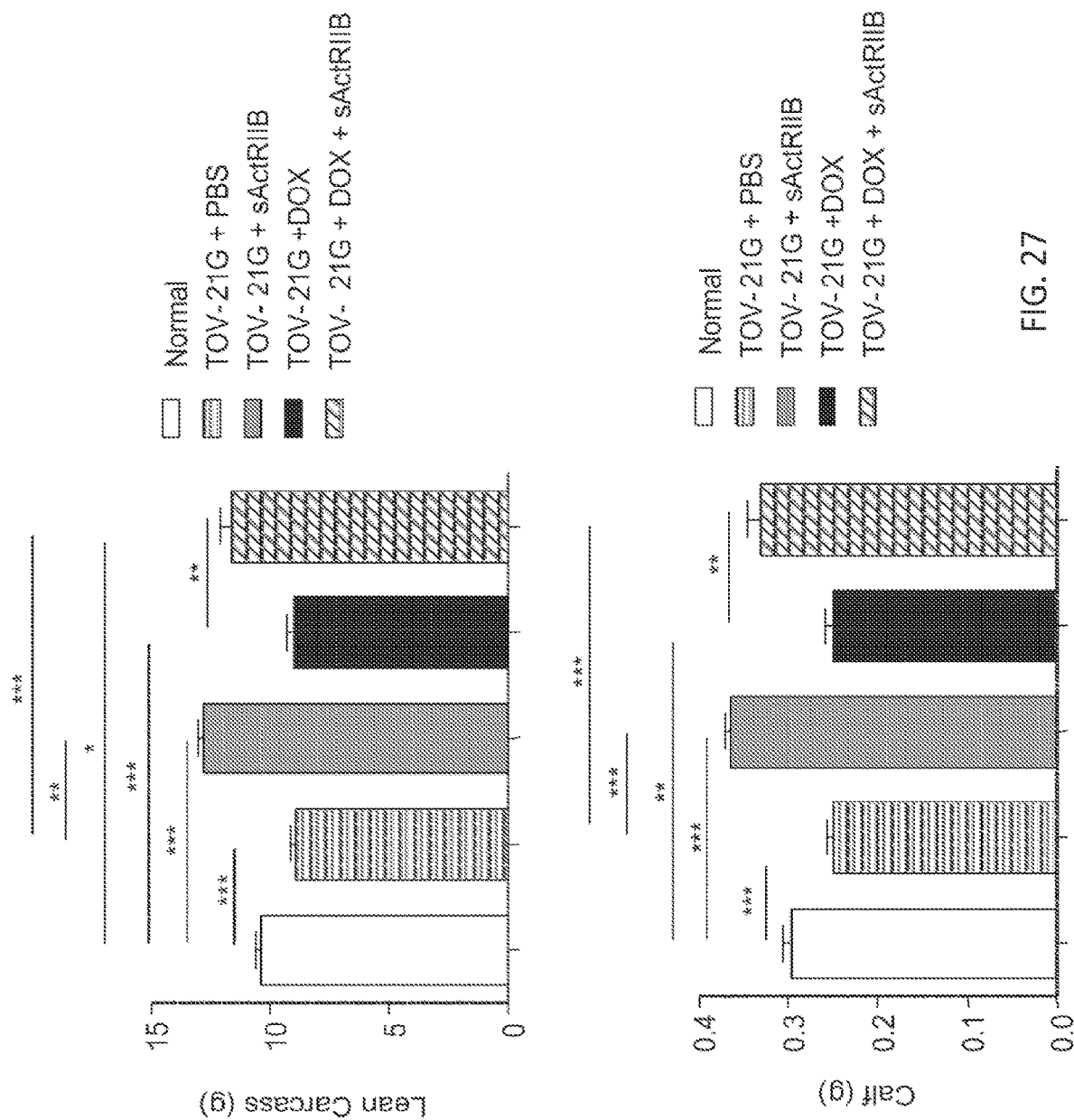
FIG. 27 shows bar graphs illustrating the effect of sActRIIB in combination with doxorubicin on muscle mass in TOV-21G tumor-bearing mice. Lean carcass and calf muscle weights were determined at terminal necropsy. Data were plotted as mean±SEM; n=10 to 18/group. Statistical significance is represented by * p<0.05;  p<0.01; * p<0.001.

Mouse lean carcass weight and calf muscle weight were determined via necropsy procedures at the end of the 4-week experiment. As shown in FIG. 27, TOV-21G tumor-bearing mice showed significant decreases in lean carcass weight and calf muscle mass compared with normal controls; however, administration of sActRIIB prevented the loss in lean carcass weight and calf muscle mass in TOV-21G-implanted nude mice. Doxorubicin had no effect on the loss of lean carcass weight and calf muscle mass in TOV-21G xenograft mice; however, combination treatment with sActRIIB significantly prevented the loss in lean carcass weight and calf muscle mass in TOV-21G-implanted nude mice. Thus, sActRIIB administered alone or in combination with doxorubicin was capable of preventing muscle loss in TOV-21G tumor-bearing mice.

sActRIIB administered alone or in combination with doxorubicin inhibited TOV-21G xenograft tumor growth and attenuated muscle wasting in the tumor-bearing nude mice. Moreover, sActRIIB and doxorubicin appeared to have additive effects on suppression of TOV-21G xenograft tumor growth in nude mice.

Example 10: Effects of Activin A Blockade with Activin-A Antibody on Body Weight, Muscle Mass, Lean Body and Fat Mass, Organ Weights, Ovarian Tumor Growth and Tumor Angiogenesis Factor Expression in Female Inhibin-α Knockout Mice The objectives of this study were to examine the pharmacological effects of activin-A antibody on circulating activin A level, body weight, lean body and fat mass, muscle and organ weights, and ovarian tumor weight, as well as tumor angiogenic factor (VEGF and Ang-1) expression levels in ovarian tissues, in Inhα KO mice with established ovarian tumors and cachexia.

Inhα KO mice were licensed from Dr. Martin M. Matzuk (Baylor College of Medicine, Houston, Tex.). Mice were maintained on a mixed C57BL6/129S6/SvEv genetic background and the colonies were bred at Charles River Laboratories, Inc. (Wilmington, Mass.). Genotyping of Inhα KO mice was conducted by PCR using genomic tail DNA and performed by Genetically Engineered Models and Services (Charles River Laboratories, Inc. Wilmington, Mass.).

Weekly Injection for 4 Week Experiment

| Group No. | Treatment | n | Route | Dose (mg/kg) | Conc. (mg/mL) | Volume (mL) | Dosing Schedule |
|---|---|---|---|---|---|---|---|
| 1 (WT) | PBS | 6 | SC | — | 0 | 0.1 | 1 x/week |
| 2 (WT) | Activin A Ab | 5 | SC | 20 | 6 | 0.1 | 1 x/week |
| 3 (Inhα KO) | PBS | 9 | SC | — | 0 | 0.1 | 1 x/week |
| 4 (Inhα KO) | Activin A Ab | 9 | SC | 20 | 6 | 0.1 | 1 x/week |

Eleven-week-old female Inhα KO mice were subcutaneously (SC) injected with either 20 mg/kg activin-A antibody or PBS (vehicle control). The activin-A antibody used was the same as described in the Materials section above. Age-matched WT littermate control mice were injected with 20 mg/kg activin-A antibody or PBS (served as baseline controls). The weekly injections lasted for 4 weeks. At the end of the 4-week study, terminal blood samples were drawn by cardiac puncture and serum was stored at −80° C. for activin A analysis. MSD Standard plates were used to detect free activin A levels according to the protocol provided by the manufacturer. Serum collected at necropsy was used in the assay. VEGF Immunoassay kit was used to detect VEGF (vascular endothelial growth factor) levels by following the protocol provided.

Mouse body weights were recorded once per week for 4 weeks. Body composition (lean mass and fat mass) was analyzed by nuclear magnetic resonance (NMR) imaging on week 0 and week 4 using the Mini Spec NMR imaging instrument (Bruker BioSpin GmbH, Rheinstetten, Germany) according to the protocol provided by the manufacturer. At the end of the 4-week study, all animals were euthanized in a CO2 chamber and were subjected to terminal necropsy procedures. Immediately following euthanization, the calf muscle and ovary, as well as uterus in Inhα KO mice were excised and weighed.

Mouse ovaries and ovarian tumors were fixed in Zinc-formalin for paraffin blocks. Paraffin sections of 4 µm in thickness were used for IHC. Antigen retriever was by microwaving 3 min in Unmask Solution (Vector H-3300). None specific staining blocking was in CAS (Zymed Lab 00-8120) for 30 minutes at room temperature. Primary antibodies diluted in CAS are: rabbit anti Angiopoietin 1 (Abcam ab8451) 1:500; rabbit anti VEGF (Abcam ab46154) 1:150. Incubation was at room temperature for 3 hours. The secondary antibody was linked by Vector Elite rabbit IgG ABC kit (pk-6101). Vector SG kit (SK-4700) was used for the blue/gray stain with nuclear counterstained in Fast Red (Vector H-3403). All results were expressed as the mean±standard error of the mean (SEM). Statistical significance of difference between activin-A antibody-treated groups and PBS-treated groups was analyzed for all data, using Student's 2-tailed t-test. Statistical significance between groups is represented by $p<0.05$ values.

Figure 28:
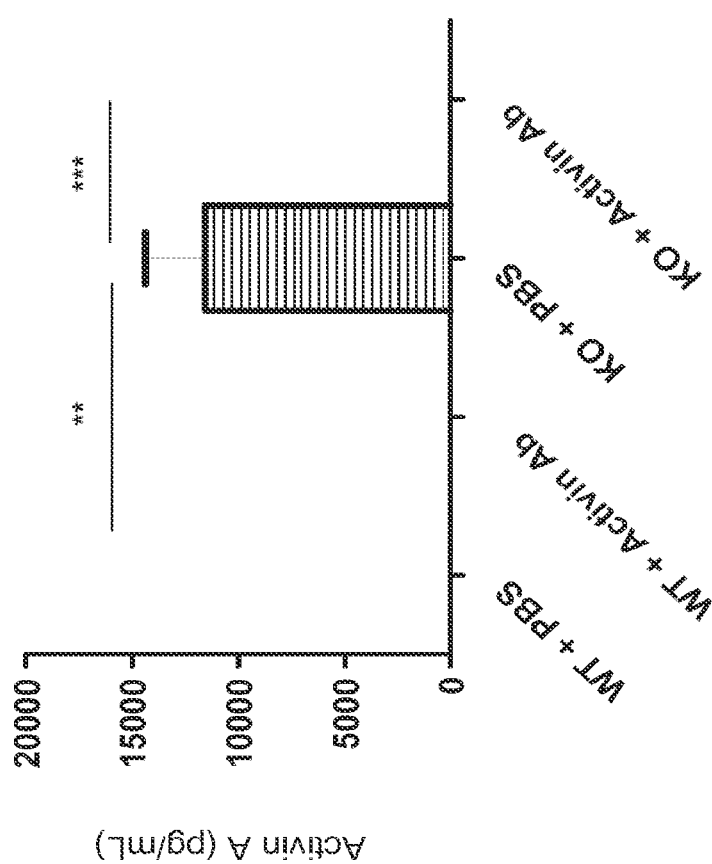
FIG. 28 shows a bar graph illustrating the effect of activin-A antibody on serum activin A levels in female Inhα KO mice and wild-type littermate control mice. Measurements of free activin A level in female Inhα KO mouse groups were plotted as the mean±SEM; *p<0.001 and p<0.01
Figure 29:
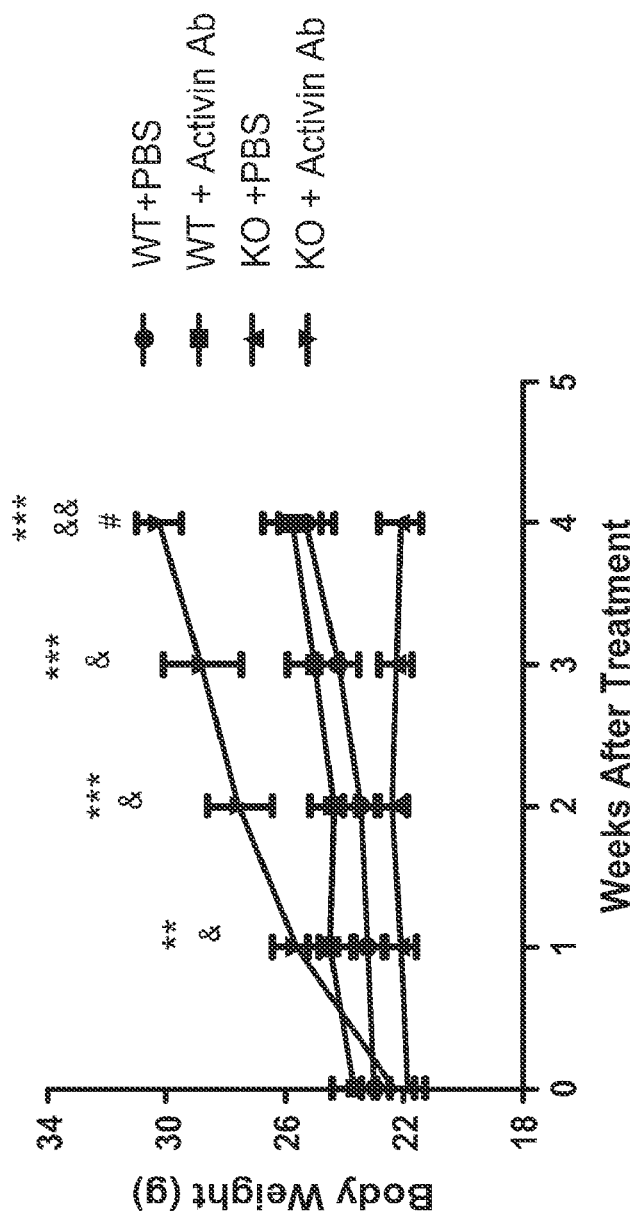
FIG. 29 shows the effect of activin-A antibody treatment on body weight in female Inhα KO mice and wild-type littermate control mice. Measurements of body weight in female Inhα KO mice were plotted as the mean±SEM;  p<0.01 and * p<0.001 for Inhα KO groups treated with activin-A antibody vs PBS. $^{&}$ p<0.05 and $^{&&}$ p<0.01 for activin-A antibody treated Inhα KO group vs PBS treated WT group. $^{#}$p<0.05 for PBS treated Inhα KO group vs PBS treated WT group.

The serum activin A levels were significantly elevated in Inhα KO mice compared to the WT control groups. The injections of activin-A antibody completely eliminated the increase in serum activin A in Inhα KO mice after 4-weeks of treatment (FIG. 28). Administration of activin-A antibody in Inhα KO mice increased body weight significantly compared to the PBS-treated Inhα KO and WT littermates within 1 week of treatment. The significant body weight increase continued through week 4. During this 4-week period, the body weight of the Inhα KO mice treated with PBS remained constant. In the WT littermate group, activin-A antibody had no effect on the body weight (FIG. 29).

Figure 30:
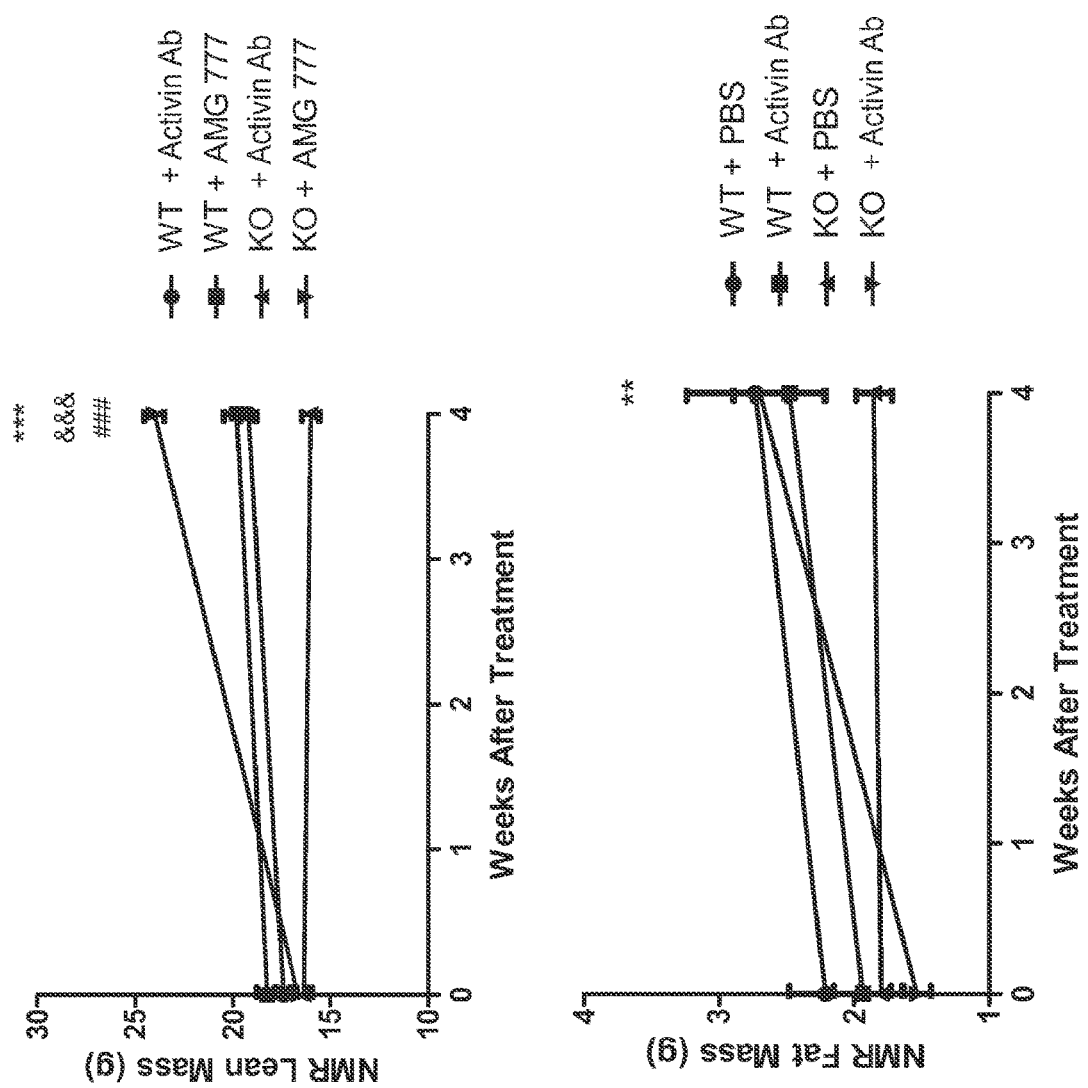
FIG. 30 shows the effect of activin-A antibody treatment on lean body mass and fat mass in female Inhα KO mice and wild-type littermate control mice. Measurements of lean mass (upper panel) and fat mass (lower panel) in female Inhα KO mouse were plotted as the mean±SEM; * p<0.001 and  p<0.01 for Inhα KO groups treated with activin-A antibody vs PBS. $^{&&&}$p<0.001 for activin-A antibody treated Inhα KO group vs PBS treated WT group. $^{####}$p<0.001 for PBS treated Inhα KO group vs PBS treated WT group.

As revealed by NMR imaging, administration of 20 mg/kg activin-A antibody in female Inhα KO mice led to the significant increase of lean body mass beyond that of the PBS-treated Inhα KO mice and WT littermates by week 4. Conversely, Inhα KO mice treated with PBS had significantly lower lean body mass compared to the WT mice and activin-A antibody-treated Inhα KO mice. In the WT littermate control groups, activin-A antibody had no effect on lean body mass. Activin-A antibody in Inhα KO mice increased fat mass to the levels of WT littermate control group by the end of the 4-week treatment period, and it was significantly higher than that of Inhα KO mice treated with PBS. In the WT littermate control groups, activin-A antibody had no significant effect on fat mass (FIG. 30).

Figure 31:
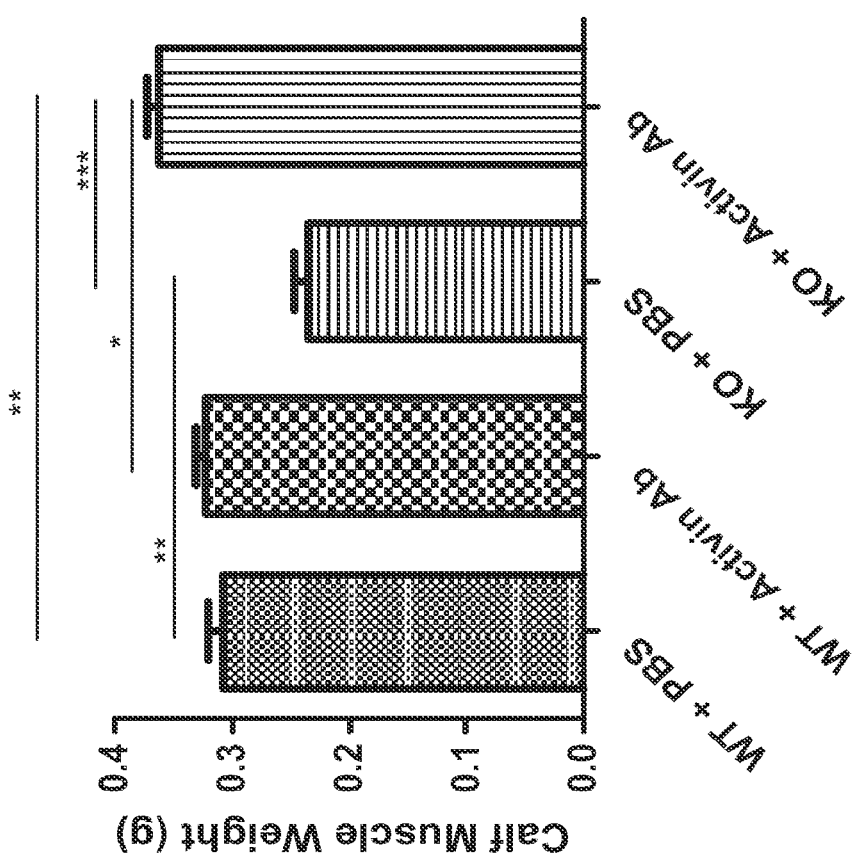
FIG. 31 shows a bar graph illustrating the effect of activin-A antibody treatment on calf muscle weight in female Inhα KO mice and wild-type littermate control mice. Calf muscle weights were plotted as mean±SEM; *p<0.001, p<0.01, *p<0.05.

The calf muscle mass was measured at the end of the study via terminal necropsy procedures. Activin-A antibody administration of Inhα KO mice resulted in significantly increased muscle mass compared to the PBS-treated Inhα KO mice and WT littermate control groups. Activin-A antibody had no significant effect on calf muscle mass in the WT littermate control groups (FIG. 31).

Figure 32A:
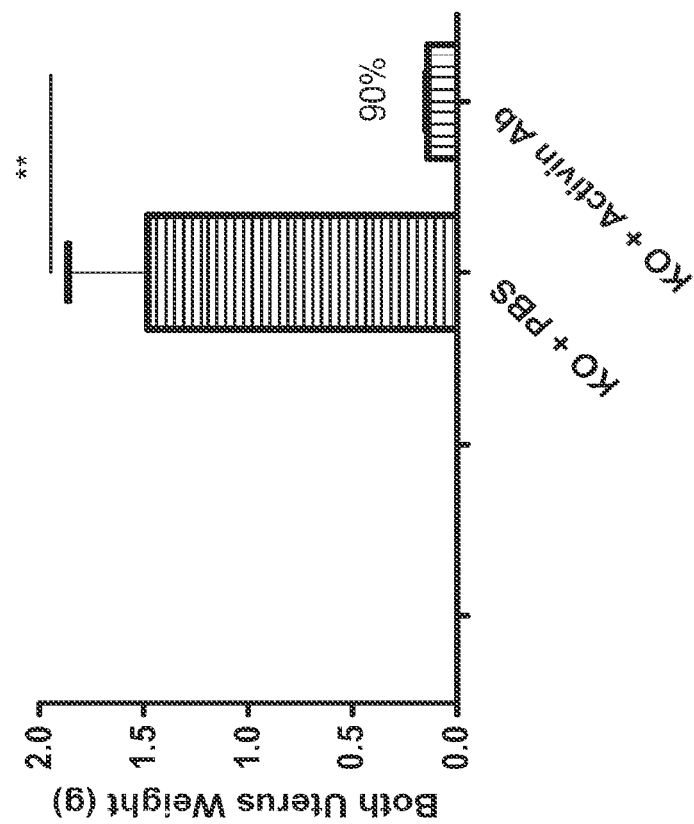
FIG. 32A shows the effect of activin-A antibody treatment on ovary weight in female Inhα KO mice and wild-type littermate control mice. Data was plotted as mean±SEM; *p<0.001, p<0.01.
Figure 32B:
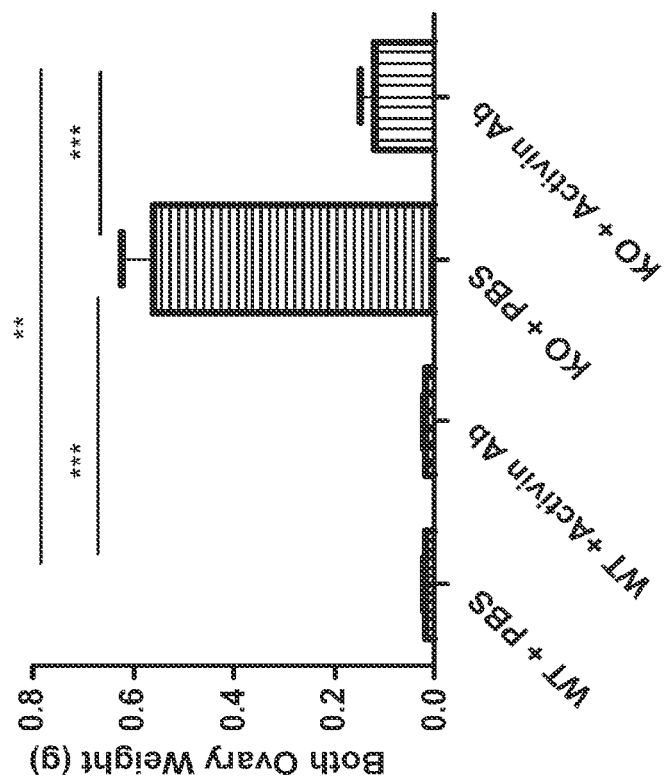
FIG. 32B shows the effect of activin-A antibody treatment on uterus weight in female Inhα KO mice and wild-type littermate control mice. Data was plotted as mean±SEM; *p<0.001, p<0.01.

Ovaries and uterus (Inhα KO mice only) were examined at the end of the study via necropsy procedures. The data revealed that all the female Inhα KO mice developed large hemorrhagic ovarian tumors. Gross weights of the ovaries of Inhα KO mice were significantly higher than that of the WT littermate control group. Administration of activin-A antibody in Inhα KO mice led to a significantly reduced tumor sizes in comparison to the tumors in the Inhα KO mice treated with PBS. Furthermore, most of the uterus in the Inhα KO group with PBS were enlarged full of fluid. The activin-A antibody treatment significantly reduced the uterus weight by 90%. Activin-A antibody had no effect on ovaries weights in the WT littermate control groups (FIG. 32).

Figure 33:
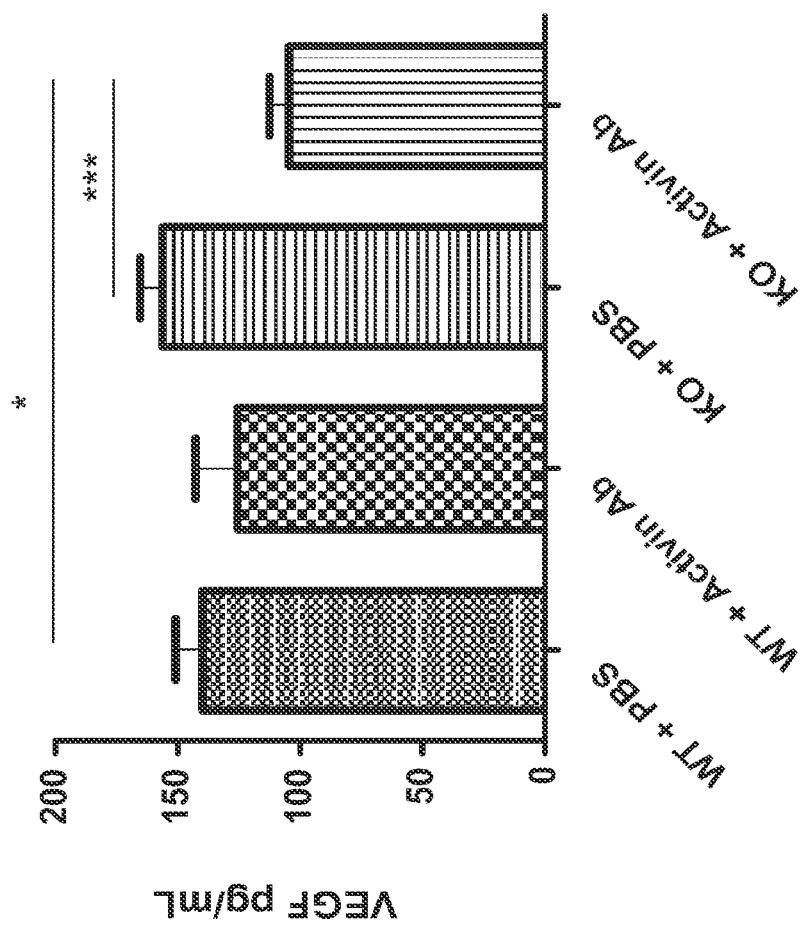
FIG. 33 shows a bar graph illustrating the effect of activin-A antibody treatment on serum VEGF levels in female Inhα KO mice and wild-type littermate control mice. Measurements of serum VEGF level were plotted as the mean±SEM; ***p<0.001, *p<0.05.
Figure 34:
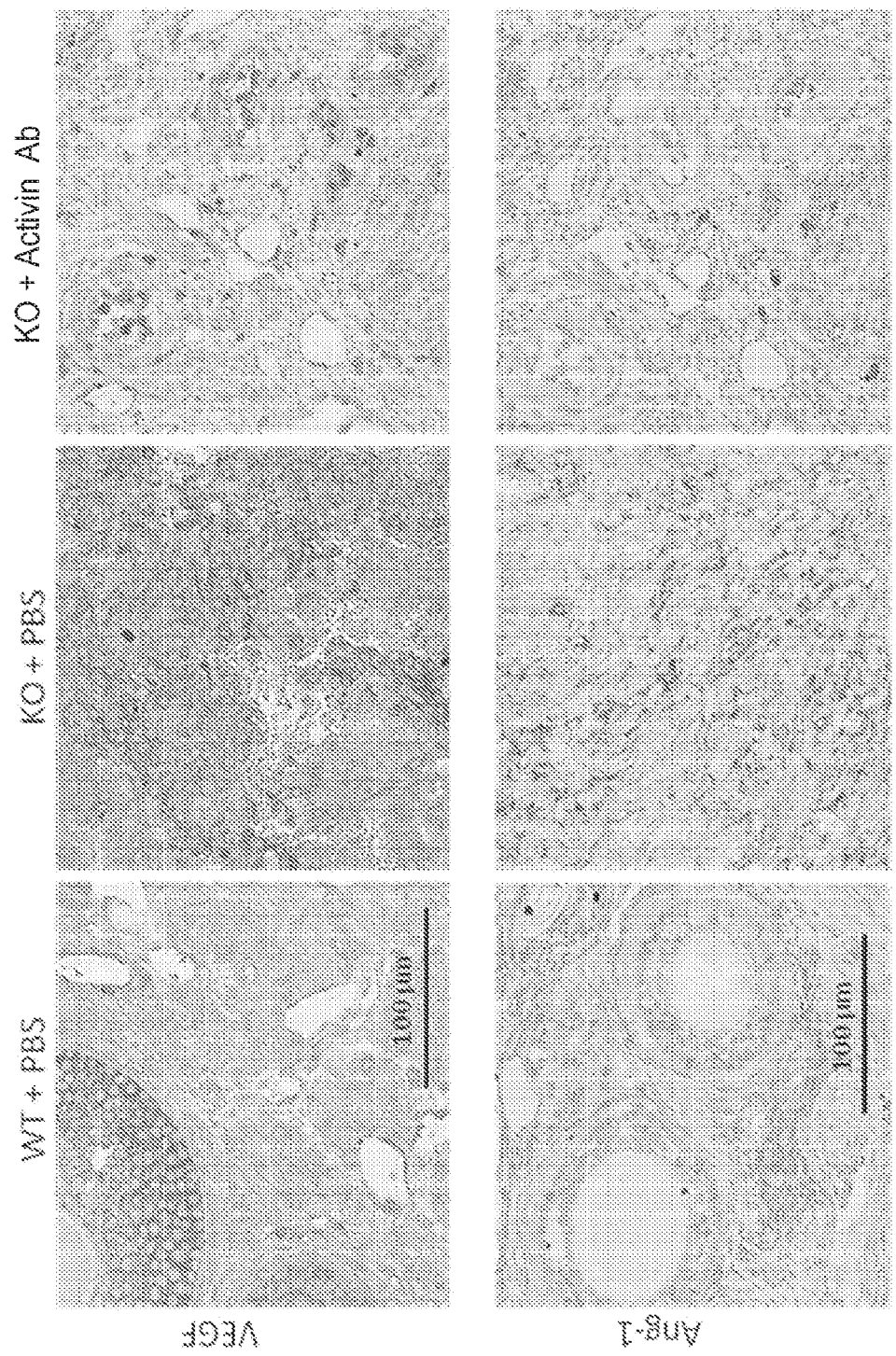
FIG. 34 shows the effect of activin-A antibody treatment on VEGF and angiopoietin-1 protein expression levels in ovarian tumor tissues of Inhα KO mice and wild-type littermate control mice. Upper panel: Representative images of VEGF and Ang-immunostaining (grayish blue) on ovarian tissue sections. Nuclei were counter stained with Fast Red. Bar graphs: VEGF and Ang-1 immunoreactivities in ovarian sections from 3 animals per group were quantified by imaging with Metamorph software and plotted as the mean±SEM. ***p<0.001 and *p<0.05
Figure 34:
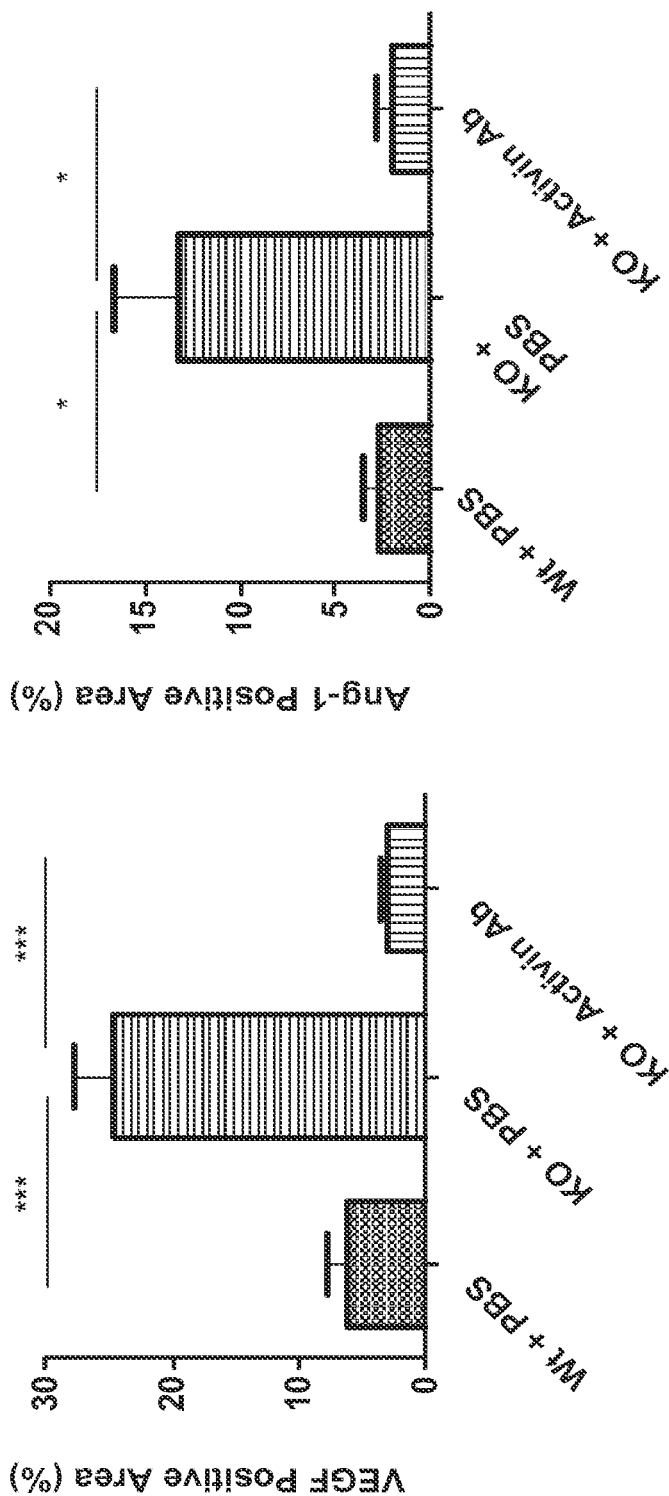

Serum VEGF ELISA revealed that the Inhα KO mice with advanced ovarian tumors had greatly increased levels of VEGF in their circulation (FIG. 33). Both VEGF and angiopoietins-1 (Ang-1) immunoreactivities were significantly increased in the sections of ovarian tumors from PBS-treated Inhα KO mice. Activin-A antibody treatment abolished the VEGF and Ang-1 inductions in the ovaries (FIG. 34).

The results from the present study indicate that weekly dose of 20 mg/kg activin-A antibody for 4 weeks reduced circulating activin levels, ameliorated cachexia, suppressed ovarian tumor growth and decreased the expression of tumor angiogenesis factors in female Inhα KO mice. Activin-A antibody administration significantly increased body weights and skeletal muscle mass, decreased ovarian tumor size, and abolished VEGF and Ang-1 overexpression in the ovaries in Inhα KO mice.

Example 11: Effects of Activin-A Antibody in Combination with Doxorubicin on Tumor Growth, Body Weight and Muscle Mass in Nude Female Mice Implanted with TOV-21G Ovarian Carcinoma The objective of this study was to examine the effects of pharmacological administration of activin-A antibody, doxorubicin, and activin-A antibody plus doxorubicin, on body weight, tumor growth and muscle mass in nude mice implanted with TOV-21G ovarian xenograft tumors. The activin-A antibody used was the same as described in the Materials section above. Eight-week-old female Athymic nude mice were each injected with $2.2 \times 10^6$ TOV-21G cells subcutaneously (SC) into the left site of the lower flank of the mice. On day 12 post tumor implantation, the mice were divided into 4 groups by body weight and tumor size and then treated with vehicle, activin-A antibody, doxorubicin, or the combination of activin-A antibody and doxorubicin. In addition, a group of non-tumor bearing mice was used as normal control and received PBS. The dosing and treatment schedule are indicated in the table below:

| Group | n | Test Article | Dose mg/kg | Conc. mg/mL | Volume mL/20 g | Route | Regimen |
|---|---|---|---|---|---|---|---|
| Normal | 8 | PBS | NA | NA | NA | SC | 1 x/week |
| TOV-21G + PBS | 14 | PBS | NA | NA | NA | SC | 1 x/week |
| TOV-21G + Activin-A Ab | 14 | Activin-A Ab | 20 mg/kg | 2 | 0.2 | SC | 1 x/week |
| TOV-21G + DOX | 14 | DOX | 4 mg/kg | 0.4 | 0.2 | IP | 1 x/week 4 consecutive IP injections |
| TOV-21G + Activin-A Ab + DOX | 14* | Activin-A Ab DOX | 20 mg/kg 4 mg/kg | 2 0.4 | 0.2 0.2 | SC IP | 1 x/week 1 x/week 4 consecutive IP injections |

*Two mice in Group 5 were killed by other mice in the cage, they were multicaged (4 mice/cage).

Mice were weighed weekly. Body weight data were recorded longitudinally. Tumor size was measured longitudinally by using an electronic caliper (Fred V. Fowler Company, Inc.). The following formula was used to calculate actual tumor volume (Tomayko and Reynolds, 1989): Volume of a rectangular solid tumor: Tumor volume (mm³) =length (mm)×width (mm)×height (mm) of tumor. At the end of the study, mice in all groups were subjected to terminal necropsy and lean carcass weight (excluding skin, adipose tissue, internal organs, and head) was determined by using standard anatomical dissection procedures. The calf muscles from left and right sides of each mouse were excised and weighed. All results were expressed as the mean±SEM. For statistical analysis, a standard 2-tailed t-test was used to determine the statistical differences. Any p value less than 0.05 was considered to be statistically significant.

Figure 35:
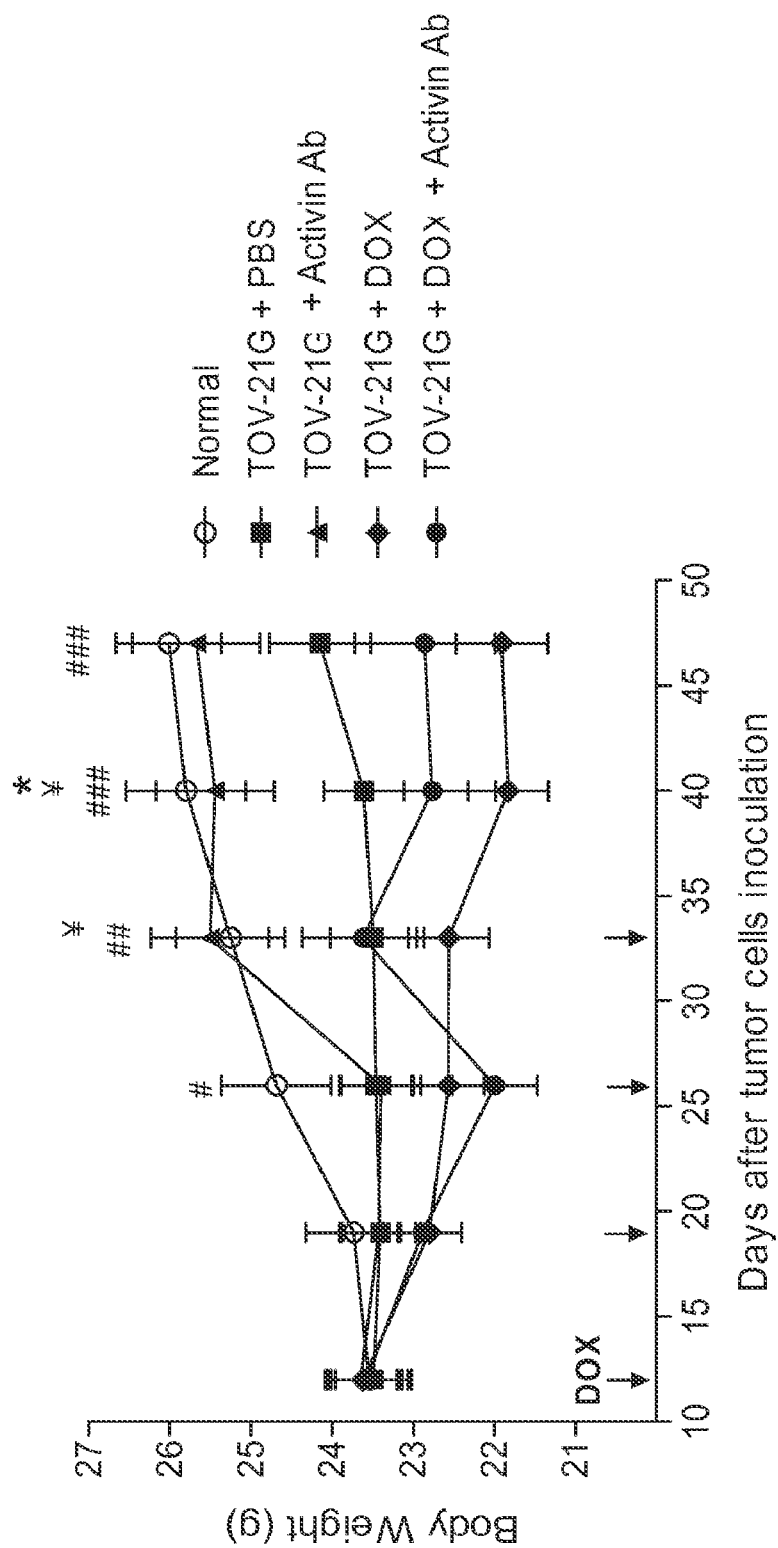
FIG. 35 shows the effect of activin-A antibody in combination with doxorubicin on body weight in TOV-21G tumor-bearing mice. Body weight was recorded longitudinally. Arrows point to timings of doxorubicin dosing. Data were plotted as mean±SEM; n=8-14 per group. Standard 2-tailed Student's t-test (MS Excel 5.0) was used to analyze the differences between groups. Statistical significance is represented by *: p<0.05: Normal vs. TOV-21G+PBS; $^{#}$: p<0.05, $^{##}$: p<0.01, $^{###}$: p<0.001: Normal vs. TOV-21G+DOX; $^{¥}$: p<0.05: TOV-21G+PBS vs. TOV-21G+Activin Ab.

As shown in FIG. 35, TOV-21G tumor-bearing mice showed a significant loss in body weight compared with non-tumor-bearing normal control mice. Activin-A antibody administration prevented the weight loss in TOV-21G tumor-bearing mice. Doxorubicin treatment led to further decline (non-statistically significant) in body weight in TOV-21G implanted mice. Combination treatment with activin-A antibody and doxorubicin appeared to cause less weight loss (non-statistically significant) than doxorubicin treatment alone.

Figure 36:
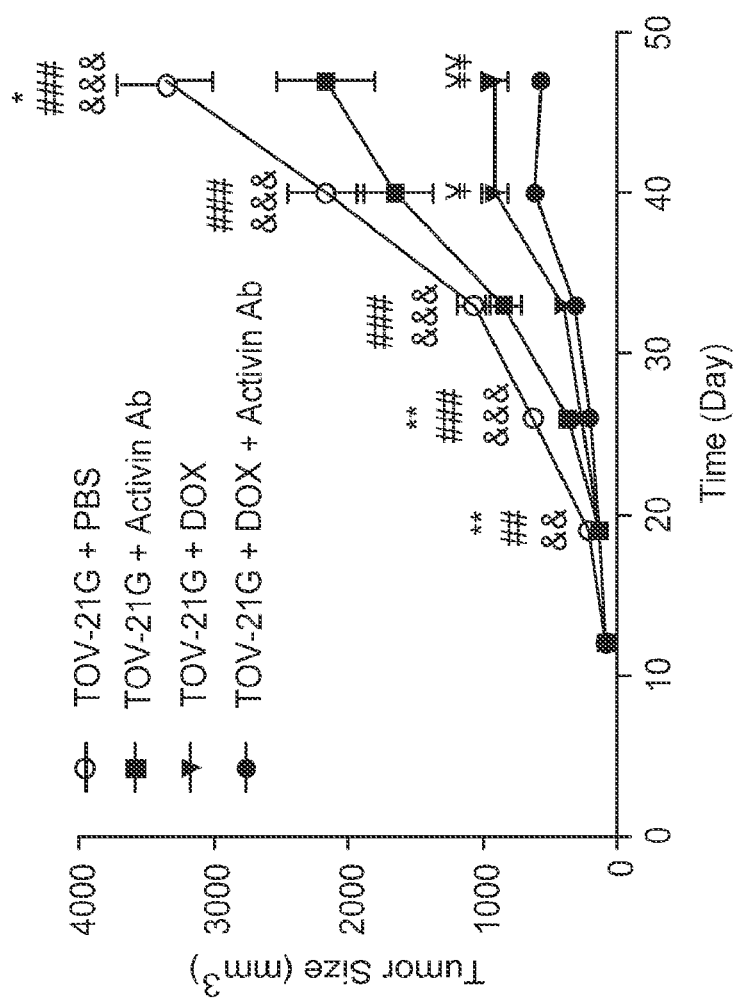
FIG. 36 shows the effect of activin-A antibody in combination with doxorubicin on tumor size in TOV-21G tumor-bearing mice. Measurements of tumor size were plotted as the mean±standard error of the mean (SEM); n=8-14 per group. Standard 2-tailed Student's t-test (MS Excel 5.0) was used to analyze the differences between groups. Statistical significance is represented by * p<0.05, ** p<0.01: TOV-21G+Activin Ab vs. TOV-21G+PBS, $^{##}$p<0.01; $^{###}$: p<0.001: TOV-21G+DOX vs. TOV-21G+PBS; $^{&&}$p<0.01; $^{&&&}$ p<0.001: TOV-21G+DOX+Activin Ab vs. TOV-21G+PBS; $^{¥}$p<0.05; $^{¥¥}$p<0.01: TOV-21G+DOX+Activin Ab vs. TOV-21G+DOX.
Figure 37:
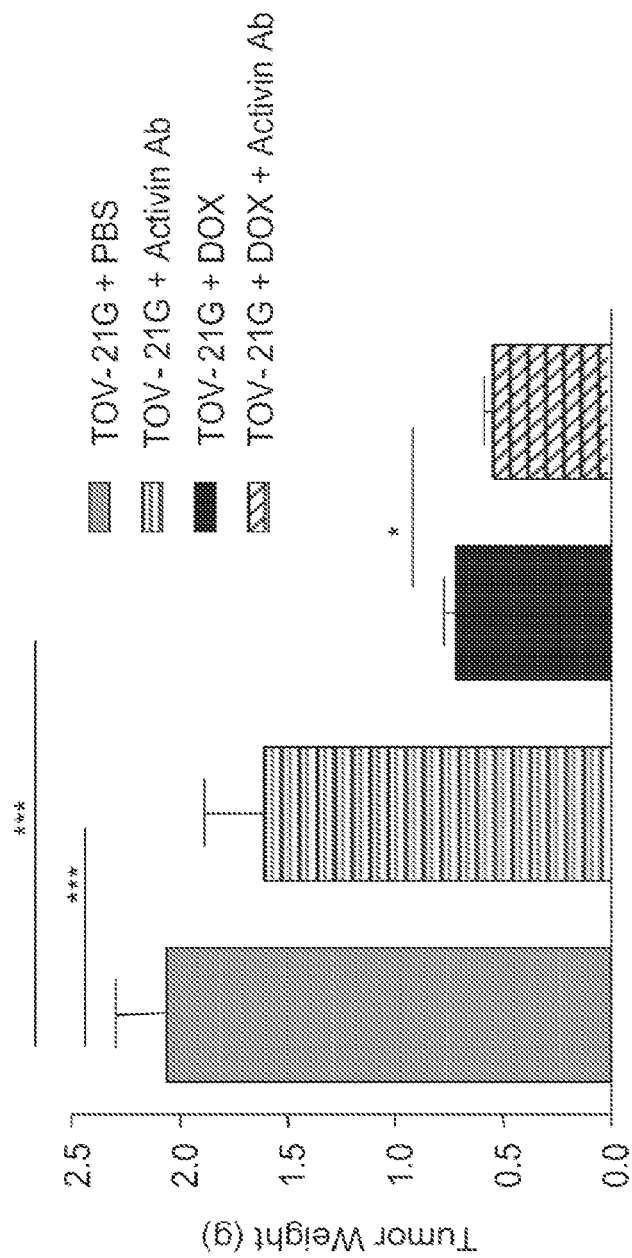
FIG. 37 shows the effect of activin-A antibody in combination with doxorubicin on tumor weight in TOV-21G tumor-bearing mice. Measurements of tumor weight were plotted as the mean±standard error of the mean (SEM); n=8-14 per group. Standard 2-tailed Student's t-test (MS Excel 5.0) was used to analyze the differences between groups. Statistical significance is represented by *: p<0.05; : p<0.01; *: p<0.001.

Tumor size of each individual mouse was measured every week throughout the 5-week study period. Tumor weights were recorded via terminal necropsy procedures at week 5. As shown in FIG. 36 and FIG. 37, statistically significant decreases in the tumor size and tumor weight at day 47 were observed in activin-A antibody-treated TOV-21G-bearing mice versus the vehicle-treated TOV-21G-bearing mice. In addition, combination treatment with activin-A antibody and doxorubicin had an additive effect on tumor suppression. Thus, activin-A antibody or doxorubicin was each capable of inhibiting TOV-21G tumor growth in nude mice and when these two agents were combined, they led to greater inhibition of TOV-21G tumor growth.

Mouse lean carcass weight and calf muscle weight were determined via necropsy procedures at the end of the 5-week experiment. As shown in FIG. 38, TOV-21G tumor-bearing mice showed significant decreases in lean carcass weight and calf muscle mass compared with normal controls; however, administration of activin-A antibody prevented the loss in lean carcass weight and calf muscle mass in TOV-21G-implanted nude mice. Doxorubicin treatment had no effect on the loss of lean carcass weight and calf muscle mass in TOV-21G xenograft mice; however, combination treatment with activin-A antibody attenuated the loss in lean carcass weight and calf muscle mass in TOV-21G-implanted nude mice. Thus, activin-A antibody administered alone or in combination with doxorubicin was capable of preventing muscle loss in TOV-21G tumor-bearing mice.

Activin-A antibody administered alone or in combination with doxorubicin inhibited TOV-21G xenograft tumor growth and also attenuated muscle wasting in the tumor-bearing nude mice. Moreover, activin-A antibody treatment appeared to have an additive effect with doxorubicin chemotherapy on suppression of in vivo growth of TOV-21G xenograft tumors in nude mice.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

Alibhai, S M H, Gogov S, Allibhai Z. Long-term side effects of androgen deprivation therapy in men with non-metastatic prostate cancer: a systematic literature review. Crit Rev Oncol/Hematol. 2006; 60:201-15.

Chang K P, Kao H K, Liang Y, et al. Overexpression of activin A in oral squamous cell carcinoma: association with poor prognosis and tumor progression. Ann Surg Oncol. 2010; 17:1945-1956.

Cobellis L, Reis F M, Luisi S, et al. High concentrations of activin A in the peritoneal fluid of women with epithelial ovarian cancer. J Soc Gynecol Investig. 2004; 11:203-206.

de Kretser D M, Hedger M P, and Phillips D J. Activin A and follistatin: their role in the acute phase reaction and inflammation. Journal of Endocrinology. 1999:161:195-198.

Doherty T J. Aging and sarcopenia. J Appl Physiol. 2003; 95:1717-27.

Do T V, Kubba L A, Antenos M, Rademaker A W, Sturgis C D, and Woodruff T K. The role of activin A and Akt/GSK signaling in ovarian tumor biology. Endocrinology. 2008; 149:3809-16.

Gabizon A, Martin F. Polyethylene glycol-coated (pegylated) liposomal doxorubicin: rationale for use in solid tumours. Drugs. 1997; 54 (suppl 4):15-21.

Harada K, Shintani Y, Sakamoto Y, Wakatsuki M, Shitsukawa K, and Saito S. Serum immunoreactive activin A levels in normal subjects and patients with various diseases. J Clin Endocrinol Metab. 1996; 81:2125-2130.

Hubner G, Alzheimer C, and Werner S. Activin: a novel player in tissue repair processes. Histology & Histopathology. 1999; 14:295-304.

Jones K L, de Kretser D M, Patella S, and Phillips, D J. Activin A and follistatin in systemic inflammation. Molecular & Cellular Endocrinology. 2004; 225:119-125.

Lambert-Messerlian G M, DePasquale S E, Maybruck W M, Steinhoff M M, and Gajewski W H. Secretion of activin A in recurrent epithelial ovarian carcinoma. Gynecol Oncol. 1999; 74:93-97.

Lee S J, Reed L A, Davies M V, et al. Regulation of muscle growth by multiple ligands signaling through activin type II receptors. Proc Natl Acad Sci USA. 2005; 102:18117-22.

Lee S J, McPherron A C. Regulation of myostatin activity and muscle growth. Proc Natl. Acad. Sci., USA. 2001; 98:9306-9311.

Luisi S, Florio P, Reis F M, and Petraglia F. Expression and secretion of activin A: possible physiological and clinical implications. European Journal of Endocrinology. 2001; 145:225-236.

MacDonald N, Easson A M, Mazurak V C, Dunn, G P, Baracos V E. Understanding and managing cancer cachexia. J Am Coll Surg. 2003; 197:143-61.

Matzuk M M, Finegold M J, Su J G J, Hsueh A J W, Bradley A. α-inhibin is a tumour-suppressor gene with gonadal specificity in mice. Nature. 1992; 360:313-19.

Matzuk M M, Finegold M J, Mather J P, Krummen L, Lu H, Bradley A. Development of cancer cachexia-like syndrome and adrenal tumors in inhibin-deficient mice. Proc Natl Acad Sci USA. 1994; 91:8817-21.

Morley J E, Thomas D R, Wilson M-M G. Cachexia: pathophysiology and clinical relevance. Am J Clin Nutr. 2006; 83:735-43.

Muscaritoli M, Bossola M, Aversa Z, Bellantone R, Fanelli F R. Prevention and treatment of cancer cachexia: new insights into an old problem. Eur J Cancer. 2006; 42:31-41.

Provencher D M, Lounis H, Champoux L, et al. Characterization of four novel epithelial ovarian cancer cell lines. In Vitro Cellular & Developmental Biology Animal. 2000.36:357-361.

Roth S M, Walsh S. Myostatin: A therapeutic target for skeletal muscle wasting. Curr Opin Clin Nutr Metab Care. 2004; 7:259-63.

Roubenoff R. Origins and clinical relevance of sarcopenia. Can J Appl Phys. 2001; 26:78-89.

Roubenoff R, Heymsfield S B, Kehayias J J, Cannon J G, Rosenberg I H. Standardization of nomenclature of body composition in weight loss. Am J Clin Nutr. 1997; 66:192-96.

Tomayko M and Reynolds C P. Determination of subcutaneous tumor size in athymic (nude) mice. Cancer Chemother Pharmacol. 1989; 24:148-154

Wildi S, Kleeff J, Maruyama H, Maurer C A, Buchler M W, and Korc M. Overexpression of activin A in stage IV colorectal cancer. Gut. 2001; 49:409-417.

Yoshinaga K, Mimori K, Yamashita K, Utsunomiya T, Inoue H, and Mori M. Clinical significance of the expression of activin A in esophageal carcinoma. Int J Oncol 2003; 22:75-80.

Zhou X, Wang J L, Lu J, et al. Reversal of cancer cachexia and muscle wasting by ActRIIB antagonism leads to prolonged survival. Cell. 2010; 142: 531-543.

Zimmers T A, Davies M V, Koniaris L G, et al. Induction of cachexia in mice by systemically administered myostatin. Science. 2002; 296:1486-88.

The invention claimed is:

1. A method for treating serous ovarian cancer in a subject in need thereof comprising administering a therapeutically effective amount of an anti-activin-A antibody and a chemotherapeutic compound to the subject wherein the anti-activin-A antibody comprises:

(a) a light chain variable domain sequence of SEQ ID NO: 275; and
(b) a heavy chain variable domain sequence of SEQ ID NO: 278 wherein said antigen binding protein binds to human activin-A; and wherein the chemotherapeutic compound is capecitabine.

* * * * *